United States Patent
Rapaport et al.

(10) Patent No.: US 7,209,550 B1
(45) Date of Patent: Apr. 24, 2007

(54) MEDICAL INFORMATION SYSTEM HAVING INTERACTIVE MESSAGING INTERFACE

(76) Inventors: Seymour A. Rapaport, 1050 Crooked Creed Dr., Los Altos, CA (US) 90240; Jeffrey A. Rapaport, 362 W. Olive Ave., Suite 16, Sunnyvale, CA (US) 94086; Kent Don, 373 Oxford Ave., Palo Alto, CA (US) 94301

( * ) Notice: Subject to any disclaimer, the term of this patent is extended or adjusted under 35 U.S.C. 154(b) by 1649 days.

(21) Appl. No.: 09/717,915

(22) Filed: Nov. 21, 2000

Related U.S. Application Data

(63) Continuation of application No. 08/906,726, filed on Aug. 5, 1997, now Pat. No. 6,192,112, which is a continuation-in-part of application No. 08/581,749, filed on Dec. 29, 1995, now Pat. No. 5,926,526.

(51) Int. Cl.
*H04M 1/64* (2006.01)
(52) U.S. Cl. .................... 379/88.12; 379/88.22
(58) Field of Classification Search ............. None
See application file for complete search history.

(56) References Cited

U.S. PATENT DOCUMENTS

| | | | | |
|---|---|---|---|---|
| 4,625,081 A | * | 11/1986 | Lotito et al. ............ | 379/88.26 |
| 4,853,952 A | * | 8/1989 | Jachmann et al. ....... | 379/88.11 |
| 5,325,294 A | * | 6/1994 | Keene ..................... | 705/3 |
| 5,649,003 A | * | 7/1997 | Kapsales et al. ......... | 379/88.25 |
| 5,737,396 A | * | 4/1998 | Garcia .................... | 379/88.16 |
| 5,995,594 A | * | 11/1999 | Shaffer et al. .......... | 379/88.12 |
| 6,333,973 B1 | * | 12/2001 | Smith et al. ............ | 379/88.12 |
| 7,034,691 B1 | * | 4/2006 | Rapaport et al. ....... | 340/573.1 |

* cited by examiner

*Primary Examiner*—Fan Tsang
*Assistant Examiner*—Joseph T. Phan
(74) *Attorney, Agent, or Firm*—MacPherson Kwok Chen & Heid LLP; Gideon Gimlan

(57) ABSTRACT

A system for providing medical information to a patient is provided. The system includes a medical information server, including a software engine, coupled to a memory location. The memory location stores a plurality of voice mailboxes. A voice mailbox includes at least two segments. A first segment for test results, or an upload-source note, and a second segment for account owner information, or a chart note. An upload-source, such as a testing facility or laboratory, is coupled to the server and provides test results to the mailbox. An interactive voice response (IVR) software interface is also coupled to the engine. The IVR provides the medical information in the mailbox responsive to a user input. The system may also include a patient database. Further, the engine generates alerts to the account owner based upon particular events. The system is also configured to prevent conflicting accesses by users. The system is convenient to use due to reporting features and an identifier function used to locate particular voice mailboxes.

19 Claims, 66 Drawing Sheets

MEDICAL INFORMATION SYSTEM HAVING INTERACTIVE MESSAGING INTERFACE

CONTINUATION APPLICATION INFORMATION

This application is a continuation of U.S. application Ser. No. 08/906,726, filed Aug. 5, 1997, entitled A MEDICAL INFORMATION SYSTEM INCLUDING A MEDICAL INFORMATION SERVER HAVING AN INTERACTIVE VOICE RESPONSE INTERFACE, which subsequently issued as U.S. Pat. No. 6,192,112 on Feb. 20, 2001 and which itself was a continuation-in-part of U.S. application Ser. No. 08/581,749 filed Dec. 29, 1995 that subsequently issued as U.S. Pat. No. 5,926,526 on Jul. 20, 1999 with the title METHOD AND APPARATUS FOR AUTOMATED PATIENT INFORMATION RETRIEVAL. The disclosures of said cross-referenced applications are incorporated herein by reference.

FIELD OF THE INVENTION

The present invention relates to providing medical information such as laboratory test results to patients.

DESCRIPTION OF RELATED ART

Medical providers and testing facilities are typically deluged with demands on their time and have limited support for delivery and tracking of test results. Primary care and other medical providers often order various tests during their office evaluation of patients. The tests may range from a pregnancy test with a single yes-no type answer that will be reported the next day to batteries of tests with more than fifty result values that may come back at different times over several weeks. The task of reporting these results to patients can be horrendously complex and consuming, but, at the same time, errors or lapses in reporting can be life threatening. The task is often accomplished with great effort and not uncommonly with less than ideal perfection or completeness.

U.S. patent application entitled, "Method and Apparatus for Automated Patient Information Retrieval," Seymour A. Rapaport, M.D., Jeffrey A. Rapaport et al., filed Dec. 29, 1995 referenced above and incorporated by reference, describes an approach for patient information retrieval that significantly eases this work and can allow essentially complete reporting of test results to the patients in a professional practice. The approach described there increases the medical provider's efficiency and effectiveness in accomplishing the test result reporting task many fold. However, despite the fact that the provider's medical practice and patient care is significantly improved in that it is possible for essentially all tests to be reported, the provider must accomplish some added tasks, and therefore there are some added demands on the provider's time.

SUMMARY

The present disclosure of invention provides methods and/or systems that may streamline the provider's tasks so that the provider is involved time-wise only to the extent that he or she wants to and has to be. This results in essentially complete reporting of patient tests and other appropriate patient messages in the medical practice with little added efforts on the providers' part and improved patient care and safeguards to patients' health.

There are several additions and innovations that enable these goals: The system improves the use of standard patient messages and allows for extensive uploading of results of tests by testing facilities directly into the account owner's patient message database for access by the account owner's patients. This significantly eases the burden of test reporting for the provider, but comes with the cost of making the provider less aware than is desirable to certain test results—e.g., critical results, results that the provider is especially interested in knowing, results that the testing facility feels need direct provider attention, and time-sensitive results. To prevent such occurrences, the system has several types of alerts for the providers and upload-sources (testing facilities).

Upload-sources may upload specific results into an upload-source note field that is in the mailbox for account owners to review. The content in this field is available only to medical personnel and not the patient.

A finder function and patient identifier feature enables the account owner to quickly locate the proper mailbox for a patient on the system for placing a patient message when the test results return.

The system may be configured to include a database with patient record data that automatically uploads much of the information needed for the mailbox on the system when needed; text-to-speech software allows this information to be converted to speech which may be played over a telephone line by a interactive voice response system.

A plurality of reports is composed by the system to aid account owners and upload-sources. These reports automatically record the functioning of the system including account owner placement and retrieval of messages and alerts, patient message retrieval, and a summary of message content.

An array of parameters allows for significant customization of a particular system at the account level, mailbox pool level, and system level. This customization allows features of the system to be available as desired thereby offering a highly customized solution to the many different needs of a variety of users of the system.

The system shares information resources through a variety of interfaces and also supports a public application programming interface (API), which allows access to third party software and solutions.

The system may be configured to serve several members of the same provider group with the same access means, e.g. telephone number, with the inclusion of a mailbox number that is linked to an account.

According to one aspect of the present disclosure, a system for providing medical information to a patient is provided. The system comprises a medical information software engine. A memory location having a voice mailbox is coupled to the engine. The voice mailbox is accessible by the patient, the upload-source, such as a laboratory test facility, and the account owner, such as a medical provider. The voice mailbox includes a first segment for storing a patient message for the patient, a second segment for account owner information supplied by the account owner, and a third segment for storing upload-source information, such as test results. The upload-source is coupled to the medical information software engine and may provide the test results. An interactive voice response system interface is coupled to the medical information engine and the voice mailbox. The interface provides the account owner information in the second segment responsive to an account owner input.

Upload-Source Uploading Patient Messages and Patient Retrieval Alerts into Mailboxes that Have Associated Account Owner Chart Notes According to an aspect of the present invention, a set of pre-recorded patient messages are stored in the appropriate patient mailboxes in response to account owner input or input from an expert system where the expert system responds to test result data at the upload-source. The expert system rule-base is in agreement with the standards and practices of the upload-source and account owners involved.

According to an aspect of the present invention, messages may include textual data which is translated into speech data using text-to-speech software and stored in a patient voice mailbox.

According to an aspect of the present disclosure, both the account owner and the uploading source may be notified by a patient-retrieval alert if a patient does not access the voice mailbox within specified time period.

According to another aspect of the present disclosure, when data is uploaded into a mailbox, the upload-source may assign responsibility of the mailbox to a particular account owner. The account owner would have the mailbox assigned to his or her account database, and have corresponding information sent to the account owner regarding the patient message and mailbox. The information may include alert information.

According to an aspect of the present disclosure, a patient voice mailbox may have a segment for storing an upload-source note wherein the upload-source may upload specific test results or messages into the upload-source note that the account owner can access but not the patient.

According to an aspect of the present disclosure, the system alerts a particular account owner when an upload-source note is uploaded into an assigned patient voice mailbox but a patient message is not stored in the assigned patient voice mailbox.

According to an aspect of the present disclosure, the upload-source may overwrite data in a mailbox if the patient voice mailbox data has not been accessed by patient or altered by an account owner. If the account owner has accessed the mailbox, and the upload-source alters data in the voice mailbox, the account owner is notified by an upload-source-change alert According to an aspect of the present disclosure, patients cannot receive certain pre-recorded patient messages without prior review and/or approval by the account owner.

Configurations with PD Access and Configurations Without PD Access

According to an aspect of the present disclosure, each account may have an associated patient database (PD) containing records with fields having: 1) a unique patient identification code, 2) other identifying data, 3) contact data, 4) and other information regarding the patients in the practice of the account owner.

According to an aspect of the present disclosure, when an account is configured to have access to a patient database, appropriate data from fields in this database can be entered into a particular mailbox using a patient finder code ("PFC") to locate the proper patient identification code ("PIC"). In this configuration the account owner's chart notes are associated with the PIC.

According to an aspect of the present disclosure, the upload-source can assign a mailbox to the account owner's account.

According to an aspect of the present disclosure, all chart notes for a specific patient in a PD provided by the accessing account owner will first be presented in order of date of formation and then chart notes placed by other account owners for this PIC will be presented in order of date of formation. In another aspect, the chart notes provided by other account owners are preceded by the system playing the name of the account owner who provided the chart note.

According to an aspect of the present disclosure, a patient database may contain other fields pertinent to the patient's health such as drug allergies and current medications or have means of accessing such data on an electronically stored patient record elsewhere.

According to an aspect of the present disclosure, for an account with access to a patient database there is available an alert, called the test-number alert, which indicates the number of tests remaining to be retrieved by a patient. The alert is activated according to the following: The account owner enters into the system the number of mailboxes that will be used to report results to the patient over a specified time period subsequent to the office visit wherein the tests were ordered. This number is decremented whenever the patient retrieves a patient message stored in a mailbox within this set time period. If all patient messages in mailboxes that are to inform the patient of results have not been retrieved, the patient is informed of this prior to the end of the patient's access to the system. According to another aspect of the disclosure, if there are remaining unfilled or unretrieved patient messages after the account owner pre-set time, the account owner may be so informed by this alert if it is activated. If by the deadline set for this alert, the patient has additional tests ordered to be reported on the system, the account owner is prompted to reset the test number alert information.

Alerts

According to an aspect of the present invention, for an account with patient database (PD) access, the account owner can assign a completion notification request (CNR) to a mailbox corresponding to a PIC. A completion notification request (CNR) utilizes a series of numeric digits which is communicated to the upload-source and associated with the chart note stored when the test is ordered. The upload-source accordingly can associate the upload message with the CNR string and alert the account owner that a patient message or upload-source note has been uploaded into the patient mailbox. The CNR string has an associated account owner input of a deadline whereby an alert to the account owner is activated by the system (compliance alert) if a patient message or upload-source note is not uploaded by the upload-source within this deadline.

According to an aspect of the present disclosure, for an account without PD access, when the account owner stores a chart note at the time of test ordering, he or she may set a deadline for the system to notify him or her if there is no upload-source note or patient message uploaded to that mailbox within an account owner specified deadline. This alert is referred to as a compliance alert.

According to an aspect of the present disclosure, for an account without PD access, when storing a chart note, the account owner may cause the system to notify him or her when an upload-source note or patient message is uploaded to that mailbox within an account owner specified deadline. This alert is referred to as a completion alert.

According to an aspect of the present disclosure, the upload-source when uploading data into a mailbox can activate an alert for notifying the account owner that an upload-source note or patient message in a particular mailbox has been uploaded. In another aspect of the present invention, the particular upload-source name is communicated to the account owner during playing of alert information. This alert is referred to as an upload alert.

According to another aspect of the present disclosure, the upload-source can set a deadline by which the account owner must access the upload-source note or patient message in a particular mailbox which the upload-source has uploaded or the upload-source is automatically notified of the lack of access by the account owner. This alert is referred to as a timed-upload alert.

According to an another aspect of the present disclosure, whenever an upload-source sets an upload alert in a mailbox, the corresponding mailbox will have an owner alert activated at the time of upload.

According to still another aspect of the present disclosure, if the notification deadline in the aforementioned timed-upload alert is less than a parameter value, the upload-source is periodically notified of the status of the access of the mailbox by the account owner and the system can initiate means to contact the account owner or a designated alternate regarding the alert by pager or other means. This alert is referred to as a panic alert.

According to an aspect of the present disclosure, the upload-source is notified by, for example, fax to inform the upload-source of the retrieval or non-retrieval of an upload alert or panic alert.

According to an aspect of the present disclosure, the account owner is prompted by the system to record an alert note number when the account owner sets an alert for the patient. The alert note includes patient contact information, e.g. the patient's phone. The alert note is only available to the account owner when an alert is activated. In an embodiment, the upload-source may set the alert note information when uploading information.

According to an aspect of the present disclosure, when the patient retrieves a patient message with a patient-retrieval alert associated with the patient message, the patient-retrieval alert is automatically removed from the corresponding account's alerted mailbox list.

According to an aspect of the present disclosure, a mailbox can not be removed or deleted from the system if a panic alert has been activated for the mailbox and the account owner has not addressed the panic alert.

According to an aspect of the present disclosure, the deadline until a patient-retrieval alert is activated can be set individually for each patient message by the account owner or upload-source at the time of patient message placement.

According to an aspect of the present disclosure, the various types of alerts on the system are presented to the account owner in a pre-designated order, sorted by alert type.

According to another aspect of the present disclosure, the alerts of a particular type can be further ordered to be presented to the account owner in order of the date of their creation.

According to an aspect of the present disclosure, the system has a built in default capability of assigning an alert precedence if a mailbox has more than one alert.

In an embodiment if a mailbox has more than one alert flag set, then the alert information for the mailbox is presented to the account owner as if the mailbox only had the highest precedence alert. For example, if a mailbox has both a panic alert flag set and a patient-retrieval alert flag set, the mailbox is presented to the account owner as if the mailbox only had a panic alert flag set; or, for example, if a mailbox had both patient-retrieval alert flag set and upload-source-change alert flag set, the alert information is presented as if the mailbox only had an upload-source-change alert flag set.

In an embodiment if a mailbox has more than one alert, the contents of the mailbox are presented to the account owner only once during the account owner's accessing of his or her alerts.

Prevention of Conflicting Demands and Results on System

According to an aspect of the present disclosure, a mailbox may only be accessed by one user at a time.

According to an aspect of the present disclosure, after a patient retrieves a patient message from a particular mailbox, neither the account owner or the upload-source can edit any field in that mailbox.

According to an aspect of the present disclosure, mailboxes in a particular mailbox pool are either in a protected range or not in a protected range. If a particular mailbox is in the protected range then when mailbox information is uploaded and/or changed by uploading file information, the upload file information for that mailbox must contain the appropriate mailbox security code.

In an embodiment, for an account with PD access, the mailbox security code can be a patient security code or other type of patient security code for a particular patient in a PD.

Reporting Functions

According to an aspect of the present disclosure, the system maintains a count of entries in the expired-timed-upload alerts collection: When this count reaches a parameter value or when the number of days since the last such report was sent to the upload facility is above a parameter value, the system sends the upload facility an expired-timed-upload alert report. The expired-timed-upload alert report indicates, but is not limited to, the deadline set for alerting the account owner of the uploaded information and the time of account owner access of such information.

According to an aspect of the present disclosure, the system compiles and sends a report to the upload-source that lists the results of the system's processing of the last upload file received by the system from this source. This report is compiled and sent once the uploaded file is processed. This report lists those mailboxes that failed to upload information and an error code that indicates the reason for the failure. The report for an account with PD access includes the mailbox number assigned by the system to each uploaded result and/or patient message; this mailbox number may be used by the upload-source to subsequently edit the mailbox. The report may also include for each mailbox a patient name, a PIC, pre-recorded patient message code, upload-source note or upload-source code, a name of account owner for the mailbox, and date and time of upload.

In an embodiment, for accounts without PD access, a mailbox number is reported in place of the PIC.

According to an aspect of the present disclosure, patient message titles may summarize pre-recorded patient messages and be presented to account owners when appropriate to inform them of mailbox contents more rapidly. According to another aspect of the present disclosure, the account owner may use standard patient message codes or text to summarize the content of custom recorded patient messages so that these codes and what they represent may appear on reports generated by the system. These codes and messages may be appended.

According to an aspect of the present disclosure, the account owner when accessing alerts can place information regarding his or her disposition of each alert and associated information in a file for subsequent transcription to the patient's records. The account owner may store in an electronic medical record associated with the patient the actions taken secondary to and results of his or her accessing an alert for that patient.

Patient Identifier Functionality

According to one aspect of the present disclosure the system uses a finder function and a patient identifier to locate a particular patient message and/or mailbox.

According to an aspect of the present disclosure, a two digit numeric entry, called a patient identifier, corresponds to a subset of mailboxes containing the mailbox desired and is used by the finder function to retrieve the mailbox for data entry in the mailbox. The patient identifier has several unique characteristics that allow efficient location of the appropriate mailbox.

According to an aspect of the present disclosure, the patient identifier can be used only to access a mailbox in the account of the account owner who assigned the patient identifier to a specific patient mailbox.

According to an aspect of the present disclosure, the patient identifier can be used only by the account owner who is authorized to leave a patient message in the particular mailbox—e.g., the patient identifier is available to the account owner using the system and only after the account owner gains access to the system using the appropriate security code.

According to an aspect of the present disclosure, the patient identifier is selected by the person who stores a patient message in the mailbox.

According to an aspect of the present disclosure, the patient identifier can only access mailboxes that do not contain patient messages.

According to an aspect of the present invention, the patient identifier can only access mailboxes that do not contain patient messages, or that have had patient messages stored less than a specific time period.

According to an aspect of the present disclosure, upon entering the patient identifier, information is presented to the user on the matching mailboxes to allow discrimination between the mailboxes. This allows the user to identify the appropriate mailbox. Typically, a patient identifier consisting of two digits will result in some redundancy—i.e., several mailboxes will have the same patient identifier and, often, the same patient since several tests may have been ordered on one patient.

According to an aspect of the present disclosure, the patient identifier is used on the system in conjunction with storing the patient name and then playing the associated account owner's chart note. This allows for rapid identification and choice of the proper mailbox by the account owner, since the system allows the listening account owner to "skip forward" at any time by pushing an appropriate touch tone telephone key.

According to an aspect of the present disclosure, a particular mailbox is only accessible by a patient identifier until a patient message has been stored in the mailbox. Thus, as patient messages are stored, there is a progressive decrease in the number of choices presented to the account owner when the system is entered to store another patient message. This aids in the speed and efficiency of an account owner's use of the system.

According to an aspect of the present disclosure, the system may retrieve in rank order the closest matches to a particular entered patient identifier.

According to an aspect of the present disclosure, once a set of mailboxes has been identified by entering a particular patient identifier, the system retrieves and presents the particular data in fields of each mailbox sequentially to the account owner in an order that allows the most discriminating fields to be presented first.

According to an aspect of the present disclosure, the patient identifier is a voice signal that the account owner voices into the system. The system records the vocal characteristics of the spoken patient identifier. When the account owner subsequently enters the system to place a patient message, the account owner may voice the patient identifier into the system and the system presents, in rank order, the nearest matches of the vocal characteristic electronic signal so inputted from which the account owner would choose the correct mailbox.

Interactive Voice Response Interface

According to another aspect of the present disclosure, the prompts heard by a particular user in the interactive voice response interface automatically change in response to the number of user entries by the particular user into the system and/or logic block of the system. The number of entries controlling this change is adjustable by the system administrator. A similar function operates for the same purpose if interfaces other than interactive voice response are used.

Per another aspect of the present disclosure, the value representing the number of entries that determines which prompt is played decays (decreases) over time.

Per another aspect of the present disclosure, the threshold that triggers change from one prompt to another changes over time.

According to an aspect of the present disclosure, several account owners who may work as a group may give patients the same telephone number to access the system to retrieve their messages. There are three numbers on a card given to the patient: The first number, is the telephone number, and is used to indicate which mailbox pool is being accessed. The second number, the mailbox number, is used to determine the mailbox number as well as the account that has the particular mailbox. The third number, the security code, is used to provide secure access to the mailbox with the patient message.

DETAILED DESCRIPTION

I. System Overview

Figure 1:
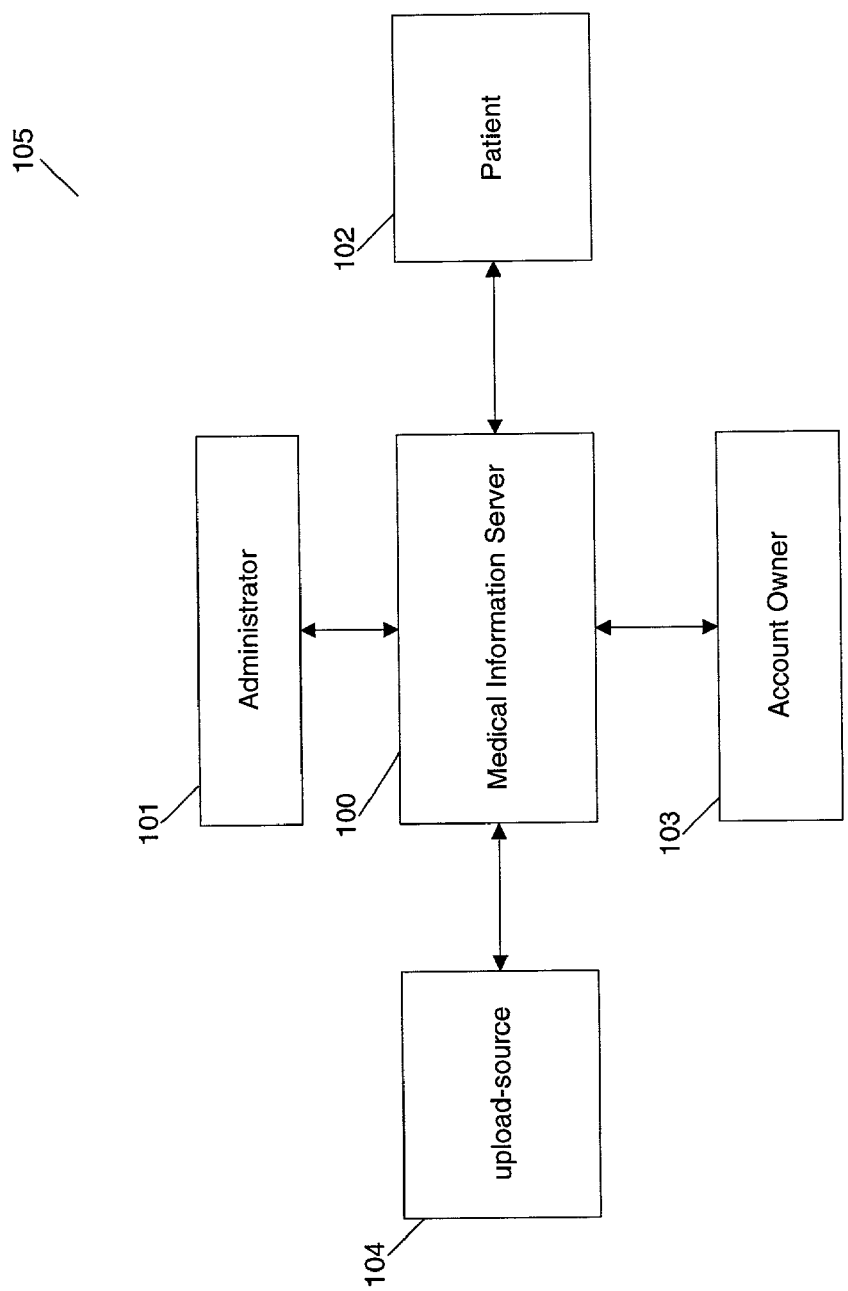
FIG. 1 illustrates a simplified block diagram of a medical information system and its interactions with users in accordance with the present disclosure.

A system for providing and delivering medical information between (1) account owners such as medical providers, physicians and testing facilities, (2) upload-sources such as laboratories and testing facilities, and (3) patients, using a medical information server is described below. Section II describes typical users of the system. Section III provides definitions which may be used in conjunction with the present disclosure. Section IV describes reports generated by the system. Section V describes the system software and hardware architecture.

In the preferred embodiment an interactive voice response system (IVR) is used as an interface to the system and is described in Section VI. Flow chart diagrams for a system having a IVR interface are also described.

II. Users of the System (1) Patients: A patient retrieves patient messages from the system by contacting the system through an input device, such as a touch tone telephone, and enters appropriate information such as mailbox number and security code.

(2) Account owners: Account owners are assigned an account on the system and may access the system to store or change messages for patients or make changes to their account parameters. Account owners, for example, could be medical providers such as physicians or their agents. An account owner may also be a medical facility that performs tests, such as a mammogram center or cancer screening centers. Account owners may access the system via IVR menus.

(3) Upload-source: The upload-source transfers patient test results and other information to the system using electronic data transfer.

(4) System administrator: The system administrator may use system screens and menus to configure the system and manage accounts and upload-sources, as well as provide general administration of the system.

III. Definitions (1) Account—An Account is a collection of data that is used by the system to serve the account owner. An account may include, but is not limited to, the following data: Account configuration data, Mailbox collection, Mailbox loading activity list (lists of mailboxes with patient messages placed by account owner/mailboxes with messages uploaded today), mailbox status reports (account activity report), administrator voice mail messages, and recorded name of the account owner.

In an embodiment, an account may have an account message collection which contains pre-recorded patient messages for each account owner.

There are three account types to fit the needs of various account owners. The three account types are:

A) Account with patient database (PD) access—this account type uses a patient database.

B) Account with patient identifier feature and no patient database (PD) access—this account type uses the patient identifier feature to aid the account owner in placing patient messages and the account does not have access to a patient database.

C) Account without patient identifier feature and no patient database (PD) access—this account type does not have the patient identifier feature nor patient database (PD) access.

(2) Account message—patient message pre-recorded by account owner which can be stored in a mailbox.

(3) Account message title—short recorded description of an account message.

(4) Account Number—a number that identifies the account owner's account on the system.

(5) Account Owner—A user that has an account on the system and can access the system to use the account owner menus.

(6) Account security code—a code that allows account access.

(7) Activate alert—set an alert flag in a mailbox to "New" and if the mailbox is not in the account's list of alerted mailboxes, then add alert to the list.

(8) Alerts: Alerts are generated by the medical information server to notify the account owner and/or upload-source of important events. There are several types of alerts. Alerts that are used to inform account owners are referred to as owner alerts.

The following is a list of alert types:

A. Patient-retrieval alert: Either an account owner or an upload-source may request notification in the event that a patient does not retrieve a patient message within a deadline specified when setting the alert. In this situation, the system fulfills the request by activating an alert signal and delivering the alert signal to the account owner and/or upload-source. This alert serves to notify the account owner and upload-source of important results not successfully communicated to the patient so that other means and efforts may be undertaken to notify patient of their test results.

B. Upload-source-change alert: When an upload-source alters data in a mailbox and the account owner has accessed that data prior to the data alteration, the system activates an upload-source-change alert indicating that the data has been altered by an upload-source. The alert is communicated to the account owner.

C. No-message alert: An alert activated by the medical information server when the upload-source uploads information such as test results into an upload-source note in a mailbox without uploading a corresponding patient message in the mailbox. This alert is received by the account owner and serves as notification that the account owner should store an appropriate patient message in the mailbox for the patient.

D. Non-timed-upload alert: This alert notifies the account owner that test information has been uploaded into a mailbox. The alert is set by the upload-source at the time of upload and is activated by the system for the account owner. This alert may serve to notify the account owner that test information he or she was particularly interested in has been placed in the mailbox.

E. Timed-upload alert: This alert is similar to a non-timed-upload alert but adds the following feature: If the account owner does not retrieve the upload alert within a deadline specified when setting the alert, the system will notify the upload-source of this fact as part of either an expired-timed-upload alert (ETUAR) report or a Panic report. If the time period specified is within a pre-defined panic range then the alert is considered to be a panic alert. If an upload alert that is a panic alert and is not received by the account owner within the deadline, the alert will appear on a Panic report. In an embodiment, this report is may be sent by the system by fax. All timed-upload alerts that do not appear on a Panic report will appear on an Expired-timed-upload alert Report (ETUAR).

The timed-upload alert is used to notify the uploading source when an account owner has accessed information that has been uploaded into a patient message mailbox. The upload-source is notified through this alert activation if the account owner does not retrieve or access this information within the deadline specified by the upload-source. The upload-source may be notified of the time of retrieval of the information in a fax report. An account owner alert is set when an upload alert information is placed in a patient mailbox.

If the account owner retrieves this upload alert with Panic Status (i.e., accesses the patient message and/or upload-source note) within a parameter value number of days or hours, a signal, such as a fax, is generated with this retrieval information and sent to the upload-source.

In the preferred embodiment, whether or not the account owner retrieves the mailbox information within the specified deadline, a signal, such as a fax, is generated and sent to the upload-source within a parameter value set time. This signal (fax) indicates receipt or non-receipt of alert.

The panic alert serves to notify the account owner of critical results that need timely review and allows notification of the upload-source if account owner notification has been received or not within an upload-source set time.

In an embodiment, when a mailbox in an account has a panic alert, the system sends a signal, such as an electronic notification signal to a pager, to the account owner who has the mailbox assigned to him or her.

In an embodiment, when a mailbox in an account has a panic alert, and the account owner who has the mailbox assigned to him or her does not retrieve the panic alert by the upload-source set deadline, the system sends a signal, such as an electronic notification signal to a pager, to the account owner.

F. Patient-attempt alert: This is an alert activated by the system when the patient contacts the system to retrieve a patient message but no patient message is available. The patient-attempt alert is delivered to the account owner who has initialized the mailbox in an account without PD access, or placed a chart note for the patient in an account with PD access and informs the account owner that the patient is attempting to access information that has not as yet been stored in the mailbox.

In an embodiment if the mailbox belongs to a mailbox pool without PD access, and the mailbox has not been initialized then a patient-attempt alert is not activated for the mailbox.

G. Completion alert (for accounts without Patient Database access): This is an alert set by the account owner at the time the test is ordered for the patient. This alert is activated by the system and is delivered to the account owner when a patient message or upload-source note is placed in the mailbox by an upload-source. The purpose of this alert is to allow a means for the account owner to know the test result regardless of the outcome. For example, if the patient has been anemic and treated, the account owner might want to know the blood level even if the blood level test had returned to the normal range.

The completion alert is useful because in a situation where results are uploaded to the mailbox in the form of a pre-recorded patient message, the account owner may not be notified if the results are normal. Hence, a means such as this allows for account owner notification if desired regardless of the test results.

H. Compliance alert (for accounts without Patient Database access): This is an alert set by the account owner when the test is ordered. The system will activate this alert if a patient message or upload-source note has not been placed in the mailbox within the deadline specified when setting the alert. A compliance alert may be activated, for example, as a result of the patient not having the test done or if the test specimen is lost, since the test results won't be entered if these events occur. This may also be used to notify the account owner if the test result is not entered into the system by the time that the account owner informed the patient the test result would be available. This alert type is needed since at times an account owner may order a test that is important to be done timely and/or the account owner may feel that the patient may not comply with having an important test done.

In an alternative embodiment, the compliance alert can be set by the upload-source. This may be of use so that if the upload-source does not receive the test specimen within a time frame and wishes to communicate this fact to the account owner.

I. Completion/compliance alerts (for accounts with Patient Database access): For accounts with patient database access, the account owner does not assign mailbox numbers for the patient to obtain test results. The mailboxes are automatically assigned by the system. Accordingly, the account owner needs to assign a numeric sequence of digits that identifies a chart note which reflects the testing circumstances. This allows the system to associate a particular chart note to a particular mailbox via the particular numeric sequence of digits for a completion or compliance alert.

Thus, in an embodiment, the medical information server allows an account owner to place a completion notification request (CNR) for a patient's test result. The account owner provides a CNR identifying signal or number when the chart note is placed. The CNR identifying signal or number is unique to that chart note and the associated test and patient. The account owner at the time of generation of the CNR specifies a time limit in days to determine the CNR deadline. The account owner then transmits the unique CNR identifying signal or number to the upload-source. When the mailbox information is uploaded, the CNR allows identification of the mailbox so that the completion alert is activated for the account owner for the corresponding medical information. If no information is uploaded into the mailbox by the CNR deadline, then a compliance alert is activated for the mailbox.

In an alternative embodiment, the CNR code could be furnished to the account owner by the system in response to an account owner request.

J. Trace alerts (for accounts with Patient Database access): An account owner can choose to activate a trace for a patient at the time that a chart note is recorded. The account owner will specify a deadline in days for the trace which is used to determine the trace deadline. In the length of time prior to the trace alert deadline, whenever a mailbox is uploaded for this patient the account owner will receive a trace alert indicating a mailbox was uploaded. If more than one account has a trace set for a patient, each account will receive a trace alert for each mailbox uploaded. If no mailbox has been uploaded prior to the trace alert deadline, then a trace alert indicating this fact will be activated for the account and the trace alert setting will be removed. Each trace alert will have a status flag that indicates whether or not patient information was uploaded into the mailbox.

These alert communications can be via fax report, electronic mail, ASCII data file, sound file, voice file, voice mail, or other means and can include the patient name and name of the account owner and/or upload-source that set the alert information and/or entered information in the patient mailbox.

In an embodiment, only the account owner and/or upload-source who sets an alert will receive the alert if an alert is activated.

(9) Chart Note—a chart note is a text message and/or voice recording placed by the account owner in a mailbox that typically contains information the account owner will find useful in placing patient messages relating to test results coming back for the patient.

In an embodiment, a chart note is used with a patient identifier in the patient finder function to allow the account owner to identify the proper mailbox in which to place information.

In an alternate embodiment chart notes can be ASCII text that can be translated into speech using text-to-speech software.

(10) Completion Notification Request (CNR)—a request from the account owner to be notified when a mailbox is uploaded. Typically, a two digit CNR code will uniquely identify the CNR within the group of CNRs for a patient and account.

(11) Custom patient message—patient message recorded by account owner specifically for one patient.

(12) Deadline (Alert Deadline)—time period for an action to occur so that the associated alert flag is changed to New.

(13) Delete alert—setting an alert flag to unused and clears any alert deadline information for the alert and if there is no other active alert in the mailbox, then remove the alert from the account's list of alerted mailboxes.

(14) Expired patient message—Patient message that has been unretrieved before an account configuration parameter time period.

(15) Expired timed-upload alert—a timed-upload alert that was not retrieved by the account owner within deadline specified in the alert setting.

(16) Mailbox—a group of data relating to a single patient that may include, but is not limited to, a patient message and other information such as notes from an upload-source and/or account owner, and flags and information relating to various alerts, time message was uploaded, time message was retrieved by patient.

(17) Mailbox number—a number that uniquely identifies the mailbox within a mailbox pool.

(18) Mailbox pool—a group of mailboxes that account owners, upload sources, and their patients can access.

(19) Mailbox security code—a series of numeric digits that allows patient access to certain contents of a mailbox.

(20) Note—a text or voice recording placed by an account owner or upload-source containing information; this information is not accessible by patients.

(21) Patient Database (PD)—a database of patient records from which patient data can be utilized to reduce the amount of data the account owner must enter to set up a mailbox.

(22) Patient Finder Code (PFC)—a series of numeric digits used to identify a patient record that is not necessarily unique within the PD. The PFC is typically a short-hand version of the PIC that is more convenient for the account owners to input: If PFC use results in several patient matches in the PD, the system presents these to the account owner for the account owner to choose the correct entry.

(23) Patient Identification Code (PIC)—a series of numeric digits used to identify a patient that is unique for each patient in the PD.

(24) Patient message digits—digits that are spoken to patient after the pre-recorded patient message and may give a specific test result—e.g., "Your cholesterol is" "200". The "200" is the patient message digits and represents the value of cholesterol for this test.

(25) Pre-Recorded patient message codes—Pre-recorded patient messages have a code that can be entered by the account owner to identify their content on reports and lists of patient messages. These codes are also used to specify which pre-recorded patient message is placed in a patient mailbox.

(25) PSC "Patient Security Code"(accounts with PD access only)—a series of numeric digits used to secure access to a patient's test results that is unique within the PD. The PSC may consist of two parts. Part A is a fixed length of digits for all patients in the PD. Part B can be variable length (up to 20 digits) and is typically used if Part A is not unique in the PD, But Part A and Part B together are unique to the PD.

(26) Reported mailbox—a mailbox that has appeared on an account activity report.

(27) Retired mailbox—mailbox that has had a patient message either expired or retrieved.

(28) Set Alert—alert information, such as an alert deadline, is placed in alert fields of the mailbox.

(29) System patient message—a pre-recorded patient message available to all account owners to place in patient mailboxes.

(30) System patient message title—short, recorded description of a system patient message.

(31) System prompt—pre-recorded voice message that either delivers information to the caller or requests caller input.

(32) Upload-source note—an upload-source note is a text message and/or voice recording placed in a mailbox by an upload-source containing information to the appropriate account owner who is assigned the mailbox and not the patient. The upload-source note is accessible only by the account owner and the upload-source that placed the upload-source note.

IV. Reports Generated by the System

In order to allow various users of the system to track pertinent activities including delivery of patient messages the system generates and automatically delivers to the account owners and upload sources several types of reports. These include the following:

1. Account Activity report: A report sent to an account owner that lists all mailboxes assigned to the account in which the patient message has either expired or been retrieved. This report can include the patient name, date that the patient message was placed by the account owner or upload-source, the account owner name, if patient retrieved the message, the date when the patient message was retrieved by the patient, indication if the patient message was not retrieved, if upload-source entered information then upload source identification, a code or synopsis that reflects the content and or type of patient message, and the types of alerts set for a mailbox, if any, together with the time information regarding alert flags and whether or not the account owner received these alert messages.

2. Upload Acceptance report: A report sent to an upload-source that lists the results of processing the last upload data file received by the system from this upload-source. This report includes any mailboxes that failed to accept information that was sent by the upload-source along with an error code that indicates the reason for the failure. This report may include the patient name, patient identifier (if report to account without PD access) or PIC (if the report is to an account with PD access), mailbox number, pre-recorded patient message code, the upload-source note, pertinent alert information, the name of the account owner, and the date and time of the data upload.

3. Upload Activity report: A report sent to an upload-source that lists all mailboxes which information has been uploaded by the upload-source and in which the patient message has either expired or been retrieved. This report can also include pertinent information as in other reports noted above for the Upload Acceptance report and the Account Activity report. This report also can indicate if a message has been accessed by the account owner who is assigned the mailbox and the time of this access.

4. Expired Timed-Upload Alert Report (ETUAR): A report sent to an upload-source that lists all expired-timed-upload alerts that do not have panic status. This report can also include pertinent information as noted above for other reports.

5. Panic report: A report sent to an upload-source that lists a single expired panic alert. In addition, this report can include the name of the account owner and/or the name of an alternative back-up provider for whom the alert was set as well as relevant information regarding content of this mailbox.

In an embodiment, the Panic report may include means and results of contact attempts regarding the account owner, alternate backup provider and the patient involved as well as other pertinent information noted above for other reports.

6. Summary Panic report: A report sent to both the upload-source and account owner that lists all panic alerts for a particular time period, the date and time the message and alert status was entered into a mailbox for each listed panic alert, and the date and time the alerts were retrieved by the account owner and the name of the account owner, an indication if alert(s) were not retrieved and any back-up provider(s) that were contacted and/or attempted to be contacted. This report can also include pertinent information as noted above for other reports.

In alternate embodiments, these reports may be faxed, e-mailed, or sent over a local or wide area network.

V. Medical Information System Software and Hardware Architecture

1. Medical Information System Hardware.

Figure 2:
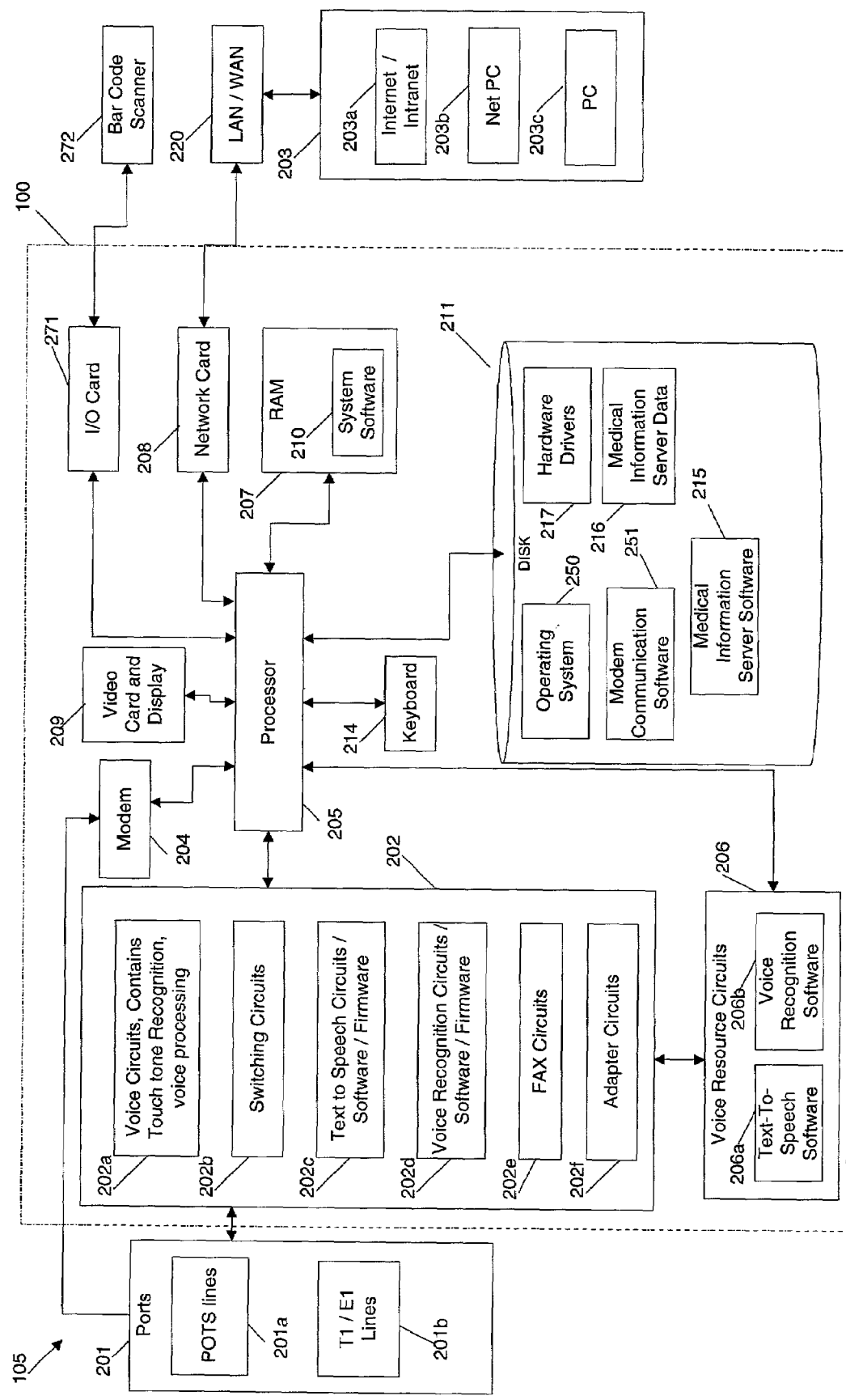
FIG. 2 illustrates a simplified hardware block diagram of a medical information system and associated input and output devices in accordance with the present disclosure.

FIG. 1 illustrates a simplified block diagram 105 of a system which interfaces with users of the system in accordance with the present disclosure. The Medical Information Server 100 interfaces with the system administrator 101, the patient 102, the account owner 103, and the upload-source 104. FIG. 2 illustrates a simplified hardware block diagram of the medical information server 100 according to the present invention. In an embodiment server 100 includes processor 205 which in the preferred embodiment is an Intel Pentium™200 megahertz microprocessor. Processor 205 is coupled with disc 211, modem 204, network card 208, I/O card 271, random access memory (RAM) 207, video card and display 209, keyboard 214, telephony circuits 202 and voice resource circuits 206.

In a preferred embodiment, disc 211 will be a four-gigabyte hard disk drive. Disc 211 contains Windows NT 4.0 operating system 250, modem communication software 251, medical information server software 215, medical information server data 216, and hardware drivers 217. Hardware drivers include, Dialogic voice/fax card drivers, video drivers, modem drivers, and other drivers. Medical information server software 215 and medical information server data 216 are detailed further in FIG. 5.

In an alternate embodiment, medical information server programs and data may be stored at a remote location and accessed via network by server 100.

In an embodiment, modem 204 may be a 28.8 k bps modem, which provides remote access to server 100 for service and maintenance from telephony ports 201 which include plain old telephone service lines ("POTS lines") 201a or through T1/E1 lines 210b.

RAM 207, in an embodiment, includes 64 megabytes of random access memory and contains Windows NT 4.0, along with appropriate device drivers.

In an embodiment, RAM 207 contains system software and includes the following products available from Artisoft Inc, Computer Telephony Products Group located at 5 Cambridge Center, Cambridge, Mass. 02142: (a) Visual Voice Pro Dialogic edition version 3.02 for Microsoft Windows NT 4.0, (b) Visual Voice Text-To-Speech 2.0 for Microsoft Windows NT 4.0, (c) Visual Fax 2.0 for Microsoft Windows NT 4.0, (d) Visual Voice Recognition Support 2.0 for Microsoft Windows NT 4.0.

In an embodiment, the following software products are loaded into Server 100 and are supported under Visual Voice Recognition support 2.0: The AT&T Watson™ SAPI engine, and the PureSpeech RECITE!™ Recognition engine for use on Dialogic Antaries™ Board. These software products are available from Artisoft™ Inc. The Dialogic Antaries™ voice board is available from Dialogic Corporation located at 1515 Route Ten, Parsippany, N.J. 07054.

In an embodiment, Visual Voice™ Text-To-Speech software utilizes the DECtalk™ text-to-speech engine, which is also available from Artisoft Inc.

In an alternative embodiment, Antaries™ board can utilize other speech recognition technology such as Applied Language Technologies' SpeechWorks™. In an embodiment, Applied Language Technologies software Speech-Forms™, SpeechQuery™, and SpeechAgent™ are used in conjunction with SpeechWorks™. Applied Language Technology is located at 695 Atlantic Avenue, Third Floor, Boston, Mass. 02111.

In the embodiment, Dialogic Board Device drivers for Microsoft Windows NT 4.0 are loaded into RAM 207 and are available from Dialogic Corporation.

Figure 66:
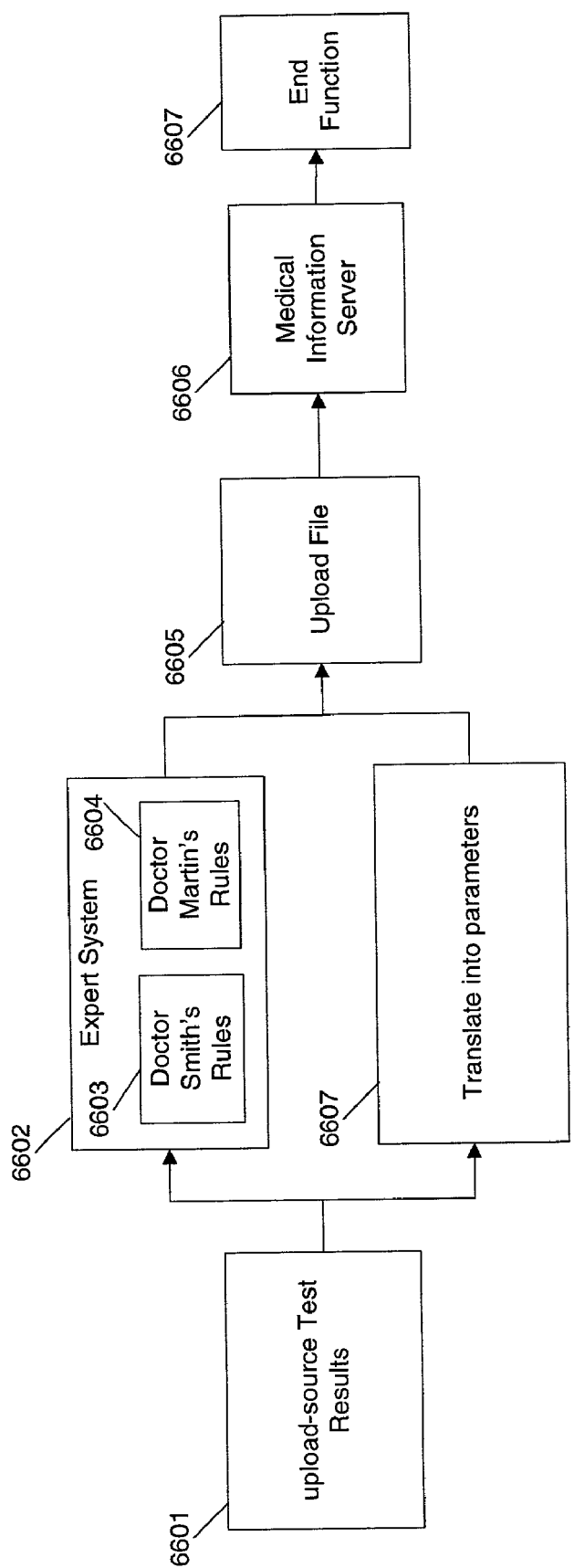
FIG. 66 illustrates a logic flow diagram for message uploading from an upload-source into the medical information system in accordance with the present disclosure.

Appropriate run-time software Visual Basic 5.0, as well as communications software is loaded in RAM 207. The voice software interacts with processor 205 and telephony circuits 202 and voice resource card 206 and disk 211, to handle, for example, voice processing, voice recognition, faxing, and text-to-speech processing. Flow control charts as illustrated by FIGS. 6 through 66 are described in detail below and illustrate the operation of IVR interface program 215e (illustrated in FIG. 5) in Server 100.

In an embodiment, T-NetX™, Inc's Speak EZ Voice Print™ speaker verification software for Antares™ is installed in Server 100. T-NetX™, Inc is located at 67 Inverness Drive East, Englewood, Colo. 80112.

Manuals for specific software named above from Applied Language Technologies, Artisoft, Digital Equipment Corporation, PureSpeech, and Dialogic are incorporated by reference.

Patients, or those interested in obtaining medical information, as well as account owners and the system administrator, access server 100 by way of POTS lines 201a, or T1/E1 lines 201b. In an embodiment, an account owner or patient uses a touch-tone telephone to access telephony ports 201. In alternate embodiments, other data communication services, such as wireless services, can be used instead of telephony ports and may be directly coupled to telephony circuits 202.

In an embodiment, information upload from upload-source is via modem 204 or network card 208 or via scanner device such as a bar code scanner 272 through I/O card 271. In alternate embodiments other input devices such as optical information entry and translation, electromagnetic or RF devices may be used.

Telephony circuits 202 include, among other circuits, circuits for interfacing with telephony ports 201. These circuits include voice circuits 202a having a touch tone recognition circuit and voice processing circuit, as well as other circuits. Other circuits include switching circuits 202b, text-to-speech circuits 202c which have appropriate software and firmware, voice recognition circuits 202d which may include appropriate software/firmware, fax circuits 202e, and adapter circuits 202f.

In an embodiment, telephony circuits 202 may be a Dialogic D41ESC board, and Fax circuits may be a Dialogic VFX daughter board.

In an embodiment, Voice Resource Circuits 206 include a Dialogic Antaries board which contains Text-To-Speech software 206a and/or Voice Recognition software 206b. In an embodiment, the connection between Voice Resource circuits 206 and Telephony circuits 202 is via a Signal Computer ("SC") connector.

In an embodiment, network card 208 is connected to a local area network (LAN) or wide area network (WAN) 220 which provides Server 100 access to other devices, and other devices access to Server 100. Some of these devices are represented by block 203 which contains Internet/Intranet 203a, a Net-PC 203b, and PC 203c.

System software 210 is primarily responsible for operating system 105, and in particular server 100.

Figure 3:
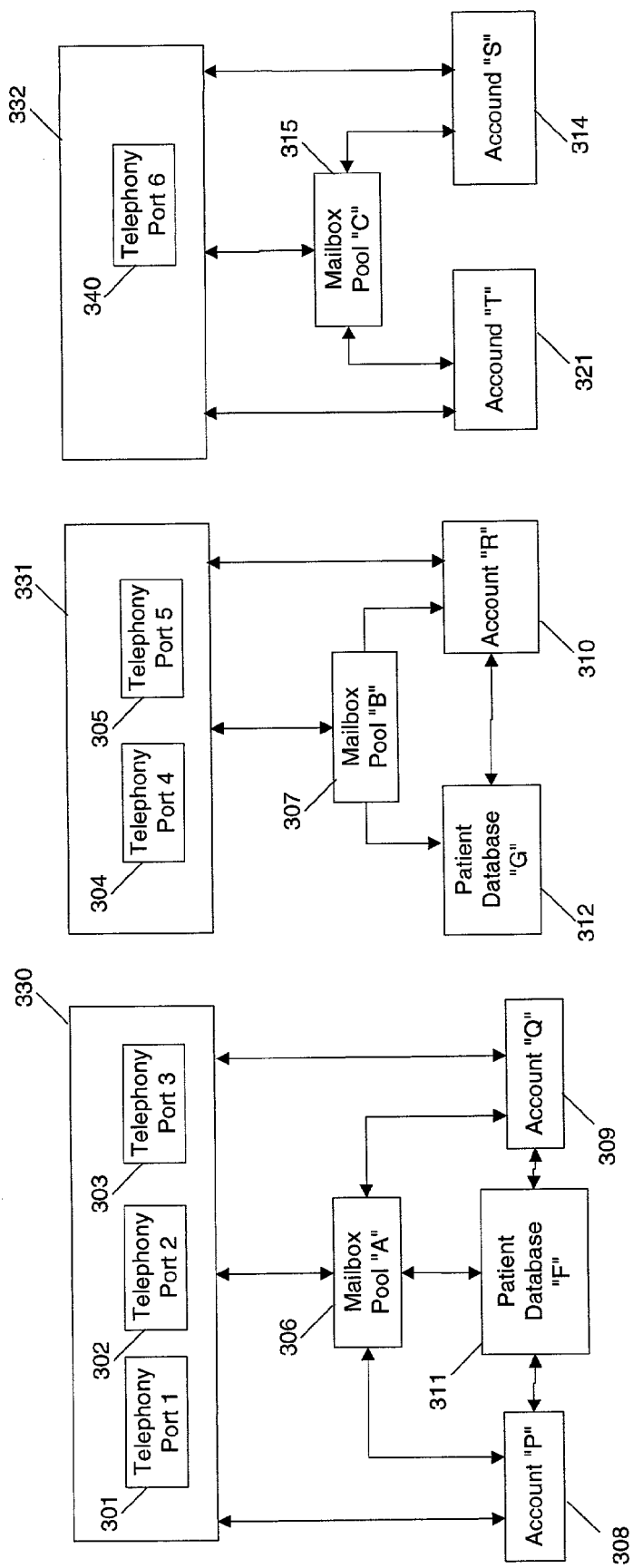
FIG. 3 illustrates a simplified block diagram of relationships between telephony ports, mailbox pools, accounts, and patient databases in a medical information system in accordance with the present disclosure.

FIG. 3 illustrates various embodiments of telephony ports, mailbox pools, users of accounts, and patient databases intercoupled in accordance with the present disclosure. Blocks 330331 and 332 represent telephony port groups. Telephony port group 330 consists of telephony ports 1, 2, and 3 represented by blocks 301, 302, and 303, respectively. Telephony port group 331 consists of telephony ports 4 and 5 represented by blocks 304 and 305 respectively. Telephony port group 332 consists of telephony port 6 represented by block 340. Telephony port groups 330, 331, and 332 have access to mailbox pool A as illustrated in block 306, mailbox pool B as illustrated in block 307 and mailbox pool C as illustrated in block 315, respectively.

In an embodiment, Mailbox Pool A has access to Patient Database F as illustrated in block 311 by account owner P as illustrated in block 308 and account owner Q in block 309 who may likewise access mailbox pool A by way of telephony port group 330.

Mailbox Pool B has access to Patient Database G as illustrated in block 312. Account owner, R as illustrated in block 310, may access Mailbox Pool B.

In an alternate embodiment, mailbox pool C does not have access to a patient database. Account owner S as illustrated in block 314 and account owner T as illustrated in block 321 are able to access mailbox pool C by telephony port group 6.

These embodiments illustrate that more than one account owner can interact with a single patient database and more than one account owner can access and use a single mailbox pool. Further, a single system can service account owners with or without access to a patient database.

In an embodiment, a patient database may be located on a remote server.

Figure 4:
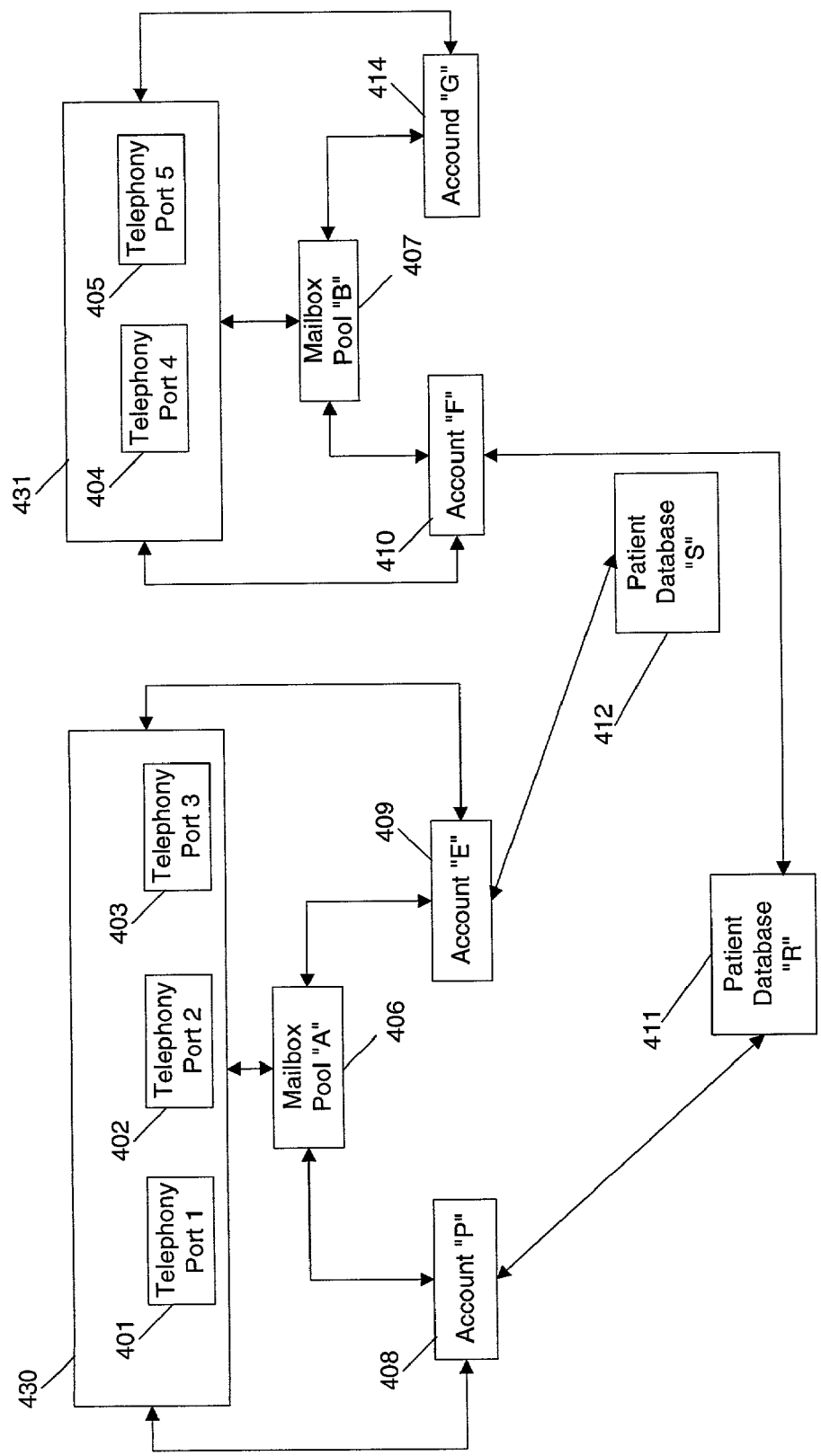
FIG. 4 illustrates a simplified block diagram of an alternative configuration of telephony ports, mailbox pools, accounts, and patient databases in a medical information system in accordance with the present invention.

FIG. 4 illustrates a simplified block diagram of an alternative embodiment of telephony ports, mailbox pools, account owners, and patient databases in the medical information system 105. Blocks 430 and 431 consist of groups of telephony ports: Block 430 consists of telephony port 1 in block 401, telephony port 2 in block 402, and telephony port 3 in block 403. Block 431 consists of telephony port 4 in block 404 and telephony port 5 in block 405.

Mailbox pool A is represented by block 406 and Mailbox pool B is represented by block 407. Patient database R is represented by block 411 and patient database S is represented by block 412.

Account owner P as illustrated by block 408 interacts with telephony ports in block 430, Mailbox pool A represented by block 406, and patient database R represented by block 411.

Account owner E as illustrated by block 409 interacts with telephony ports in block 430, Mailbox pool A represented by block 406, and patient database S represented by block 412.

Account owner F as illustrated by block 410 interacts with telephony ports in block 431, Mailbox pool B represented by block 407, and patient database R represented by block 411.

Account owner G as illustrated by block 414 interacts with telephony ports in block 431, and mailbox pool B represented by block 407 and does not have access to a patient database.

FIG. 4 illustrates that system 105 may be configured so that more than one account owner can access a particular mailbox pool and that the accounts that access a particular mailbox pool may access different patient databases and that some of the account owners that access a particular mailbox may also have access to a patient database while others do not.

Figure 5:
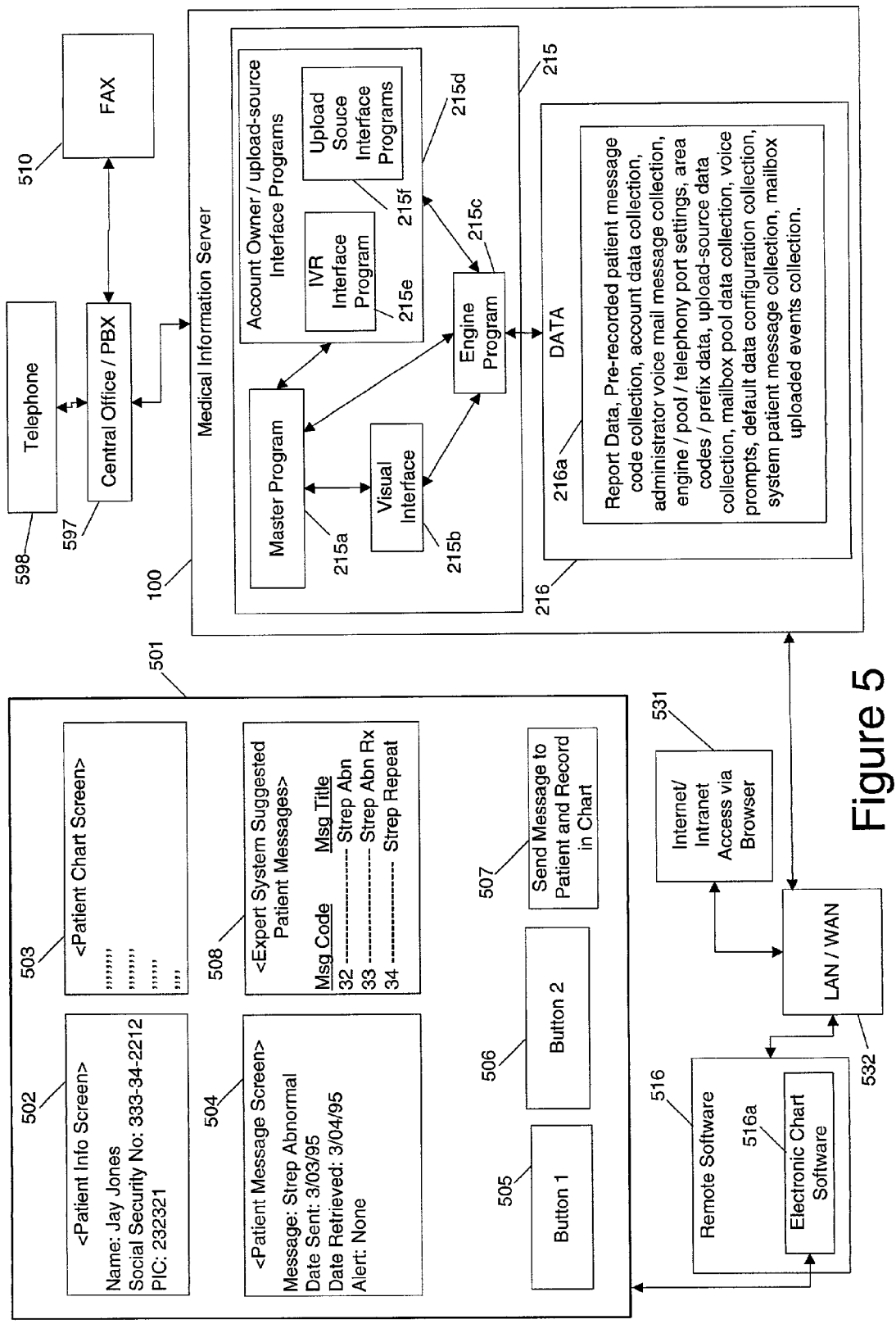
FIG. 5 illustrates the medical information server and interfaces to other components of the system in accordance with the present invention.
Figure 6:
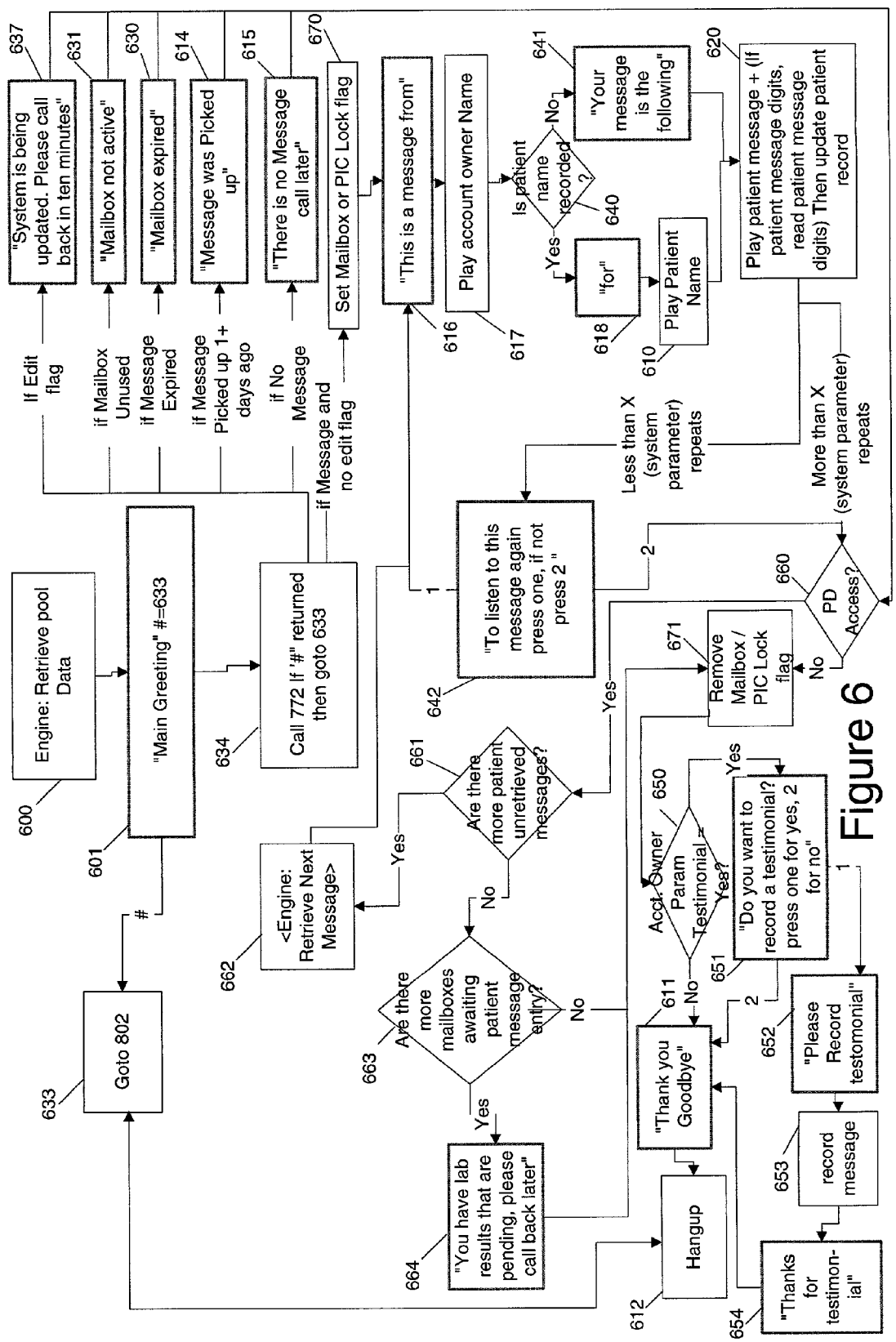
FIG. 6 illustrates a logic flow diagram of a patient attempting to retrieve a patient message in a medical information system in accordance with the present disclosure.

FIG. 5 illustrates a medical information server 100 having GUI screens, electronic chart software, and other interfaces. Server 100 software 215 includes master program 215a, Visual Interface program 215b, engine program 215c, and account owner/upload-source interface programs 215d (with IVR interface programs 215e, and upload-source interface program 215f).

Medical Information System ("MIS") data 216 includes, for example: (a) Report data, (b) Patient Pre-recorded Message Code collection, (c) Account data collection, (d) administrator voice mail messages, (e) engine/pool/telephony port settings, (f) area codes/prefix data (for area codes and prefixes that medical information server can dial out to), (g) upload-source data, (h) PD data collection, (i) mailbox pool data, (j) voice prompts, (k) default configuration data, and (l) system patient message collection. (m) mailbox uploaded events collections, and (n) mailbox collections. In the embodiment, server 100 interacts with users via touch-tone telephone 598 and Fax 510 through a central office or PBX 597. Server 100 interacts through local or wide area networks 532 and internet/intranets 531. Remote software 516 can allow interaction with electronic chart software 516a or a graphic user interface ("GUI") 501.

Block 501 illustrates a GUI of an Electronic Chart Software Screen. The screen contains a plurality of informational display screens and control buttons to facilitate information delivery and receipt. Screen segment 502 represents a patient information screen that displays pertinent information regarding a patient. Screen segment 503 represents the patient chart screen, where information on patient's medical chart is displayed. Screen segment 504 represents a patient message screen where information regarding messaging to the patient is displayed utilizing the Medical Information Server 100; uploaded test results may be represented as text here or accessed by sound device. Screen segment 508 represents patient messages suggested by an expert system in response to the test results represented in screen segment 504. An account owner may click on these to load the results into the appropriate mailbox. Buttons represented by blocks 505 and 506 are used to control content of patient chart screen 502 and patient info screen 504.

A user can extract information from the patient screen and use other input to place a patient message into a patient mailbox in server 100 by patient-message-send button represented by block 507. Button 507 allows electronic chart software to extract information from patient message screen as well as user input to place a patient message in medical information server 100 into a patient mailbox. The results of patient message delivery, including alert information are reported in patient information screen 504.

The system software Interface's public application programming interface facilitates the interactions noted above. Through these means a plurality of different interface embodiments are possible for handling test result information. The interfaces may present and receive data through a GUI and accept input from appropriate expert system suggested selections for possible patient messages. The account owner may then click on one such patient message to have the specific chosen message loaded into the patient mailbox.

In an embodiment, panic or other alert types may be communicated on the account owner's GUI screen for notification, acknowledgment, and reaction through the use of information resources available by way of medical information server 100.

2. Medical Information Server Software and Data.

Medical information server software and data includes, but is not limited to, (a) several databases, (b) a master program, that starts and stops the medical information server, (c) an engine or collection of software routines, (d) upload-sources data, (e) graphical user interface screens for the administrator and account owner, and (f) an interactive user interface, which in the preferred embodiment is an interactive voice response (IVR) interface. Interactive response interfaces include interactive voice telephony response interfaces, graphical user interfaces (GUI), video delivery mechanisms, wireless delivery mechanisms, or combinations of these.

Typical Data Groupings:

The engine references data in collections, wherein items can be added, deleted or edited; lists, wherein items can be added or deleted but not edited; and tables, wherein items can be edited but not added or deleted.

The engine interacts with at least the following data collections: (a) patient database (PD) data collection, (b) the patient message code collection, (c) the system patient message collection, (d) the administrator voice mail message collection, (e) the mailbox pool collection, (f) the upload-source data collection (a database consisting of data characterizing the upload-sources), (g) the disallowed prefix data collection, (h) the allowed area code/prefix data collection, (i) the default configurations data for the engine, mailbox pools, accounts, and upload-sources, (j) account collection, (k) engine/port/mailbox pool/accounts/upload-sources configuration data collection.

The patient database collection typically includes patient databases (PD) which contain (a) PD record data, (b) a PD chart note collection, (c) PD trace collection, and (d) a CNR list containing numbers of mailboxes with CNR's.

The Patient Message Code collection contains a group of patient message codes. In an embodiment, each patient message code contains the following data: (a) a series of digits that identifies the message, (b) a flag indicating whether or not the message is available for use, (c) a flag indicating whether or not the message is time sensitive (whether or not a patient-retrieval alert can be set or activated), (d) a flag indicating whether or not the message includes patient message digits, (e) a flag indicating whether or not the message includes a custom recorded segment that is appended to pre-recorded message, (f) a descriptive code that can be written on reports to describe contents of pre-recorded message.

The system patient message collection includes pre-recorded patient messages that are available on the entire system for all account owners.

The administrator voice mail message collection includes messages to the administrator from account owners on the system.

The mailbox pool collection contains a group of mailbox pools. In an embodiment, each mailbox pool contains (a) pool configuration data, (b) a collection of unused mailboxes, and (c) an account collection.

Each account in the account collection contains account configuration data and a collection of mailboxes.

In an embodiment, mailboxes may contain upload-source notes, chart notes, and alert notes (e.g. alert notes typically contain the patient telephone number) which may be voiced or in ASCII format, or ASCII translated to voice via a text-to-speech method.

In an embodiment, each account also contains a list of noted mailboxes with a chart and/or upload-source note loaded and no patient message loaded, a list of messaged mailboxes with patient messages loaded, a list of retired mailboxes, a list of mailbox coded events, a list of mailbox uploaded events, a list of alerted mailboxes, a list of mailboxes wherein the patient message has been reported, an account activity reports collection containing account activity reports for the account, an account message collection and an administrator voice mail message collection.

The upload-source data collection contains a group of upload-sources. In an embodiment, each upload-source contains (a) a retired mailbox list, (b) an upload activity reports collection, (c) a timed-upload alerts collection, (d) an expired-timed-upload alerts collection, (e) an expired-timed-upload alert report list, (f) a list of Panic reports, (g) data relating to the upload activity report format and Panic reports formats, and (h) upload-source configuration data.

The Disallowed Prefix data collection includes data that the medical information server uses in preventing connection via telephone with undesirable locations—e.g., in an interactive voice response interface embodiment, numbers such as 911 cannot be called.

The Allowed Area Code/Prefix collection includes data that limits the system to contacting only certain desirable locations—e.g., in an interactive voice response interface embodiment, the area codes that the system is allowed to call out to, which in the present software has been described as resident in the architecture illustrated in FIG. 5. In an another embodiment this software may be stored on an article of manufacture, such as a magnetic or optical medium.

A. The Engine

The engine is a collection of software routines that manage the storage of, the access to, and the transfer and manipulation of data relating to the following: engine/port/mailbox pool/account/upload-source configuration, patient databases, mailbox pools including mailbox and account data, and upload-source data. The engine handles all automatic processing of this data including checking for expirations and activating alerts and generating reports. The engine interacts with interface software so as to allow use of the system across several different modes of operation and platforms with minimal reconfiguration. Similarly, the engine interacts with database access software to allow the use of a variety of database servers with little or no added reconfiguration.

1. Engine Interaction with Configured Data

The engine is started and stopped via the master control program 215*a*. The engine on start-up reads the engine configuration data and the other system components configuration data. The engine also reconfigures the system in response to changes in configuration data via administrator screens. The engine provides access to the disallowed prefix collection and Allowed Area Code collections and deletes expired system logs and mailboxes.

2. Engine Interaction with Patient Databases

The engine has the capability to add or delete to their respective collections a PD, trace alert, upload-source note, and chart note. The engine can also allow editing an existing PD, trace alert, upload-source note and chart note.

The engine allows additions to the PD by upload-sources and the administrator. The engine also allows the administrator to make changes and deletions in the PD. The engine also can retrieve data from, add data to, and delete records from the PD database. The engine can verify validity of access by checking the patient identification code (PIC) prior to allowing these actions.

The engine also searches for records using a particular patient finder code (PFC). The IVR interface and the engine allow the user to identify the correct patient if necessary from the group selected by the PFC.

In an embodiment the engine may use text-to-speech software to convert uploaded ASCII strings in patient name fields and upload-source note fields to voice files. The engine can retrieve and delete and write data to and from chart notes, upload-source notes, and alerts.

The engine can retrieve a patient name voice recording from a PD record.

The engine can also retrieve a list of chart notes for (1) a specific PIC, (2) for a specific PIC and specific creation date, (3) for a specific medical account owner and PIC, and (4) for a specific PIC, creation date or range of dates and particular account owner.

The engine can check for and delete any PD chart notes that have exceeded a parameter set maximum stay on the system.

In an account without PD access, the engine can check for and delete any chart notes that have exceeded a parameter set maximum stay on the system.

The engine is able to: (1) allow only the account owner who originally created a chart note to add to, replace or delete the particular chart note; (2) allow any account owner to listen to any chart note for any patient in a PD to which the account has access. Any number of account owners can create a chart note for the same patient on a particular day.

When creating the chart or upload-source note the engine can assign an unique identifying number (CNR) associated with the account owner number and PIC and sets the creation date for this upload-source or chart note to the current date. The engine also converts, if needed, ASCII text to a voice recording file using text-to-speech software.

The engine is able to set and/or activate one trace alert per patient for each account owner. Several account owners may have trace alerts set and/or active for a particular patient. The engine checks trace alert deadlines and activates compliance alerts accordingly and places them in the appropriate mailbox. Likewise, when test results are uploaded, the engine activates the completion alerts in the appropriate mailbox.

3. Engine Interaction with Messages

The engine allows pre-recorded patient messages to be accessed through patient pre-recorded message codes from a patient pre-recorded message code collection. Codes and messages may be added or deleted from this collection. The engine can check if a particular patient pre-recorded message code entry exists and respond appropriately. The patient pre-recorded message collection contains fields for each patient pre-recorded message code specifying if the patient pre-recorded message code is active or not on the system, is time sensitive, and if the pre-recorded message requires patient message digits or has custom recorded segment which is played after the patient pre-recorded message to specify test result values, a time for an appointment, or other patient information.

The engine also enables creation of system patient messages for corresponding message codes and can add, retrieve, or delete these recordings. The engine can associate a system patient message title with each system patient message code that summarizes the message content.

The engine also enables creation of administrator voice mail messages, which are added to an administrator voice mail message collection. The engine allows addition or deletion as well as retrieving such messages and a count of such messages. Data in a voice mail message may include message identification number, account owner number that sent the message, account owner name that sent message, status of message (new or old), and the message voice recording or the memory location of the file that contains the messages.

The engine also maintains a count of new and saved administrator voice mail messages.

4. Engine Interaction with a Mailbox Pool Collection

The engine maintains a mailbox pool data collection and is capable of adding and deleting mailbox pools and retrieving data from a mailbox pool.

In an embodiment, each mailbox pool contains the following configuration data: Pool number, pool name, and whether or not the pool functions with a patient database enabled and, if so, the patient database number.

Each mailbox pool may have a range of mailboxes available that are accessible by upload-sources for data entry without a security code. This is termed the unprotected mailbox range.

In an embodiment, each pool includes at least the following additional parameters:

Expiration Parameters: (a) maximum days a patient message can stay unretrieved in a mailbox, (b) number of days after a mailbox is reported before mailbox is deleted, (c) maximum days a mailbox can have a chart note and no patient message loaded, (d) maximum days an account activity report will be kept, (e) maximum days an upload activity report will be kept, (f) maximum days a mailbox can remain unused.

Report parameters: (a) text to display on account activity report after last entry, (b) threshold number of entries to trigger an account activity report, (c) maximum number of days between an account's activity reports, (d) maximum number of entries per page on an account activity report, (e) title for account activity reports, (f) title for expired-timed-upload alert reports.

Voice recording parameters: (a) maximum size of patient name in seconds, (b) maximum size of chart note in seconds, (c) maximum size of account message in seconds, (d) maximum size of custom patient message in seconds, (e) maximum size of account name recording in seconds, (f) maximum size of alert note in seconds, (g) maximum size of voice message left for administrator in seconds.

For the above mailbox pool parameters that affect accounts, the account configuration parameters are adjusted by the engine to ensure that every account accessing the mailbox pool has parameter values within the mailbox pool parameter limits.

The engine can send a voice mail message to any or all accounts in a pool.

The engine is able to move an unused mailbox to the list of mailboxes for an account.

The engine can interact with a list of unused mailboxes: The engine can remove such mailboxes from the list when the mailbox is assigned to an account or if the mailbox's expiration date has passed. The engine also allows the system administrator to remove a mailbox.

The engine maintains a count of unused mailboxes. The engine can also check a range of mailbox numbers for any existing mailboxes and output those mailbox numbers found or not found and indicate any mailboxes containing patient message data in this range. The engine can create a range of mailboxes not in use and add these to an unused mailbox list.

The engine can also write a list of newly created mailboxes and their security codes to a file. The engine searches the list of unused mailboxes daily and removes those with expired dates.

Unused mailboxes have data fields containing a security code and expiration date. The administrator may remove an unused mailbox.

5. Engine Interaction with an Account Data Collection

The engine interacts with an account data collection. The engine is able to retrieve a list of accounts, create an account and add the account to the collection and delete the account and remove the account from the collection. An account can not be deleted if the account has any entries in the account's mailbox collection. The engine can retrieve and write account data. The engine can search the collection and retrieve an account using a specific security code. This process can be used to check if a new security code is already in use.

In an embodiment, each account in the account data collection has fields for the following data: account number, flag that determines if the account is currently activated, the account type (account with PD access, account with patient identifier feature and without PD access, account without patient identifier feature and without PD access), flag that determines whether or not patient-retrieval alerts are available (i.e. alert can be set or activated), recording of account owner's name, account owner telephone number, flag that determines whether or not there is tracking of upload events available for the account owner to review, a flag that determines whether or not the account will accept uploads of test information without a security code being entered first, a flag that determines whether or not the number of mailboxes available are unlimited, the number of mailboxes left for the account, a listing of the last access time by the account owner, the account owner's email address, a flag that determines whether or not patient database access is enabled, the length of time the patient database chart note can exist before expiration, a flag that determines whether or not automatic fax reports are sent, a flag that determines whether or not faxes are available, the limit on number of faxes for the account, the number of mailboxes left for this account, the fax phone number for the account, the end date of the last activity report for the account, a flag that determines whether or not panic alert notification should be by voice message or pager, the panic alert phone number, the panic alert number to display on pager, alternate provider name, and the alternate provider phone number.

The engine has the capability of interacting with other programs to create messages, such as a voice mail message, to the account.

The engine has functions for the following internal processes relative to an account. The engine can create an account using an account number as input, reset the count of available faxes at a particular time interval, change the number of mailboxes left for an account, send reports to account owners or, if a report can not be sent successfully, re-route the report to a separate administrator file location for this purpose.

6. Engine Interaction with an Account Mailbox Collection

The engine maintains a count of the mailboxes in the account mailbox collection.

The engine is able to retrieve a patient message from a mailbox and retrieve the account number associated with a mailbox.

In an account without PD access the engine is able to add a mailbox to an account. In doing this the engine activates an unused mailbox, decrements the count of mailboxes available for that account, sets the initialization date of the mailbox to the current date, sets the mailbox initialized flag and writes data to the mailbox.

In an account with PD access the engine can create a new mailbox for the account. The engine adds this mailbox to the account's mailbox collection while decreasing the available mailbox count for the account, setting the mailbox initialization date to the current date, and flagging the mailbox as initialized. The engine also loads data into the mailbox from the PD record using the PIC provided and writes data to the mailbox. Any data (e.g., patient name) provided as part of the creation request is not replaced with the corresponding data in the PD record.

In an embodiment, a parameter controls which data in the PD record can be replaced by the corresponding data given in the creation request.

The engine can search an account mailbox collection looking for a mailbox that contains an unretrieved patient message that matches a specific patient pre-recorded message code.

The engine is able to create a list of all mailboxes matching a specified patient identifier by searching the mailbox collection for the account for mailboxes that have not been retrieved or expired.

The engine is able to create a list of all mailboxes that have a specific PIC and have unretrieved patient messages.

The engine is able to read data from a mailbox after locking the mailbox record to prevent any writing to the record during this process. The engine is capable of writing data to the mailbox only if no such lock is in place.

If a patient enters a mailbox to access a patient message, a lock is placed on the mailbox so that the account owner cannot enter or change data in the mailbox during the time the patient is accessing the patient message.

Tasks carried out by the engine on the mailbox collection include setting the patient message retrieved flag to Yes in a mailbox when a patient calls and retrieves his or her messages.

The engine adds the patient retrieved mailbox to the list of reported mailboxes and sets the report date to the current date.

When a mailbox expires or has the message retrieved by a patient, the engine removes the mailbox from the list of messaged mailboxes and adds the mailbox to the list of retired mailboxes for that account. If any data in the mailbox was uploaded by an upload-source, then this change in status of the mailbox is communicated in a report (such as a faxed report) to the appropriate upload-source. As a further consequence, the alert flags for the mailbox are set to Unused and this mailbox is deleted from the account's list of alerted mailboxes. The patient message is made no longer accessible by the patient.

The engine is able to remove a mailbox from the mailbox collection and then increment the count of mailboxes available for the corresponding account.

In an embodiment, mailboxes have associated with them the following data fields: (a) account number, (b) security code number, (c) patient identifier, (d) upload-source note, (e) chart note, (f) report date, (g) upload-source number, (h) patient message, (i) appeared in upload activity report flag, (j) patient first name string, (k) patient last name string, (l)

patient name recording path/file name string, (m) created/edited by account owner flag (Y/N), (n) initialization date (the earliest date of when the chart or upload-source note or patient message was recorded, (o) initialized (Y/N)—set when chart/upload-source note or patient message added, (p) compliance deadline date, (q) completion notification flag (Y/N), (r) PIC string, (s) PD name recording flag (Y/N), (t) PSC string, and (u) owner-entered-mailbox-with-no-subsequent-change alert flag (Y/N). Each mailbox also has a data structure that contains alert data. Each type of alert has a status field (flag) that indicates whether the alert is New, Saved, or Unused. Each alert may also have additional data fields that contain information related to the alert.

In an embodiment, each mailbox has alert information data fields for the following information, with the potential inputs as indicated in parentheses: (a) mailbox number, (b) patient-retrieval alert (New/Saved/Blank), (c) patient-retrieval alert deadline, (d) no-message alert (New/Saved/Blank), (e) compliance alert (New/Saved/Blank), (f) compliance alert deadline, (g) upload-source-change alert (New/Saved/Blank), (h) completion alert (New/Saved/Blank), (i) completion alert deadline, (j) upload alert (New/Saved/Blank), (k) upload panic alert (Y/N), (l) upload alert retrieval deadline date/time, (m) message expired flag, (n) owner-entered-mailbox flag.

In the case of an account having PD-access, the above fields (a–n) and the following additional fields are included in a mailbox: (o) trace alert (New/Saved/Blank), (p) trace alert deadline, (q) compliance/completion alert (New/Saved/Blank), (r) compliance/completion alert deadline, and (s) PD identification number.

In an embodiment, the engine is set so that an upload-source cannot alter data in a mailbox, remove data from a mailbox, or delete a mailbox unless the data affected was placed there by that upload-source and the mailbox has not been accessed or changed by an account owner. Also a mailbox cannot be deleted if a panic alert is in the mailbox and the account owner has not accessed the alert.

In an embodiment, trace alerts to a particular PIC of a PD, can be deleted by the account owner.

7. Engine Software Routines

The engine has the following processes or software routines for performing various functions.

(a) Add a chart or upload-source note to a mailbox: The engine creates a mailbox if the mailbox does not exist, then creates and adds a note to the mailbox. If the mailbox does not contain a patient message, the mailbox is added to the list of noted mailboxes.

(b) Add a patient message to a mailbox: The engine creates a mailbox if the mailbox does not exist, then creates and adds the patient message to the mailbox. If the patient message has been uploaded and the account is configured to track upload events, an entry is added to the mailbox uploaded events list. If the account owner has added the patient message, an entry is added to the mailbox coded events list. If the mailbox is in the list of noted mailboxes, the mailbox is removed from that list. The mailbox is added to the list of messaged mailboxes. The patient identifier for the mailbox is deleted.

(c) Remove a patient message from a mailbox: The engine can clear the patient message from the mailbox. If the message was uploaded by an upload-source and the account is configured to track upload events, the engine removes the entry from the mailbox uploaded events list. If the patient message was added by the account owner, the engine removes the entry from the mailbox coded events list for that account. If the mailbox contains either a chart note or an upload-source note, the mailbox is added to the list of noted mailboxes. The mailbox is removed from the list of messaged mailboxes. The engine removes any alert from the upload-source's timed-upload alerts collection, from the upload-source's expired-timed-upload alerts collection and from the mailbox. The engine also deletes any patient retrieval or compliance alerts from the mailbox.

(d) Add a compliance deadline to a mailbox: The engine uses the number of compliance days to calculate and set the compliance deadline.

(e) Add a patient retrieval deadline to a mailbox: The engine uses the number of days entered to calculate and set the patient-retrieval alert deadline.

(f) Clean out a mailbox and its contents: The engine removes the mailbox from any list the mailbox is on and from any collections containing the mailbox for both the account and the upload-source. All data related to the mailbox except for security code is removed. If the mailbox pool has PD access disabled, then the mailbox is added to the pool's collection of unused mailboxes. A mailbox cannot be cleaned out if a panic alert is in the mailbox and the account owner has not yet accessed the panic alert. In an embodiment, when cleaning out a mailbox and its contents, if the corresponding mailbox pool has PD access, then the mailbox is added to the pool's collection of unused mailboxes.

(g) Delete a mailbox: The engine removes the mailbox from any lists and collections for both the account and the upload-source. All data is removed from mailbox and the mailbox is not added to the pool's collection of unused mailboxes. A mailbox cannot be deleted if the mailbox has a panic alert and the account owner has not yet accessed the panic alert.

(h) Record patient's name.

(i) Convert patient's name text to voice recording: The engine is able to convert patient name text to a voice recording using text-to-speech software.

(j) Process patient messages at expiration time: The engine deletes the chart note and upload-source note from the mailbox but the patient's name and patient message are kept. The message expired flag is set to indicate the message has expired.

(k) Retrieve patient name recording: The engine can play the patient name if there is a file with a recording of the name in the mailbox; if not and if the account configuration parameter, PD-Name-Recording is set, then the engine plays the recording from the PD database.

(l) The engine can set a flag indicating that an account owner accessed the mailbox and set the appropriate flag indicating if the account owner changed any data in the mailbox subsequent to entering the mailbox. In the event the account owner changed any data in the mailbox, an upload-source can no longer edit any of the contents of the mailbox. If the account owner accesses the mailbox, but does not change any of the mailbox's contents, the upload-source may change contents in the mailbox if the particular upload-source was the upload-source who uploaded the message in the mailbox, and if the patient has not accessed the mailbox, and this action will activate an upload-source-change alert.

(m) Load data into mailbox from the PD: The engine can load data such as the patient name text and patient telephone number text from the PD record into a mailbox. The engine can create voice recordings for the patient name and the phone number using text-to-speech software. If the patient's name recording is already stored in the PD, this recording may be used in preference to the text-to-speech output.

(n) Activate an alert: The engine activates an alert in a mailbox by setting the appropriate alert status flag in the mailbox to New. Any data associated with the alert is written to the appropriate alert data fields. The account's alert counts are then updated. If the mailbox does not already exist in the account's list of alerted mailboxes, it is added to this list. The mailbox's panic alert flag is set if appropriate.

(o) Set an alert: The engine can set alert deadlines and other alert information.

(p) Update alert information in timed-upload alert collection: The engine can write the alert receipt date/time for the corresponding entry in the upload-source's timed-upload alert collection.

(q) Update alert information in collection/list: The engine can write alert information and add/remove entries in collections and/or lists containing alerts.

(r) Save an alert: Sets the alert status flag to Saved and updates the account's alert counts.

(s) Delete an alert: sets the alert flag to Unused and clears the corresponding alert data fields for the alert being deleted. If there are no remaining New or Saved alerts flags in the mailbox, then the mailbox is removed from the account's alerted mailbox list. The account's alert counts are updated. If there are no other alerts in the mailbox, the mailbox is removed from the accounts list of alerted mailboxes.

In an embodiment, if one alert is deleted for a mailbox with several types of alerts set, then all alerts are deleted for the mailbox.

8. Engine Interaction with a Patient Message

In an embodiment, a patient message in a mailbox includes (a) Content data and (b) Status data.

In an embodiment, the content data includes: (i) A patient message identification signal or code, (ii) The patient message text, (iii) The patient message voice recording, And (iv) patient message digits.

In an embodiment, the status data includes: (i) patient message retrieved (Y/N), (ii) patient message expired (Y/N), (iii) patient message loaded (Y/N), (iv) patient message source (upload-source or account number), (v) patient retrieval alert active (YIN), (vi) retrieval date, (vii) retrieval deadline days, (viii) retrieval deadline date, and (ix) message loaded date.

The engine can interact with patient messages in the following ways:

(a) Clear patient message: The engine sets all data items to their default settings.

(b) Create a patient message: The patient message is loaded with a patient pre-recorded message code or placement of a custom message, patient message digits (if required) and patient message source. The message loaded date is set to the current date. If specified, the retrieval deadline date and days are set.

(c) Retrieve a patient message. The engine sets the retrieval date to the current date and sets the patient message retrieved flag to indicate the message has been retrieved by the patient. The engine plays the patient message voice recording and sets the patient-entered-mailbox flag.

(d) Convert patient message text to voice recording using text-to-speech software.

(e) Record custom patient message voice recording.

(f) Play patient message voice recording for account owner and set the owner-entered-mailbox flag.

The account contains a list of messaged mailboxes—i.e., mailboxes with patient messages loaded.

The engine maintains a count of entries in this list.

The engine can interact with the list of messaged mailboxes via the following steps:

(a) The engine checks the list of messaged mailboxes daily to see if any mailbox has a patient message with a patient-retrieval alert deadline date that has passed with no patient-retrieval alert. If so, a patient-retrieval alert is activated in the mailbox.

(b) The engine can check for expired patient messages: The engine checks this list daily to see if any mailbox has a patient message that has remained unretrieved for a maximum number of days. The maximum number of days is a mailbox pool configuration parameter. Any mailbox that has remained unretrieved for a longer than parameter maximum number of days is retired.

9. Engine Interaction with Notes

In an embodiment, alert notes, chart notes, and upload-source notes each have respective data fields for:
  (a) Whether or not they are loaded on the system,
  (b) Their respective text content,
  (c) Voice recordings of their content,
  (d) Their creation date, and
  (e) Source that created the note. (upload-source or account owner)

The engine interacts with each of these note types via the following steps:

(a) Create a note: The engine creates or recreates a note setting the creation date to the current date and setting the loaded flag.

(b) The engine can check to see if a note is loaded.

(c) The engine can retrieve the contents of the note; in doing so the engine sets the owner-entered-mailbox flag.

(d) The engine can convert the note text into a voice recording.

The account contains a list of noted mailboxes, which are mailboxes that have only a note loaded.

The engine maintains a count of entries in this noted mailboxes list.

The engine can interact with this noted mailboxes list via the following steps:

(a) Check for compliance alerts to activate: The engine checks this list daily to see if any mailbox has a compliance deadline set that has passed and the mailbox has no compliance alert. If such a situation is found, a compliance alert is activated for the mailbox.

(b) Expire mailboxes without a patient message: The engine checks daily the list of mailboxes with notes to see if any mailbox has been on the list for the maximum number of days. If so, the mailbox is deleted. The mailbox will not appear on any account activity report or on any upload activity report. The maximum number of days is a mailbox pool configuration parameter.

(c) The engine can search the list for mailboxes with a specific patient identifier and retrieve this subset.

10. Engine Interaction with Retired Mailboxes

The server contains a list of retired mailboxes.

The engine maintains a count of entries in this list.

The engine can interact with the retired mailboxes list via the following steps:

(a) The engine can check daily for patient messages received prior to the present day to see if the patient message in the mailbox was retrieved. If so, in an embodiment, any chart note or upload-source note in the mailbox is deleted. The patient message, patient name, and alert note are kept in the mailbox.

(b) The engine checks periodically to see if an Account Activity report is to be generated. The engine checks this list daily and, if the number of entries is above a threshold, a report is generated. Also if the number of days since the last Account Activity report is greater than a maximum number of days, such a report is generated. The threshold and maximum number of days are mailbox pool configuration parameters.

11. Engine Interaction with Reported Mailboxes

An account contains a list of reported mailboxes. The engine maintains a count of entries in this list.

The engine checks this list daily to process any mailbox that has been on the list, check whether or not the patient message has been retrieved, check if the reported mailbox has been on the list for a maximum number of days. Each such mailbox on the list greater than this maximum number of days is deleted unless the mailbox contains information that was stored by an upload-source and has not yet appeared on an Upload-Source Activity report.

12. Engine Interaction with Alerted Mailboxes

An account has an alerted mailbox list. This list is maintained as a linked list with a sort order. Any mailbox that contains an active alert will appear only once in this list. The position that a mailbox appears in the list of alerted mailboxes is determined by the highest-ranking alert type that the mailbox contains. All New alerts, i.e., alerts that have not as yet been accessed by the account owner and not deleted, are ranked higher than Saved alerts, which are alerts that have been accessed by the account owner and not deleted. Further, within each of these groups the alerts are ranked by type of alert for example: timed-upload alert, patient-retrieval alert, no-message alert, compliance alert, upload-source-change alert, completion alert, non-time upload alert. The engine maintains counts of each type of alert.

The engine can create and retrieve the current list of alerted mailboxes.

The engine can also write changes (including adding or deleting an entry to the alerted mailbox list and sorting the alerted mailbox list).

The engine maintains the following alert counts for each account: total number of active alert entries, number of New alerts, number of Saved alerts, number of panic alerts, and number of New panic alerts.

13. Engine Interaction with Mailbox Coded Events

The server has a mailbox coded events list for each account. The engine can create a list of mailbox numbers in which an account owner placed patient messages on a particular date. The engine can add an entry to the list and checks the list daily and removes any entries dated prior to a particular date. Each mailbox coded event in this list contains fields for the mailbox number and the date the patient message was placed in the mailbox.

14. Engine Interaction with Mailbox Upload Events

The server has a mailbox upload events list for each account owner. The engine maintains a count of entries in this list and controls the maximum size of the list and the duration the entries may stay in the list. The engine can interact with an external interface to retrieve a list of mailbox upload events for an account and can delete all mailbox upload events in a list. The engine can add an entry to the list; if the list is at its maximum size, the oldest entry is removed before the new one is added. The engine also checks this list daily and purges any entry that has exceeded the maximum length of time the entry is allowed to stay on the list.

Each mailbox upload event contains fields for the mailbox number and the date the upload occurred, and the upload-source that uploaded.

15. Engine Interaction with Account Activity Reports

An account has an account activity reports collection. The engine maintains a count of the entries in this collection. The engine checks the collection of account activity reports daily and deletes any report that has existed for longer than a maximum number of days.

Each account activity report contains a data field indicating the date that the report was created. When the engine places a mailbox on such a report, the mailbox is moved from the list of retired mailboxes to the list of reported mailboxes and the mailbox is marked as reported. Unless the account is deactivated, the report is sent to the account owner.

16. Engine Interaction with an Account Message Collection

An account has an account message collection. The engine can retrieve and write account messages. The engine can also record or play an account message or its title.

Each account message has fields for the account message voice recording and a title voice recording, and a patient message code.

17. Engine Interaction with a Account Administrator Voice Mail Message Collection The server has an account administrator voice mail message collection. The engine can add an administrator voice mail message to the collection, allow the administrator voice mail message to be heard by the recipient, or delete the administrator voice mail message. The administrator voice mail message has fields for indicating an account number, whether or not to broadcast the message to all account owners on the system or a subset of such account owners, and whether or not the message is to an individual account owner.

18. Engine Interaction with an Account with PD Access with a List of Active Mailboxes For a mailbox pool with PD access there is a list of active mailboxes in the pool. The engine is able using the PFC to search this list and find all records that match the PFC specified and output the number of matches found. The engine can also do a narrow PFC search taking as input single digits or characters of the PFC in succession to narrow the previously mentioned search by adding sequentially specified digits or characters to the previous PSC. The engine outputs the number of matches so found and can present these matches to the account owner for further account owner selection.

19. Engine Interaction with an Upload Source Data Collection

The system maintains an upload-source data collection which is a collection of parameters and data regarding the upload-sources. The entries are referenced by unique upload-source numbers in a specified range. The engine maintains a count of entries and an upload field requirements table which contains all the upload fields (See below) that can be configured by the administrator to be either required or not.

The engine can interact with an external interface to create an upload-source, add the upload-source to the collection and set all upload-source parameter data to the default configuration. The engine can delete the upload-source from the collection and read and write upload field requirement table entries.

In an embodiment, the following data fields characterize the upload-source parameter data: (a) upload-source number, (b) minimum number of alerts for the expired time upload activity report (ETUAR), (c) maximum days for ETUAR, (d) date of last ETUAR, (e) panic alert time threshold in days:hours, (f) security code, (g) fax telephone number, (h) report upload activity (Y/N), (i) minimum retired mailboxes for report, (j) maximum days between upload activity reports, (k) date of last upload activity report, (l) company name, (m) contact name, (n) PD update access (Y/N), (O) PD access code, (p) email address, (q) allowed to set patient retrieval alert deadlines (Y/N).

The engine can interact with an external interface regarding the upload-source to send a report to upload-source with a cover sheet displaying company name and contact name. If the report is successfully sent, the file is placed in an appropriate directory. If unsuccessful, the report is sent to the administrator and the file is placed in another directory for such unsuccessfully sent reports. Reports can be faxed or may be sent via electronic file transfer.

The engine, when a mailbox is retired, can add that mailbox to the retired mailbox list if the upload-source has a parameter set to report upload activity.

The system maintains a retired mailbox list. The engine maintains a count of the entries of this list and checks this list daily to see if the number of entries has reached the minimum number of upload events for a report whereupon an upload activity report is generated. If the number of days since the last report exceeds a threshold number of days, then a new report is generated also.

The system maintains an Upload Activity reports collection. The engine maintains a count of entries in this collection and checks the collection daily and deletes any report that has existed for a pool parameter maximum number of days.

The Upload Activity reports contain a field for the creation date; the engine generates the report to the upload-source and flags a mailbox as reported once the mailbox data is added to a report. The mailbox is also moved from retired to reported mailbox list.

20. Engine Interaction with Timed-Upload Alert List

The server maintains a timed-upload alerts list. The engine maintains a count of entries in this list and is able to activate a timed-upload alert and add the alert to the collection. The engine checks for mailboxes that contain timed-upload alerts that have either been accessed by the account owner or have expired. If such a mailbox is found, the corresponding entry in this list is removed. If the entry has panic alert then a Panic report is generated; otherwise, the alert is added to the list of expired-timed-upload alerts.

In an embodiment, each timed-upload alert has fields for the following: mailbox number, upload alert deadline, receipt date/time, patient phone number, and panic status (Y/N). The engine has a process to set timed-upload alerts that sets the mailbox number, the deadline for the alert, and the panic status; the engine can also set the receipt date/time when the alert information is received by account-owner or sent to the upload-source.

The system has an expired-timed-upload alerts list. The engine maintains a count of entries in this list and checks this list daily to see if the count of entries is at or above the minimum number of alerts for report whereupon the system generates an ETUAR. Also, if the number of days since the last report is greater than the maximum days for report and there is at least one entry in the collection, then an ETUAR is generated. Once an entry appears on an ETUAR the entry is removed from this list.

In an embodiment, each expired-timed-upload alert has the following data: Mailbox number, Patient message text, Patient message code, Receipt date/time, Patient message loaded date/time, and Entry added date/time.

21. Engine Interaction with Reports

The server maintains an Expired Timed-Upload Alert report (ETUAR) List and a count of entries in this list.

The Expired Timed-Upload Alert report (ETUAR) is organized by account number and includes the account phone number. The engine generates these reports using data in the expired-timed-upload alert to create report entries. The ETUAR report is sent to upload-source.

The engine is able to generate a Panic report using data in timed-upload alert to create report entry. This report is sent to the upload-source.

The Upload Activity report contains the following fields: account number, mailbox number, patient name, date created, date patient message retrieved, patient message text (includes patient message code), upload-source note text (if available). Indicators such as: "*"=patient retrieval alert activated, "**"=Panic report generated.

In an embodiment, the Panic report contains:

(1) Account owner fields: name, practice name, phone number, email address, and account owner last system access date/time, whether or not an account owner accessed the mailbox and when as well as (2) Mailbox fields: Patient Name, Patient message text (if any), upload-source note text (if any), patient message loaded date/time, date/time alert was activated, patient phone number (if any).

22. Engine Interaction with Disallowed Prefix Collection

In an embodiment, the server contains a Disallowed Prefix Collection. In an IVR embodiment, the engine can interact with an external interface to: (a) Create a prefix and add the prefix to collection, (b) Delete a prefix and remove the prefix from the collection, (c) Check for existence of a prefix in the collection; or (d) Remove the collection and load all new entries from a file into collection.

The prefix data can be up to six (6) digits to handle area code/prefix combinations. '?' can appear anywhere in prefix as a wild card, so, for example, '???911' would disallow any phone number with second 3 digits as 911.

23. Engine Interaction with Allowed Area Code Prefix Collection

In an embodiment, the server has an Allowed Area Code Collection. In an IVR embodiment the engine can interact with an external interface to do the following: (a) Create an allowed area code and add the area code to collection, (b) Delete an area code and remove the area code from the collection, (c) Check for existence of an area code in collection; or (d) Delete the collection and load all new entries from a file into the collection.

24. Engine Interaction with Default Configuration Collection

The server has a default configuration collection for the engine, mailbox pool, accounts, and upload-source parameter configurations. The engine can interact with an external interface to read and write a default configuration by interacting with configuration software that has the type of configuration as a variable.

25. Engine Interaction with Upload Data Interface

In an embodiment, the upload interface reads from an uploaded data file in disk (211). This data file is uploaded data input via modem (204).

The engine periodically checks for upload files to process and uploads these into an particular upload subdirectory where upload data is processed. The files are given an identifying extension and the first line of each file contains header data with each field separated. If the supplied security code is not valid, a single error will appear in the upload acceptance report and the upload file will not be processed. If the fax number is specified, the fax number will be written to the upload-source parameter data record. The PD access code is also optional.

The upload file header will typically contain the upload-source number, security code, fax number, and PD access code.

Each subsequent line in the file is processed as an upload file entry. Once the upload file is processed, an upload acceptance report is generated.

The engine interacts with the upload-source data by reading the data in a file that has been electronically uploaded into a disk (211). The engine processes each upload-source entry, applies data validation for each field of each entry, and responds to the commands noted below at the start of the upload entry. Data fields for entries are specified as either always-required ('R') or required if specified in the upload field requirements table pertaining to that upload-source ('T').

Typically each upload file entry is required to have one of the following commands as the first two characters:
NM—Create a new mailbox (mailbox number provided)
NP—Create a new mailbox (PIC provided)
CM—Change a mailbox field (mailbox number, field name, and new value provided)
DM—Delete a mailbox (mailbox number provided)
AP—Add patient to PD (PIC required)

In an embodiment, in an account without PD access, an upload-source may initialize a mailbox on behalf of an account or upload-source. In this embodiment, the upload-source uploads the mailbox number, the account number, a patient identifier, and a chart note. In this embodiment, text-to-speech software translates the chart note text into speech.

If a required field has no data or a field has invalid data, then an upload error is generated and the entry is not processed. Once the data is validated, the mailbox will be added to the account's mailbox collection if necessary; then the specified data is stored in the mailbox. If the entry includes a patient retrieval alert deadline, a patient retrieval deadline can only be set for the mailbox if the upload-source is allowed to set patient retrieval deadlines by checking appropriate flag. The system uses text-to-speech software to create voice recordings from the following fields: patient message text, patient name text, upload-source note text, and/or patient phone number text (alert note recording). Some fields must have data and others are optional. Any fields that are optional will be so designated in the Upload Field Requirements Table. Whether or not fields are optional or required in this table may be changed.

If the entry specifies upload notification, a time limit can be specified in days and hours. An upload alert is activated for the mailbox. If a time limit is specified, the upload alert is added to the upload-source's timed-upload alerts list. If the time limit is less than the panic threshold, the alert is given panic status. If the alert has panic status and the account has requested panic alert notification, a notification phone call will be placed. If the entry contains an upload-source note but no patient message, then a no-message alert is created and is added to the mailbox. If the mailbox is newly created (not just edited) and the upload entry has completion notification specified, then a completion alert is activated for the mailbox.

If a PIC is supplied in the entry, the patient last name in the upload entry will be cross-checked against the last name in the PD record. If the patient last name and PIC do not match then an upload error is generated and the upload request is not processed. If the PIC is not found in the PD, then an upload error is generated and the upload request is not processed. The number of the mailbox created is added to the entry before the entry is added to the upload acceptance report. Then if the upload-source wishes to edit or delete the mailbox, the upload-source will have the mailbox number.

In an embodiment, in order for the upload-source to add a patient to the PD, the upload-source must have PD update access and must provide the correct PD access code. If an upload-source tries to add a PIC that already exists in the PD, then an upload error is generated and the upload request is not processed.

If an entry includes a change to any information in a mailbox and that mailbox has a flag set to indicated the mailbox has been "entered" by the account owner but no changes in any data field of that mailbox have been made by the account owner, then an upload-source-change alert is activated for the mailbox. If the account owner has changed any field in the mailbox in this situation, then this entry by the upload-source is blocked and an error code is generated.

When a mailbox is created by upload, the upload-source field in the mailbox is set to the upload-source number that uploaded the file.

If the following situations occur, an upload error is generated and the entry is not processed:
(a) Account number or mailbox number missing,
(b) New mailbox command and the count of mailboxes available for the account is not unlimited and is at zero,
(c) The upload alert has panic status and an upload-source note is not provided,
(d) Entry does not include either an upload-source note or a patient message, (e) Mailbox security code is not provided and the mailbox is not in the mailbox pool's unprotected range, (f) No first name or last name provided, (g) A patient message is specified but a patient message was already retrieved, (h) If the mailbox security code is not provided and the account is not configured to accept uploads without security code, (i) An entry attempts to change or delete a mailbox that was not created by that upload-source, (j) An entry attempts to change or delete a mailbox that has been modified by the account owner, or (k) Upload-source note specified with no patient message and no no-message alert set.

For an account without PD access the engine typically processes the following fields and does data validation as required for each entry: (a) Mailbox pool number, (b) account number, (c) mailbox number, (d) mailbox security code, (e) patient phone number, (f) patient message code (if patient pre-recorded message, patient pre-recorded message code, if custom then code is "0"), (g) patient message digits, (h) patient message text, (i) patient-retrieval alert deadline, (j) upload notification flag—Y/N, (k) upload notification time limit days, (l) upload notification time limit hours, (m) upload-source note text, (n) patient identifier. For an account with PD access the engine typically processes the above (a through n) plus the following additional fields for each entry: (O) Patient Identification Code (PIC)—(Can not be empty), (p) patient last name—at least one letter, (q) patient first name—at least one letter. (r) patient middle initial—can be blank.

Upload Acceptance report: The engine generates this report in response to the upload of a file by the upload-source. The report contains the time of the upload with, for example, the following format: "Uploaded at DD-MMM-YY,HH:MM", where DD=day, MMM=Month, YY=Year, HH=hour and MM=minute. The report will typically contain the data from the original file followed by a comma and one of the descriptions of the result from the list below.

If all mailboxes were coded successfully, then the line "All mailboxes uploaded successfully" appears on the last line. Otherwise the line will read "The following mailboxes were not uploaded successfully: xxxx(yyyy), xxxx(yyyy), . . . ". The legend "(xxxx(yyyy) where xxxx=Account number, yyyy-mailbox number)" will appear as the last item on the report. Upload result descriptions:

In an embodiment, the Upload Acceptance report will contain codes that describe the results of the upload attempt. These, for example, could include the following:

000—mailbox coded successfully
2XX: ACCOUNT ERRORS
201—ERROR, doctor not active
202—ERROR, doctor has no more mailboxes left
203—ERROR, mailbox not active
204—ERROR, mailbox already contains another patient message
205—ERROR, mailbox cannot be edited because placed by or edited by doctor.
206—ERROR, mailbox must contain patient message or upload-source note
3XX: MISSING DATA ERRORS
301—ERROR, account number is required
302—ERROR, mailbox number is required
303—ERROR, patient last name field requires at least one character
304—ERROR, protected mailbox, mailbox security code required
305—ERROR, mailbox must contain patient message or upload-source note
306—ERROR, upload-source note must have either patient message or upload alert setting in upload entry.
4X: DATA TYPE ERRORS
402—ERROR, invalid mailbox number
403—ERROR, mailbox security code not correct
404—ERROR, last name not valid
405—ERROR, first name not valid
406—ERROR, patient phone number not valid
407—ERROR, patient message not valid—invalid patient pre-recorded message code
408—ERROR, patient message not valid—invalid patient message digits
409—ERROR, patient message not valid—patient message digits required and not specified
410—ERROR, patient message not valid—patient message digit specified and not required
411—ERROR, patient message not valid—text string not valid
412—ERROR, Alert Retrieval Days not valid
413—ERROR, Upload-source Alert data not valid
414—ERROR, Upload-source note data not valid
5XX EDITING/DELETING ERRORS
501—ERROR, correction rejected—patient message already retrieved
502—ERROR, correction rejected—original not uploaded
503—ERROR, field (field name) missing required data
504—ERROR, edit not accepted—account holder created/edited patient message
505—ERROR, cannot delete patient message, edited/created by account holder
506—ERROR, cannot delete patient message, different upload-source uploaded patient message
6XX PD ERRORS
601—ERROR, upload data does not match patient record
602—ERROR, patient record not found
603—ERROR, access to patient database denied
604—ERROR, cannot add patient—record already exists
9XX MISC ERROR CODES
901—ERROR Upload list rejected—Upload-source Upload Security Code Not valid.

B. System Graphic User Interface (GUI)

The server 100 may interact with users through several screens. In an embodiment, these screens and their characteristics include the following:

(a) Screen for Administrator Interface:

The administrator screen interface provides access to the data engine to add, delete or edit information relating to the following: (i) engine configuration, (ii) patient databases, (iii) mailbox pools, (iv) accounts, (v) upload-source, (vi) mailboxes.

In addition this interface will allow the administrator to startup and shutdown the system, configure the upload, IVR, and other interfaces, manage system diagnostics, and set appropriate parameters.

(b) Screen for SYSTEM MENU OPTION: This displays, among other options, windows to configure engine data defaults, set system defaults, copy files and initialize the system:

(c) Screen for MAILBOX POOL MENU OPTION: This displays, among other information, lists of mailbox pools, and accounts as well as windows for configuring the accounts and mailbox pools.

(d) Screen for UPLOAD MENU OPTION: This displays, among other information, lists of upload-sources and allows the user to add and delete upload-source configuration data.

(e) Screen for PRE-RECORDED PATIENT MESSAGE MENU OPTION: This displays pre-recorded patient messages and allows the user to add or delete patient messages.

(f) Screen for PATIENT DATABASE MENU OPTION: This displays PD collection information as well as allows a user to add or delete a PDs.

(g) Screen for DIAGNOSTICS MENU OPTION: This displays diagnostic and statistic information, such as calls per month.

(h) Screen for IVR INTERFACE MENU, and related information. This displays telephony ports. This screen also enables a user to load system prompts and displays to user information regarding allowable phone number prefixes and area-codes.

(i) Screen for HELP MENU OPTION: This displays help information, such as indexes.

VI. IVR Interface

An interactive voice response (IVR) interface is an example of an interface structure provided in accordance with the present disclosure.

In an embodiment, the IVR interface provides the following functionality:

Patient Access—The patient calls the system and provides a mailbox number and security code. If mailbox is generated from an account with PD access then the patient enters their patient identification code (PIC) and their security code (PSC). The patient will then hear the patient message and may be asked to record a testimonial.

Account Owner Access—The account owner calls the system and enters a security code. If the account is new, then the caller will go through an account initialization process on this first call. The caller will then hear any voice mail messages that the account has waiting and the number of alerts that have been activated for the account. The caller can then create mailboxes, alter or delete mailbox contents, edit account configuration, send messages to the administrator, and review alerts.

Administrator Access—The system administrator calls the system and enters a security code. The caller can then configure accounts, retrieve messages from accounts, send messages to accounts, add mailboxes to pools, record system prompts, initiate system shutdown, or configure parameter settings.

In an embodiment, the IVR interface includes the following components:

(A) A telephony port data collection with processes to add and remove a telephony port from the collection. Each telephony port has specifications regarding its application (inbound or outdial) and the pool number associated with the telephony port and processes to read and write telephony port configuration data.

(B) A system message queue for debug messages and fax requests waiting to be processed.

(C) An invalid access log and associated file. Entries to this log are generated whenever a caller fails in three attempts to provide a valid account number, mailbox number or security code. Each item contains date, time, account number, mailbox number, prompt number, and digits entered by the caller. The entry may also contain information from caller-id services.

(D) An account owner configuration collection. Each account may contain data for the following fields and parameters: (a) pool number, (b) account number, (c) PD number, (d) first access (Y/N), (e) prompt for alert note (Y/N), (f) prompt for testimonial (Y/N), (g) read mailbox number (Y/N), (h) compliance alerts available (Y/N), (i) account change code required (Y/N), (j) quickfill (Y/N), (k) play chart note with alert (Y/N), (l) account change code, (m) PD enabled (Y/N), (n) say chart notes during Patient message Read (Y/N), (O) say upload-source notes during patient message read (Y/N), (p) maximum age of chart note heard (number of days), (q) hear other account chart notes (Y/N), (r) hear account name before chart note (Y/N)

(E) IVR interface status data: Is the account currently being accessed (Y/N); has alert information been heard by account owner (Y/N).

(F) A process to create the account configuration; all account data is initially set using the default configuration. The engine also has processes to read and write data, as indicated in the following flow diagrams.

(G) A mailbox configuration collection in which each mailbox configuration includes data relating to pool number, account number, mailbox number, and PIC and IVR interface status data such as whether or not a mailbox is currently in edit mode.

(H) A process to read and write data to mailboxes and tables.

(I) An Interface Configuration Table with the following parameters:
I01: Administrator's password
I02: Maximum number of times patient can listen to patient message
I03: Set automatic fax reports during first access (Y/N)
I04: Volume level (J) Fax parameters
F01: Number of times to retry a fax call
F02: Minutes pause between fax call retries
F03: Outgoing fax id that appears in fax header
F04: Instructions faxed from ASCII/TIFF file (A/T)
F05: system name (fax cover sheet)
F06: system description (fax cover sheet)
F07: Company name (fax cover sheet)
F07: Company phone number (fax cover sheet)
F09: Company fax number (fax cover sheet)

1. IVR Flow Charts.

Figure 64:
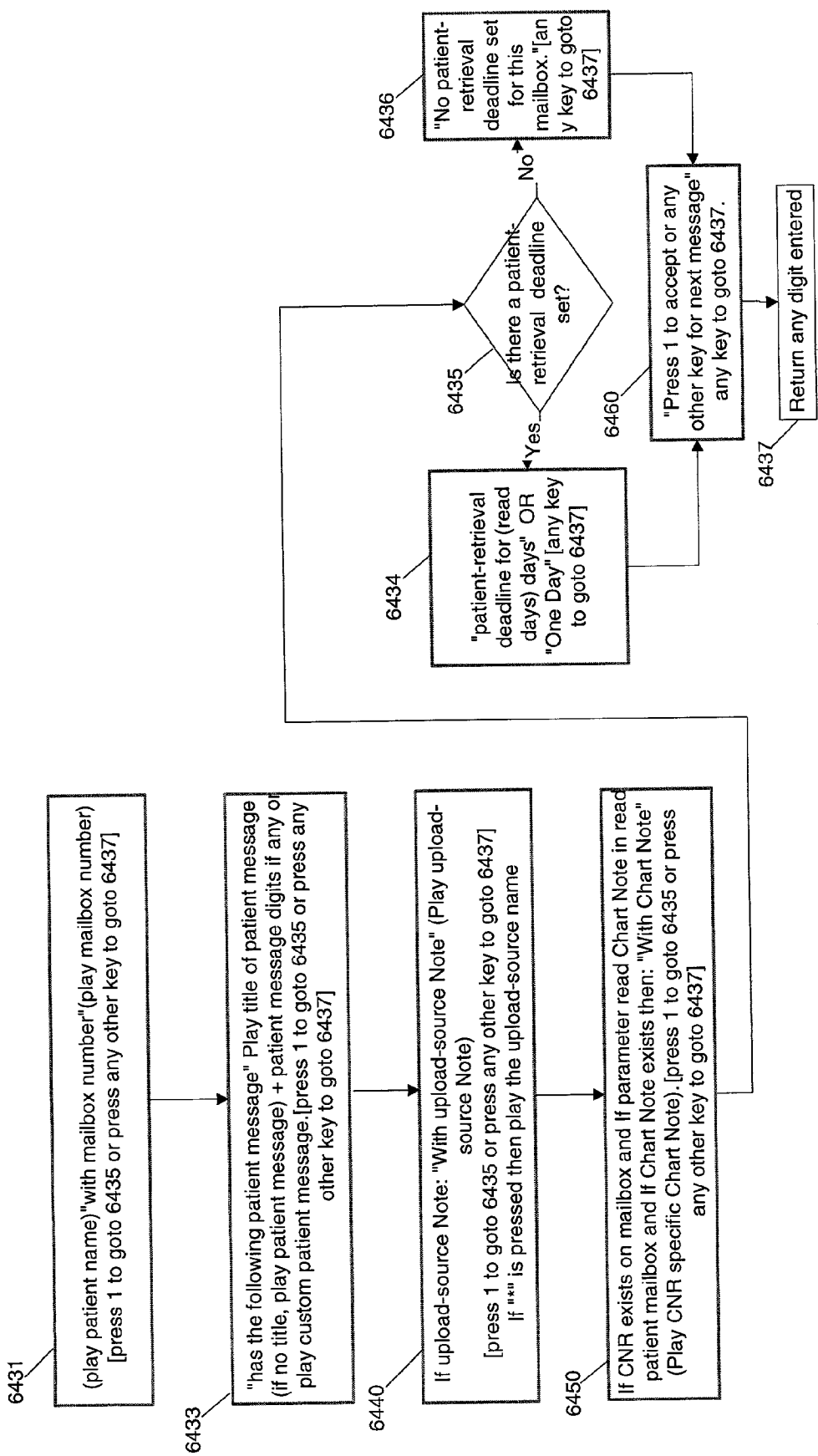
FIG. 64 illustrates a logic flow diagram in a medical information system with patient database access for presenting the data in a particular mailbox in accordance with the present disclosure.

FIGS. 6 to 64 illustrate the operation of a medical information system having an interactive voice response interface. These figures illustrated logic flow diagrams and the operation of system 105 with an IVR interface.

FIG. 6 illustrates a logic flow diagram of a patient obtaining a medical message on Server 100 illustrated in FIG. 1. The patient, for example, contacts Server 100 using a touch-tone telephone through central office via POTS line represented in 201a. An account owner may similarly access Server 100 to access or place information or patient messages. While the preferred embodiment of the present invention interface is described using a touch tone telephone for accessing and inputting information, other forms of electronic information and entry means such as voiced information recordings, voice commands, and/or electronic data files may be inputted or received by a user to access, record information, control, or otherwise use Server 100.

Figure 7:
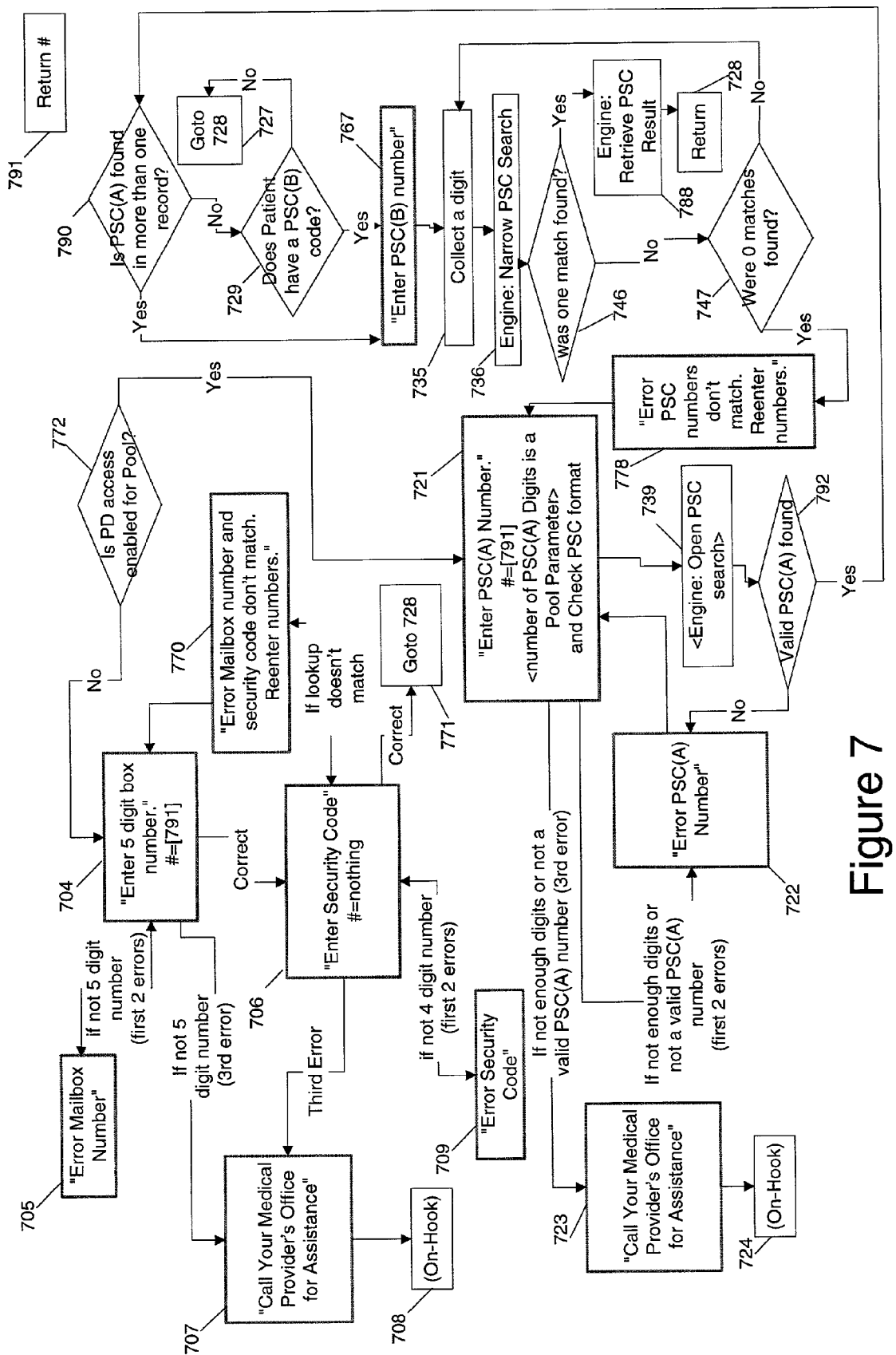
FIG. 7 illustrates a logic flow diagram of a patient entering a mailbox number, if required, and security code(s) in a medical information system in accordance with the present invention.

FIG. 6 illustrates a main greeting being generated in the system at logic block 601 after the user telephones the Server 100 and the system engine initializes the system and retrieves mailbox pool data in logic block 600. The processor 205 accesses the main greeting message from disc 211 to generate this greeting message. The system then, in the case of a patient desiring to retrieve an account owner patient message, transfers control to logic block 634 where control is transferred to logic block 772 illustrated in FIG. 7. The user is subsequently requested to enter identification numbers that are verified or not as illustrated in FIG. 7.

Figure 8:
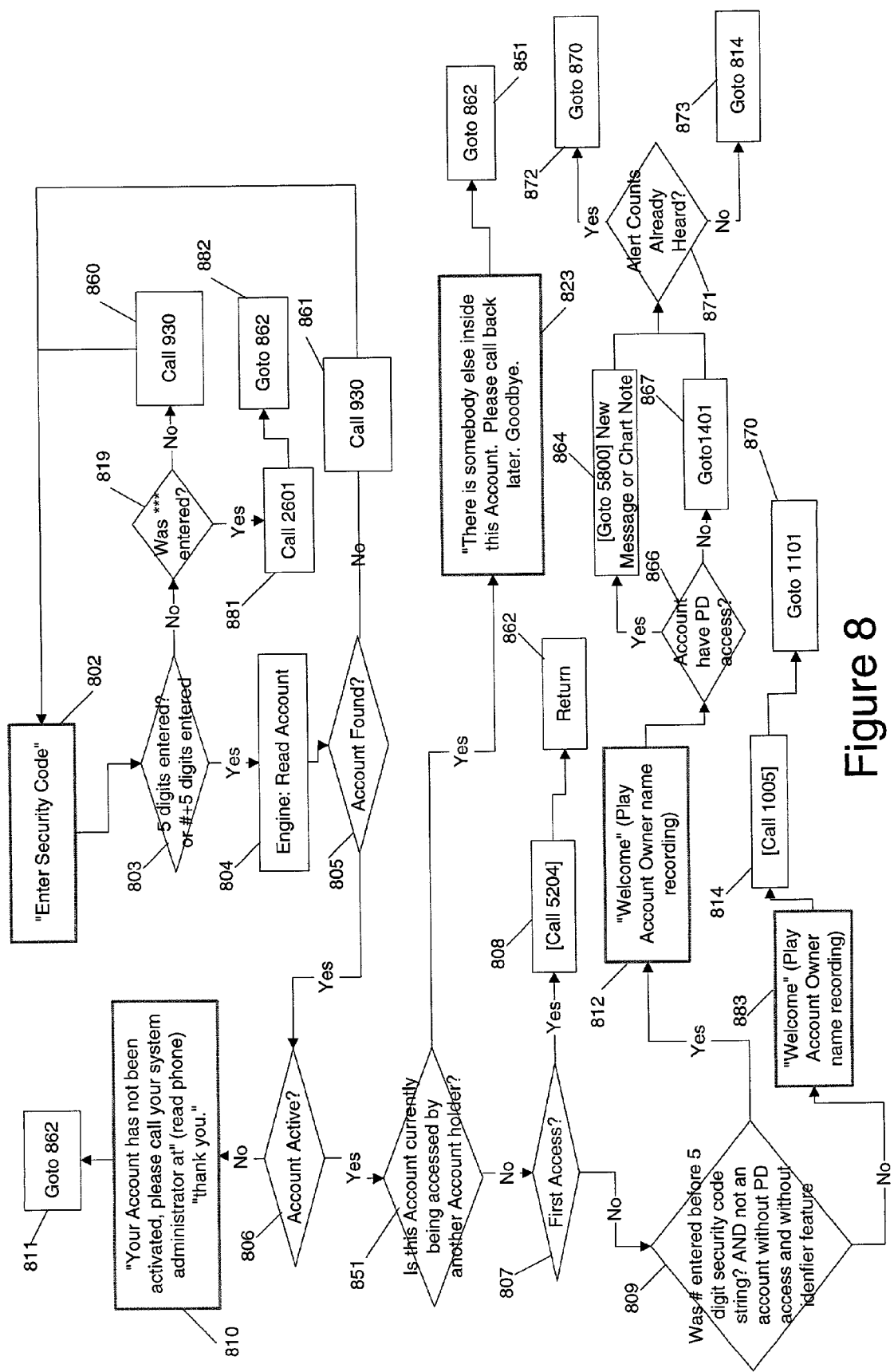
FIG. 8 illustrates a logic flow diagram of an account owner or system administrator entering a medical information system in accordance with the present disclosure.

If the user enters "#" subsequent to logic block 601, control is transferred to logic block 633 and the system thereupon transfers control to logic block 802 illustrated in FIG. 8. Here the user is prompted to enter an account owner security code and the account owner subsequently proceeds as illustrated in FIG. 8 below. When control is returned from the logic illustrated in FIG. 8 to logic block 633, control is passed to logic block 612 where the system hangs up.

If a patient desiring to retrieve an account owner patient message correctly enters the appropriate identification numbers, control is then transferred to either (a) logic block 637 where, if an edit flag is currently set for the mailbox number the patient entered or the patient's PIC, the patient is informed that the system is being updated and to call back later; or (b) to logic block 631 where, if the mailbox is unused, the patient is informed that the mailbox is inactive; or (c) to logic block 630 where, if the patient message has expired, the patient is informed of this fact; or (d) to logic block 614 where, if the patient message has already been retrieved more than one day ago, the patient is so informed; or (e) to logic block 615 where, if there is no patient message in the mailbox, the patient is so informed and asked to call back later and the system activates a patient-attempt alert for the appropriate account owner if available.

If all of the above are not true and there is a patient message pending patient retrieval in the mailbox, control is transferred to logic block 670 where the system locks out other access for the mailbox being accessed if the system is functioning without patent database access or sets a lock for all mailboxes with the PIC being accessed if the system is functioning with a patient database access. This lock prevents other users from entering the mailbox being accessed by the patient while the patient is retrieving the message.

Control then passes to logic block 616, which results in the following announcement to the patient: "This is a message from". Then control passes to logic block 617 which plays the appropriate account owner name which typically is the account owner name given the patient when the patient obtained the information for retrieving the patient message. Control is then transferred to logic block 640 where the system determines if the patient name is recorded in the mailbox. If so, control is transferred to logic blocks 618 and 610 and the prompt "for" followed by the patient's name is played by the system. If not, control is transferred to logic block 641 and the prompt "Your message is the following" is played. Control is then transferred to logic block 620 where the patient message in the mailbox is played and any associated patient message digits regarding specific test results are read; the patient record is also updated by the system to acknowledge the receipt of the message by the patient and the time and date of receipt. A parameter allows control to be transferred to logic block 642 a specified number of times so that the patient can hear the message again as control cycles through logic blocks 616617,640 and either 618 and 610 or 641, and then 620. Control is then transferred from logic block 642 or 620 to logic block 660 where a determination is made whether or not the account has access to a patient database (PD) or not.

If not, control passes to logic block 671 where the mailbox lock that was set previously to prevent other user access is removed. Control then passes to logic block 650 where, according to a parameter, control may be transferred to logic block 611 where the system plays a prompt thanking the patient before hanging up in logic block 612 or to logic block 651 where the patient is queried regarding recording a testimonial. If the patient responds negatively here, control is transferred again to block 611 before the system hangs up in block 612. If the patient responds affirmatively, the patient is next asked to record a testimonial in logic block 652. This action is carried out next in logic block 653, and the patient is thanked in logic block 654 before control is again transferred to logic block 611 prior to the system hanging up in logic block 612.

If the system has a patient database configuration, control passes from logic block 660 to logic block 661 where a determination is made whether or not there are more unretrieved patient messages for the patient with same PSC. If so, control passes to logic block 662 where the engine retrieves the next patient message before passing to logic block 616 where the system proceeds as described previously to play the patient message.

If a determination is made in logic block 661 that there are no more patient messages with the entered patient security code to be played, control passes to logic block 663 where a determination is made whether or not there are other mailboxes with this patient security code awaiting placement of patient messages or test results for future delivery. If not, control passes to logic block 671 where the previously set lock for mailboxes with the current PIC being accessed is removed prior to control passing to logic block 650 for processing as described above. If there are such mailboxes awaiting test results to allow placement of patient messages, control passes to logic block 664 where the patient is informed of this and how many such mailboxes there are. Control then passes from logic block 664 to logic block 671 for processing as discussed before.

FIG. 7 illustrates the system obtaining and verifying the mailbox number to be accessed from the patient and the corresponding security codes. In an embodiment, the system can be configured to operate with or without a patient database containing records with demographic, identification, and other information about each patient in the practice stored in a system disc like 211. If the account is functioning without access to a patient database, the account owner typically provides the patient the account owner identification number, which could be a phone number, a patient identification number, security number, and information on how to contact Server 100 when the tests are ordered.

If the account is functioning with patient database access, the account owner merely provides the patient an account owner identification number and a patient security code, and information on how to contact Server 100. Thus, in an account functioning without access to a patient database (non-PD), the account owner might hand the patient a card at the office visit listing the phone number to dial (account owner identification number), a mailbox number (patient identification number), and a security code. For an account with access to a patient database (PD) the account owner could merely ask the patient to call a phone number (account owner identification number) and enter a security code that is readily known to both the account owner and the patient. This security code could, for example, be a patient number, the patient's initials plus birthdate, a portion of the social security number or some combination of these. The system could use DNIS, dialed number identification service, to automatically identify the account owner identification number.

Control is transferred to logic block 772 from logic block 634 as illustrated in FIG. 6 and a determination is made if the mailbox message was stored in an account with access to a PD. If this is the case, control is transferred to logic block 721 where the patient is asked to enter the first part of his or her patient security code. The patient security code (PSC) is unique within the particular PD and consists of two parts: PSC(A), a fixed length string for all patients; this suffices for entry into the system if the entry is unique in the PD; and PSC(B), an additional identifying sequence used if PSC(A) is not unique in the PD. Control is then transferred to logic block 739 where the system's engine performs a search for the entered PSC.

The system determines in logic block 721 if the entered PSC or PSC(A) is valid. If the PSC(A) is entered incorrectly or is not valid, control is transferred to logic block 722 where the patient is so informed and asked to re-enter the patient identifier for a total of two failed attempts; on the third error, control is transferred to logic block 723 where the patient is requested to call the account owner's office for assistance before the system hangs up in logic block 724. If the PSC(A) entered has a valid format, control is then transferred to logic block 739 where the system's engine performs a search for the entered PSC. Control is then transferred to logic block 792 where a determination is made whether or not a valid matching PSC(A) is found by the engine. If not, control passes to logic block 722 for processing as above.

If a valid PSC(A) is found in logic block 792, control is transferred to logic block 790 where a determination is made whether or not more than one PSC(A) exists in the PD. If this is not the case, control is transferred to logic block 729 where a determination is made whether or not there is a patient PSC(B) code. If this is not the case, control is transferred to logic block 727 and then to logic block 728 before being returned to logic block 634 illustrated in FIG. 6 for further processing of patient message delivery. If there is a PSC(B), then control is transferred to logic block 767 where the patient is requested to enter the PSC(B). If in logic block 790 a determination is made that the PSC(A) entered is not unique in the PD, control is also transferred to logic block 767.

Control is next transferred to logic blocks 735 and then 736 where the system does a narrow search of the PD to identify the PSC. In logic block 735 a single digit of the entered PSC(B) is collected and then in logic block 736 the system's engine performs a narrow search of the appropriate PD records. In logic block 746 a determination is made if one and only one match was found. If a single match is found, control is transferred to logic block 788 where the engine retrieves the PSC result and then to logic block 728 and then returned to logic block 634 illustrated in FIG. 6 for further processing of patient message delivery. If a single match was not found, control is transferred to logic block 747 where a determination is made whether or not no matches were found. If this is the case, then the PSC does not match any in the PD and control is transferred to logic block 778 where the user is so informed prior to being transferred to logic block 721 and re-entry of the PSC is requested. If more than one match exists, control is transferred from logic block 747 back to logic block 735 for the system to collect and process another digit which is appended to prior PSC(B) digits through logic blocks 736,746, and 747 as above. In this way the unique PSC in the PD is identified.

If the mailbox being accessed has no access to a PD, control is transferred from logic block 772 to logic block 704 where the patient is requested to enter, for example, a five digit mailbox number previously supplied by the account owner. If the mailbox number is not valid, control is transferred to logic block 705 where the user is so informed for the first two errors and then to logic block 707 on the third error where the user is requested to call the account owner's office before the system goes on-hook in logic block 708. If the mailbox number entered is correct, control is transferred to logic block 706 where the patient is requested to enter the security code for the mailbox given by the account owner. If the entered security code does not correctly correspond to the previously entered mailbox number, control is transferred to logic block 770 where the user is so informed prior to the control being transferred back to logic block 704 where another request is made to enter the mailbox number. If there are other errors on entry of the security code, control is transferred to logic block 709 where the user is so informed on the first two errors and then to logic block 707 on the third error where the user is asked to contact the account owner's office. The system then goes on hook when control is next transferred to logic block 708. If the correct security code is entered, control is transferred to logic block 771 and then to logic block 728 whereupon control returns to logic block 634 illustrated in FIG. 6 for further processing of retrieval of the patient message.

If "#" is entered in logic block 704 or logic block 721 control is transferred to logic block 791 and "#" is returned to logic block 634 illustrated in FIG. 6 for further processing.

FIG. 8 illustrates a logic flow diagram of an account owner or system administrator entering the automated patient information retrieval system. Control is received from logic block 633 illustrated in FIG. 6 and transferred to logic block 802 where the user is requested to enter a security code. The system determines in logic block 803 if 5 digits or "#" plus 5 digits was entered by the user; if not, control is transferred to logic block 819 where a determination is made whether or not "*" was entered block 803. If not, control passes to logic block 860 prior to being transferred to logic block 930 illustrated in FIG. 9. If "*" was entered in logic block 819 control is transferred to logic block 881 prior to being transferred to logic block 2601 of the administrator menu illustrated in FIG. 26. On return of control from the logic illustrated in FIG. 26 to logic block 881 control is transferred to logic block 612 in illustrated in FIG. 6 for hang up through logic blocks 882, 862, and 633.

If in logic block 803 five digits or "#" plus five digits were entered, control is transferred to logic block 804 where the system's engine reads account data. Control is transferred then to logic block 805 where a determination is made whether or not the account was found. If not, control is transferred to logic block 861 prior to being transferred to logic block 930 illustrated in FIG. 9. If the account was found, control is transferred to logic block 806 where a determination is made whether or not the account is active. If not, control is transferred to logic block 810 where the account owner is advised that the account has not been activated and to call the system administrator before control is transferred to logic block 612 illustrated in FIG. 6 for hang up through logic blocks 811, 862, and 633. If the account is active, control is transferred to logic block 851 where a determination is made whether or not the account is currently being accessed by another account owner. If so, control is transferred to logic block 823 where the current entering medical is so notified and asked to call back later; control is then transferred to logic block 612 illustrated in FIG. 6 for hang up through logic blocks 851, 862, and 633. This prevents two account owners from accessing an account at the same time and possible confusion and errors.

If there is no other account owner accessing the account, control is transferred to logic block 807. Here a determination is made whether or not this is the first access of this account on the system by the account owner so that the account owner may install their account name and account security code. In this situation an initial access code is provided the account owner by the system administrator for initial access use in logic block 803. Server 100 compares this initial access code stored on disc 211 with the account number in logic block 805 and proceeds as previously noted depending on the results. If this is the first access, control is transferred to logic block 808 whereupon control is then transferred to logic block 5204 illustrated in FIG. 52 where a welcome message is then generated. Upon return of control from logic illustrated in FIG. 52, control is then passed to logic block 862 whence control is returned to the logic block that originally transferred control to logic block 802.

Figure 58:
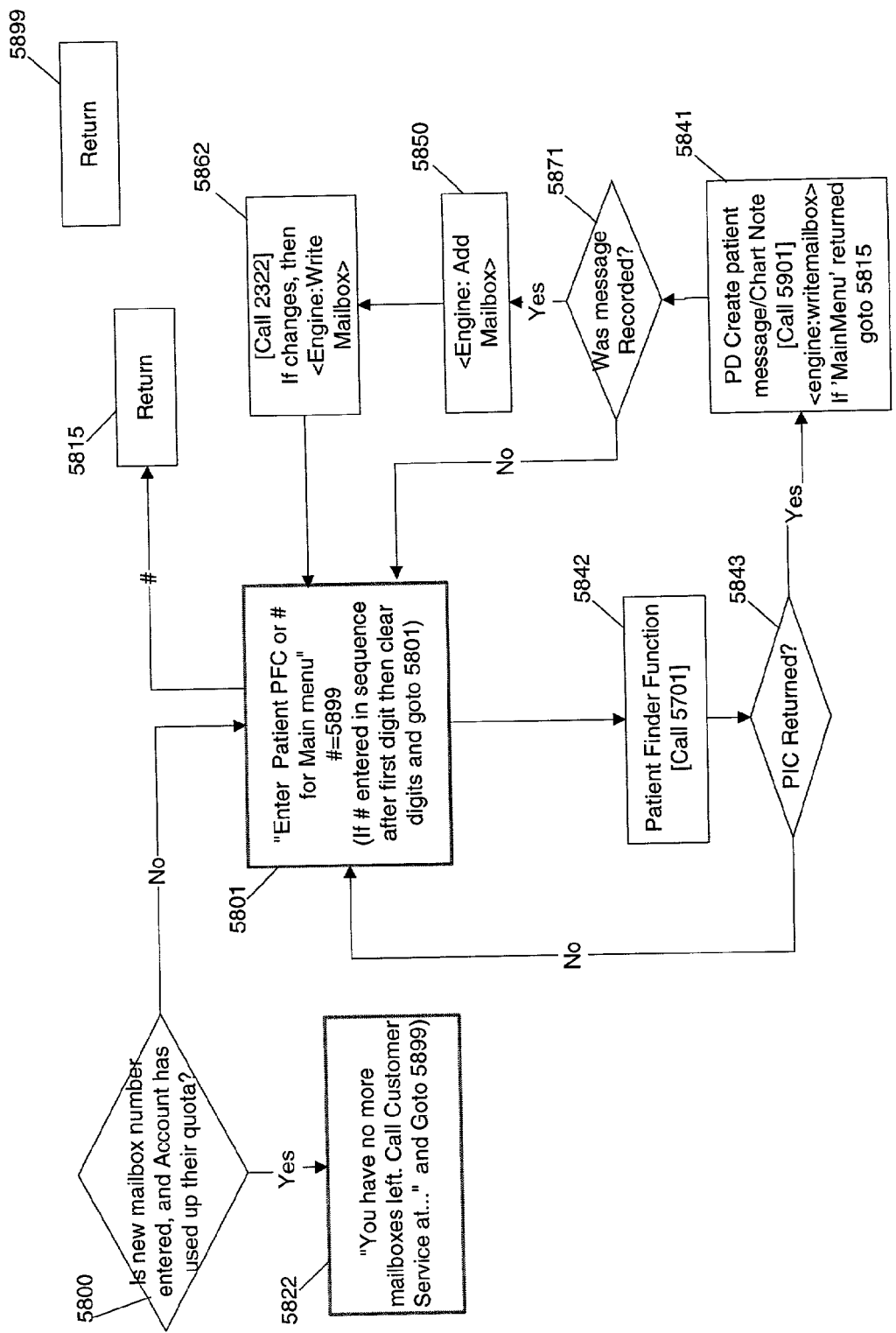
FIG. 58 illustrates a logic flow diagram in a medical information system with patient database access for placing a patient message or chart note in accordance with the present disclosure.

If this is not the first access, control is then transferred to logic block 809 where a determination is made whether or not "#" was entered before the five digit security code and that the account is not an account with no patient identifier feature and no PD access. This is to allow the account owner to speed dial into the system to rapidly place a chart note or patient message without hearing alert counts. If a "#" was entered, control is transferred to logic block 812 where a welcome message is generated to the account owner and thence to logic block 866 where a determination is made whether or not the account has PD access. If yes, control is then transferred to logic block 864 and thence to logic block 5800 as illustrated in FIG. 58 which illustrates the placement of a patient message or chart note in a system with the PD access. If the account does not have PD access, control is transferred to logic block 867 and thence to logic block 1401 illustrated in FIG. 14 that illustrates a flow diagram for setting up a mailbox for future retrieval for patient message placement and setting compliance and completion alerts for the mailbox. Subsequent to the return of control from the called logic to logic block 864 or logic block 867 control is transferred to logic block 871 where a determination is made whether or not the account owner has already heard the alert counts currently on this access to the system for this account. If yes, then control is transferred to logic block 1101 as illustrated in FIG. 11 that illustrates accessing the main menu of the system via logic blocks 872 and 870. If not, control is transferred to logic block 1005 as illustrated in FIG. 10 that illustrates the logic flow diagram of an account owner accessing administrator and alert information on the system via logic blocks 873 and 814.

If "#" was not entered before the five digit security code, control is transferred to logic block 883 where the system plays a welcome message using the account owner's name. Control is then transferred to logic block 1005 illustrated in FIG. 10 where administrator messages and alert information are accessed via logic block 814 before being transferred to logic block 1101 as illustrated in FIG. 11 that illustrates the system's main menu access via logic block 870.

Figure 9:
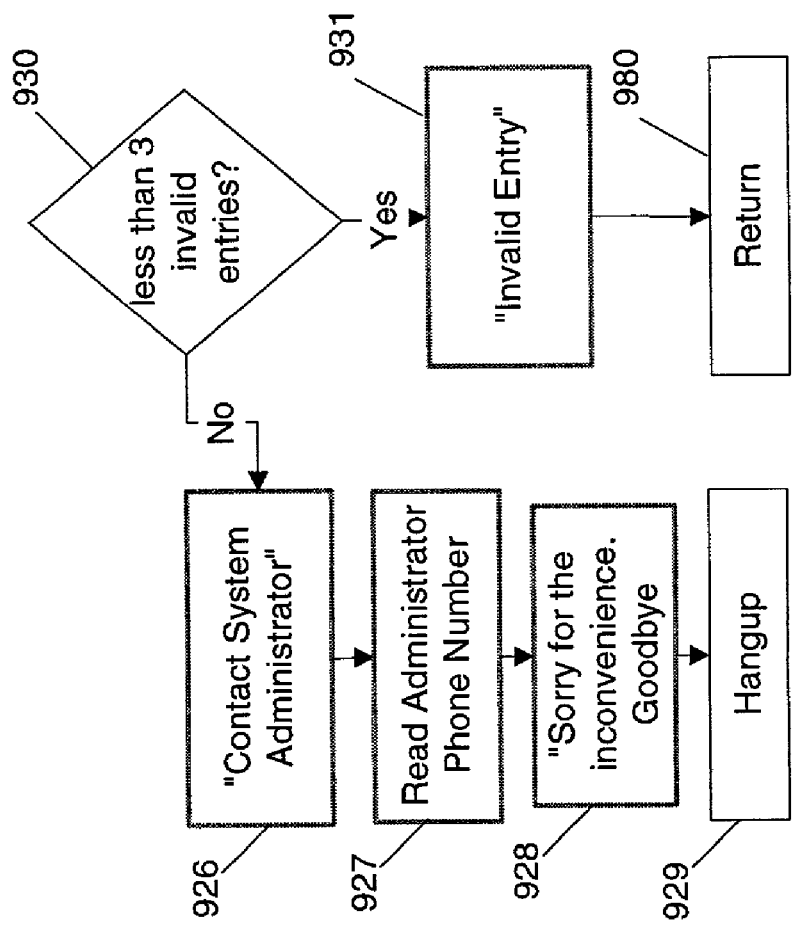
FIG. 9 illustrates a logic flow diagram for handling invalid security code entries of an individual entering a medical information system as an account owner or administrator in accordance with the present disclosure.

FIG. 9 illustrates a logic flow diagram for handling invalid security code entries of an individual entering the system as an account owner or system administrator. Control is transferred from logic block 930 to logic block 931 if there are less than three invalid entries of the security code in question where the user is informed of the invalid entry. Control is then passed to logic block 980 whence control is return to the logic block that called logic block 930 illustrated in FIG. 9. If there have been three invalid entries of the security code in question, control is transferred from logic block 930 to logic block 926 where the user is asked to contact the system administrator. Control is next passed to logic block 927 where the system administrator's customer service phone number is read and then to logic block 928 where a goodbye message is read before control is transferred to logic block 929 for hang up.

Figure 10:
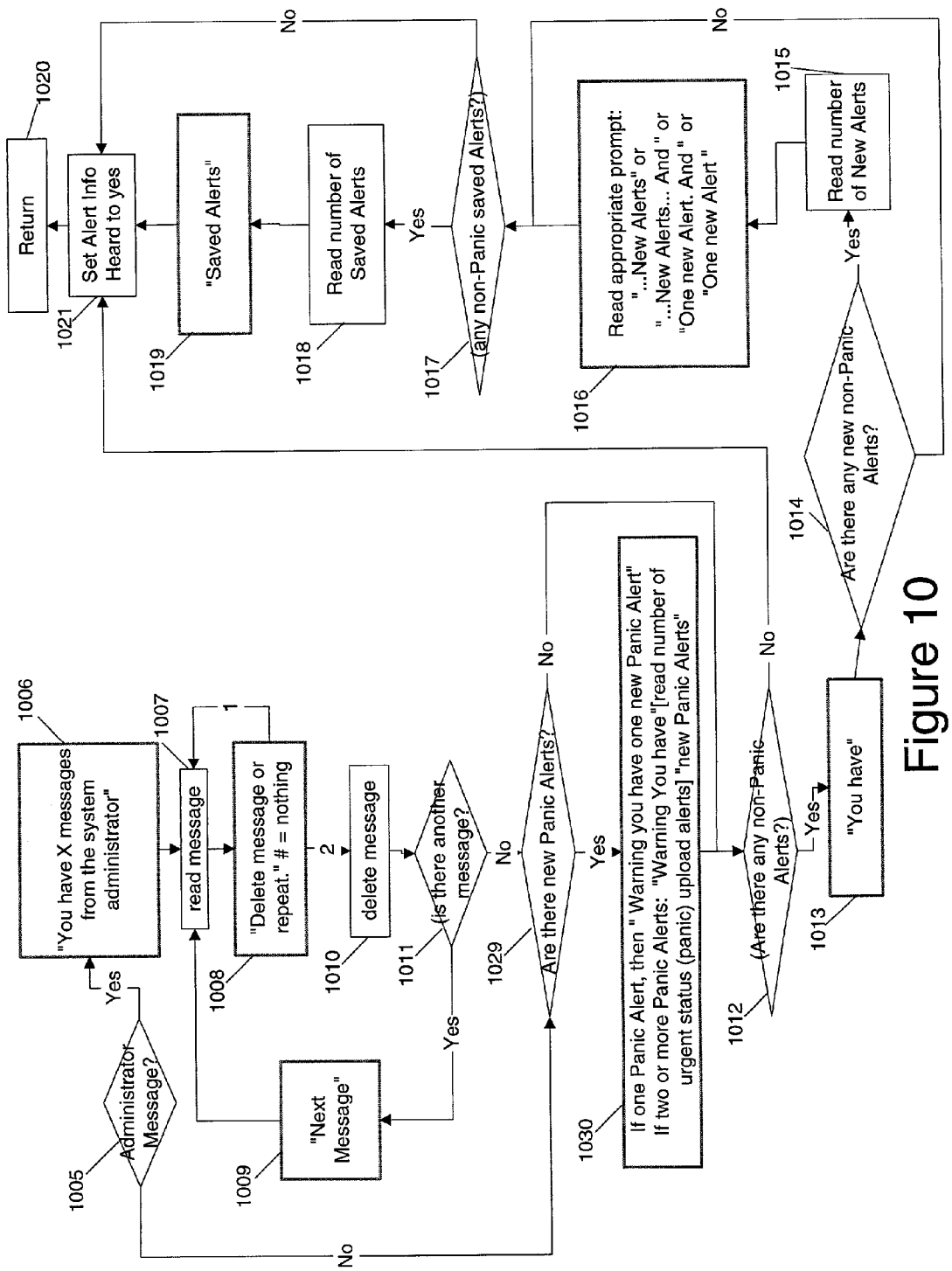
FIG. 10 illustrates a logic flow diagram of an account owner accessing administrator and alert information in a medical information system in accordance with the present invention.
Figure 11:
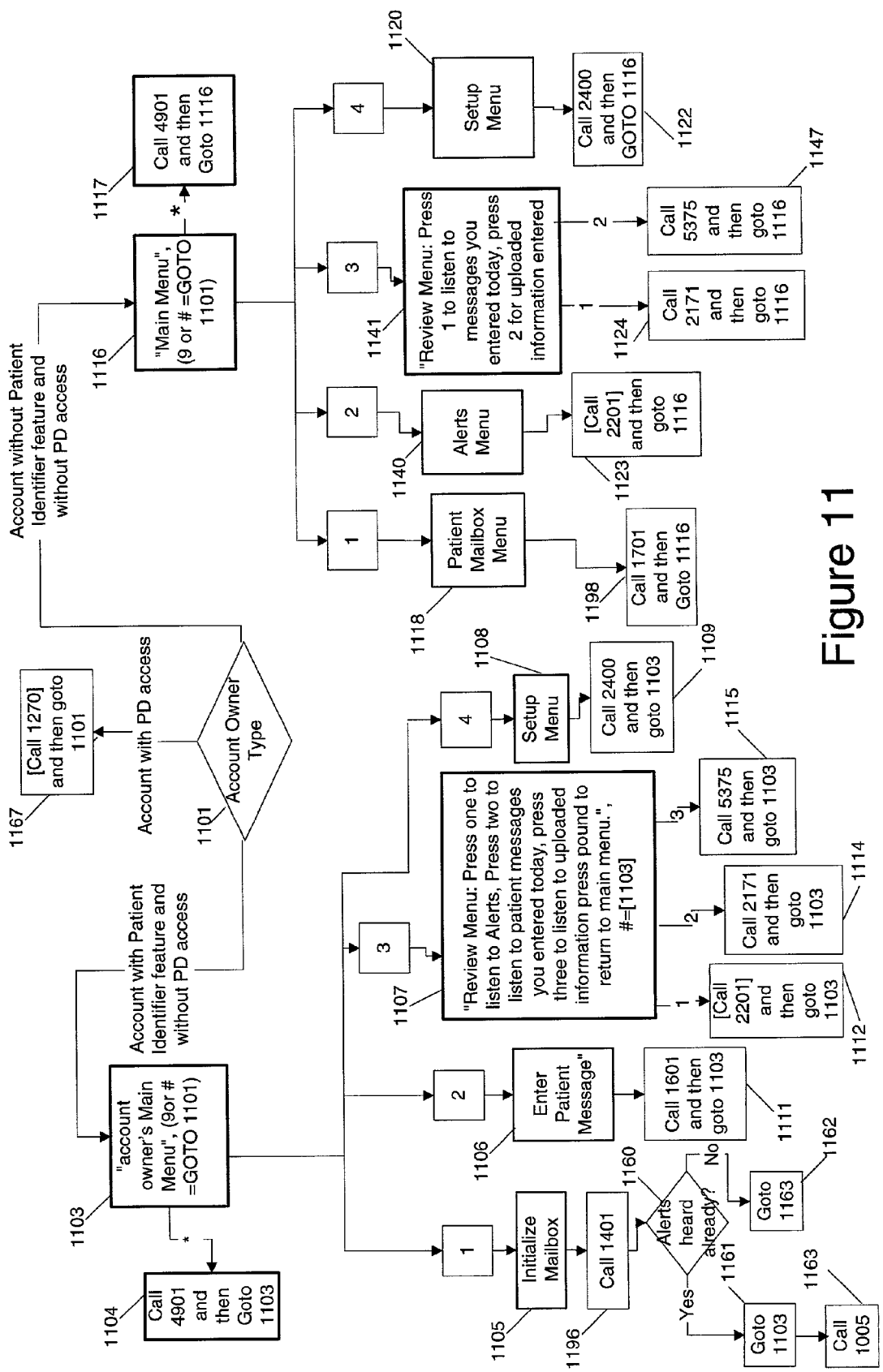
FIG. 11 illustrates logic flow diagrams of an account owner accessing the main menu in several available configurations of a medical information system in accordance with the present disclosure.

FIG. 10 illustrates a logic flow diagram of an account owner accessing administrator messages and alert information on the system. In logic block 1005 a determination is made if there are messages for the account owner from the administrator. If not, control is transferred to logic block 1029 and the logic flow diagram proceeds as described below. If yes, control is transferred to logic block 1006 where the account owner is informed of the number of messages from the system administrator. These messages are then presented as indicated in logic blocks 1007, 1008, 1010, 1011, and 1009: The first message is read in logic block 1007 and control is transferred to logic block 1008 where the account owner is asked if the message should be repeated or deleted. If the account owner chooses to hear the message again, control is transferred back to logic block 1007 for this purpose; otherwise, control is transferred to logic block 1010 where the message is deleted. Then control transfers to logic block 1011 where a determination is made if there are more administrator messages. If so, control is transferred to logic block 1009 which causes the prompt "Next Message" to be played and the next message to be retrieved before control is transferred to logic block 1007 for playing of this message. If there are no further such messages, control is transferred to logic block 1029 where a determination is made if the account owner has any panic alerts. If not, control is transferred to logic block 1012. If yes, control is transferred to logic block 1030 where the account owner is informed of the number of panic alerts currently in his account prior to control being shifted to logic block 1012. If there are no other active alerts on this account, logic block 1012 causes control to shift to logic block 1021 where the alert information is updated to indicate retrieval for any alerts that have been heard and then to logic block 1020 and return to the logic block that called this function. If there are other alerts, control is transferred to logic block 1013 which plays the prompt "You have" and then to logic block 1014 where a determination is made if there are new alerts or not. If not, control is transferred to logic block 1017 and the system proceeds as indicated below. If so, control transfers to logic block 1015 where the number of new alerts is read and then to logic block 1016 where an appropriate prompt identifies these as new alert(s). Control is then transferred to logic block 1017 where a determination is made whether or not there are saved alerts or not. If not, control is transferred to logic block 1021; if there are, control transfers to logic blocks 1018 where the number of saved alerts is read and then to logic block 1019 which identifies this as the number of saved alerts. Control then transfers to logic block 1021 where the system sets a flag to indicate alert information for this account has been heard before going to logic block 1020 which causes control to return to the logic block that originally called the function as illustrated in FIG. 10.

FIG. 11 illustrates logic flow diagrams of an account owner accessing the main menu in several different available configurations of the system. In logic block 1101 the type of account is determined: Account with patient database access, account with patient identifier feature and no patient database access, or account with no patient identifier feature and no patient database access.

Figure 49:
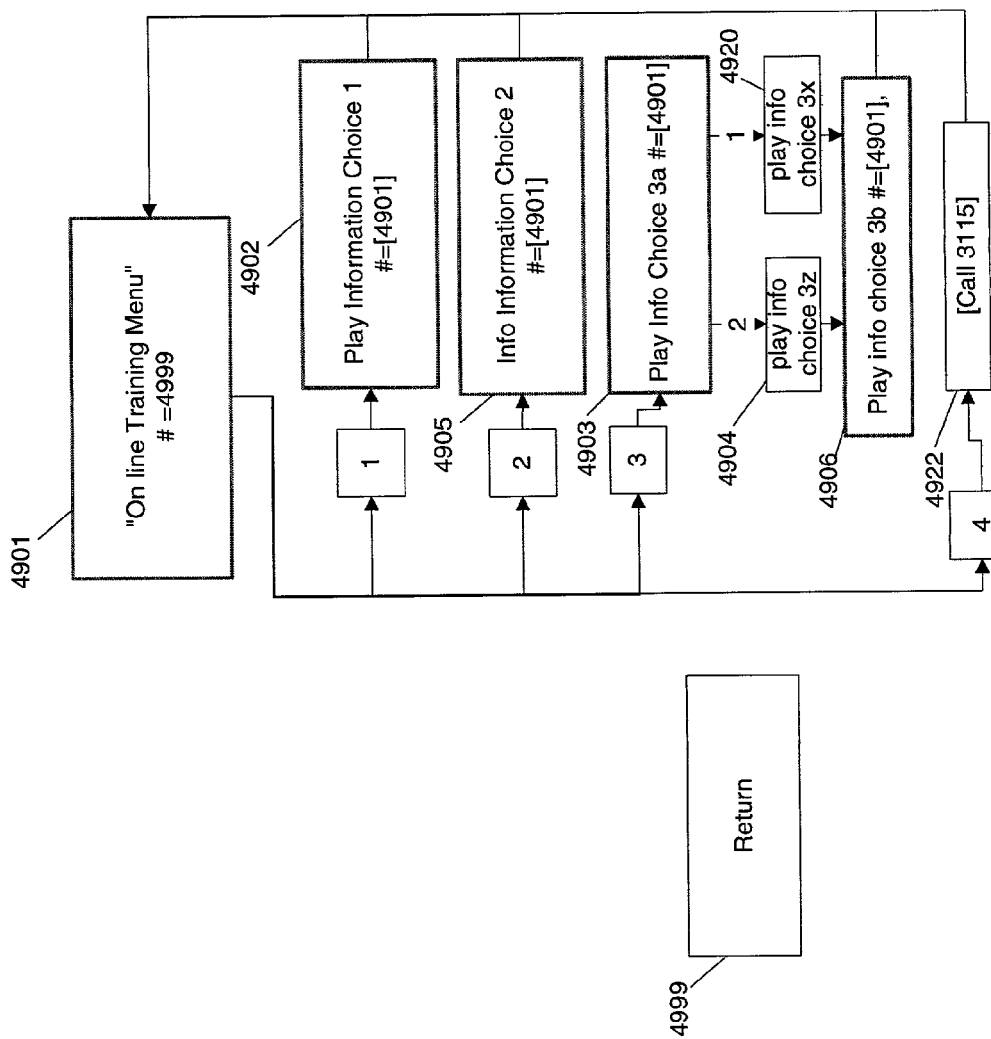
FIG. 49 illustrates a logic flow diagram for on-line training in a medical information system in accordance with the present disclosure.

If the entered security code corresponds to an account without access to a PD, control is transferred to logic block 1103 where the account owner is given four alternatives that may be chosen by pressing numbers 1 to 4 on a touch tone telephone or a choice to press "*" to transfer control via logic block 1104 to logic block 4901 illustrated in FIG. 49 that illustrates a logic flow diagram for on-line training and for accessing help in using the system. The numbered alternatives include: initialize mailbox in logic block 1105; enter patient message in logic block 1106; access to listen to alerts, or a list of patient messages the account owner entered that day, or a list of uploaded messages entered the system in logic block 1107; and Setup Menu in logic block 1108.

Figure 14:
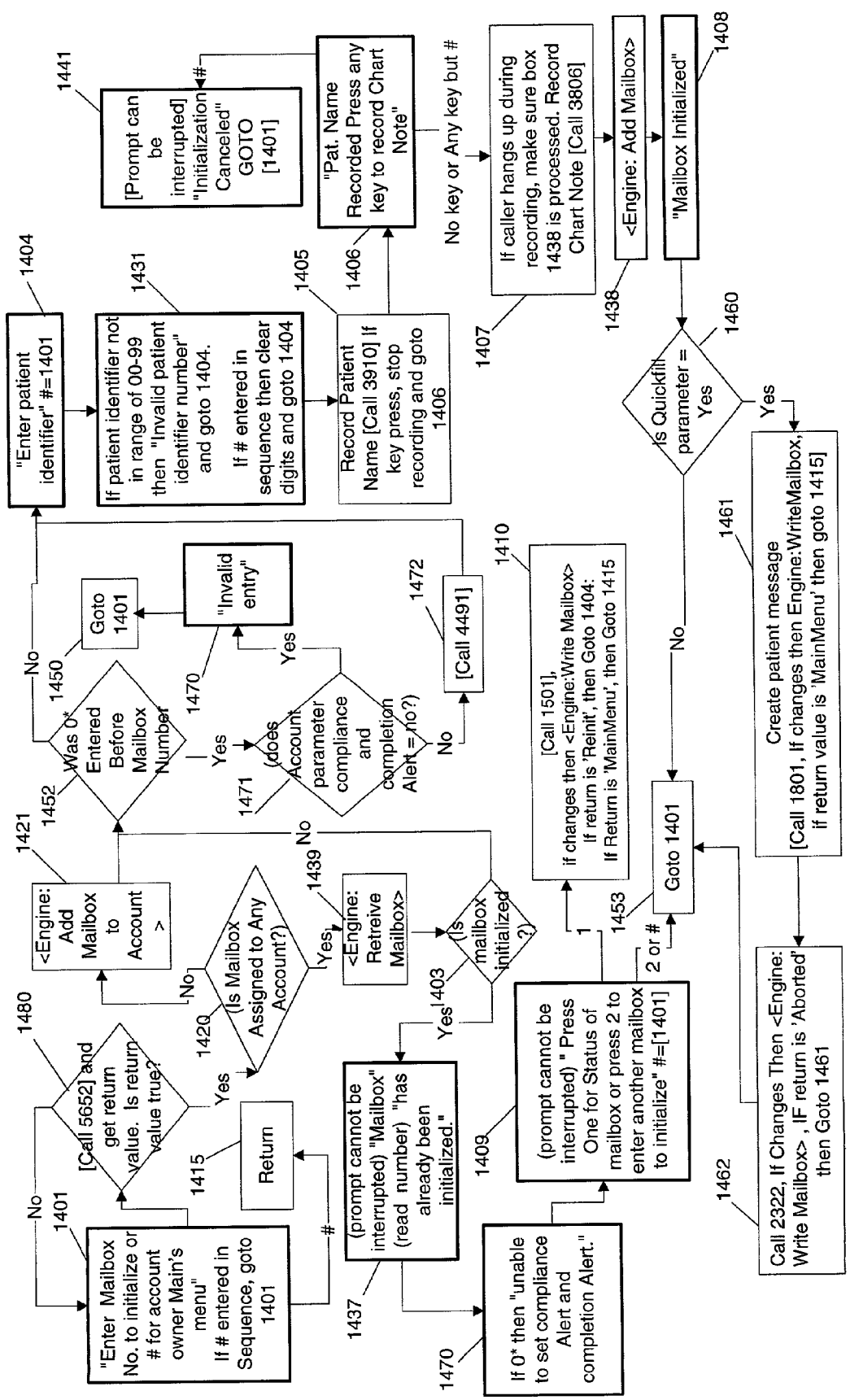
FIG. 14 illustrates a logic flow diagram of setting up a mailbox for chart note storage for future retrieval and/or access for patient message storage and setting a compliance or completion alert for mailboxes in a medical information system in accordance with the present disclosure.

Control is transferred from logic block 1105 via logic block 1196 to logic block 1401 illustrated in FIG. 14 which illustrates a logic flow diagram of initializing a mailbox, i.e., setting up a mailbox, for future retrieval for patient message placement, and setting compliance and completion alerts. Control returns then from the logic blocks illustrated in FIG. 14 and is transferred to logic block 1160 where a determination is made if the account owner on this entry into the system has or has not heard the alert information on the system illustrated in the logic in FIG. 10. If alert information has been heard, control is transferred to logic block 1103 via logic block 1161; if not, control is transferred to logic block 1162, then to logic block 1163 and thence to logic block 1005 and processed as heretofore described to logic block 1020; then control is returned to logic block 1163 and subsequently transferred to logic block 1103 via logic block 1161.

From logic block 1106 control is transferred via logic block 1111 to logic block 1601 illustrated in FIG. 16 which illustrates a logic flow diagram for locating the proper mailbox for patient message placement in the system and which is described in detail below. In logic block 1107 the account owner is given three alternatives that may be chosen by entering numbers 1 to 3 on a touch tone telephone. These alternatives include: (1) transfer of control via logic block 1112 to logic block 2201 illustrated in FIG. 22 which illustrates a logic flow diagram for accessing panic and other alerts on an account in the system; (2) transfer of control via logic block 1114 to logic block 2171 illustrated in FIG. 21 that illustrates a logic flow diagram for accessing a list of patient names and their messages entered into the system on a particular date; (3) transfer of control via logic block 1115 to logic block 5375 illustrated in FIG. 53 which illustrates a logic flow diagram for an account owner to access a list of patient names and messages and upload-source notes uploaded to the system by one or more upload-sources. Upon completion of each of the above transfers of control, control returns to the logic block that initiated the transfer and then is transferred back to logic block 1103.

Figure 24:
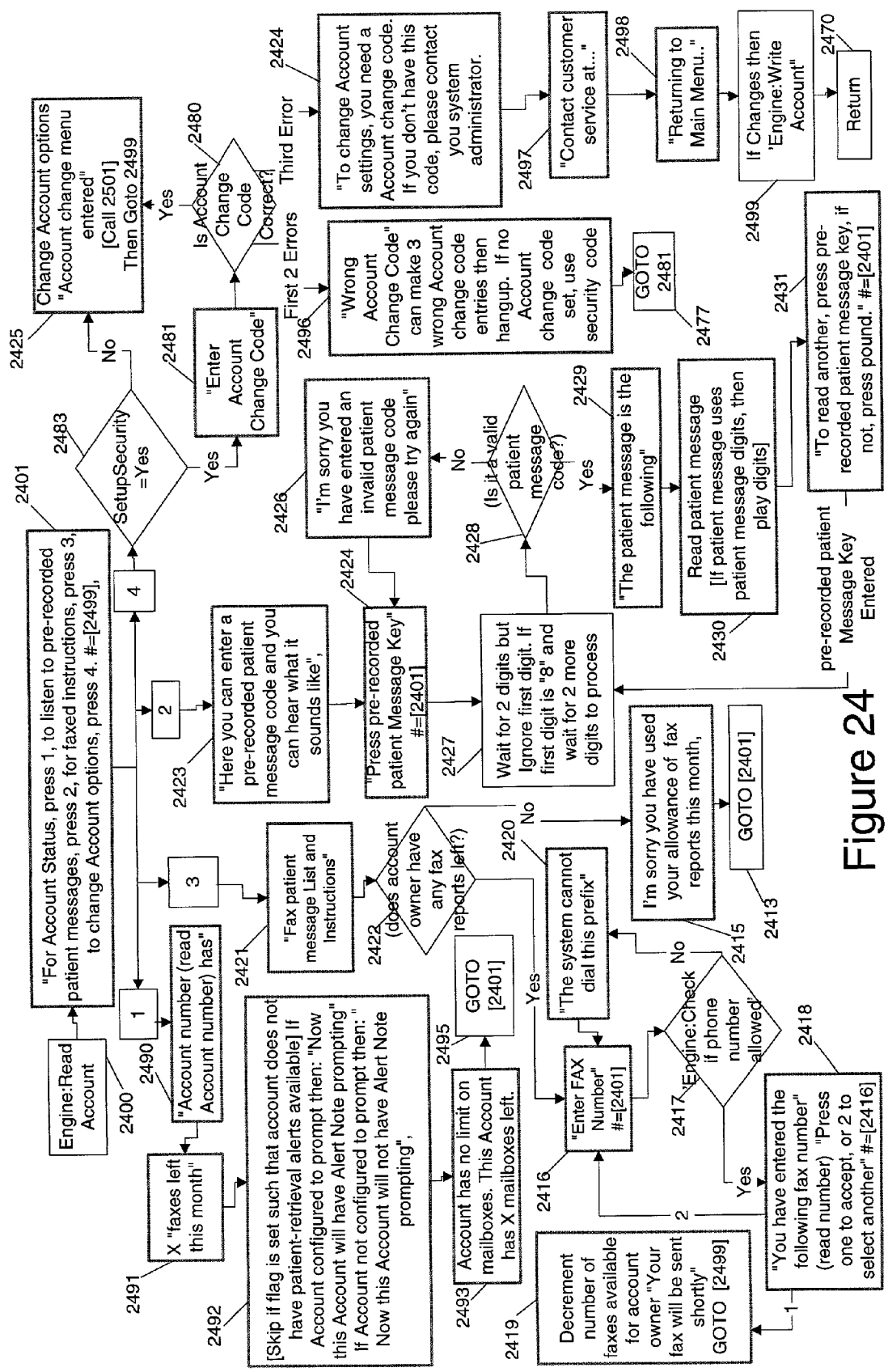
FIG. 24 illustrates a logic flow diagram for accessing and changing an account's status as well as listening to patient pre-recorded messages in a medical information system in accordance with the present disclosure.

In logic block 1108 control is transferred via logic block 1109 to logic block 2400 illustrated in FIG. 24 that illustrates a logic flow diagram for accessing account parameters in the system. Upon return from logic illustrated in FIG. 24 control is transferred back to logic block 1109 and thence to logic block 1103.

If the security code entered corresponds to an account type with patient database access, control is transferred from logic block 1101 to logic block 1116 where the account owner is given four alternatives which may be chosen by pressing numbers 1 to 4 on a touch tone telephone. The account owner may also choose to press "*" to transfer control via logic block 1117 to logic block 4901 illustrated in FIG. 49 that illustrates a logic flow diagram for on-line training and accessing help in using the system. The numbered alternatives include: transfer of control via logic block 1118 and then logic block 1198 of the Patient Mailbox Menu to logic block 1701 illustrated in FIG. 17 which illustrates a logic flow diagram for entering a message edit menu, recording a patient name, recording a patient message for a mailbox, and accessing chart notes and upload-source notes related to a particular mailbox in the system; transfer of control via logic block 1140 of the Alerts Menu and then logic block 1123 to logic block 2201 illustrated in FIG. 22 which illustrates a logic flow diagram for accessing panic and other alerts on an account in the system; transfer of control to logic block 1141 of the Review Menu; and transfer of control via logic block 1120 of the Setup Menu and then logic block 1122 to logic block 2400 illustrated in FIG. 24 which illustrates a logic flow diagram for accessing account parameters in the system so as to change or review these parameters.

Figure 21:
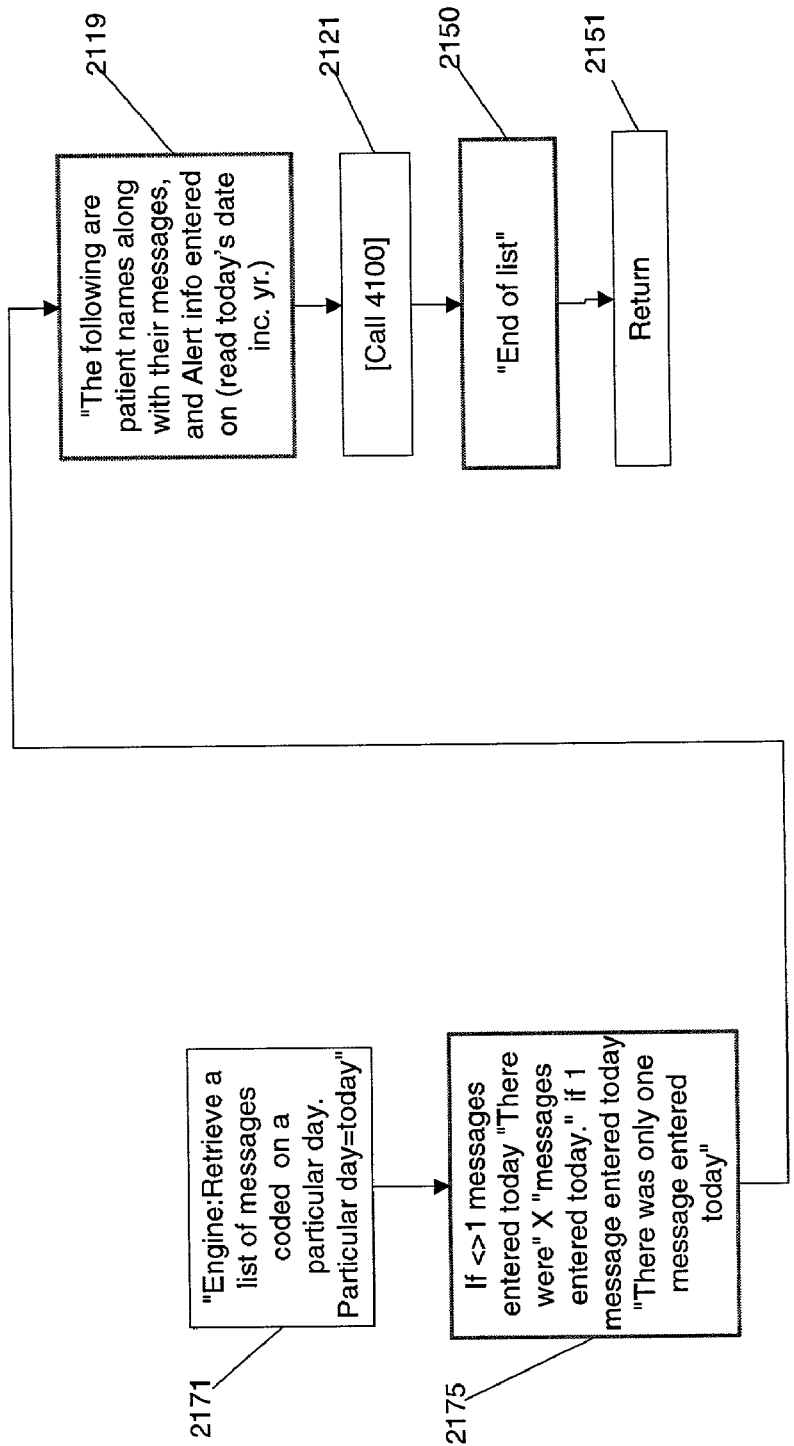
FIG. 21 illustrates a logic flow diagram for accessing a list of patient mailboxes with corresponding names and their messages entered on a particular date in a medical information system in accordance with the present disclosure.
Figure 53:
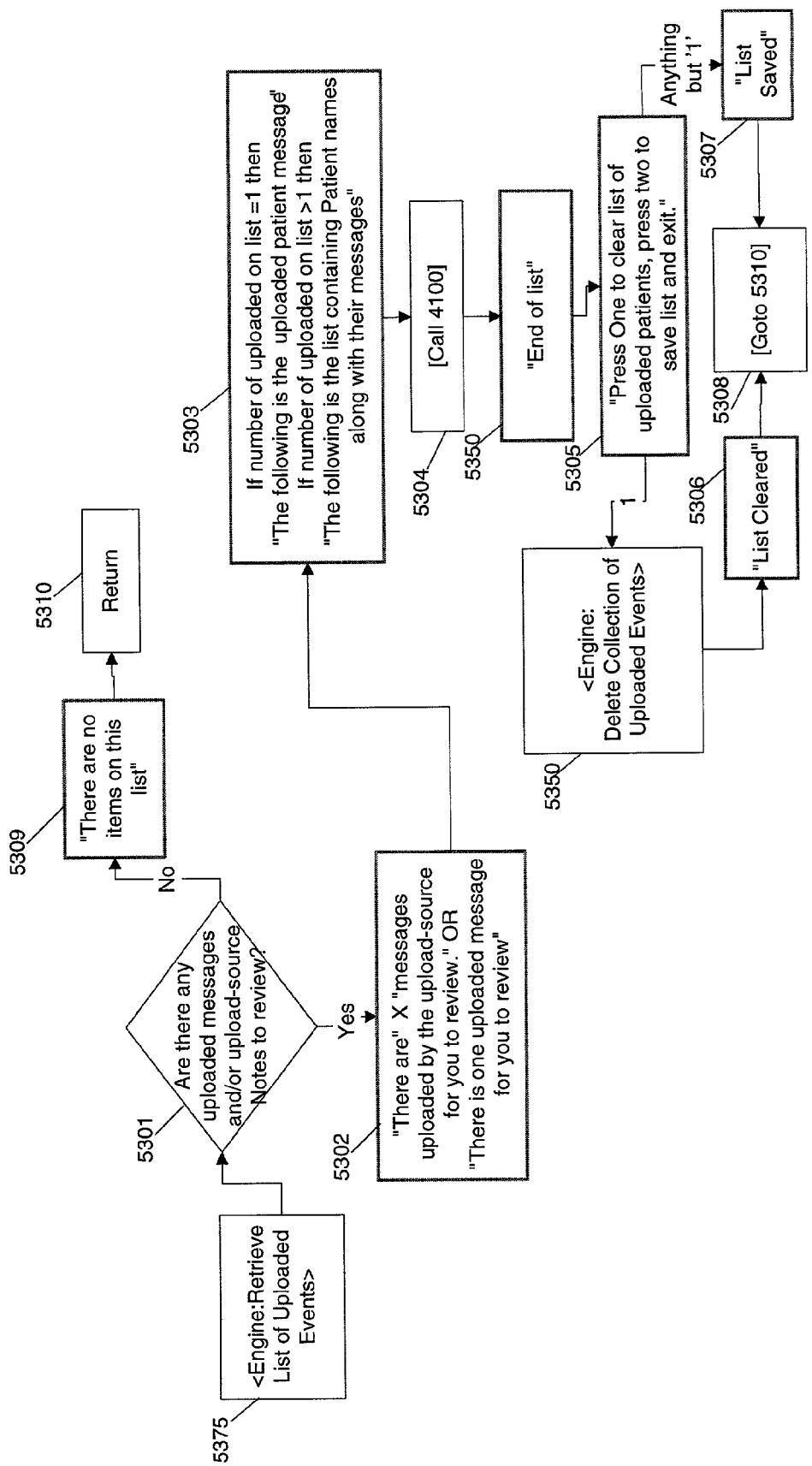
FIG. 53 illustrates a logic flow diagram for an account owner to access a list of patient names and messages and upload-source notes uploaded by one or more upload-sources in a medical information system in accordance with the present disclosure.

In logic block 1141 the user is given a choice to transfer control by entering the proper touch tone digits on a telephone to either (a) logic block 1124 whence control is transferred to logic block 2171 illustrated in FIG. 21 which illustrates a logic flow diagram for accessing a list of patient names and their messages entered into the system on a particular date by this source or (b) logic block 1147 whence control is transferred to logic block 5375 illustrated in FIG. 53 which illustrates a logic flow diagram for an account owner to access a list of patient names and patient messages and upload-source notes uploaded to the system by one or more upload-sources.

Subsequent to the completion of each of the above transfers of control to the figures indicated, control returns to the logic block that initiated the transfer and then is transferred back to logic block 1116.

Figure 12:
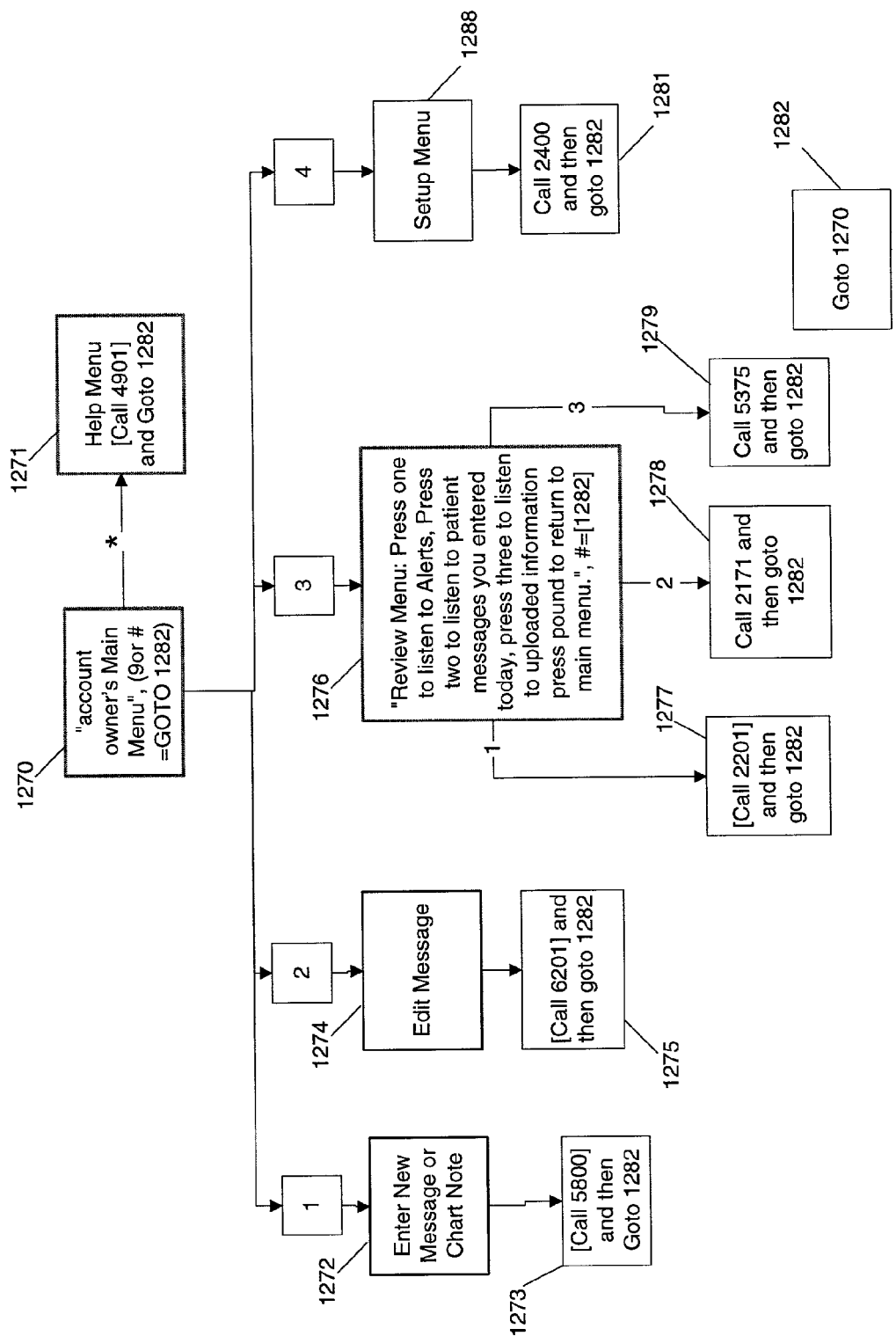
FIG. 12 illustrates a logic flow diagram of an account owner accessing a main menu in a medical information system with patient database access in accordance with the present disclosure.

If the entered security code corresponds to an account with access to a PD, control is transferred to logic block 1167 illustrated in FIG. 11 and thence to logic block 1270 illustrated in FIG. 12 where the account owner is given four alternatives that may be chosen by pressing numbers 1 to 4 on a touch tone telephone or a choice to press "*" to transfer control via logic block 1271 to logic block 4901 illustrated FIG. 49 that illustrates a logic flow diagram for on-line training and for accessing help in using the system. The numbered alternatives include: enter a new patient message or chart note in logic block 1272, edit a message in logic block 1274, a Review Menu in logic block 1276, and a Setup Menu in logic block 1288.

Control is transferred from logic block 1272 via logic block 1273 to logic block 5800 illustrated in FIG. 58, which illustrates a logic flow diagram for placing patient messages or chart notes for an account with access to a PD.

Figure 62:
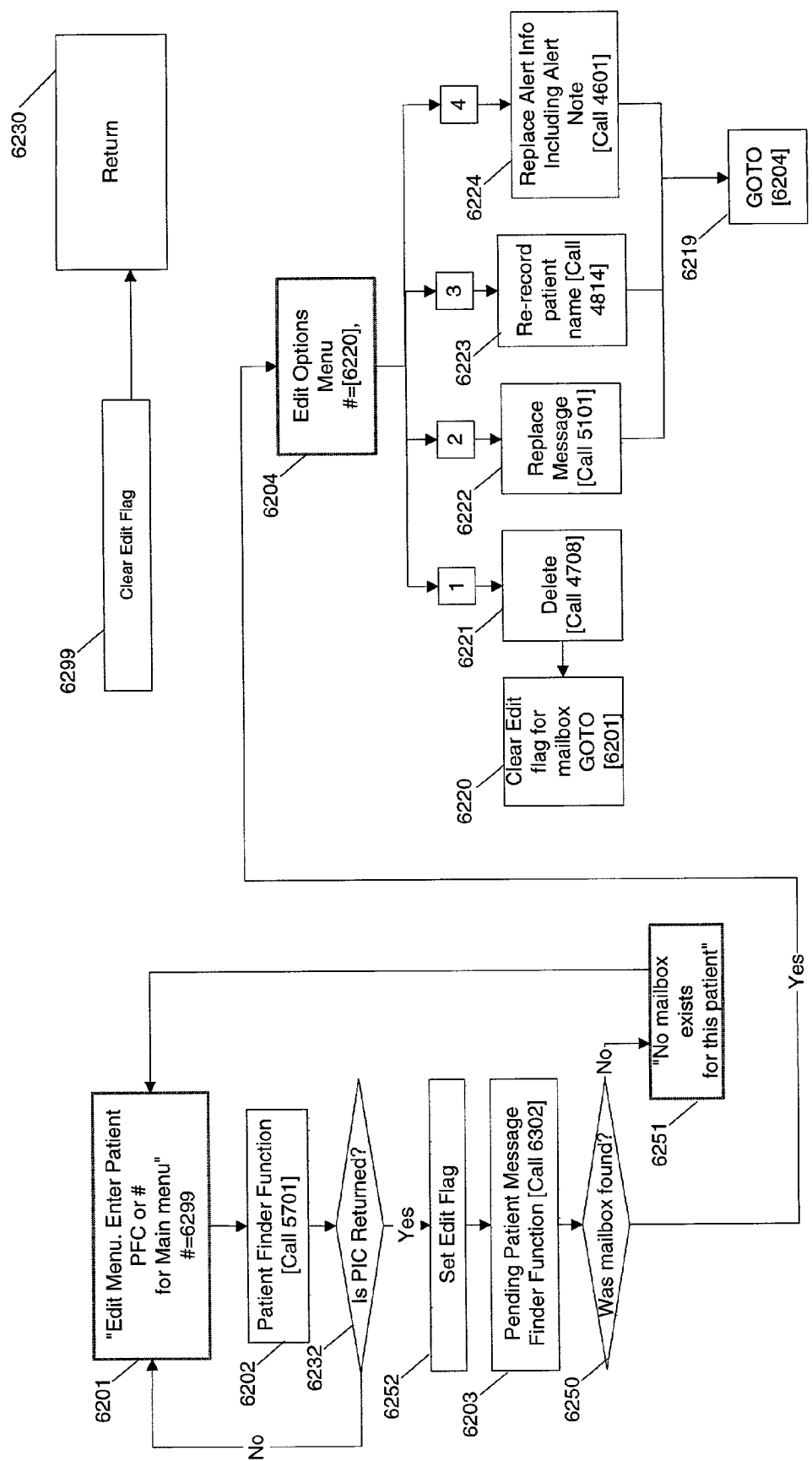
FIG. 62 illustrates a logic flow diagram in a medical information system with patient database access for editing data in a mailbox in accordance with the present disclosure.

Control is transferred from logic block 1274 via logic block 1275 to logic block 6201 illustrated in FIG. 62, which illustrates a logic flow diagram for editing data in a mailbox for an account with PD access.

The account owner is given three alternatives in the Review Menu associated with logic block 1276 that he may access by entering the proper touch tones on a telephone. Control may be transferred from logic block 1276 (a) via logic block 1277 to logic block 2201 illustrated in FIG. 22 which illustrates a logic flow diagram for accessing panic and other alerts on the account in the system, (b) via logic block 1278 to logic block 2171 illustrated in FIG. 21, which illustrates a logic flow diagram for accessing a list of patient names and their messages entered into the system on a particular date, or (c) via logic block 1279 to logic block 5375 illustrated in FIG. 53 which illustrates a logic flow diagram for an account owner to access a list of patient names and patient messages and upload-source notes uploaded to the system by one or more upload-sources.

Control is transferred via logic block 1281 from logic block 1288 to logic block 2400 illustrated in FIG. 24 which illustrates a logic flow diagram to access account parameters in the system.

Subsequent to the completion of each of the above transfers of control to the figures indicated, control returns to the logic block that initiated the transfer and then is transferred back to logic block 1270 via logic blocks 1282.

Figure 13:
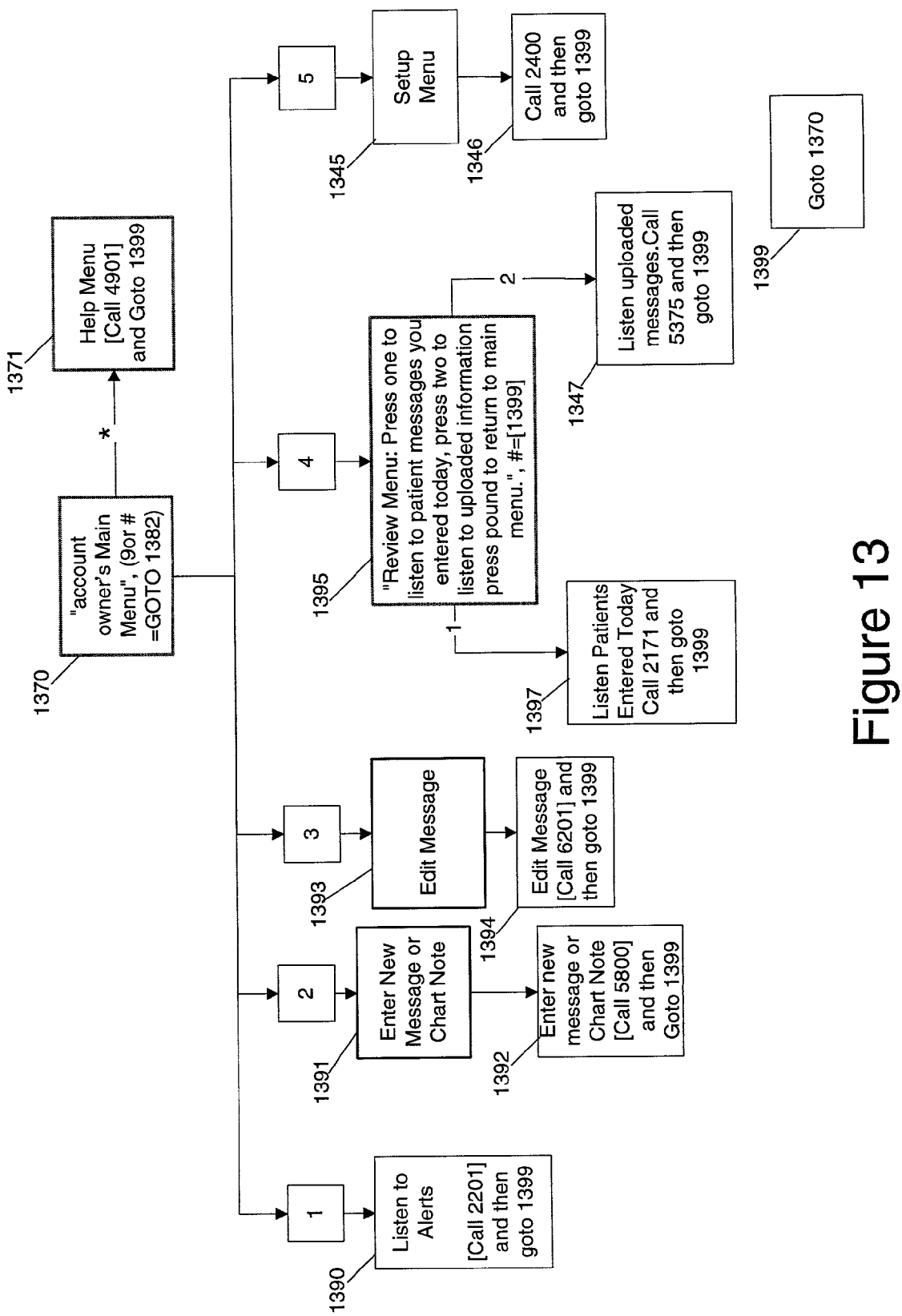
FIG. 13 illustrates a logic flow diagram of an account owner accessing an alternative main menu in a medical information system with patient database access in accordance with the present disclosure.

FIG. 13 illustrates an alternative to FIG. 12 of the logic flow diagram of an account owner accessing the main menu in a system with patient database access; a parameter allows the system to utilize logic in FIG. 13 in place of logic in FIG. 12.

FIG. 13 illustrates that logic block 1370 offers the account owner five alternatives that may be chosen by pressing numbers 1 to 5 on a touch tone telephone or a choice to press "*" to transfer control via logic block 1371 to logic block 4901 of FIG. 49 that illustrates a logic flow diagram for on-line training and for accessing help in using the system. The numbered alternatives include: listen to alerts in logic block 1390, enter a new patient message or chart note in logic block 1391, edit a message in logic block 1393, a Review Menu in logic block 1395, and a Setup Menu in logic block 1345.

Figure 22:
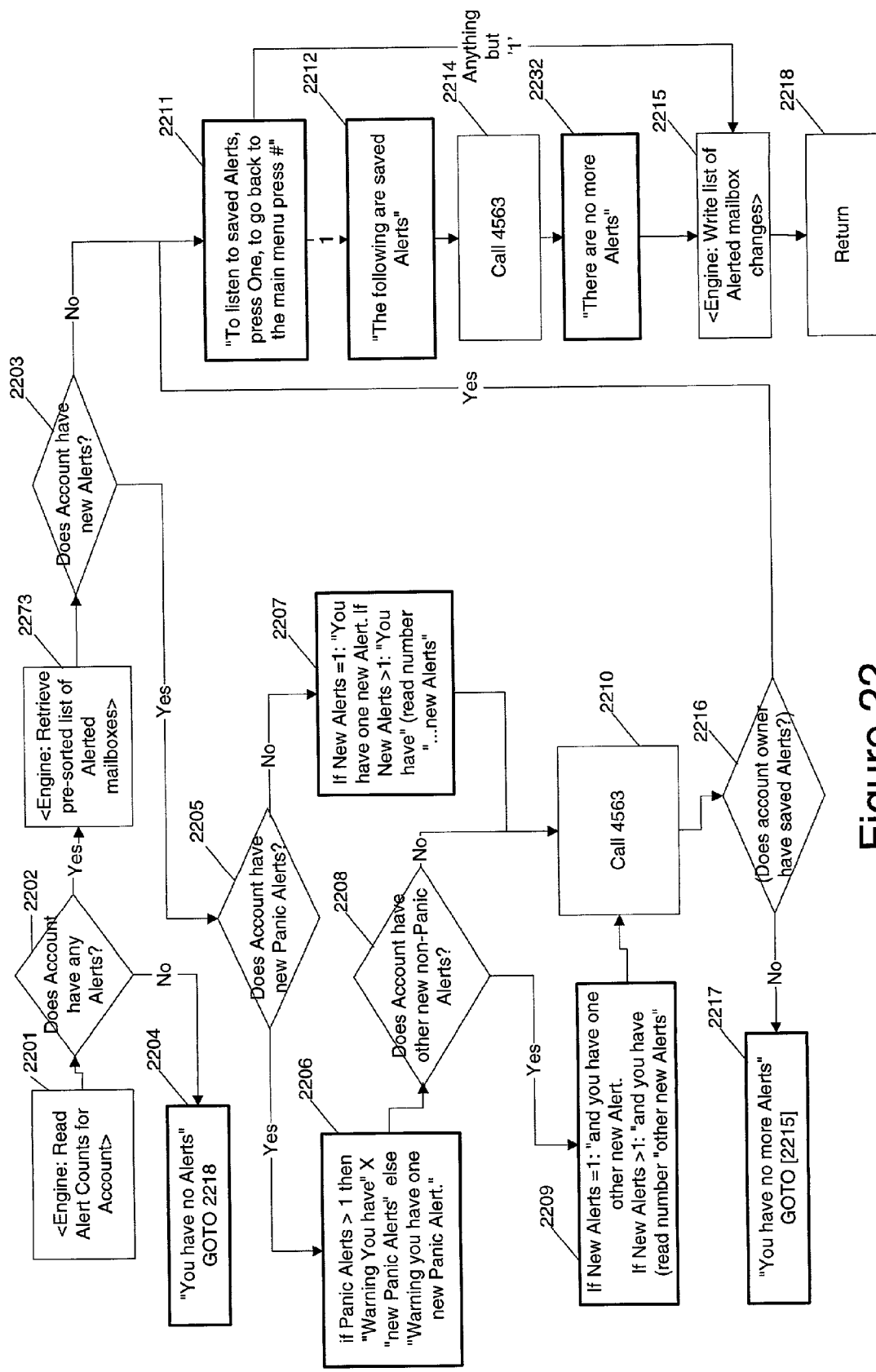
FIG. 22 illustrates a logic flow diagram for accessing panic and other alert information on an account in a medical information system in accordance with the present disclosure.

Control is transferred from logic block 1390 to logic block 2201 illustrated in FIG. 22 which illustrates a logic flow diagram for accessing panic and other alerts on the account in the system.

Control is transferred from logic block 1391 via logic block 1392 to logic block 5800 illustrated in FIG. 58 which illustrates a logic flow diagram for placing patient messages or chart notes for an account with access to a PD.

Control is transferred from logic block 1393 via logic block 1394 to logic block 6201 illustrated in FIG. 62 which illustrates a logic flow diagram for editing data in a mailbox for an account with PD access.

The account owner is given two alternatives in the Review Menu associated with logic block 1395, which may be accessed by entering the proper touch tones on a telephone. Control may be transferred from logic block 1395 (a) via logic block 1397 to logic block 2171 illustrated in FIG. 21 which illustrates a logic flow diagram for accessing a list of patient names and their messages entered into the system on a particular date, or (b) via logic block 1347 to logic block 5375 illustrated in FIG. 53 which illustrates a logic flow diagram for an account owner to access a list of patient names and patient messages and upload-source notes uploaded to the system by one or more upload-sources.

Control is transferred via logic block 1346 from logic block 1345 to logic block 2400 illustrated in FIG. 24 which illustrates a logic flow diagram to access account parameters in the system.

Subsequent to the completion of each of the above transfers of control to the figures indicated, control returns to the logic block that initiated the transfer and then is transferred back to logic block 1370 via logic block 1399.

FIG. 14 illustrates a logic flow diagram of initializing a mailbox, i.e., setting up a mailbox for future retrieval for patient message placement, and setting a compliance or completion alert. Control is transferred to logic block 1401 where the user is requested to enter the mailbox number to be initialized; a 15 if the user enters "#", control is transferred back to the logic block that transferred the control to logic block 1401. Otherwise control is transferred via logic block 1480 to logic block 5652 illustrated in FIG. 56 which illustrates a logic flow diagram to check if a mailbox number is valid on the account. If the return value from the function illustrated in FIG. 56 indicates an invalid mailbox number, control is transferred back to logic block 1401 for entry of another mailbox number; if the return value indicates a valid mailbox number, control is transferred to logic block 1420 where a determination is made whether or not this is an new mailbox number. If so, control is transferred to logic block 1421 where the engine adds this mailbox to the account; control is then transferred to logic block 1452 whence the system proceeds as discussed below.

If a determination is made that the mailbox number entered is not a new mailbox number in logic block 1420, then control is transferred to logic block 1439 where the engine retrieves this mailbox from the account's mailbox database. Control then transfers to logic block 1403 where a determination is made if the mailbox has already been initialized. If so, control is transferred to logic block 1437 where the user is so informed and then to logic block 1470 where, if a marker for setting a compliance or completion alert such as "0*" was entered, the user is informed that the mailbox has already been initialized and so neither a compliance or completion alert may be set. Control is then transferred to logic block 1409 where an uninterruptible prompt states "This mailbox has already been initialized. Press One for Status of mailbox or press two to initialize another mailbox." If the user presses one, control is transferred via logic block 1410 to logic block 1501 illustrated in FIG. 15, which illustrates a logic flow diagram for assessing the status of a previously initialized mailbox in the system. On the return of control to logic block 1410 from the logic illustrated in FIG. 15, if there are changes made to the fields in the mailbox, the engine is called to write these to the mailbox database. If the return value from the logic illustrated in FIG. 15 to logic block 1410 is "ReInit", control is transferred to logic block 1404 and the system control proceeds as described in the appropriate section below; if this return value is "Main Menu", then control is transferred to logic block 1415 and thence to the logic block that called logic block 1401. If the user presses two or "#" in response to the prompt in logic block 1409, control is transferred to logic block 1453 and thence to logic block 1401.

If a determination is made in logic block 1403 that the mailbox has not been initialized, control is transferred to logic block 1452 where a determination is made if "0*" was entered before the mailbox number. If not, control is transferred to logic block 1404 where the user is asked to enter "patient identifier." The patient identifier constitutes a string, touch-tone signal, or other signal, that the system can use to rapidly select a subset of mailboxes containing the current mailbox being initialized. This string is readily available to the account owner both at the current time of initializing the mailbox and when the test results return and the account owner needs to access the system to find this mailbox. A typical patient identifier could be the patient's initials or two digits of the patient identification number that are on the lab slips.

Figure 18:
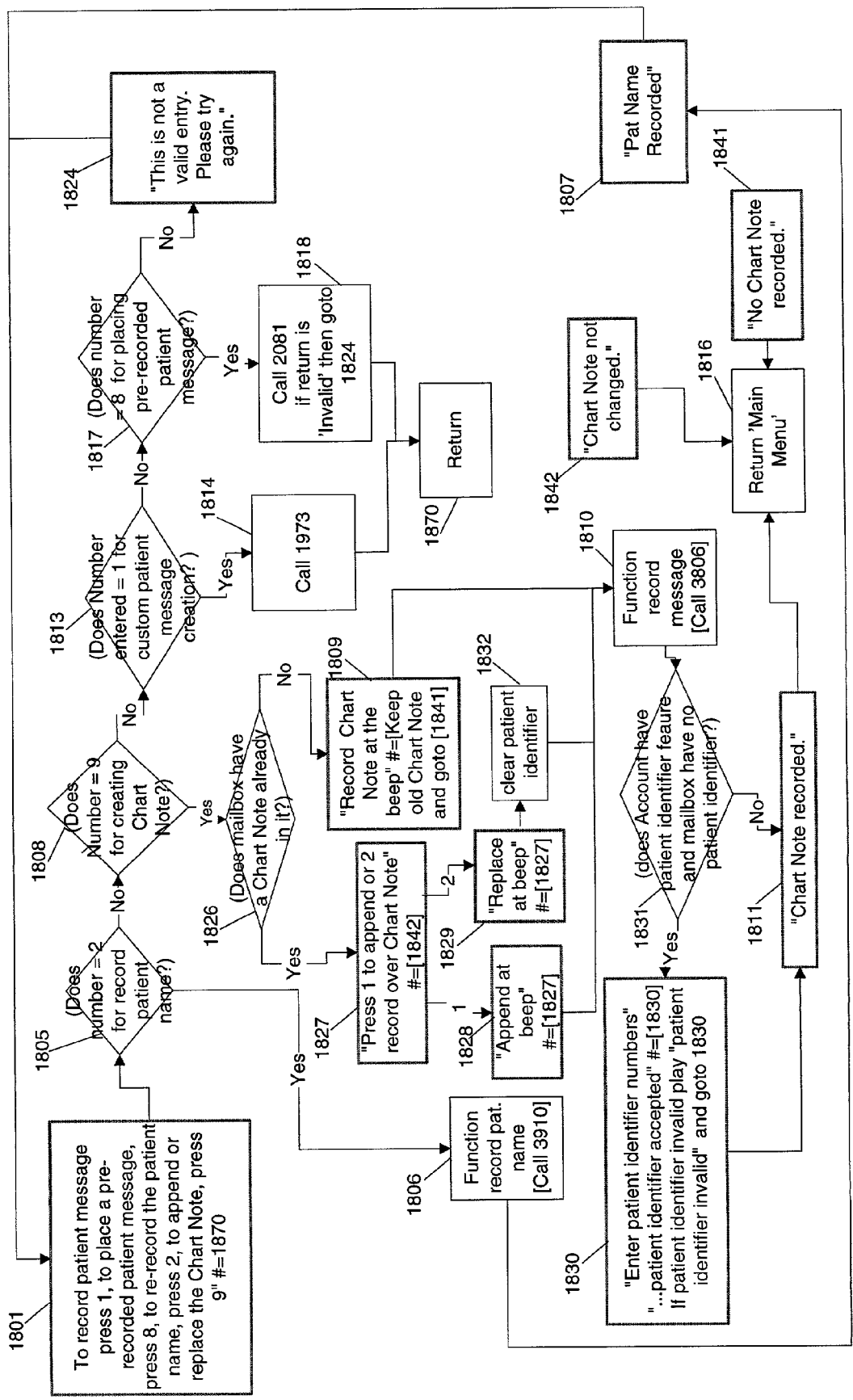
FIG. 18 illustrates a logic flow diagram for recording a patient message, placing a pre-recorded patient message, re-recording a patient name, and appending or replacing a chart note for a mailbox in an medical information system in accordance with the present disclosure.
Figure 38:
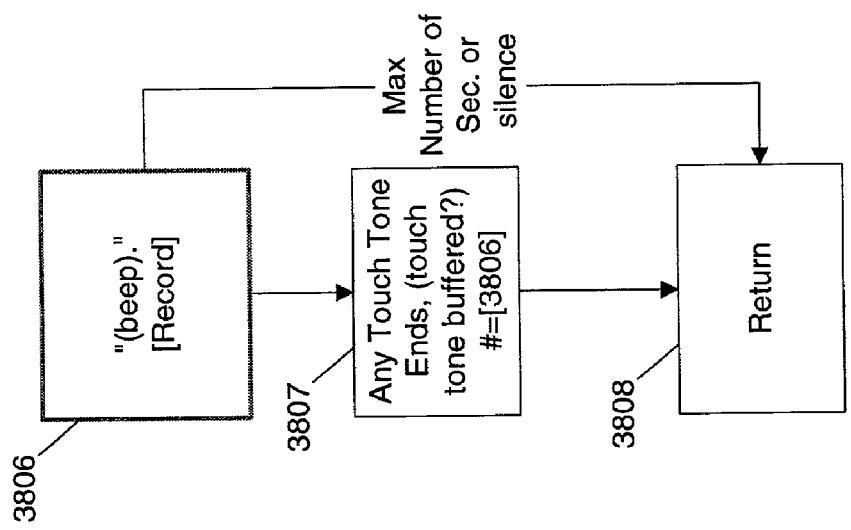
FIG. 38 illustrates a logic flow diagram for recording information with no review in a medical information system in accordance with the present disclosure.

If a determination is made in logic block 1452 that "0*" was entered before the mailbox number, control is transferred to logic block 1471 where a determination is made if the account parameter allowing the setting of compliance and completion alerts is set to "no". If this is the case, control is transferred to logic block 1470 where a prompt is played stating that the entry is invalid and the account is not set up to have compliance and completion alerts before control is transferred to logic block 1401 via logic block 1450. If this is not the case, control is transferred via logic block 1472 to logic block 4491 illustrated in FIG. 44, which illustrates a logic flow diagram for entry of completion and compliance alert information in the system. Upon return of control to logic block 1472 from the logic illustrated in FIG. 44 control is transferred to logic block 1404 where the user is asked to enter the patient identifier. From logic block 1404 control moves to logic block 1431 where a determination is made (1) if "#" was entered in the sequence for the patient identifier in which case the entry digits are cleared and control moves back to logic block 1404 or (2) if the patient identifier entered is in the range of 00 to 99. If the latter is not true, a prompt stating an invalid patient identifier was entered is played and control is transferred back to logic block 1404. If neither of the above two conditions hold, control is transferred via logic block 1405 to logic block 3910 illustrated in FIG. 39 which illustrates a logic flow diagram for recording a patient's name. Upon return of control from the logic illustrated in FIG. 39 to logic block 1405 control is next transferred to logic block 1406 where a prompt saying that the patient name has been recorded and requesting any key to be pressed to record a chart note is played. If "#" is entered at this point, control passes to logic block 1441 where a prompt stating initialization is canceled is played and the data entered in logic blocks 1404, 1405, and 1406 is discarded and control transferred to logic block 1401. If any other key besides "#" is entered at this point, control is transferred to logic blocks 1407 wherein logic block 3806 illustrated in FIG. 38 is accessed for recording a chart note with no review. Upon return of control from logic illustrated in FIG. 38 to logic block 1407 control is next transferred to logic block 1438 for the engine to add the mailbox data to the mailbox database of the account. The system is arranged so that if the caller hangs up during the recording in logic block 1407, the processes in logic block 1438 still take place. Control is next transferred to logic block 1408 where a prompt announces that the mailbox has been initialized and then passes to logic block 1460 where a determination is made whether or not the system has the "Quickfill parameter" set to "yes". The "Quickfill parameter" if set to "yes" allows the account owner to place a patient message in the mailbox just initialized at this point. If this parameter is set to "no", control is transferred to logic block 1401 via logic block 1453. If the parameter is set to "yes," control moves via logic block 1461 to logic block 1801 illustrated in FIG. 18 which illustrates a logic flow diagram for recording a patient message, placing a pre-recorded message, re-recording a patient name, and appending or replacing a chart note for a mailbox. If there are changes made in the content of the mailbox, then upon return of the control from logic illustrated in FIG. 18, the engine writes these changes to the mailbox in the account's mailbox database. If the return value from logic illustrated in FIG. 18 is "Main Menu", then control passes to logic block 1415 and thence to the logic block that called logic block 1401. Control next passes via logic block 1462 from logic block 1461 to logic block 2322 illustrated in FIG. 23 which illustrates a logic flow diagram for setting an alert note and the number of days until a patient-retrieval alert is activated. Upon return of the control from logic illustrated in FIG. 23 to logic block 1462, if there are changes made in the mailbox, the engine writes these changes to the account's mailbox database and control is passed to logic block 1453 unless "aborted" is returned in which case control is next transferred to logic block 1461. Once control is transferred from logic block 1462 to logic block 1453 is next transferred to logic block 1401.

Figure 15:
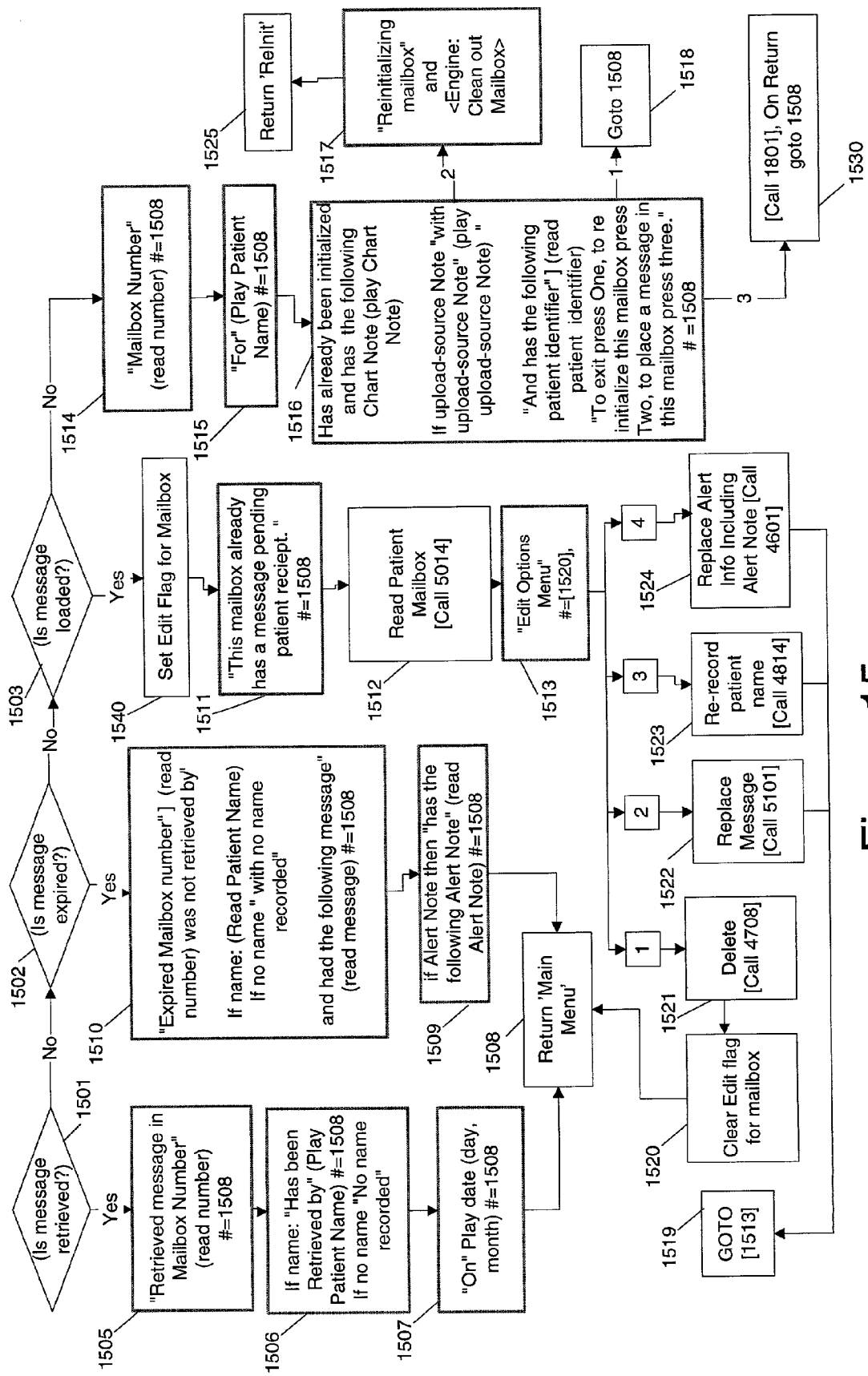
FIG. 15 illustrates a logic flow diagram for assessing the status of a mailbox, or accessing a mailbox edit menu in a medical information system in accordance with the present disclosure.

FIG. 15 illustrates a logic flow diagram for assessing the status of a previously initialized mailbox in the system. Control is transferred to logic block 1501 where a determination is made if the patient message has been retrieved. If so, control passes to logic blocks 1505, 1506, and 1507 where in logic block 1505 a prompt first states "Retrieved patient message in the mailbox number" and then the system reads the mailbox number; then another prompt in logic block 1506 follows with "has been retrieved by" and the system next plays the patients name if the name is available or "No name recorded" if that is the situation and then a prompt in logic block 1507 follows with "on" and the system plays the date on which the patient message was retrieved. Control then passes to logic block 1508 where "Main Menu" is caused to be return to the logic block that originally transferred control to logic block 1501.

If the patient message has not been retrieved, control passes to logic block 1502 where a determination is made if the patient message has expired. If this is the case, control passes to logic block 1510 where the system reads the mailbox number and states the patient message was not retrieved and then states the patient's name, if available, or that no name was recorded if the name is not available, and then reads the patient message. Control is then passed to logic block 1509 where the alert note is read if the alert note exists. Control then passes to logic block 1508 where "Main Menu" is caused to be return to the logic block that originally transferred control to logic block 1501.

If the patient message has not expired control passes from logic block 1502 to logic block 1503 where a determination is made whether or not there is a patient message present in the mailbox. If so, control is transferred to logic block 1540 where an edit flag is set for the mailbox that locks the mailbox relative to any other entry while the current account owner is in this edit mode. Control then passes to logic block 1511 where a prompt informs that the mailbox has a patient message pending patient receipt and then is transferred via logic block 1512 to logic block 5014 illustrated in FIG. 50 which illustrates a logic flow diagram for reading the contents of a patient mailbox in the system. Upon return of control to logic block 1512 from the logic illustrated in FIG. 50 control is then transferred to logic block 1513 where a prompt informs the user of four options that exist for editing the contents of the mailbox. These are accessible to the user by pressing the digits from one to four on the touch tone telephone. The numbered choices include: Deleting the patient message in which case control is transferred via logic block 1521 to logic block 4708 illustrated in FIG. 47 which illustrates a logic flow diagram for deleting the contents of a mailbox; Replacing the patient message in the mailbox in which case control is transferred via logic block 1522 to logic block 5101 illustrated in FIG. 51 which illustrates a logic flow diagram for replacing the patient message in a mailbox; Re-recording the patient name in which case control is transferred via logic block 1523 to logic block 4814 illustrated in FIG. 48 which illustrates a logic flow diagram for re-recording a patient name in a mailbox; and replace alert information including the alert note in which case control is transferred via logic block 1524 to logic block 4601 illustrated in FIG. 46 which illustrates a logic flow diagram for replacing alert information in a mailbox. Control is returned to the respective logic blocks that transferred the control initially to each of the above figures and then is transferred back to logic block 1513 via logic block 1519 in all cases except for logic block 1521. In this latter case control is then transferred to logic block 1520 where the edit flag that was set for the mailbox to prevent other user entry is cleared and then transferred to logic block 1508 where the system proceeds as described previously. If "#" is entered at logic block 1513, control is also transferred to logic block

1520 to clear the edit flag and thence to logic block 1508 where the system proceeds as described before.

If no patient message is present in the mailbox, control is transferred from logic block 1503 to logic block 1514 where the mailbox number is read and then to logic block 1515 where the prompt "for" is read followed by the patient's name and then to logic block 1516. Here a prompt is read indicating that the mailbox has already been initialized and any chart notes are then read. If there are upload-source notes in the mailbox record, they are next read; after this the patient identifier is read. The user is then prompted to press one to exit the mailbox, press two to re-initialize the mailbox or to press three to place a patient message in the mailbox. If the user presses one, control is transferred via logic block 1518 to logic block 1508 and the system proceeds as described before. If the user presses two, control is transferred to logic block 1517 where a prompt indicates the mailbox is being reinitialized and the mailbox is removed from all lists and collections that had included the mailbox for both the account being accessed and the upload-source and all data except for the security code is removed. The mailbox is added back to the collection of unused mailboxes. Control is then transferred to logic block 1525 which causes "ReInit" to be returned to the logic block that called logic in this figure. If the user enters three, control is transferred via logic block 1530 to logic block 1801 illustrated in FIG. 18 which illustrates a logic flow diagram for recording a patient message, placing a pre-recorded patient message, re-recording a patient name, and appending or replacing a chart note for a mailbox. When control returns from logic illustrated in FIG. 18 to logic block 1530, control is transferred to logic block 1508 and the system proceeds as described previously.

Figure 16:
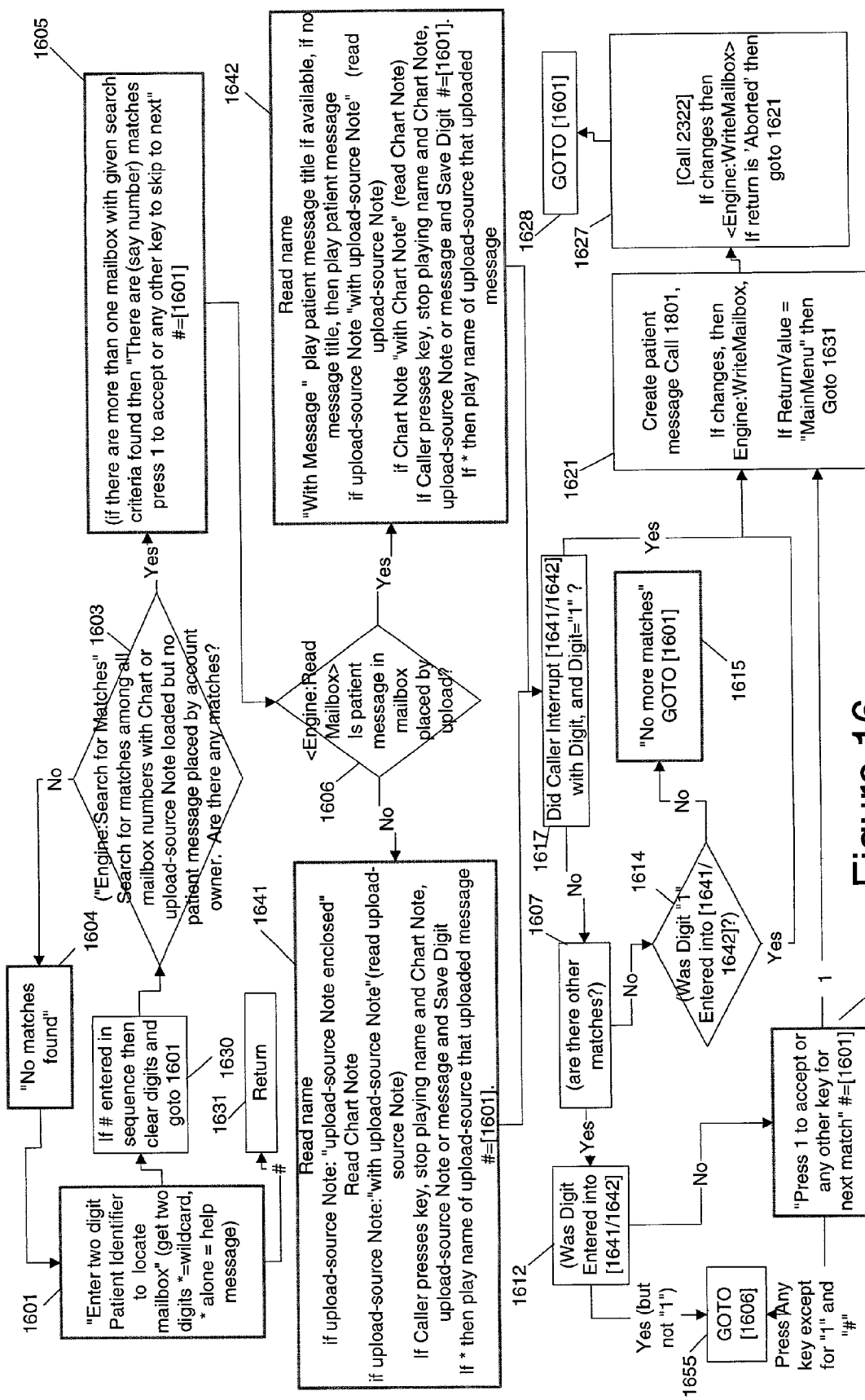
FIG. 16 illustrates a logic flow diagram for locating the proper mailbox for patient message storage in a medical information system in accordance with the present disclosure.

FIG. 16 illustrates a logic flow diagram for locating the proper mailbox for patient message placement in the system. Control is transferred to logic block 1601 where the user is requested to enter the two digit patient identifier to locate the mailbox. "*" may be used as a "wildcard" entry for one or both of these digits. If the user enters "#", control is transferred to logic block 1631 and then returned to the logic block that called logic block 1601. Otherwise, control is transferred to logic block 1630 where a determination is made whether or not "#" was entered in the sequence of digits entered in response to logic block 1601. If so, the sequence of digits is cleared and control is transferred back to logic block 1601. If not, control is transferred to logic block 1603 which results in the engine searching for matches among all mailboxes with chart or upload-source notes loaded but no patient messages placed by an account owner. A parameter in a different embodiment can narrow the results of this search to mailboxes with chart or upload-source notes loaded but no patient messages placed either by an upload-source or an account owner. Also, a parameter may expand the obtained list to include mailboxes with chart or upload-source notes with either upload-source or account owner patient messages placed. Also in an embodiment a different parameter allows inclusion in this list of matches mailboxes with patient messages loaded within another parameter number of days relative to the date of the search.

If no matches to the two digit identifier are found, control is transferred to logic block 1604 where a prompt reports this and then back to logic block 1601. If matches are found, control is transferred to logic block 1605 where the user is informed of the number of matches and asked to press one to accept a particular match in what follows or any other key except "#" to skip over the match to the next match. If "#" is pressed, the control transfers back to logic block 1601. Control is then transferred to logic block 1606 where the engine reads the contents of the mailbox via logic block 1641 or logic block 1642. Logic block 1641 obtains control if there is no patient message in the mailbox; this results in the engine causing the patient's name to be read followed by any upload-source notes and any chart notes. If there is a patient message, logic block 1642 reads the patient's name followed by the patient message or patient message title and then any upload-source notes and any chart notes. In either logic block 1641 or logic block 1642 if the user presses any key except "#", the reading is interrupted, the digit saved, and control passed to logic block 1617. If "#" is pressed in logic block 1641 or 1642, control is transferred back to logic block 1601. In logic block 1617 a determination is made if the caller interrupted with the digit "1". If not, control is transferred to logic block 1607 where a determination is made if there are any more matches to the particular patient identifier. If so, control is transferred to logic block 1612 where a determination is made whether or not the digit "1" was entered in logic block 1641 or 1642. If a digit was entered that was not "1", control is transferred back to logic block 1606 via logic block 1655. Otherwise, control is transferred to logic block 1608 where the user is prompted to press one to accept the choice or any other key for the next match. If the user presses any other key except "1" or "#", control is returned to logic block 1606 via logic block 1655. If "#" is pressed in logic block 1608, control is returned to logic block 1601. If "1" is pressed, control transfers to logic block 1621 for processing as described below.

If in logic block 1607 a determination is made that there are no more matches to the patient identifier, control is transferred to logic block 1614 where a determination is made if "1" was entered in logic block 1641 or logic block 1642. If not, control is transferred to logic block 1615 where the user is informed that there are no more matches and control is returned to logic block 1601. If "1" was entered, control is transferred to logic block 1621 and the system proceeds as described below.

Figure 23:
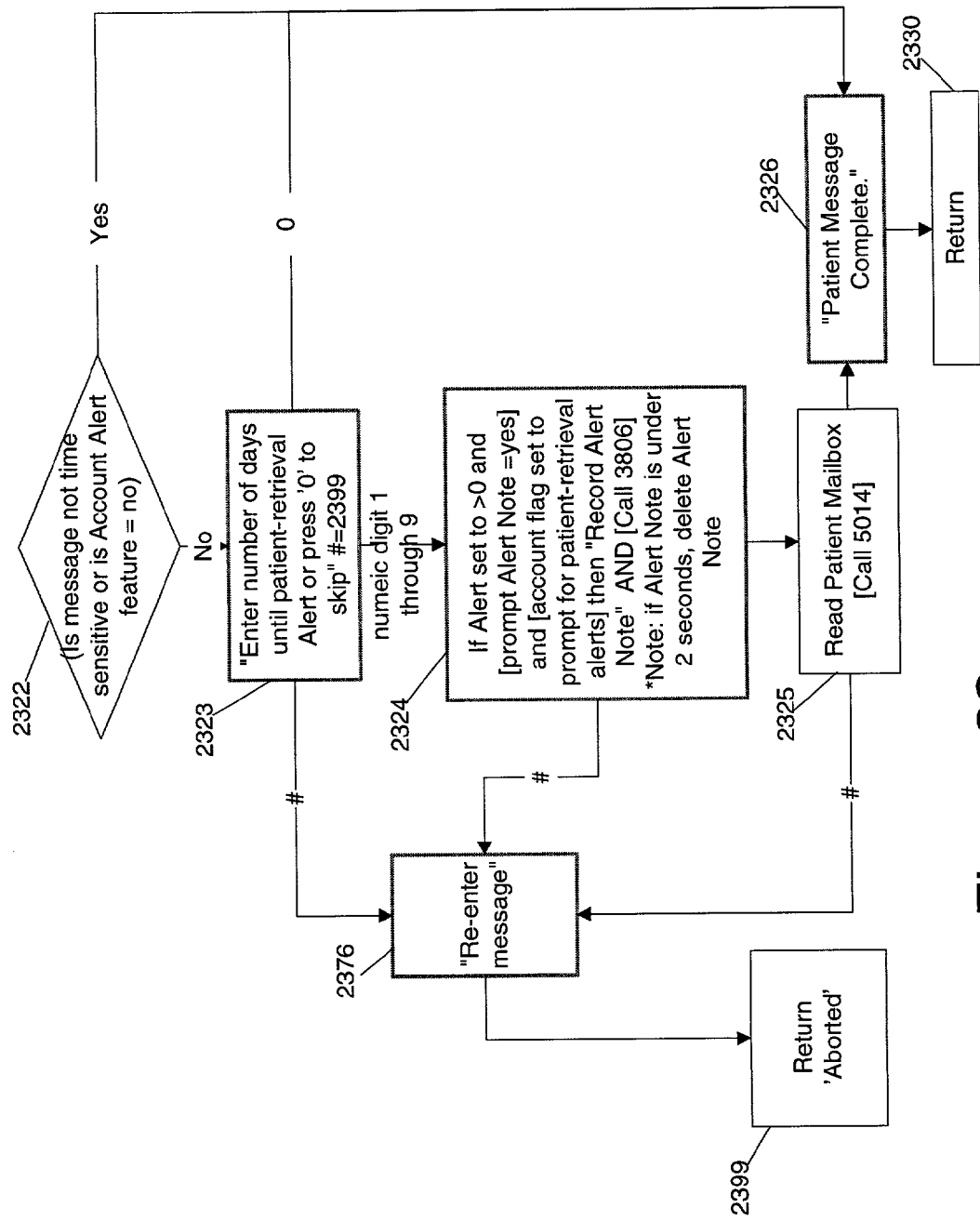
FIG. 23 illustrates a logic flow diagram for entering alert information such as setting an alert note and the number of days until a patient-retrieval alert is activated in a medical information system in accordance with the present disclosure.

If in logic block 1617 a determination is made that the user interrupted in logic block 1641 or logic block 1642 with "1", control is transferred to logic block 1621 and thence to logic block 1801 illustrated in FIG. 18 which illustrates a logic flow diagram for recording a patient message, placing a pre-recorded patient message, re-recording a patient name, and appending or replacing a chart note for a mailbox. On return of control to logic block 1621, if there are changes to the mailbox content, the engine writes these changes to the mailbox database of the account. If the return value is "Main Menu", then control is transferred to logic block 1103 via logic blocks 1111 and 1631. Otherwise, control is transferred via logic block 1627 to logic block 2322 illustrated in FIG. 23 which illustrates a logic flow diagram for setting an alert note and the number of days until a patient-retrieval alert is activated. If there are changes to the mailbox field on return of control from logic in FIG. 23 to logic block 1627 then the engine writes these changes to the mailbox database; control is then passed to logic block 1601 via logic block 1628. If the return value from logic illustrated in FIG. 23 is "Aborted", then control is transferred back to logic block 1621.

Figure 17:
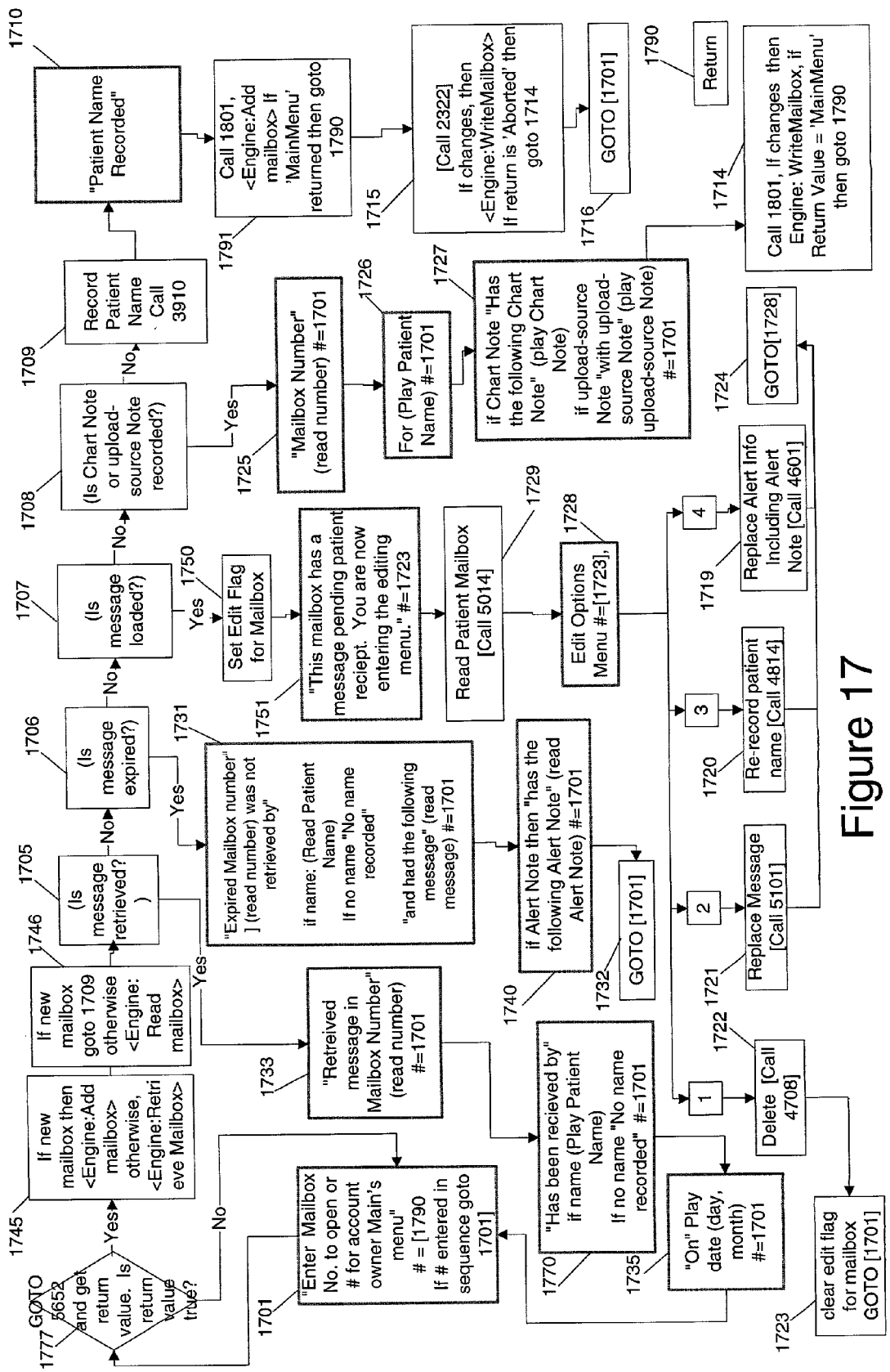
FIG. 17 illustrates a logic flow diagram for entering and retrieving mailbox information as well as accessing a mailbox edit menu, recording a patient name, recording a patient message, and accessing chart notes and upload-source notes related to a mailbox in medical information system in accordance with the present disclosure.

FIG. 17 illustrates a logic flow diagram for entering a message edit menu, recording a patient name, recording a patient message and accessing chart notes and upload-source notes related to a mailbox in the system. Control is transferred to logic block 1701 where the user is requested to enter a mailbox number to be opened or to press "#" to return to the main menu. If "#" is entered in the sequence of the mailbox number, control is returned to the beginning of the sequence of events for logic block 1701. Control is then transferred via logic block 1777 to logic block 5652 illustrated in FIG. 56 which illustrates a logic flow diagram to check whether or not a mailbox number is valid on an account in the system. If the return value from logic illustrated in FIG. 56 indicates a non-valid mailbox number, control is transferred back to logic block 1701. If the return indicates a valid mailbox number, control is transferred to logic block 1745 wherein the engine is made to add the mailbox to the account's mailbox database if this is a new mailbox number or retrieve the mailbox from the account's mailbox database if this is not a new mailbox number. Control is then transferred to logic block 1746 where control is transferred to logic block 1709 to be processed as described below if the mailbox number entered is a new mailbox number. Otherwise, the engine reads the mailbox data from the account's mailbox database and control is transferred to logic block 1705. Here a determination is made whether or not the mailbox patient message has been retrieved. If so, control is transferred to logic block 1733 where a prompt reads the mailbox number and informs the user that the patient message has been retrieved and then transfers control to logic block 1770 where the patient's name is read to the user if the name is available or the prompt "No Name Recorded" is played if the name is not available. Control then passes to logic block 1735, which informs the user of the date the patient message was retrieved. Control then passes back to logic block 1701. If the patient message was not retrieved, control is passed to logic block 1706 where a determination is made whether or not the patient message has expired. If so, control passes to logic block 1731 where the following prompt is played: "Expired Mailbox" and the number of the mailbox is played "was not retrieved by" and the patient's name is played "and had the following message" and the patient message is played. If no name was recorded, the user is so informed. Control is then passed to logic block 1740 where the alert note for the mailbox is played if alert note exists. Control is then transferred to logic block 1701 via logic block 1732.

If the patient message has not expired, control is passed to logic block 1707 where a determination is made whether or not a patient message is loaded in the mailbox. If so, control is passed to logic block 1750 where an edit flag is set that prevents other users or a patient from accessing the mailbox while the mailbox is being edited. Control is then transferred to logic block 1751 where the account owner is informed that the mailbox has a message pending patient receipt and that the edit menu is being entered. Control then passes via logic block 1729 to logic block 5014 illustrated in FIG. 50 which illustrates a logic flow diagram for reading the contents of a patient mailbox. On return to logic block 1729 control passes to logic block 1728 where the user is presented with four options for editing the contents of the mailbox. These are accessible to the user by pressing the digits from one to four on the touch tone telephone. The numbered choices include: Deleting the patient message in which case control is transferred via logic block 1722 to logic block 4708 illustrated in FIG. 47 which illustrates a logic flow diagram for deleting the contents of a mailbox; Replacing the patient message in the mailbox in which case control is transferred via logic block 1721 to logic block 5101 illustrated in FIG. 51 which illustrates a logic flow diagram for replacing the patient message in a mailbox; Re-recording the patient name in which case control is transferred via logic block 1720 to logic block 4814 illustrated in FIG. 48 which illustrates a logic flow diagram for re-recording a patient name in a mailbox; and replace alert information including the alert note in which case control is transferred via logic block 1719 to logic block 4601 illustrated in FIG. 46 which illustrates a logic flow diagram for replacing alert information in a mailbox. Control is returned to the respective logic blocks that transferred the control initially to each of the above figures and then is transferred back to logic block 1728 via logic block 1724 in all cases except for logic block 1722. In this latter case control is then transferred to logic block 1723 where the edit flag that was set for the mailbox to prevent other user entry is cleared; control is then transferred to logic block 1701. If "#" is entered at logic block 1728, control is also transferred to logic block 1723 to clear the edit flag and thence to logic block 1701.

If a determination is made in logic block 1707 that a patient message is not loaded in the mailbox, control is transferred to logic block 1708 where a determination is made if a chart note or upload-source note is recorded for the mailbox. If so, control is transferred to logic block 1725 where the mailbox number is read to the user and then to logic block 1726 where the patient's name is read to the user. Then control passes to logic block 1727 where the chart notes and upload-source notes of the mailbox are read. Control is then transferred via logic block 1714 to logic block 1801 illustrated in FIG. 18 which illustrates a logic flow diagram for recording a patient message, placing a pre-recorded patient message, re-recording a patient name, and appending or replacing a chart note for a mailbox. If, on return of control to logic block 1714 from logic illustrated in FIG. 18 there are changes to the mailbox data, the engine is directed to write those changes to the mailbox database on the account; if the return value from logic illustrated in FIG. 18 is "Main Menu", then control is transferred from logic block 1714 to the logic block that called logic illustrated in FIG. 17 via logic block 1790.

Figure 39:
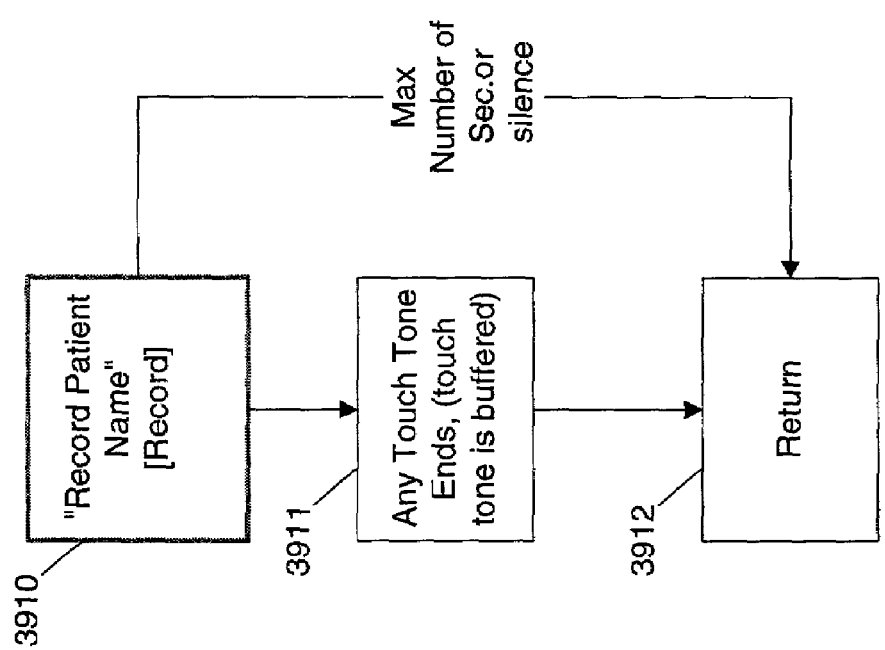
FIG. 39 illustrates a logic flow diagram for recording a patient name in a medical information system in accordance with the present disclosure.

If a determination is made that there is no chart note or upload-source note in logic block 1708 then control is passed via logic block 1709 to logic block 3910 illustrated in FIG. 39 which illustrates a logic flow diagram for recording a patient name. From logic illustrated in FIG. 39 control is transferred back to logic block 1709 and thence to logic block 1710 where a prompt informs the account owner that the patient's name has been recorded. Control is then transferred via logic block 1791 to logic block 1801 illustrated in FIG. 18 which illustrates a logic flow diagram for recording a patient message, placing a pre-recorded patient message, re-recording a patient name, and appending or replacing a chart note for a mailbox. If the return value from logic illustrated in FIG. 18 is "Main Menu", then control is transferred from logic block 1791 to logic block 1790 and then returned to the logic block that called logic illustrated in FIG. 17. If, on return of control to logic block 1791 from logic illustrated in FIG. 18 there are changes to the mailbox data, the engine is directed to write these to the mailbox database. Control is then transferred via logic block 1715 to logic block 2322 illustrated in FIG. 23 which illustrates a logic flow diagram for setting an alert note and the number of days until a patient-retrieval alert is activated. Upon return of the control from logic illustrated in FIG. 23 to logic block 1715, if there are changes made in the mailbox, the engine writes these changes to the account's mailbox database and control is passed to logic block 1716; if "aborted" is returned, control is next transferred to logic block 1714 and the system proceeds as previously described. From logic block 1716 control is transferred to logic block 1701.

In an embodiment, when a patient message is placed in a mailbox, and the patient telephone number is available, the system will call the patient and play a message indicating that a message is waiting for him or her on the system.

FIG. 18 illustrates a logic flow diagram for recording a patient message, placing a pre-recorded patient message, re-recording a patient name, and appending or replacing a chart note for a mailbox. Control is received in logic block 1801 where the account owner is prompted to press one to record a patient message, press eight to place a pre-recorded patient message, press two to re-record the patient name, or to press nine to append or replace a chart note. Control is then transferred to logic block 1805 where a determination is made whether or not two was pressed. If so, control is transferred via logic block 1806 to logic block 3910 illustrated in FIG. 39 which illustrates a logic flow diagram for recording a patient name. On return of control from logic illustrated in FIG. 39 control is transferred to logic block 1807 where a prompt informs the account owner that the patient's name has been recorded and then control is passed back to logic block 1801. If a determination is made in logic block 1805 that two was not entered, control is transferred to logic block 1808 where a determination is made whether or not nine was entered. If so, control is transferred to logic block 1826 where a determination is made if the mailbox already has a chart note. If so, control is transferred to logic block 1827 where the account owner is asked to press one to append to the chart note or two to record over the chart note. If "#" is pressed in logic block 1827, control is passed to logic block 1842 where a prompt is played stating that the chart note was not changed before control is passed to logic block 1816 whence control is returned with the return value "Main Menu" to the logic block that originally transferred control to logic block 1801. If one is pressed in response to the prompt in logic block 1827, control is transferred to logic block 1828 where the prompt "Append at beep" is played and control is transferred via logic block 1810 to logic block 3806 illustrated in FIG. 38 which illustrates recording information on the system with no review. If two is pressed, control is passed to logic block 1829 where the prompt "Replace at beep" is played and then control is transferred to logic block 1832 where the patient identifier is cleared from the mailbox database. Control is then transferred via logic block 1810 to logic block 3806 illustrated in FIG. 38. When control returns to logic block 1810 from logic illustrated in FIG. 38, control is transferred to logic block 1831 where a determination is made whether or not the account has the patient identifier feature. If the account has the patient identifier feature but the mailbox has no identifier control is transferred to logic block 1830. Otherwise, control is transferred to logic block 1811. In logic block 1830 the account owner is requested to enter the patient identifier and the system informs the account owner if the patient identifier entered is valid and, if so, of their acceptance. Control is then transferred to logic block 1811. In logic block 1811 a prompt is played that the chart note is recorded and control is passed to logic block 1816 and thence returned with the return value "Main Menu" to the logic block that originally transferred control to logic block 1801.

If in logic block 1826 a determination is made that the mailbox does not already have a chart note, control is transferred to logic block 1809 where a prompt asks the user to record a chart note at the beep. If "#" is entered, control is transferred to logic block 1841 where a prompt is played notifying the account owner that no chart note was recorded prior to control being transferred to logic block 1816 whence control is returned with the return value "Main Menu" to the logic block that originally transferred control to logic block 1801. If "#" is not entered in logic block 1809, control is transferred via logic block 1810 to logic block 3806 illustrated in FIG. 38 and the system proceeds as heretofore described.

If a determination is made in logic block 1808 that nine was not entered, control is transferred to logic block 1813 where a determination is made if one was entered. If so, control is passed via logic block 1814 to logic block 1973 illustrated in FIG. 19 which illustrates a logic flow diagram for recording a patient message. On return of control from logic illustrated in FIG. 19 to logic block 1814 control is passed to logic block 1870 which causes the control to return to the logic block that originally called logic block 1801.

Figure 20:
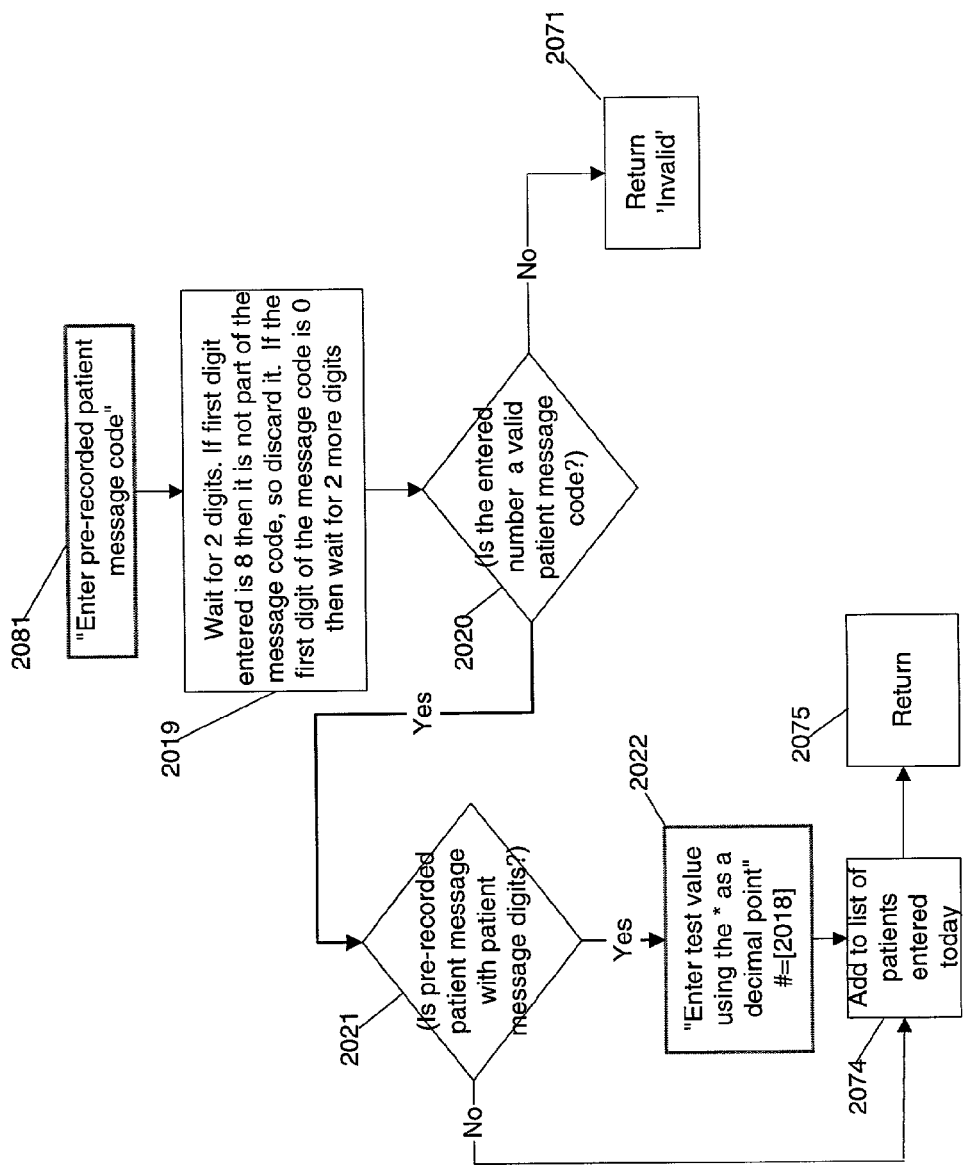
FIG. 20 illustrates a logic flow diagram for placing a pre-recorded patient message in a mailbox in a medical information system in accordance with the present disclosure.

If a determination is made in logic block 1813 that one was not entered, control passes to logic block 1817 where a determination is made if "eight" was entered. If not, control passes to logic block 1824 where a prompt informing the account owner of an invalid entry is played and the account owner is asked to retry; control is then passed back to logic block 1801. If a determination is made that "8" was entered in logic block 1817, control passes via logic block 1818 to logic block 2081 illustrated in FIG. 20 which illustrates a logic flow diagram for placing a pre-recorded patient message in a mailbox. If the return from logic illustrated in FIG. 20 is "invalid", control is transferred to logic block 1824 where the account owner is so informed and thence to logic block 1801. Otherwise, control on return from logic illustrated in FIG. 20 is passed to logic block 1870 and then returned to the logic block that called logic block 1801.

Figure 19:
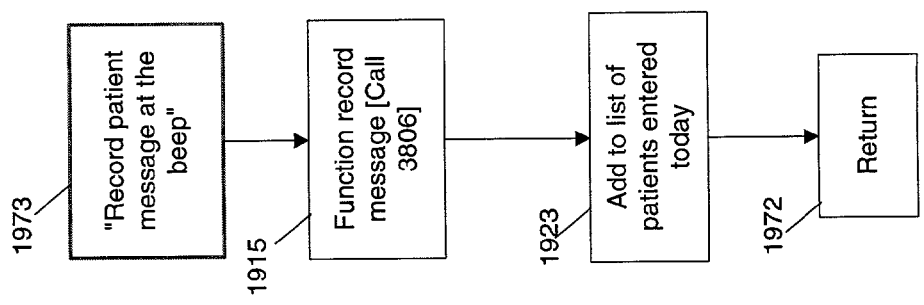
FIG. 19 illustrates a logic flow diagram for recording a patient message in a medical information system in accordance with the present disclosure.

FIG. 19 illustrates a logic flow diagram for recording a patient message in the system. Control is passed to logic box 1973 where the account owner is prompted to record the patient message at the beep. Control is then passed via logic block 1915 to logic block 3806 illustrated in FIG. 38 which illustrates a logic flow diagram for recording information with no review. Upon return of control from logic illustrated in FIG. 38 to logic block 1915 control is passed to logic block 1923 which causes the mailbox for which the patient message was just recorded to be added to the list of patients entered today. Control is then transferred to logic block 1972 which causes the control to return to the logic block that called logic block 1973.

FIG. 20 illustrates a logic flow diagram for placing a pre-recorded patient message in a mailbox in the system. Control is passed to logic block 2081 where the account owner is prompted to enter a pre-recorded patient message code. Control then passes to logic block 2019 where the system is caused to ignore the first digit entered in response to logic block 2081 if the response entered is "8" and to accept the two digits that follow "0" if the first digit entered is "0". Control is then transferred to logic block 2020 where a determination is made whether or not the entered number is a valid pre-recorded patient message code. If not, control is transferred to logic block 2071, which returns "Invalid" to the calling logic block. If a valid patient message code is entered, control is transferred to logic block 2021 where a determination is made whether or not the patient message needs patient message digits, i.e., if the message requires an account owner numerical input at the end of the pre-recorded portion on the message. If this is not the case, control is transferred to logic block 2074 and the system proceeds as subsequently described. If this is the case, control is transferred to logic block 2022 where the account owner is prompted to enter the test value using "*" as a decimal point. Control then passes to logic block 2074 where the mailbox is added to the list of patient mailboxes entered that day. Control then passes to logic block 2075, which causes control to return to the logic block that originally transferred control to logic block 2081.

In alternate embodiment, a custom recorded message segment may be appended to a pre-recorded patient message. In the flow charts, the recording of this custom pre-recorded message segment would occur in place of entering patient message digits, and the playing of this custom pre-recorded message segment would occur in place of patient message digits.

FIG. 21 illustrates a logic flow diagram for accessing a list of patient names and their messages entered into the system on a particular date. Control is received in logic block 2171 which results in the engine retrieving a list of patient messages coded on a particular day. In an embodiment the engine can retrieve a list of patient messages coded within a time period between two prompted dates. Control is transferred to logic block 2175 which informs the account owner of the number of patient messages entered that day and then passes control to logic block 2119 which plays the prompt: "The following are the Patient names along with their messages and alert information entered on" and the system then plays date of entry. Control then passes via logic block 2121 to logic block 4100 illustrated in FIG. 41 which illustrates a logic flow diagram for accessing a list of patients and their messages or patient message titles entered in the system on a particular day. On return of control to logic block 2121 from logic illustrated in FIG. 41 control is passed to logic block 2150 where the prompt "End of list" is played and then to logic block 2151 which causes control to return to the logic block that called logic block 2171.

FIG. 22 illustrates a logic flow diagram for accessing panic and other alerts on an account in the system. Control is received in logic block 2201, which causes the engine to read the alert counts for the account. Control is then transferred to logic block 2202 where a determination is made whether or not the account has any alerts. If not, control passes to logic block 2204, which informs the account owner, that there are no alerts and then passes control to logic block 2218 which returns control to the logic block that called this logic.

If a determination is made in logic block 2202 that the account has alerts, control is transferred to logic block 2273 where the engine retrieves a pre-sorted list of alerted mailboxes. Control then passes to logic block 2203 where a determination is made whether or not the account has any new alerts. If not, control is passed to logic block 2211 and the system proceeds as indicated below.

If a determination is made that there are new alerts in logic block 2203, then control passes to logic block 2205 where a determination is made if the account has new panic alerts. If not, control is passed to logic block 2207 where the account owner is informed on the number of new alerts prior to control being passed to logic block 2210 where the system proceeds as described below.

If the account has new panic alerts, control is passed from logic block 2205 to logic block 2206 where the account owner is informed of the number of new panic alerts prior to the control passing to logic block 2208 where a determination is made whether or not the account has other new, non-panic alerts. If the latter is determined not to be the case, control is transferred to logic block 2210 and the system proceeds as described below. If there are new, non-panic alerts, control is transferred to logic block 2209 where the account owner is informed of the number of these alerts prior to the control being transferred to logic block 2210. From logic block 2210 control is transferred to logic block 4563 illustrated in FIG. 45 which illustrates a logic flow diagram for deleting or saving an alert that has been accessed in the system. When control returns from logic illustrated in FIG. 45 to logic block 2210, control is transferred to logic block 2216 where a determination is made whether or not the account owner account has saved alerts.

If not, control is transferred to logic block 2217 where the account owner is informed that there are no more alerts and control is transferred to logic block 2215 and the system proceeds as described below.

If there are saved alerts, control is transferred from logic block 2216 to logic block 2211 where the account owner is prompted to press one to listen to saved alerts or press "#" to return to the main menu. If the account owner makes any other entry, control is transferred to logic block 2215 and the system proceeds as described below.

Figure 45:
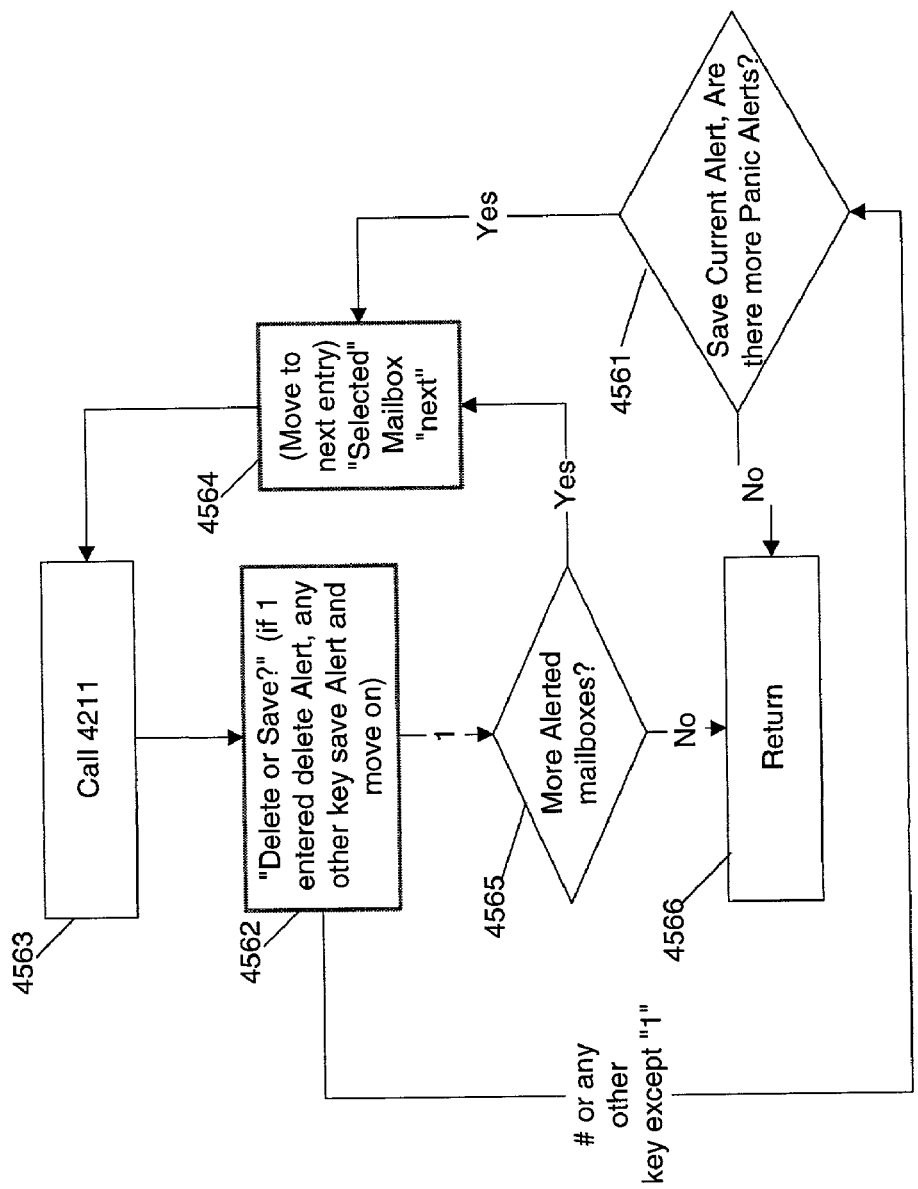
FIG. 45 illustrates a logic flow diagram for deleting or saving an alert that has been accessed in a medical information system in accordance with the present disclosure.

If the user presses one in logic block 2211, control is transferred to logic block 2212 where a prompt saying "The following are saved alerts" is played prior to the control being transferred via logic block 2214 to logic block 4563 illustrated in FIG. 45 which illustrates a logic flow diagram for deleting or saving an alert that has been accessed. On return of control from logic illustrated in FIG. 45 to logic block 2214 control is passed to logic block 2232 where a prompt stating there are no more alerts is played. Control then transfers to logic block 2215 where the engine writes a list of alerted mailbox changes to the account's databases. Control is then passed to logic block 2218 where control is returned to the logic block that called logic block 2201.

FIG. 23 illustrates a logic flow diagram for setting an alert note and the number of days until patient-retrieval alert is activated in the system. Control is received in logic block 2322 where a determination is made whether or not the mailbox patient message is not time sensitive or if the account has the patient-retrieval alert feature parameter set to "no". If so, control is transferred to logic block 2326 and the system proceeds as described below.

If not, control is transferred to logic block 2323 where the user is asked to enter the number of days until a patient-retrieval alert should be activated or to press "0" to skip. If "0" is entered, control transfers to logic block 2326 and the system proceeds as described below. If another digit is entered, control transfers to logic block 2324 where, if the alert days entered are greater than zero and the account has the flag set for prompt-alert-note to "yes" and the account patient-retrieval alert feature, the account owner is prompted to record an alert note and control is transferred to logic block 3806 illustrated in FIG. 38 which illustrates recording information on the system with no review. In logic block 2324 the system deletes the alert note if the alert note is less than two seconds in length. On return of control to logic block 2324 control is passed via logic block 2325 to logic block 5014 illustrated in FIG. 50 which illustrates a logic flow diagram for reading the contents of a patient mailbox. If "#" is entered in logic block 2325 or logic block 2324 or logic block 2323, control is transferred to logic block 2376 where a prompt "Re-enter Patient message" is played before control is transferred to logic block 2399 which causes "Aborted" to be returned to the logic block that called logic block 2322.

From logic block 2325 control is transferred to logic block 2326 which plays the prompt "Patient Message Complete" before control is transferred to logic block 2330 which returns control to the logic block that called logic block 2322.

FIG. 24 illustrates a logic flow diagram for accessing an account status in the system. Control is received in logic block 2400 and passed to logic block 2401 where the account owner is prompted to press 1 for account status, press 2 to listen to pre-recorded patient messages, press 3 to obtain faxed system instructions, or to press 4 to change account options.

If the account owner presses "1", control is transferred to logic block 2490 where the account number is read and control is next transferred to logic block 2491 where the number of faxes left this month is read to the account owner. Control then passes to logic block 2492 where the account owner is informed if the account is configured to have alert note prompting or not, unless the account configured not to have the patient-retrieval alert feature in which case this logic block is skipped. Control is then passed to logic block 2493 where the account owner is informed if the account has no limit on mailboxes or, if the account does have a limit, the number of mailboxes left. Control is then returned to logic block 2401 via logic block 2495.

If the account owner presses "2", control is transferred to logic block 2423 where the system prompts for a pre-recorded patient message code so that the account owner may hear the patient message. Control then passes to logic block 2424 where the account owner is prompted to press a pre-recorded patient message key. Control then passes to logic block 2427 where the system waits for two digits except if the first digit is an "8" in which case the system waits for two more digits. Control then transfers to logic block 2428 where a determination is made whether or not a valid patient message code has been entered. If not, control passes to logic block 2426 where the account owner is informed that an invalid code has been entered prior to control passing back to logic block 2424 prompting for another pre-recorded patient message key to be pressed.

If a determination is made that a valid patient message code has been entered in logic block 2428, control passes to logic block 2429 where a prompt stating "The patient message is the following" is played prior to control passing to logic block 2430 where the patient message is read. Control then passes to logic block 2431 where the account owner is prompted to enter another pre-recorded patient message key to hear another patient message or press "#" to return to logic block 2401. If "#" is not pressed, control returns to logic block 2427.

If the account owner presses "3" at logic block 2401, control is transferred to logic block 2421 where the account owner is informed that the system will fax a pre-recorded patient message list and instructions. Control is then transferred to logic block 2422 where a determination is made whether or not the account owner has used the month's allowance of fax reports or not. If the account owner has, control is transferred to logic block 2415 where the account owner is so informed prior to being transferred back to logic block 2401 via logic block 2413.

If the account owner has faxes left as determined in logic block 2422, control is transferred to logic block 2416 where the account owner is requested to enter a fax number. Control then passes to logic block 2417 where the engine checks if the fax number is one allowed by the system. If not, control passes to logic block 2420 where the account owner is so informed prior to control passing back to logic block 2416 for entry of another fax number. If the account owner enters "#" at logic block 2416, control transfers back to logic block 2401.

If the fax number is allowed as determined in logic block 2417, control transfers to logic block 2418 where the system reads the fax number to the account owner and asks the account owner to press one to accept and two to select another fax number. If two is entered, control returns to logic block 2416 for re-entry of a fax number. If one is entered, control passes to logic block 2419 where the number of faxes available for the account is decremented and the account owner is informed that the fax will be sent shortly. Control is then transferred to logic block 2499 and the system proceeds as described below.

If the account owner presses "4" at logic block 2401, control is transferred to logic block 2483 where a determination is made whether or not the account has the set-up-security parameter set to "yes". If not, control is transferred via logic block 2425 to logic block 2501 illustrated in FIG. 25 which illustrates a logic flow diagram for changing account options in the system. On return of control to logic block 2425 from the logic in FIG. 25 control is transferred to logic block 2499 and the system proceeds as described below.

If the account has set-up-security parameter set to "yes", control is transferred from logic block 2483 to logic block 2481 where account-owner or the agent of the account-owner is asked to enter the account change code. Control is then passed to logic block 2480 where a determination is made whether or not the entered code is correct. If so, control is transferred to logic block 2425 and the system proceeds as previously described. If the entered code is not correct, control is transferred on the first two errors to logic block 2496 where the account owner or agent of the account owner is informed of the error. If no account change code has been set on the system, the system will accept the access security code in logic block 2481. Control is then passed from logic block 2496 back to logic block 2481 for re-entry of the account change code after the account owner or agent of the account owner is informed of the error. On the third error, control is transferred from logic block 2480 to logic block 2424 where the account owner or agent of the account owner is asked to contact the system administrator. Control then passes to logic block 2497 where the account owner or agent of the account owner hears the prompt "Contact the customer service at" and then control is passed to logic block 2498 where a prompt is played that the system is returning to the main menu. Control next goes to logic block 2499 where if there are changes in the parameters, the engine writes these to the appropriate places in the account; control then passes to logic block 2470 where control is returned to the logic block that called logic block 2400.

Figure 25:
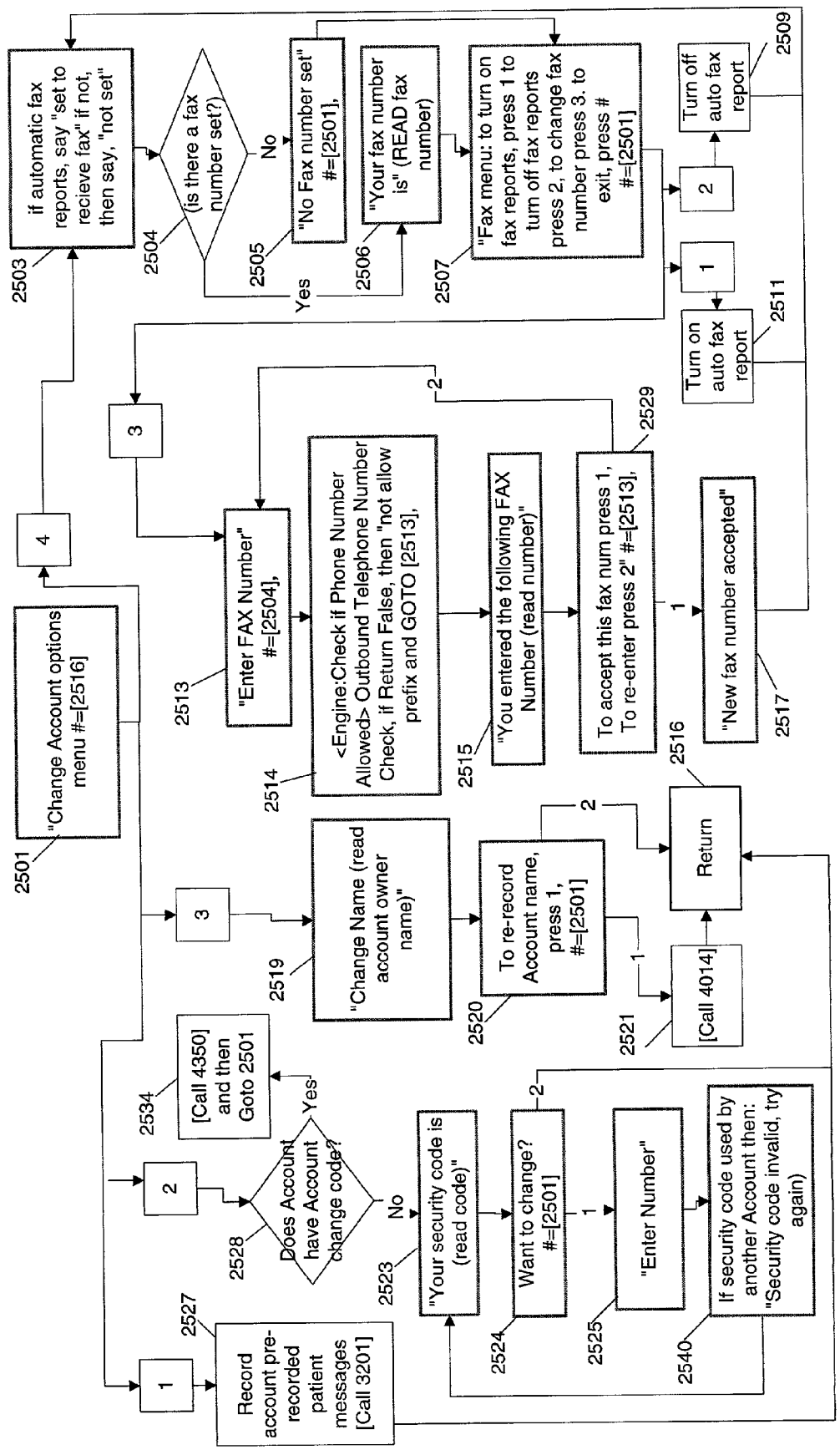
FIG. 25 illustrates a logic flow diagram for changing account options in a medical information system in accordance with the present disclosure.

FIG. 25 illustrates a logic flow diagram for changing account options in the system. Control is transferred to logic block 2501 where the account owner is presented with four options that may be chosen by entering digits from a touch tone telephone: "Press one to record a pre-recorded patient message, press two to change the security code, press three to change the name used as the account owner in prompts, press four to change the automatic fax option."

Figure 32:
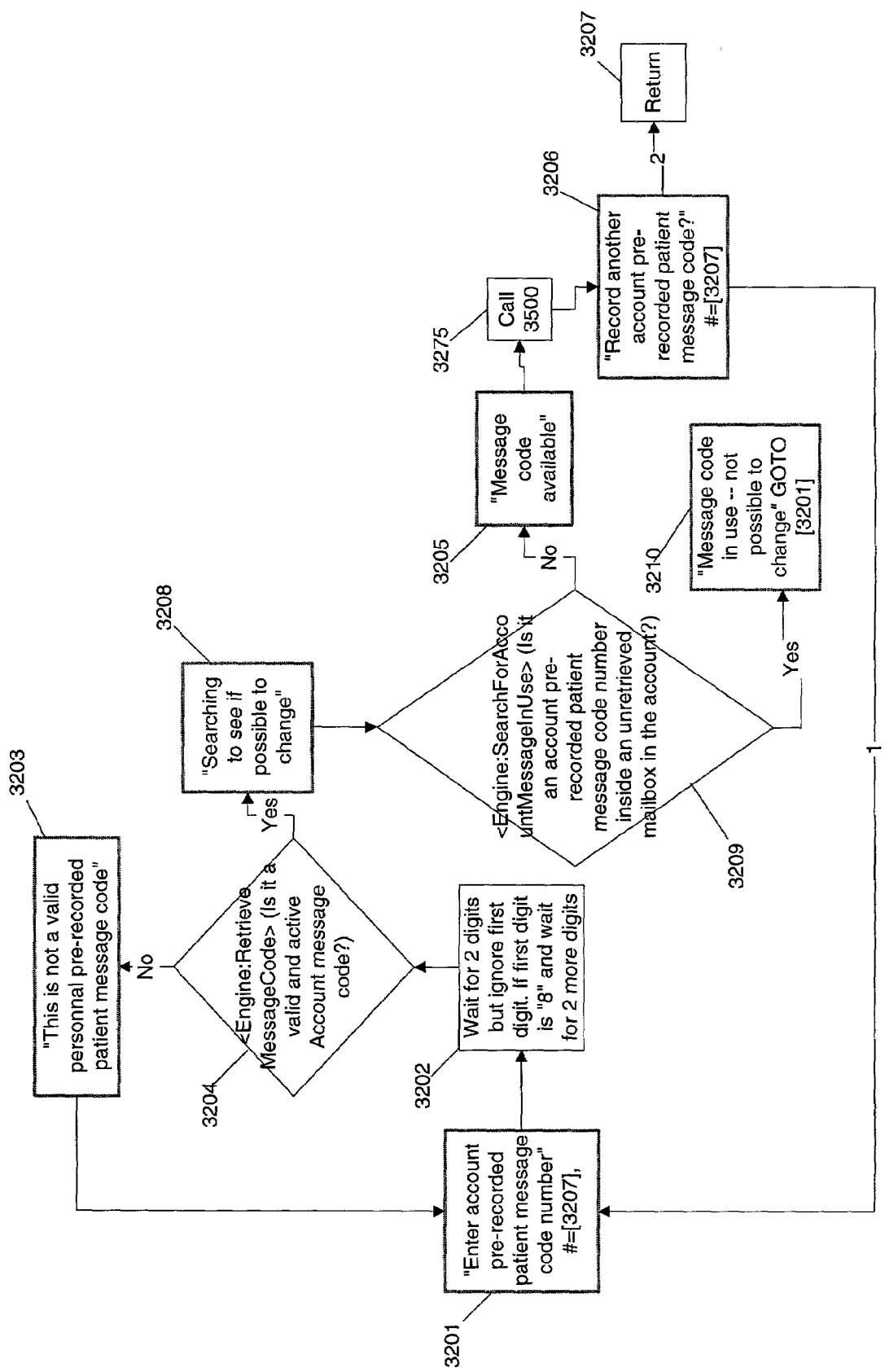
FIG. 32 illustrates a logic flow diagram for recording pre-recorded patient messages (Part I) in a medical information system in accordance with the present disclosure.

If the account owner enters "1" at logic block 2501, control is transferred via logic block 2527 to logic block 3201 illustrated in FIG. 32 which illustrates a logic flow diagram for recording pre-recorded patient messages in the system. When control is returned to logic block 2527 from logic illustrated in FIG. 32, control is transferred to logic block 2516 which causes control to return to the logic block that called logic illustrated in FIG. 25.

If the account owner enters "2" at logic block 2501, control is transferred to logic block 2528 where a determination is made whether or not the account has an account change code. If so, control transfers to logic block 4350 illustrated in FIG. 43 which illustrates a logic flow diagram for changing the access security code and/or account change code for a an account. When control returns from logic illustrated in FIG. 43, control is passed to logic block 2501. If the account does not have an account change code, control is transferred to logic block 2523 where the access security code is read. Control then passes to logic block 2524 where the account owner is asked if he or she desires to change the account security code. If the account owner answers negatively, control is transferred to logic block 2516 whence control is returned to the logic block that originally transferred control to logic block 2501. Otherwise, control passes to logic block 2525 where the account owner is asked to enter a new access security code. Control then passes to logic block 2540 where a determination is made if the code entered is in use by another account. If this is the case, a prompt stating "Security code entered is invalid" is played and the control is transferred back to logic block 2523 for processing as indicated above. If the entered access security code is acceptable, control is passed to logic block 2516 and the system progresses as described before.

If the account owner enters "3" at logic block 2501, control is transferred to logic block 2519 where the account owner is prompted to change the account owner name and control is passed to logic block 2520 where the account owner is asked to press "1" to re-record the account name or "2" to return. If the account owner presses "2", control passes to logic block 2516 where control is caused to return to the logic block that called logic illustrated in FIG. 25. If the account owner presses "1", control is transferred via logic block 2521 to logic block 4014 illustrated in FIG. 40 which illustrates a logic flow diagram for recording an account owner name. On return of control to logic block 2521 control passes to logic block 2516 which causes control to return to the logic block that called logic illustrated in FIG. 25.

If the account owner enters "4" at logic block 2501, control is transferred to logic block 2503 where the account owner is informed that the account is or is not set to receive automatic fax reports. Control then passes to logic block 2504 where a determination is made if there is a fax number set. If not, control passes to logic block 2505 where the account owner is informed that there is no fax number set; then control is passed to logic block 2507 and the system proceeds as described below. If there is a fax number set, control is transferred from logic block 2504 to logic block 2506 where the fax number is read before control is then passed to logic block 2507.

In logic block 2507 the account owner is given the choices to press one to turn on fax reports, press two to turn off fax reports, and press three to change the fax number. If the account owner presses "#", control returns to logic block 2501. If the account owner presses "1", control is transferred to logic block 2511 which causes automatic fax reports to be turned on; control is then transferred back to logic block 2503. If the account owner presses "2", control is transferred to logic block 2509 where automatic fax reports are turned off; control is then transferred back to logic block 2503. If the account owner presses "3", control is transferred to logic block 2513 where the account owner is prompted to enter a fax number. Control then passes to logic block 2514 where the engine checks if the entered phone number is allowed. If the phone number is not allowed, control is transferred back to logic block 2513. If the phone number is allowed, control passes to logic block 2515 where the entered number is read and then to logic block 2529 where the account owner is prompted to enter one to accept the number and two to re-enter the fax number. If the account owner enters "2", control is passed back to logic block 2513 and processed as above. If the account owner enters "1", control is passed to logic block 2517 where the account owner is informed that the new fax number is accepted. Control then returns to logic block 2503 and is processed as described above.

Figure 26:
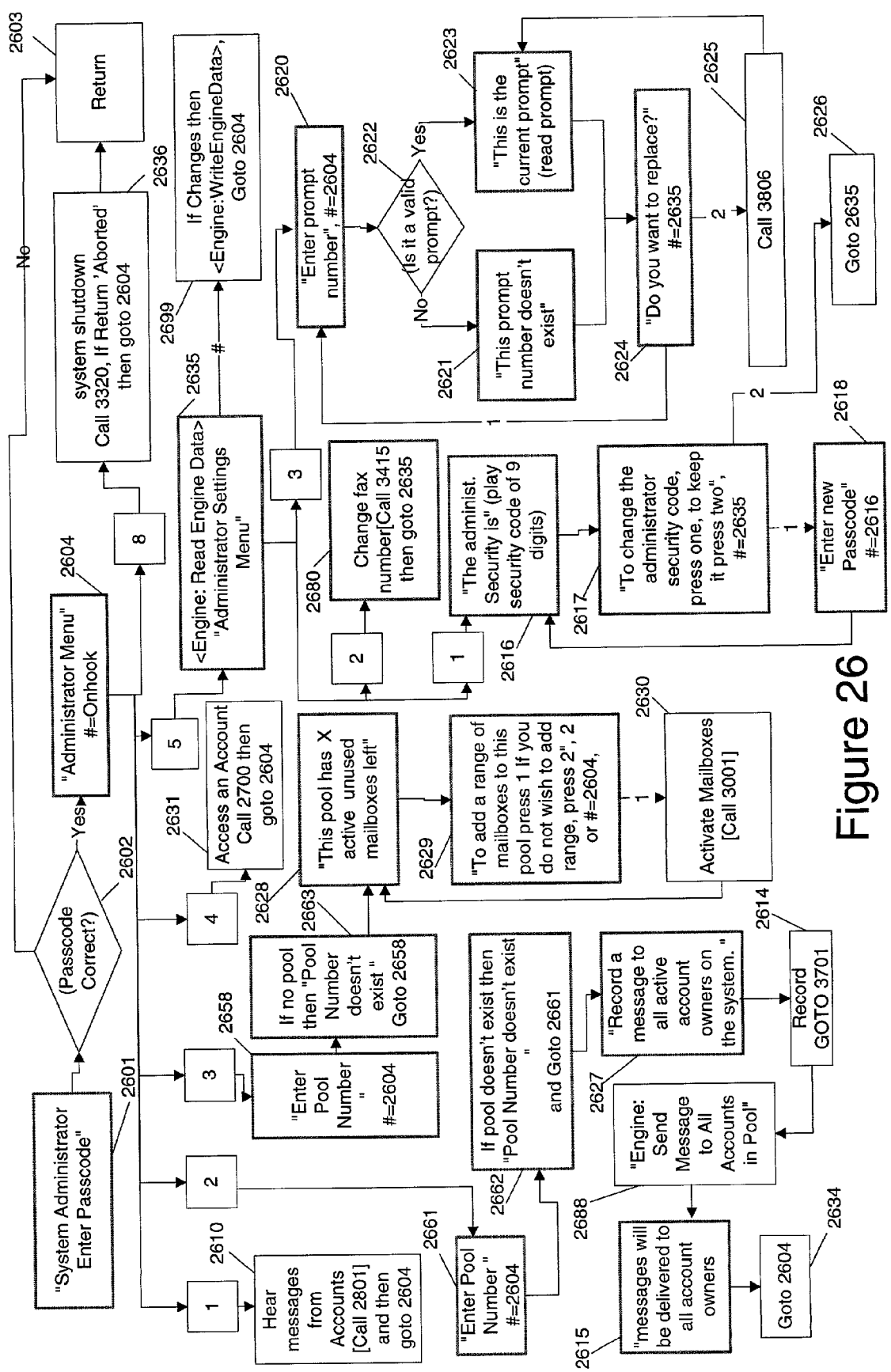
FIG. 26 illustrates a logic flow diagram for a system administrator menu in a medical information system in accordance with the present disclosure.

FIG. 26 illustrates a logic flow diagram for an administrator menu in the system. Control is transferred to logic block 2601 where the administrator is prompted to enter a passcode prior to control being passed to logic block 2602 where a determination is made whether or not the passcode entered is correct. If the entered code is incorrect, control is passed to logic block 2603 which causes control to return to the logic block that transferred control to logic block 2601. If the correct code was entered, control transfers to logic block 2604 where the administrator has six options and is prompted as follows: Press one to listen to your messages, press two to send a mass mail message to all accounts, press three for system mailbox activation, press four for checking an account's settings, press five to change the system administrator settings. The option to shutdown the system is accessed through pressing eight.

Figure 28:
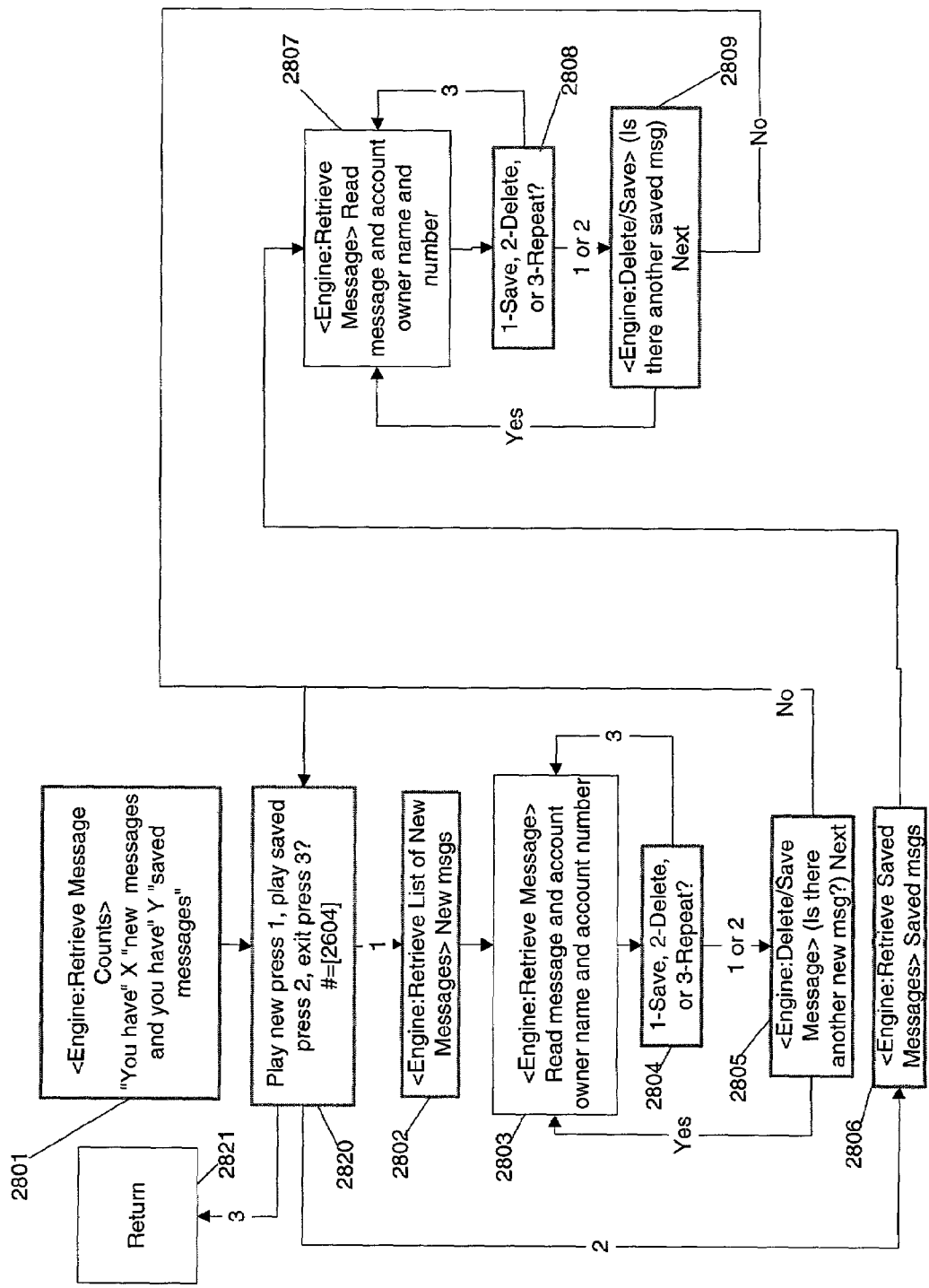
FIG. 28 illustrates a logic flow diagram for playing messages for an administrator in a medical information system in accordance with the present disclosure.

If the administrator presses "1", then control is transferred via logic block 2610 to logic block 2801 illustrated in FIG. 28 which illustrates a logic flow diagram for accessing messages for the administrator. On return from logic illustrated in FIG. 28 control is transferred back to logic block 2604.

If the administrator presses "2" at logic block 2604, then control is transferred to logic block 2661 where the administrator is prompted to enter a mailbox pool number. Control is then transferred to logic block 2662 where the system advises the administrator that the pool doesn't exist if the pool number is not found and control is transferred back to logic block 2661. If the pool number is confirmed to exist by the system, control is transferred to logic block 2627 where the administrator is prompted to record a message to all active accounts on the system. Control then passes via logic block 2614 to logic block 3701 illustrated in FIG. 37, which illustrates a logic flow diagram for recording information with review. Upon return of control from logic illustrated in FIG. 37 to logic block 2614 control is transferred to logic block 2688 where the engine sends the message to all active accounts in the pool. Control then passes to logic block 2615 where a prompt is played notifying the administrator that messages will be delivered to all account owners; control then passes to logic block 2604 via logic block 2634.

If the administrator presses "3" at logic block 2604, then control is transferred to logic block 2658 where the administrator is prompted to enter a mailbox pool number. Control is then transferred to logic block 2663 where the system advises the administrator that the pool doesn't exist if the pool number is not found and control is transferred back to logic block 2658. If the pool number is confirmed to exist by the system, control is transferred to logic block 2628 where the administrator is informed of the number of unused mailboxes left in the pool. Control then passes to logic block 2629 where the administrator is asked to enter one if he or she desires to add a range of mailboxes to the pool and two if this is not desired. If the administrator enters "2" or "#", control is transferred to logic block 2604. If the administrator presses one, control is transferred via logic block 2630 to logic block 3001 illustrated in FIG. 30 which illustrates a logic flow diagram for mailbox activation in the system. Upon return of control from logic illustrated in FIG. 30 to logic block 2630 control is transferred back to logic block 2628 where the number of unused mailboxes on the system is read to the administrator.

Figure 27:
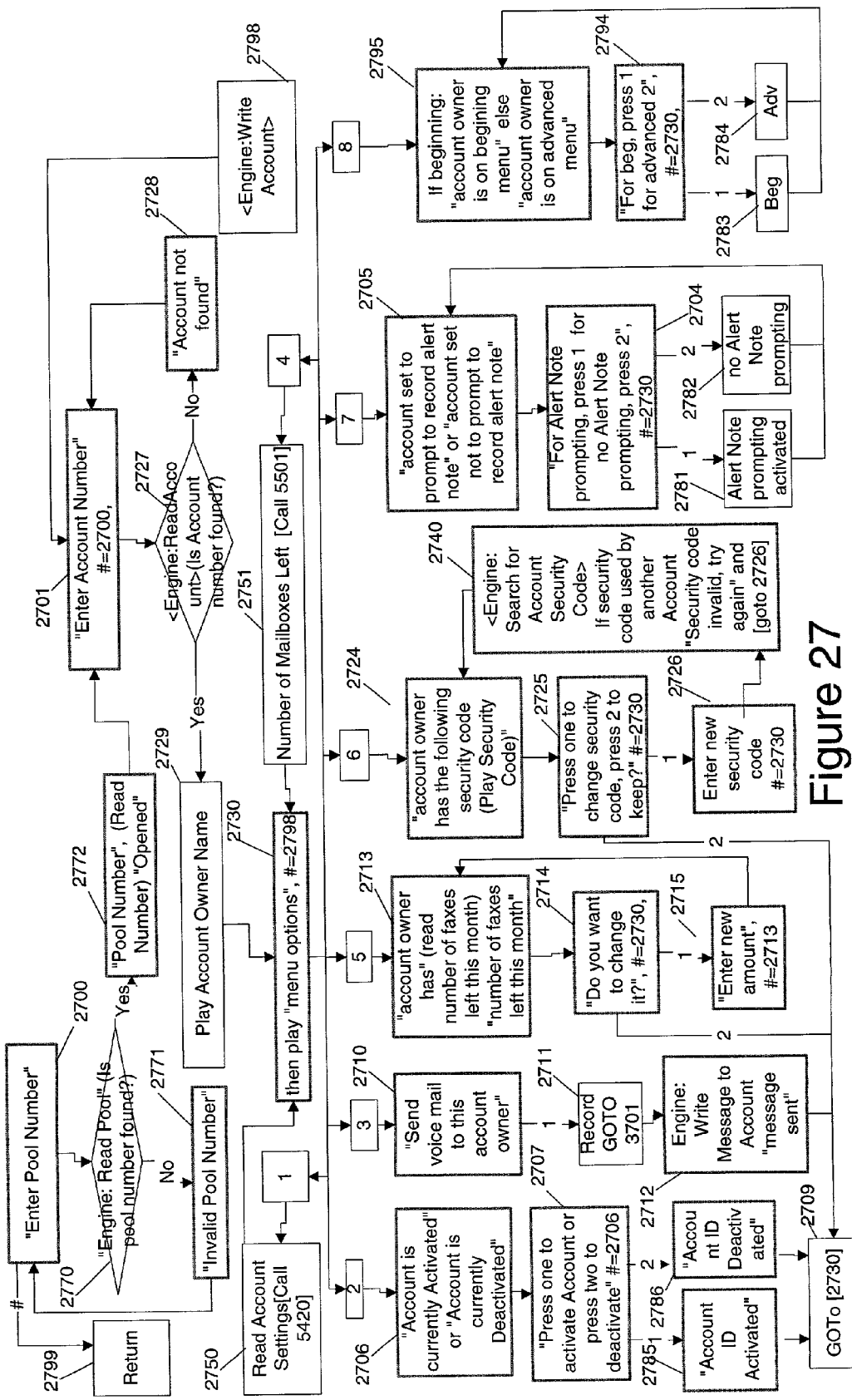
FIG. 27 illustrates a logic flow diagram for an administrator to access a mailbox pool to alter pool parameters and to change account settings in a medical information system in accordance with the present disclosure.

If the administrator presses "4" at logic block 2604, control is transferred via logic block 2631 to logic block 2700 illustrated in FIG. 27 which illustrates a logic flow diagram for an administrator to access a mailbox pool to alter pool parameters. Upon return of control to logic block 2631 from logic illustrated in FIG. 27 control is passed to logic block 2604.

If the administrator presses "5" at logic block 2604, then control is transferred to logic block 2635. Here the engine is caused to read data in the administrator settings database; if "#" is entered here, control is transferred to logic block 2699 where, if there have been changes in the settings, the engine is caused to write these to the administrator settings database. Otherwise, the administrator is prompted in logic block 2635 as follows: "Press one, to change the administrator security code; press two, to change the administrator fax number; press three, to record system prompts."

If the administrator presses "1" in logic block 2635, then control is passed to logic block 2616 where the administrator security code is played. Control next passes to logic block 2617 where the administrator is informed to press one to change the administrator security code and to press two to not change the security code. If "2" is pressed, control is transferred to logic block 2635 via logic block 2626. If "1" is pressed, control passes to logic block 2618 where the administrator is prompted to enter a new passcode; control then is transferred to logic block 2616 where the new passcode is played and the system proceeds as described previously.

Figure 34:
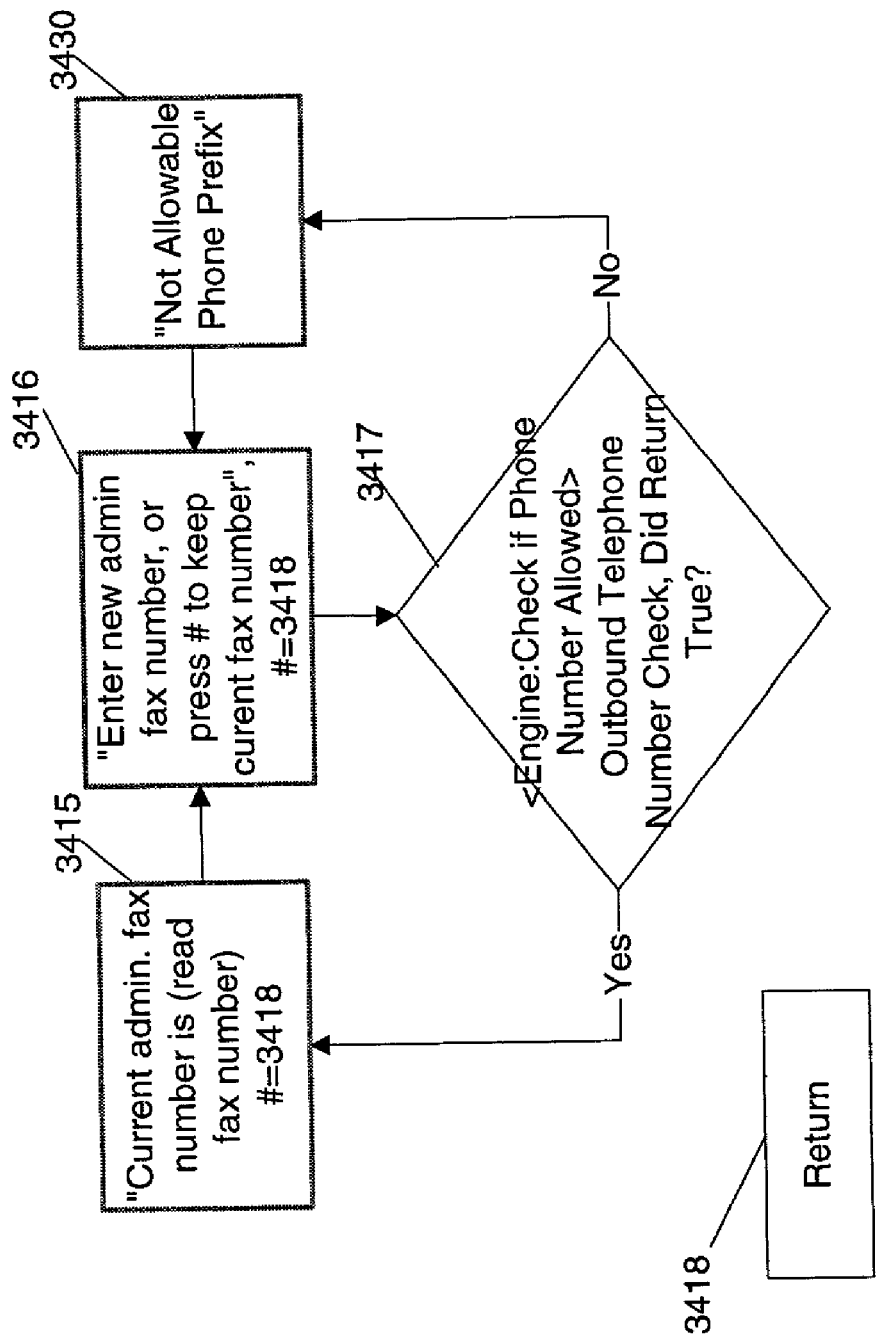
FIG. 34 illustrates a logic flow diagram for changing the administrator fax number in a medical information system in accordance with the present disclosure.

If the administrator presses "2" in logic block 2635, then control is passed via logic block 2680 to logic block 3415 illustrated in FIG. 34 which illustrates a logic flow diagram for changing the administrator fax number. On return to logic block 2680 from logic illustrated in FIG. 34 control is transferred to logic block 2635.

If the administrator presses "3" in logic block 2635, then control is passed to logic block 2620 where the administrator is prompted to enter a system prompt number. Control is then transferred to logic block 2622 where a determination is made if the entered number is a valid prompt number. If not, control transfers to logic block 2621 where the administrator is informed that the entered prompt number doesn't exist. Control then passes to logic block 2624 and the system proceeds as described below.

If the prompt number entered in logic block 2622 is valid, control is transferred to logic block 2623 where the current prompt is read to the administrator. Control then passes to logic block 2624 where the administrator is asked to enter one to keep the prompt or to press two to record over the prompt; if the administrator enters "#" control is returned to logic block 2635. If the administrator enters "1", control is passed back to logic block 2620; if the administrator enters "2", control is passed via logic block 2625 to logic block 3806 illustrated in FIG. 38 which illustrates a logic flow diagram for recording information with no review. Upon return from logic illustrated in FIG. 38 to logic block 2625 control is passed to logic block 2623 where the newly recorded prompt is read.

Figure 33:
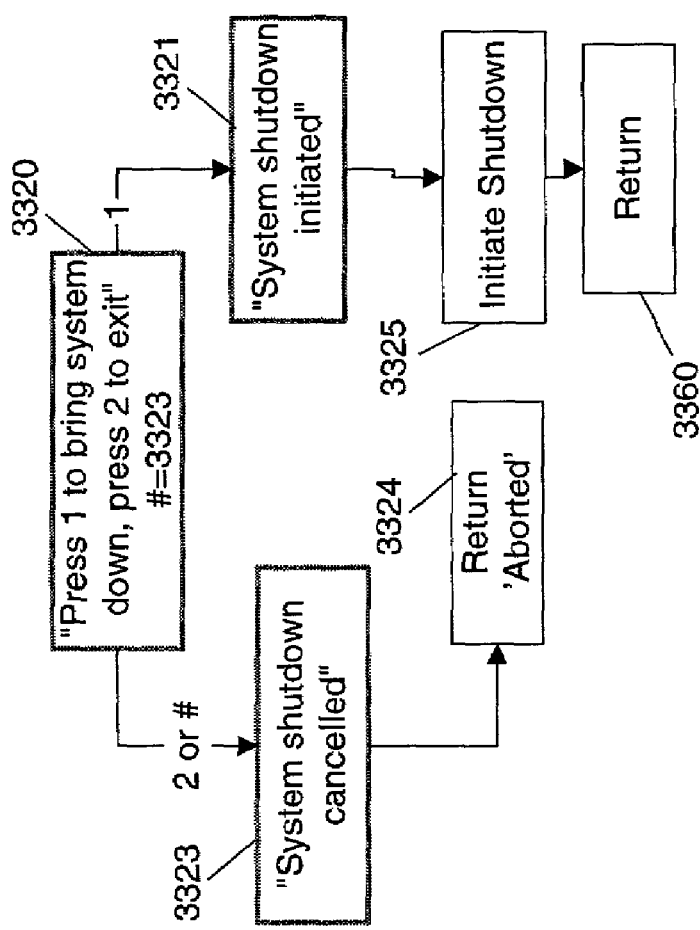
FIG. 33 illustrates a logic flow diagram for shutting down a medical information system in accordance with the present disclosure.

If the administrator presses "8" in logic block 2604, then control is passed via logic block 2636 to logic block 3320 illustrated in FIG. 33 which illustrates a logic flow diagram for shutting down the system by the administrator. If a return of "Aborted" is received back from logic illustrated in FIG. 33 into logic block 2636, control is transferred to logic block 2604 and the system proceeds as described above. Otherwise on return of control from the logic illustrated in FIG. 33 control is transferred to logic block 2603 where the system proceeds as previously described.

FIG. 27 illustrates a logic flow diagram for an administrator to access a mailbox pool to alter pool parameters. Control is transferred to logic block 2700 where the administrator is prompted to enter a mailbox pool number. If "#" is entered, control is transferred to logic block 2799 which causes the control to be transferred back to the logic block that transferred control to logic block 2700. Control is then transferred from logic block 2700 to logic block 2770 where the engine searches to system for the entered pool number. If the pool number is not found by the engine, control is transferred to logic block 2771 where the administrator is informed that an invalid pool number was entered, and then control is passed back to logic block 2700. If the engine locates the pool number, control passes to logic block 2772 where the pool number is read and the administrator informed that the pool is opened. Control is then passed to logic block 2701 where the administrator is asked to enter the account owner number. Control is then transferred to logic block 2727 where the engine determines if the account owner account number is found on the system. If not, control passes to logic block 2728 where a prompt informs the administrator that the account was not found prior to transferring control back to logic block 2701.

If the account owner account number was found in logic block 2727, control passes to logic block 2729 where the account owner name is played and then to logic block 2730 where the administrator is read the following prompt listing eight available options accessible by pressing the appropriate keys on a touch tone telephone: "Press one, for account settings; press two, for account activation; press three, to send a voice mail message to an account owner; press four, to learn the number of mailboxes left on the account; press five, to learn the number of faxes remaining on the account; press six, to change the security code; press seven, for prompting for placement of patient phone number in patient-retrieval alerts; press eight, for changing the account's setting from beginning to advanced menus.

Figure 54:
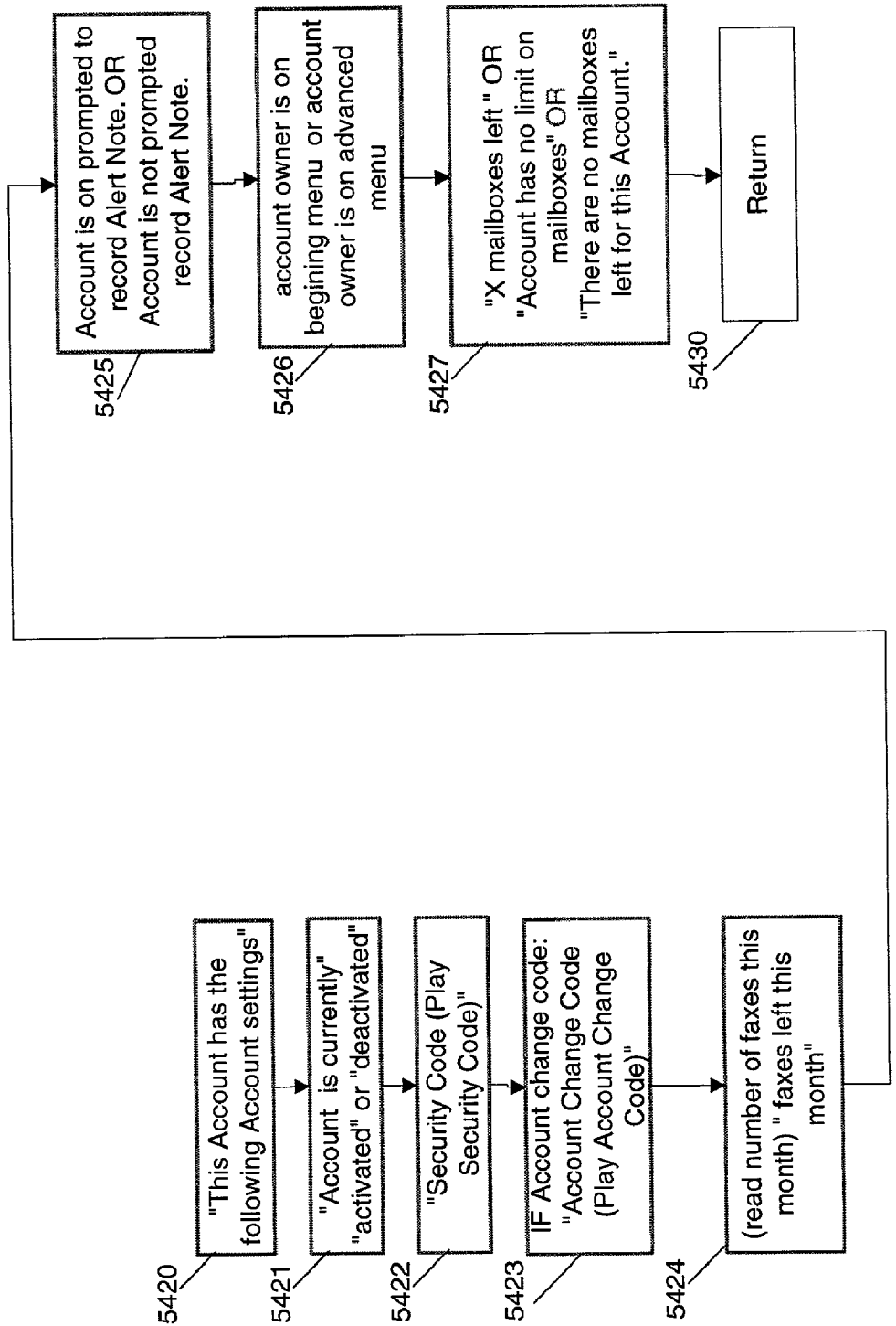
FIG. 54 illustrates a logic flow diagram for an administrator to access an account's parameters in a medical information system in accordance with the present disclosure.

If the administrator presses "1" in logic block 2730, then control is passed via logic block 2750 to logic block 5420 illustrated in FIG. 54 which illustrates a logic flow diagram for the administrator to access an account's parameters in the system. When the control returns to logic block 2750 from logic illustrated in FIG. 54, control is passed back to logic block 2730.

If the administrator presses "2" in logic block 2730, then control is passed to logic block 2706 where the administrator is informed whether or not the account is currently activated. Control then passes to logic block 2707 where the administrator is prompted to enter "1" to activate the account or "2" to deactivate the account. If "1" is entered, control is passed to logic block 2785 and a prompt is played that the account is activated before control passes back to logic block 2730 via logic block 2709. If "2" is entered, control is passed to logic block 2786 and a prompt is played that the account is deactivated before control passes back to logic block 2730 via logic block 2709.

Figure 37:
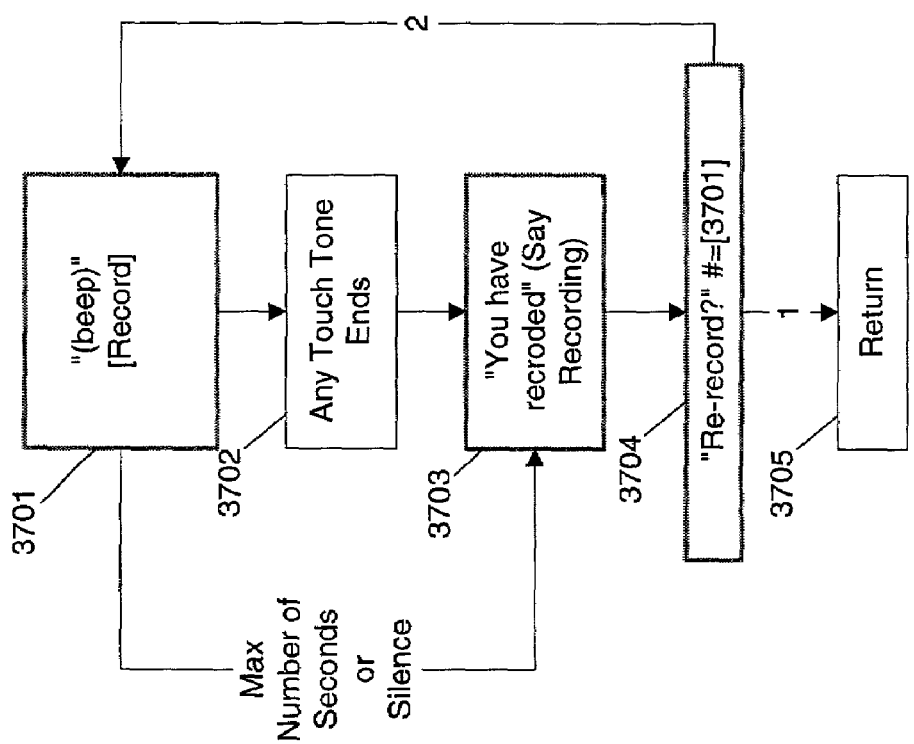
FIG. 37 illustrates a logic flow diagram for recording information with review in a medical information system in accordance with the present disclosure.

If the administrator presses "3" in logic block 2730, then control is passed to logic block 2710 where the prompt "Send voice mail to this account owner" is played before control is passed via logic block 2711 to logic block 3701 illustrated in FIG. 37 which illustrates a logic flow diagram for recording information with review in the system. Upon return of control from logic illustrated in FIG. 37 to logic block 2711 control is passed to logic block 2712 where the engine is caused to write the message to the account and then a prompt is played informing the administrator that the message was sent. Control is then passed back to logic block 2730 via logic block 2709.

Figure 55:
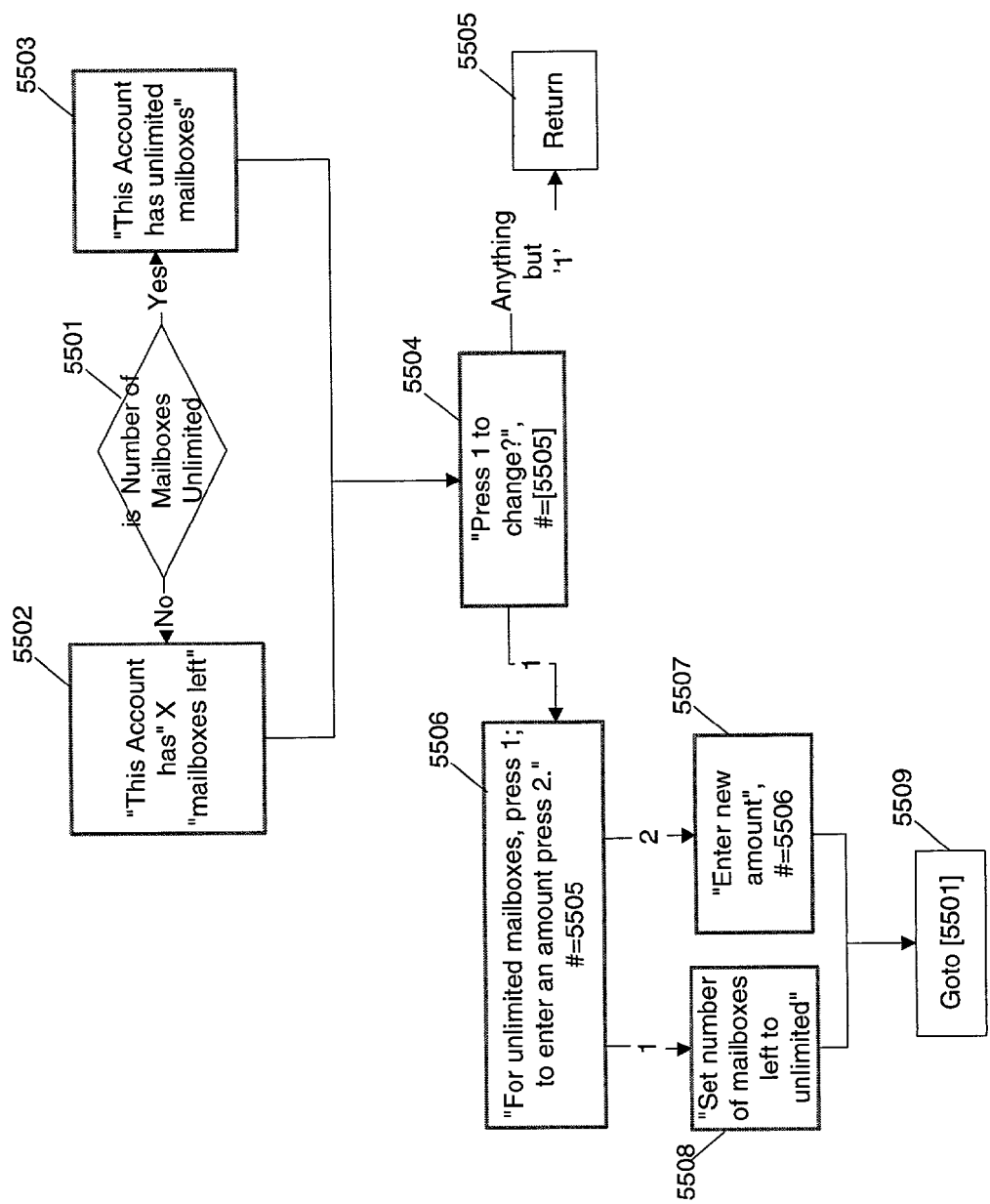
FIG. 55 illustrates a logic flow diagram for setting the number of mailboxes on an account in a medical information system in accordance with the present disclosure.

If the administrator presses "4" in logic block 2730, then control is passed via logic block 2751 to logic block 5501 illustrated in FIG. 55 which illustrates a logic flow diagram for setting the number of mailboxes on an account by the administrator. The number of remaining mailboxes on the account is accessed in the logic illustrated in FIG. 55. When control is returned from the logic illustrated in FIG. 55 to logic block 2751, control is then passed back to logic block 2730.

If the administrator presses "5" in logic block 2730, then control is passed to logic block 2713 where the administrator is informed of the number of faxes left on this account for the month. Control is then passed to logic block 2714 where the system asks the administrator to enter "1" to change the amount of remaining faxes or "2" to leave the count the same. If "2" is entered, control is passed back to logic block 2730 via logic block 2709. If "1" is entered, control passes to logic block 2715 where the system requests the administrator to enter a new number of faxes; control is then passed to logic block 2713 where the number of remaining faxes is read and the system proceeds as previously described.

If the administrator presses "6" in logic block 2730, then control is passed to logic block 2724 where the current account security code is read to the administrator and control is then passed to logic block 2725 where the administrator is asked to enter "1" to change the code or "2" to keep the code. If "2" is entered, control is returned to logic block 2730 via logic block 2709. If "1" is entered, control passes to logic block 2726 where the administrator is asked to enter a new security code and then to logic block 2740 where the engine searches the system for the newly entered security code. If this new security code is already in use by another account, the prompt "security code invalid" is played and control is transferred back to logic block 2726 and the system proceeds as previously described. If the security code is determined not to be in use, control passes to logic block 2724 where the new security code is played and the system proceeds as previously described.

If the administrator presses "7" in logic block 2730, then control is passed to logic block 2705 where the administrator is informed whether or not the account owner is prompted to record alert notes. Control then passes to logic block 2704 where the administrator is prompted to enter "1" for alert note prompting on the account or "2" for no alert note prompting on the account. If "#" is entered here, control is returned to logic block 2730. If "1" is entered, control is passed to logic block 2781 where a prompt states that alert note prompting is activated before control is passed back to logic block 2705 and the system proceeds as described previously. If "2" is entered in response to logic block 2704, control is passed to logic block 2782 where a prompt states that alert note prompting is not activated before control is passed back to logic block 2705 and the system proceeds as described previously.

If the administrator presses "8" in logic block 2730, control is passed to logic block 2795 where the administrator is informed if the account is using beginning or advanced menus. Control then passes to logic block 2794 where the administrator is prompted to enter "1" for beginning menus or "2" or advanced menus. If "1" is entered, control passes to logic block 2783 where the account is configured for beginning menus and then is passed back to logic block 2795 where the system proceeds as previously described. If "2" is entered, control passes to logic block 2784 where the account is configured for advanced menus and then is passed back to logic block 2795 where the system proceeds as previously described.

If the administrator presses "#" in logic block 2730, control transfers to logic block 2798 where the engine writes any changes to the account database. Control then transfers to logic block 2701 where the system proceeds as previously described.

FIG. 28 illustrates a logic flow diagram for playing messages for an administrator in the system. Control is transferred to logic block 2801 where the engine retrieves administrator message counts and the administrator is informed of the number of new and the number of saved messages for the administrator. Control is then passed to logic block 2820 where the administrator is asked to press "1" to play new messages, "2" to play saved messages, and "3" to exit. If "3" is pressed, control is transferred to logic block 2821 where control is returned to the logic block that transferred control to logic block 2801. If "2" is pressed, control is transferred to logic block 2806 where the system proceeds as described below.

If "1" is pressed in logic block 2820, control is passed to logic block 2802 where the engine retrieves a list of new administrator messages and then to logic block 2803 where the engine retrieves a message from the aforesaid list and where the message, account owner name, and account owner account number are read. Control then transfers to logic block 2804 where the user is asked to press "1" to save the message, "2" to delete the message, or "3" to repeat the message. If "3" is entered, control passes back to logic block 2803 where the system proceeds to reread the message, account owner name, and account owner number, as noted above. If "1" or "2" is entered, control passes to logic block 2805, and the engine either deletes or saves the message as directed. It is also ascertained here if there are more new messages. If so, control is passed back to logic block 2803 and the system proceeds as previously described. If there are no more new messages, control is transferred to logic block 2820 and the system proceeds as previously described.

Figure 29:
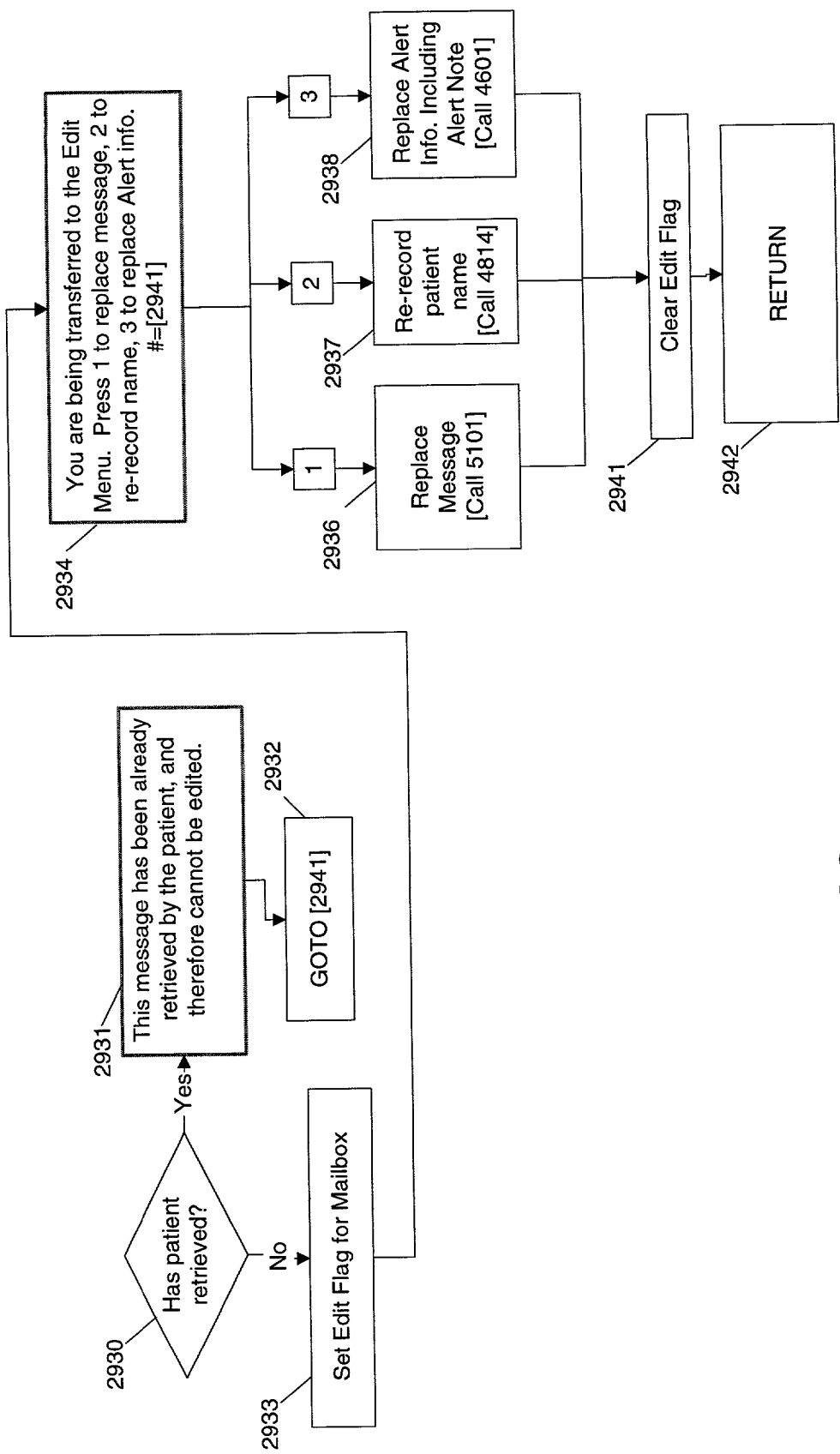
FIG. 29 illustrates a logic flow diagram for editing a patient message without playing the message in a medical information system in accordance with the present disclosure.

If there are saved messages and the administrator presses "2" in logic block 2820, control passes to logic block 2806 where the engine retrieves a list of saved message. Then control passes to logic block 2807 where the engine retrieves a saved message from the list and the message, account owner name, and account owner account number are read. Control then transfers to logic block 2808 where the user is asked to press "1" to save the message, "2" to delete the message, or "3" to repeat the message. If "3" is entered, control passes back to logic block 2807 where the system proceeds as noted above to reread the message, account owner name, and account owner number. If "1" or "2" is entered, control passes to logic block 2809, and the engine either deletes or saves the message as directed. It is also ascertained if there are more saved messages. If so, control is passed back to logic block 2807 and the system proceeds as previously described. If there are no more saved messages, control is transferred to logic block 2820 and the system proceeds as previously described FIG. 29 illustrates a logic flow diagram for editing a patient message without the system reading the patient message to the account owner. Control is passed to logic block 2930 where a determination is made whether or not the patient has retrieved the patient message. If so, control passes to logic block 2931 where the account owner is so informed and told that the patient message can not be edited. Control is then passed to logic block 2932 and thence to logic block 2941. Here the system clears any edit flags and then control is passed to logic block 2942 where control is returned to the logic block that passed control to logic block 2930.

If the patient message has not been retrieved, control is passed from logic block 2930 to logic block 2933 where an edit flag is set for the mailbox that prevents access by the patient, other account owners, or upload-sources while the mailbox is being edited. Control is then transferred to logic block 2934 where the account owner is given choices of pressing "1" to replace the patient message, "2" to re-record the patient name, and "3" to replace the alert information.

Figure 51:
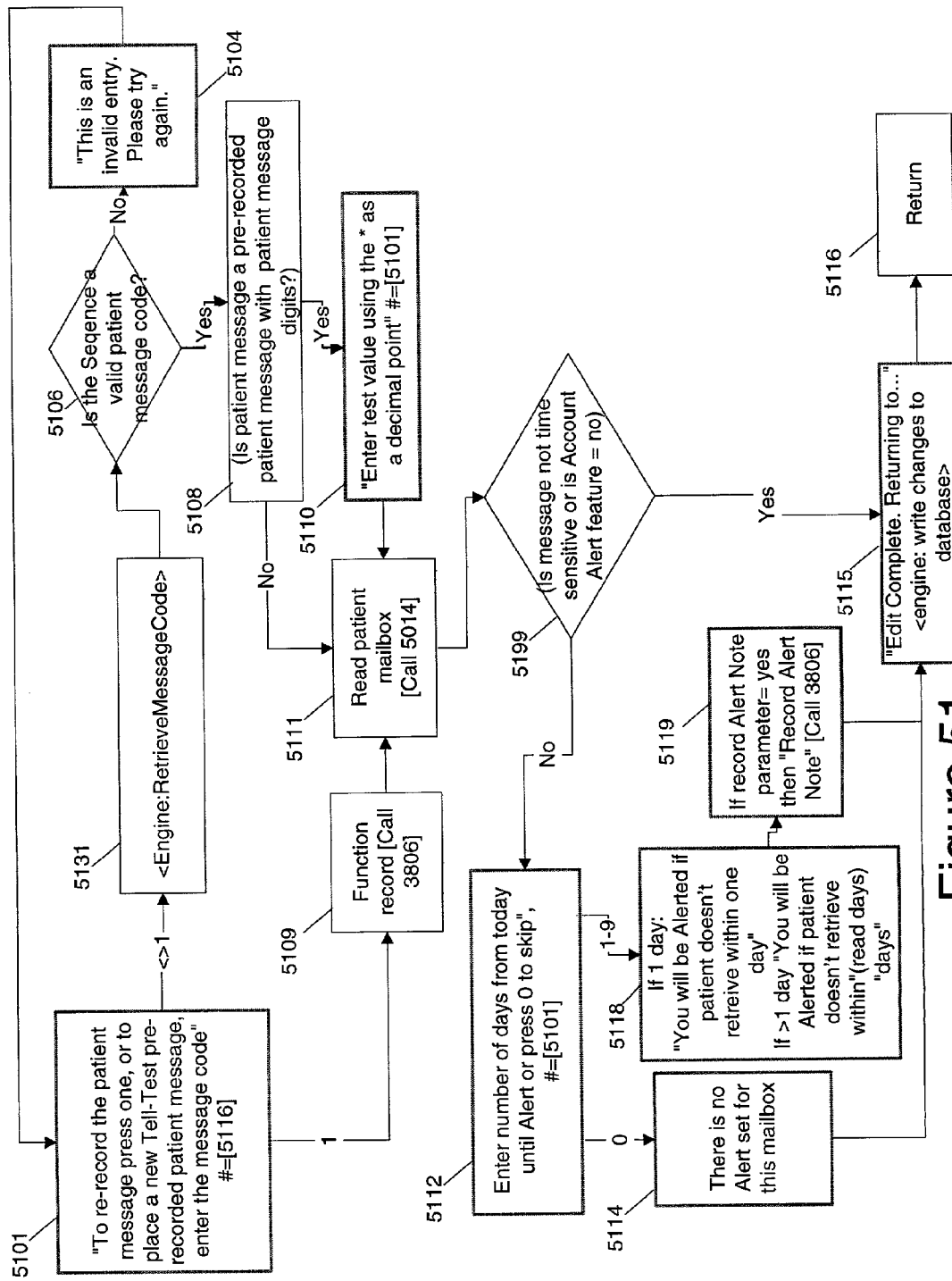
FIG. 51 illustrates a logic flow diagram for replacing a patient message in a medical information system in accordance with the present disclosure.

If "1" is entered, control is passed via logic block 2936 to logic block 5101 illustrated in FIG. 51 which illustrates a logic flow diagram for replacing a patient message.

Figure 48:
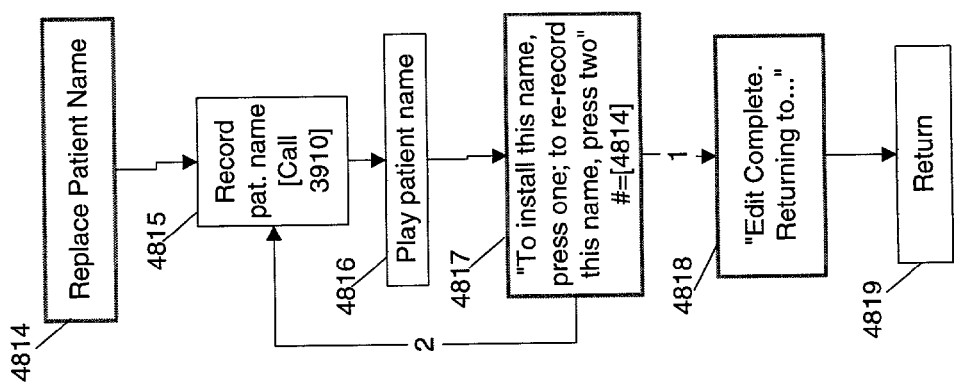
FIG. 48 illustrates a logic flow diagram for re-recording a patient name in a medical information system in accordance with the present disclosure.

If "2" is entered, control is passed via logic block 2937 to logic block 4814 illustrated in FIG. 48 which illustrates a logic flow diagram for re-recording a patient name.

Figure 46:
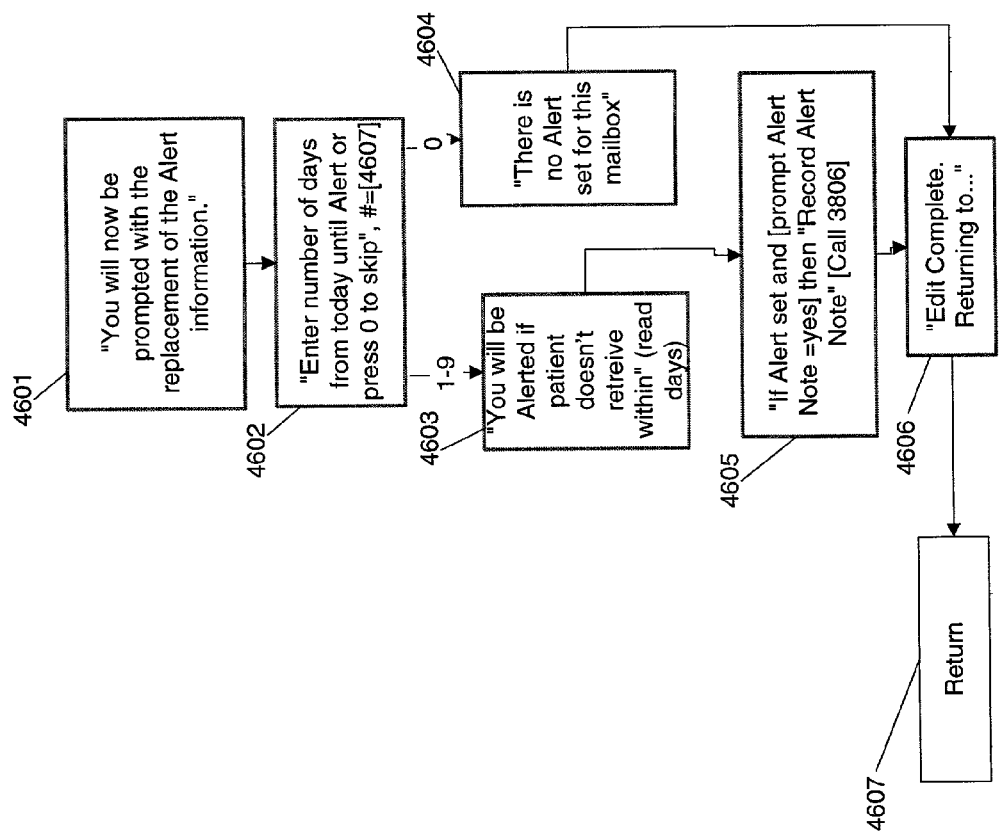
FIG. 46 illustrates a logic flow diagram for replacing alert information in a medical information system in accordance with the present disclosure.

If "3" is entered, control is passed via logic block 2938 to logic block 4601 illustrated in FIG. 46 which illustrates a logic flow diagram for replacing alert information.

When control returns to each of the above logic blocks from the logic called above, control is transferred to logic block 2941 where the edit flag is cleared. Control then passes to logic block 2942. From here control is returned to the logic block that passed control to logic block 2930.

Figure 30:
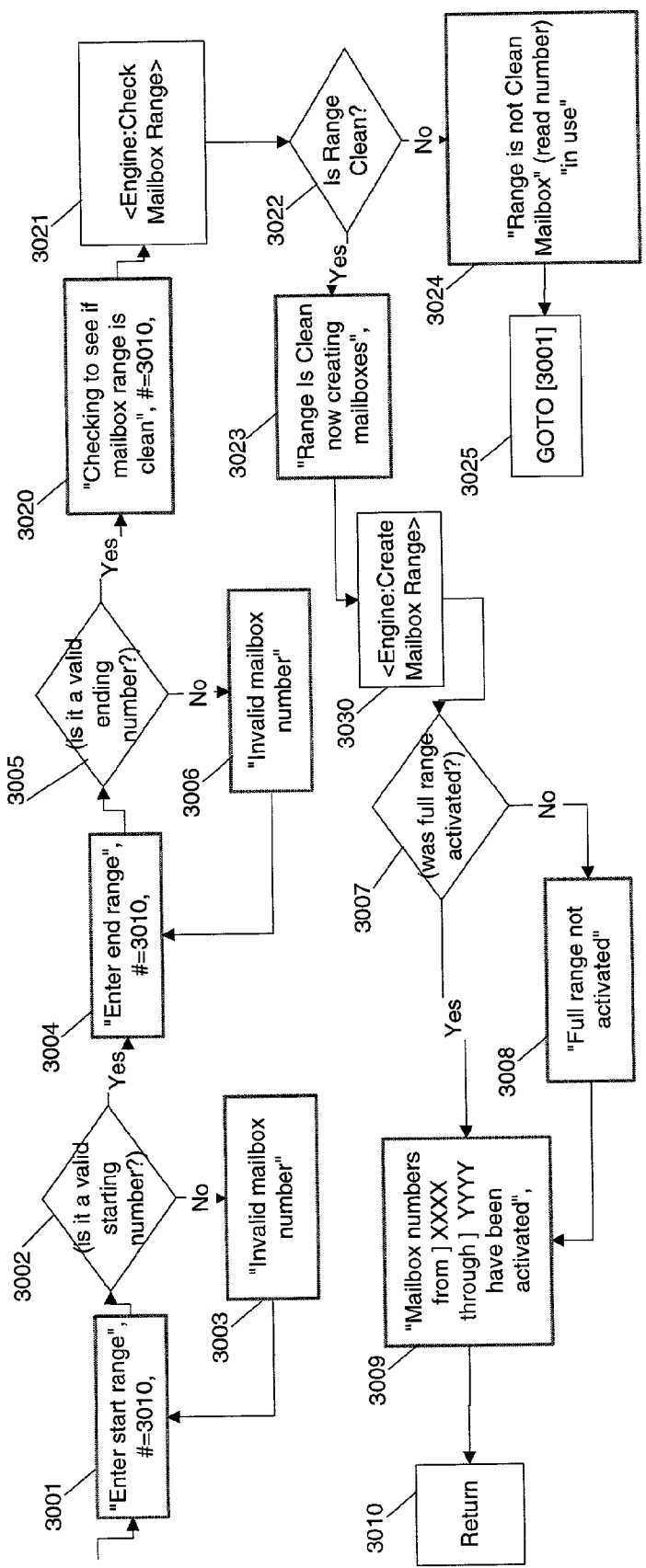
FIG. 30 illustrates a logic flow diagram for mailbox activation in a medical information system in accordance with the present disclosure.

FIG. 30 illustrates a logic flow diagram for mailbox activation. Control is passed to logic block 3001 where the administrator is prompted to enter the start of the range of mailboxes to be activated. Control then passes to logic block 3002 where a determination is made whether or not this is a valid starting number. If not, control is transferred to logic block 3003 where the administrator is informed that the entered number is invalid; control then passes back to logic block 3001.

If the entered number is determined to be valid in logic block 3002, control passes to logic block 3004 where the administrator is prompted to enter the end of the range of mailboxes to be activated. Control passes then to logic block 3005 to check if this is a valid ending number. If not, control passes to logic block 3006 where the administrator is so informed prior to control passing back to logic block 3004 for another entry.

If the number is determined to be valid in logic block 3005, control is passed to logic block 3020 to see if the indicated mailbox range is clean. By this is meant that there are no mailbox numbers in the range planned to be activated that are currently in use; the system is designed so that the system will not allow a mailbox number in use to be re-activated. Control is passed from logic block 3020 to logic block 3021 where the engine checks the indicated range. Control then is transferred to logic block 3022 and thence to logic block 3024 if the range is not clean where the user is so informed. Control then passes to logic block 3001 via logic block 3025. If the range is clean, control is passed from logic block 3022 to logic block 3023 where the administrator is notified that the range is clean and that the system is creating the mailboxes. Control next passes to logic block 3030 where the engine creates the mailboxes. Control next passes to logic block 3007 where a determination is made if the full range of mailboxes was activated. If not, control passes to logic block 3008 where the user is so informed prior to passing to logic block 3009 where the system proceeds as described below. If the full range of mailboxes was activated, control passes to logic block 3009 where the range of mailboxes that have been activated is read. Control then passes to logic block 3010 from whence control is returned to the logic block that transferred control to logic block 3001.

Figure 31:
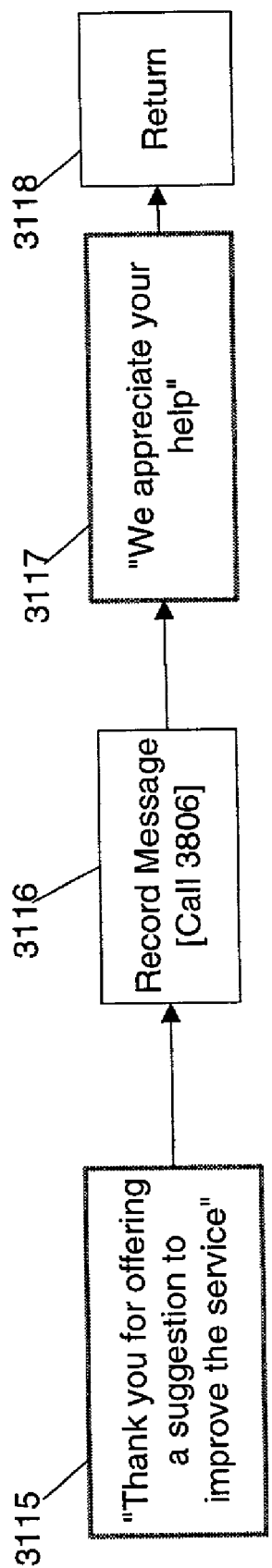
FIG. 31 illustrates a logic flow diagram for placing suggestions in a medical information system in accordance with the present disclosure.

FIG. 31 illustrates a logic flow diagram for an account owner to place suggestion messages to the administrator of the system. Control is passed to logic block 3115 where the account owner is thanked for offering a suggestion before being passed via logic block 3116 to logic block 3806 illustrated in FIG. 38 which illustrates recording information on the system with no review. When control returns from the logic illustrated in FIG. 38 to logic block 3116, control is transferred to logic block 3117 where the account owner is thanked. Control is then passed to logic block 3118 from whence control is returned to the logic block that passed control to logic block 3115.

FIG. 32 illustrates a logic flow diagram for recording pre-recorded patient messages on the system. Control is transferred to logic block 3201 where the account owner is requested to enter a pre-recorded patient message code. Control passes to logic block 3202 where two digits are retrieved except in the case where the first digit is "8"; in this case, the following two digits are retrieved. Control then passes to logic block 3204 where the engine retrieves the patient message code and determines if the entered code is valid and not a currently active account pre-recorded patient message code. If this is not the case, control is transferred to logic block 3203 where the user is notified the number is not suitable prior to control being passed back to logic block 3201 for entry of another number.

If the entered number is suitable, control is transferred to logic block 3208 where a prompt informs the account owner that the system is searching to determine whether or not the system may change the patient message associated with this number. Control then passes to logic block 3209 where the engine searches account patient messages to ascertain if the indicated pre-recorded patient message is currently in use in an unretrieved mailbox on the account. If so, control passes to logic block 3210 where a message is played indicating that a patient message code in use can not be changed; control is then returned to logic block 3201.

If the patient message code in question is not in use as determined in logic block 3209, control is passed to logic block 3205 where the account owner learns that the pre-recorded patient message code is available. Control then passes via logic block 3275 to logic block 3500 illustrated in FIG. 35 which illustrates a logic flow diagram for recording pre-recorded patient messages. When control returns from the logic illustrated in FIG. 35 to logic block 3275, control is passed next to logic block 3206 where the user is queried if another pre-recorded message is to be recorded. If the indicated answer is "yes", control is passed back to logic block 3201; if not, control is passed to logic block 3207 whence control is returned to the logic block that passed control to logic block 3201.

FIG. 33 illustrates a logic flow diagram for the administrator to shut down the system. Control is transferred to logic block 3320 where the administrator is told to press "1" to bring the system down and "2" to exit. If "2" or "#" is entered, control is transferred to logic block 3323 where the system shutdown is canceled and the administrator so informed. Control then passes to logic block 3324 where "Aborted" is caused to be returned to the logic block that transferred control to logic block 3320. If "1" is entered in response to the prompt in logic block 3320, control is transferred to logic block 3321 where system shutdown initiation is announced; then control passes to logic block 3325 where system shutdown is initiated. Control then passes to logic block 3360 whence control is returned to the logic block that passed control to logic block 3320.

FIG. 34 illustrates a logic flow diagram for changing the administrator fax number. Control is transferred to logic block 3415 where the current administrator fax number is read and thence to logic block 3416 where the administrator is prompted to enter a new fax number or press "#" to keep the current fax number. If "#" is entered, control is passed to logic block 3418 and thence to the logic block that passed control to logic block 3415. Otherwise, control passes to logic block 3417 where the engine determines if the entered phone number is allowed. If not, control is passed to logic block 3430 where the administrator is so informed prior to being transferred back to logic block 3416 for entry of another number. If the entered number is acceptable, control is passed from logic block 3417 back to logic block 3415 where the new fax number is read. If "#" is entered at logic block 3415, control passes to logic block 3418 whence the system proceeds as described above.

Figure 35:
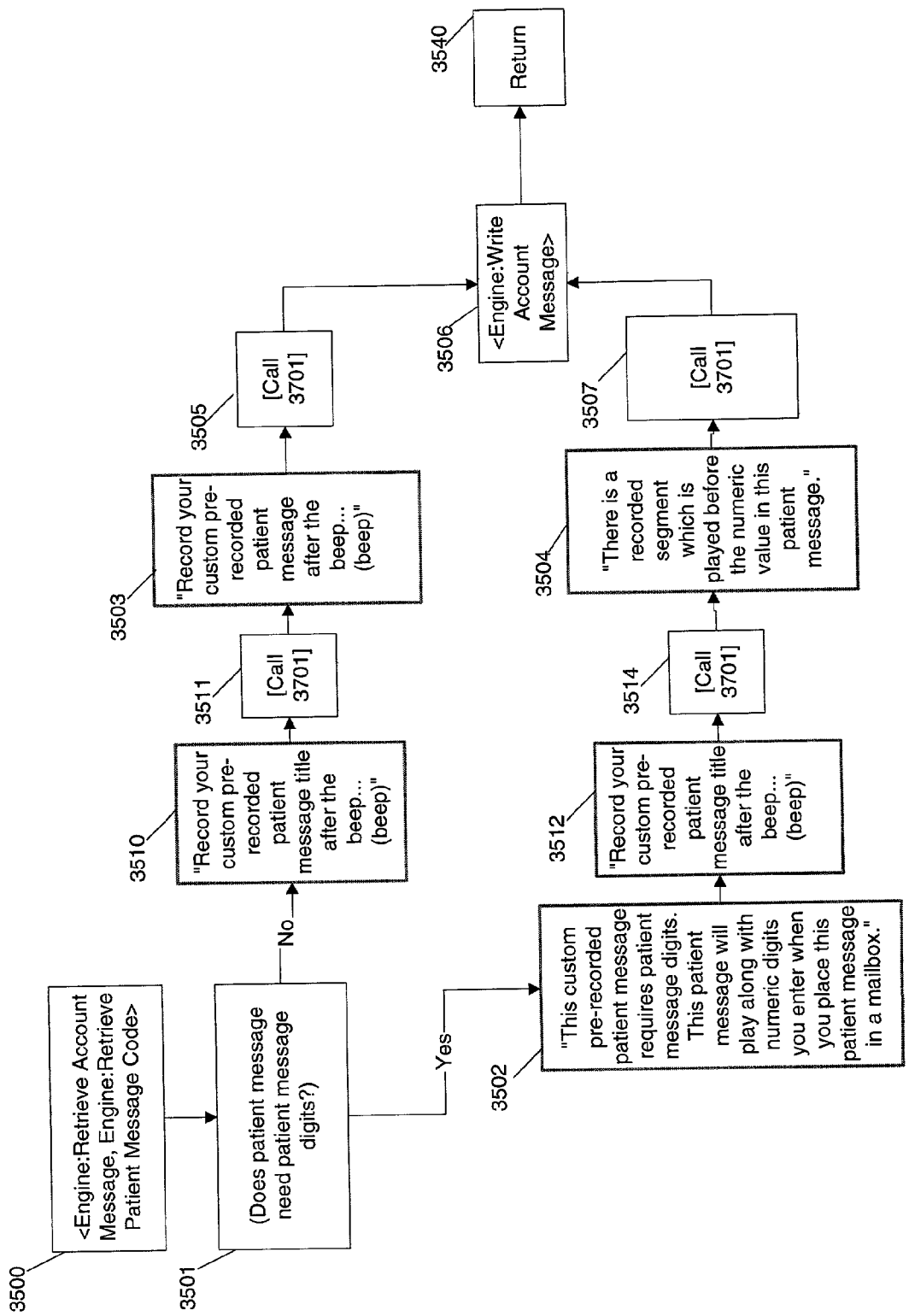
FIG. 35 illustrates a logic flow diagram for recording pre-recorded patient messages and titles to the messages (Part II) in a medical information system in accordance with the present disclosure.

FIG. 35 illustrates a logic flow diagram for recording pre-recorded messages in the system. Control is passed to logic block 3500 where the engine retrieves a patient message code and the corresponding patient message for the account. Control is then passed to logic block 3501 where a determination is made whether or not the message needs patient message digits or custom recorded message segment.

In an embodiment, the above logic flow diagram, including logic blocks 3502, 3512, 3504, 3507, 3506 can be modified to record custom recorded message segment that the system will append to a pre-recorded message.

If not, control is passed to logic block 3510 where the account owner is asked to record a custom pre-recorded patient message title after the beep. Control then passes via logic block 3511 to logic block 3701 illustrated in FIG. 37, which illustrates logic flow diagrams for recording information with review. When the control returns from the logic illustrated in FIG. 37 to logic block 3511, control is passed next to logic block 3503 where the account owner is asked to record a custom pre-recorded patient message after the beep. Control is next transferred via logic block 3505 to logic block 3701 illustrated in FIG. 37, which illustrates logic flow diagrams for recording information with review. Upon return of control from the logic illustrated in FIG. 37 to logic block 3505 control is transferred to logic block 3506 where the engine writes the previously recorded patient messages to the account database. Control then passes to logic block 3540 whence control returns to the logic block that passed control to logic block 3500.

If a determination is made in logic block 3501 that the patient message needs patient message digits (a pre-recorded message that will also play values of digits) or a custom recorded message segment, control is passed to logic block 3502 where the account owner is so informed and then transferred to logic block 3512 where the account owner is asked to record a title for the custom pre-recorded patient message after the beep. Control then passes via logic block 3514 to logic block 3701 illustrated in FIG. 37, which illustrates logic flow diagrams for recording information with review. When the control returns from logic illustrated in FIG. 37 to logic block 3514, control is passed next to logic block 3504 where the account owner is asked to record a custom pre-recorded patient message segment that is played before the patient message digits after the beep. Control is next transferred via logic block 3507 to logic block 3701 illustrated in FIG. 37, which illustrates logic flow diagrams for recording information with review. Upon return from the logic illustrated in FIG. 37 to logic block 3507 control is transferred to logic block 3506 where the engine writes the previously recorded patient messages to the account database. Control then passes to logic block 3540 whence control returns to the logic block that passed control to logic block 3500.

Figure 36:
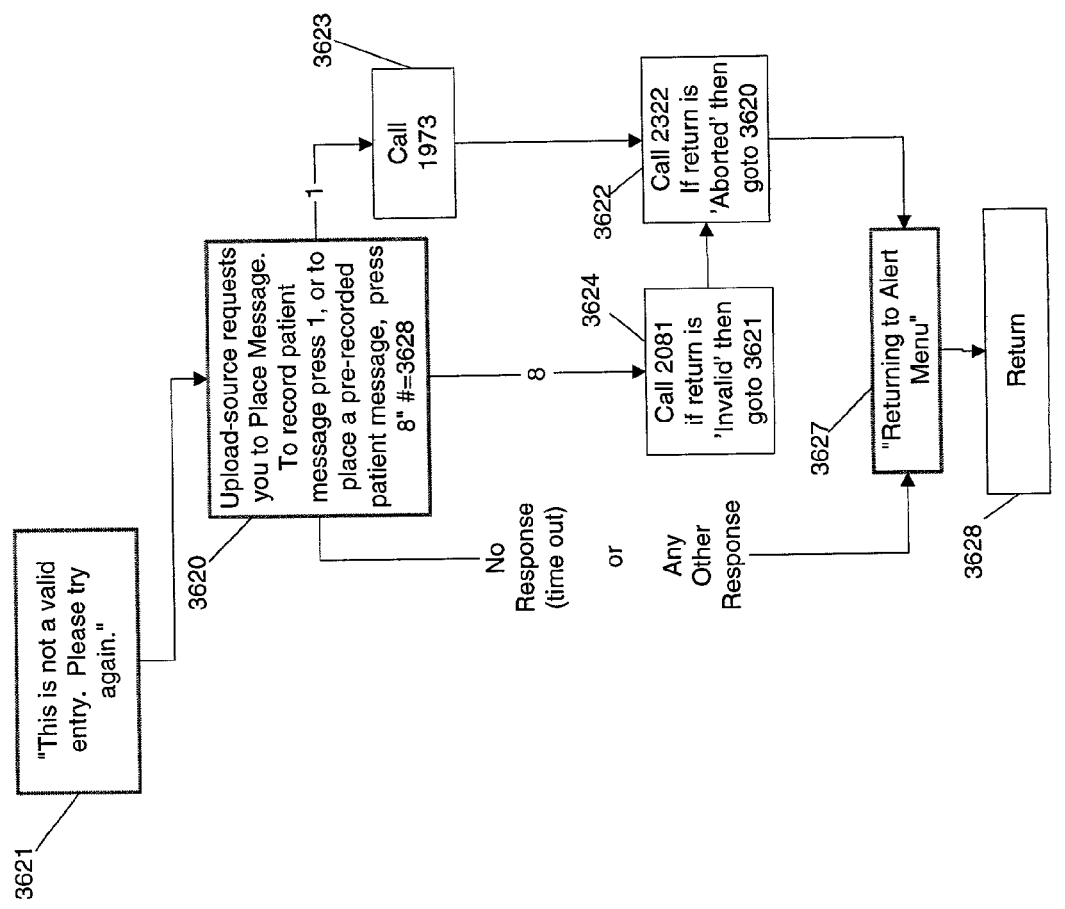
FIG. 36 illustrates a logic flow diagram for storing patient messages in response to an no-message alert in a medical information system in accordance with the present disclosure.

FIG. 36 illustrates a logic flow diagram for placing patient messages in response to a "no-message alert" in the system. Control is transferred to logic block 3620 where the account owner is informed that the upload-source requests a patient message be placed by the account owner in response to the upload-source note in the mailbox. The account owner is asked to press "1" to record a patient message or "8" to enter a pre-recorded patient message. If "1" is entered, control is passed via logic block 3623 to logic block 1973 illustrated in FIG. 19 which illustrates a logic flow diagram for recording a patient message. When control returns from logic illustrated in FIG. 19 to logic block 3623, control is next passed via logic block 3622 to logic block 2322 illustrated in FIG. 23 which illustrates a logic flow diagram for setting an alert note and the number of days until a patient-retrieval alert is activated. When control returns from logic illustrated in FIG. 23 to logic block 3622, control is passed next to logic block 3627 and the system proceeds as described below unless the return value from logic illustrated in FIG. 23 is "aborted" in which case control passes to logic block 3620 and the system proceeds as described herein.

If "8" is entered in response to the prompt in logic block 3620, control is passed via logic block 3624 to logic block 2081 illustrated in FIG. 20, which illustrates a logic flow diagram for placing a pre-recorded patient message in a mailbox in the system. Control is returned from the logic illustrated in FIG. 20 to logic block 3624. If the return is "Invalid", then control is passed to logic block 3621 where the account owner is so informed and asked to re-enter a pre-recorded patient message code; control is then passed back to logic block 3620 and the system proceeds as described herein. If the return value from logic illustrated in FIG. 20 to logic block 3624 is not "Invalid", control is passed to logic block 3622 and the system proceeds as described herein.

Control is passed from logic block 3622 to logic block 3627 where the account owner is informed that the system is returning to the alert menu.

If there is no response within a specific time interval to the prompt in logic block 3620 or if the response is other than "1" or "8", control passes from logic block 3620 to logic block 3627.

Control is passed from logic block 3627 to logic block 3628 whence control is returned to the logic block that passed control to logic block 3620.

FIG. 37 illustrates a logic flow diagram for recording information with review in the system. Control is passed to logic block 3701 with the user having been prompted to record at the beep. A beep is played in logic block 3701 and control is passed to logic block 3702 unless there is silence for a parameter maximum number of seconds in which case control is passed to logic block 3703. In logic block 3702 any touch tone ends the recording and control is transferred to logic block 3703 where a prompt plays first "You have recorded" and then the message that was just recorded. Control is then passed to logic block 3704 where the account owner is asked to press one to accept the recording and two to re-record. If the account owner presses "2", control passes back to 3701 for re-recording; if "1" is pressed, control passes to logic block 3705 where the control is returned to the logic block that originally passed control to logic block 3701.

FIG. 38 illustrates a logic flow diagram for recording information with no review in the system. Control is passed to logic block 3806 with the account owner having been prompted to record at the beep. A beep is played in logic block 3806 and control is passed to logic block 3807 unless there is silence for a parameter maximum number of seconds in which case control is passed to logic block 3808. In logic block 3807 any touch tone ends the recording and control is transferred to logic block 3808 where the control is returned to the logic block that originally passed control to logic block 3806.

FIG. 39 illustrates a logic flow diagram for recording a patient name in the system. Control is passed to logic block 3910 where the account owner is prompted to record the patient name. Control is then passed to logic block 3911 where any touch tone ends the recording. If there is silence for a parameter maximum number of seconds in logic block 3910 or logic block 3911, control is passed to logic block 3912. From logic block 3912 the control is returned to the logic block that originally passed control to logic block 3910.

Figure 40:
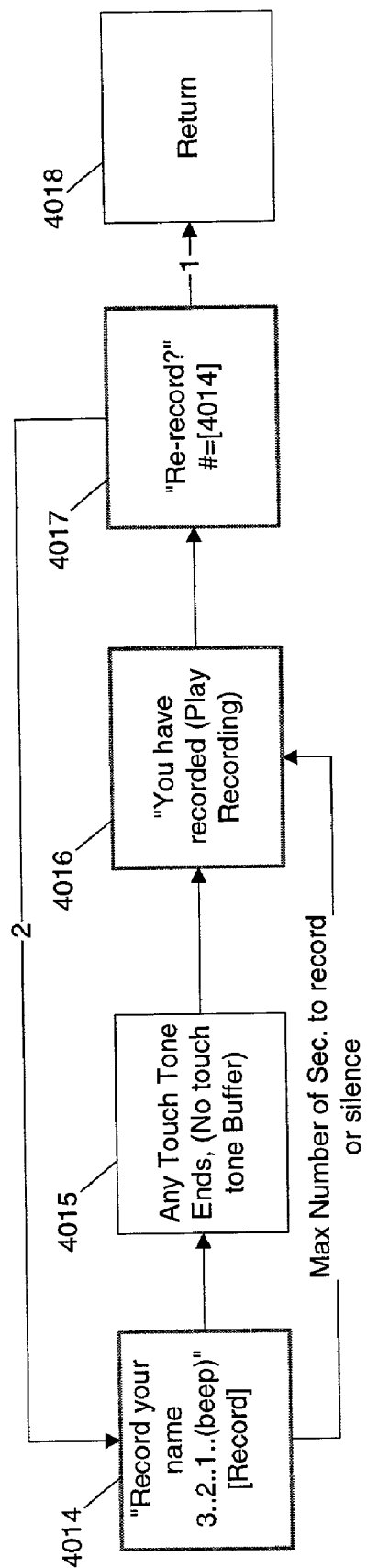
FIG. 40 illustrates a logic flow diagram for recording an account owner name in a medical information system in accordance with the present disclosure.

FIG. 40 illustrates a logic flow diagram for recording an account owner name in the system. Control is passed to logic block 4014 where the account owner is prompted to record the account owner name after a count down to a beep. Control is then passed to logic block 4015 where any touch tone ends the recording. If there is silence for a parameter maximum number of seconds in logic block 4014 or logic block 4015, control is passed to logic block 4016 where a prompt plays first "You have recorded" and then the name that was just recorded. Control is then passed to logic block 4017 where the account owner is asked to press one to accept the recording or two to re-record. If the recorder presses "2", control passes back to 4014 for re-recording; if "1" is pressed, control passes to logic block 4018 where the control is returned to the logic block that originally passed control to logic block 4014.

Figure 41:
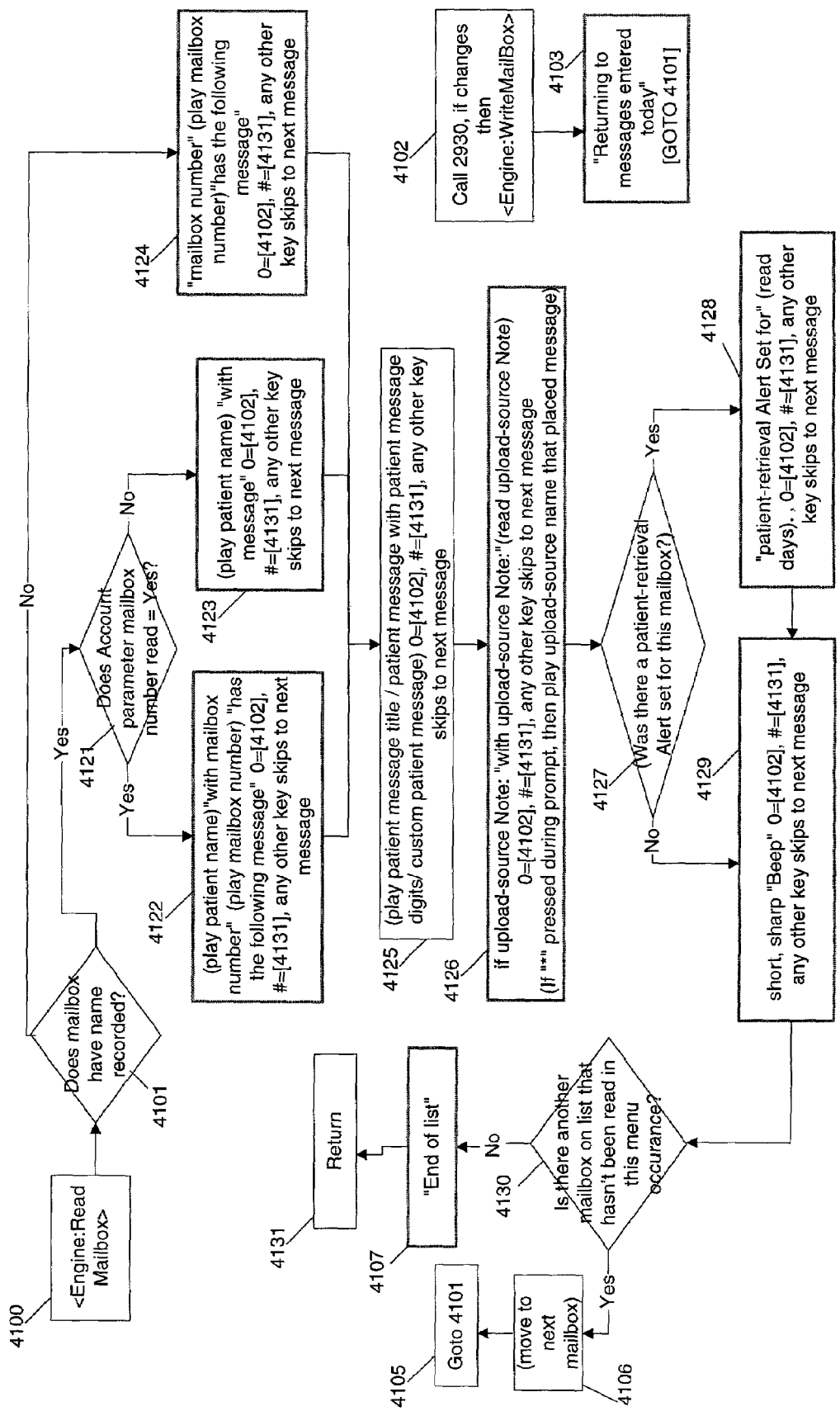
FIG. 41 illustrates a logic flow diagram flow for accessing a list of patients and their messages or message titles entered on a particular day in a medical information system in accordance with the present disclosure.

FIG. 41 illustrates a logic flow diagram for accessing a list of patients and their messages or patient message titles entered into the system on a particular day. Control is transferred to logic block 4100 where the engine reads the mailbox record and then control passes to logic block 4101 where a determination is made if the mailbox has the patient name recorded. If not, control is passed to logic block 4124 where prompts play the following messages: "Mailbox number" and the system then plays the mailbox number "has the following message". Control then passes to logic block 4125 and proceeds as described below.

If a determination is made in logic block 4101 that the account does have a name recorded, control passes to logic block 4121 where a determination is made if the account parameter that determines if the mailbox number is read is set to "yes" or "no". If "no", control is transferred to logic block 4123 where prompts produce the following statements: The system plays the patient name and then the prompt "with message". Control is then passed to logic block 4125 and the system proceeds as described below. If a determination is made that the parameter for mailbox number read is set to "yes", then control is transferred to logic block 4122 where prompts produce the following statements: The system plays the patient name, and next the following prompt "with mailbox number", and then the mailbox number, and next the following prompt: "has the following message". Control is then passed to logic block 4125 and the system proceeds as described below.

In logic block 4125 the system either plays the patient message title or a patient message with patient message digits or custom patient message (recorded at the time of message entry); control is then transferred to logic block 4126 where the upload-source note for the mailbox is read if there is any. Control then passes to logic block 4127 where a determination is made if patient-retrieval alert is active for this mailbox. If no, control passes to logic block 4129 where the system proceeds as described below. If yes, control passes to logic block 4128 where the system informs the account owner of the patient-retrieval alert and the day for which the alert is set. Control then passes to logic block 4129 where a short sharp beep plays prior to control being transferred to logic block 4130 where a determination is made whether or not there is another mailbox on the list that has not been read in this menu access. If not, control passes to logic block 4107 which states the end of the list has been reached and then to logic block 4131 whence control returns to the logic block that originally passed control to logic block 4100.

If a determination is made in logic block 4130 that there is another mailbox to read, control passes to logic block 4106 wherein the next mailbox to be read is retrieved prior to control returning to logic block 4101 via logic block 4105. The above sequence then repeats. Note that in logic blocks 4122, 4123, 4124, 4125, 4126, 4128, and 4129 if the account owner interrupts with (a) "0" control is transferred to logic block 4102 and the system proceeds as described below or (b) "#" control is transferred to logic block 4131 and the system proceeds as described before or (c) any other key in which case the system skips ahead to the next message. If "*" is entered in logic block 4126 by the user, the system plays a prompt stating "This result was uploaded by" and then states the name of the upload-source that uploaded the upload-source note in question. Control is transferred back to logic block 4126 after this.

If control is transferred to logic block 4102 by the user pressing "0" in one of the above logic blocks, control then passes to logic block 2930 illustrated in FIG. 29, which illustrates a logic flow diagram for editing a patient message without reading the message. If changes are made in the patient message, then the engine writes these changes to the mailbox database. After this and upon return of the control to logic block 4102 from logic illustrated in FIG. 29, control passes to logic block 4103 where the user is informed that the system is returning to reading the patient messages entered today and control is passed back to logic block 4101.

Figure 42:
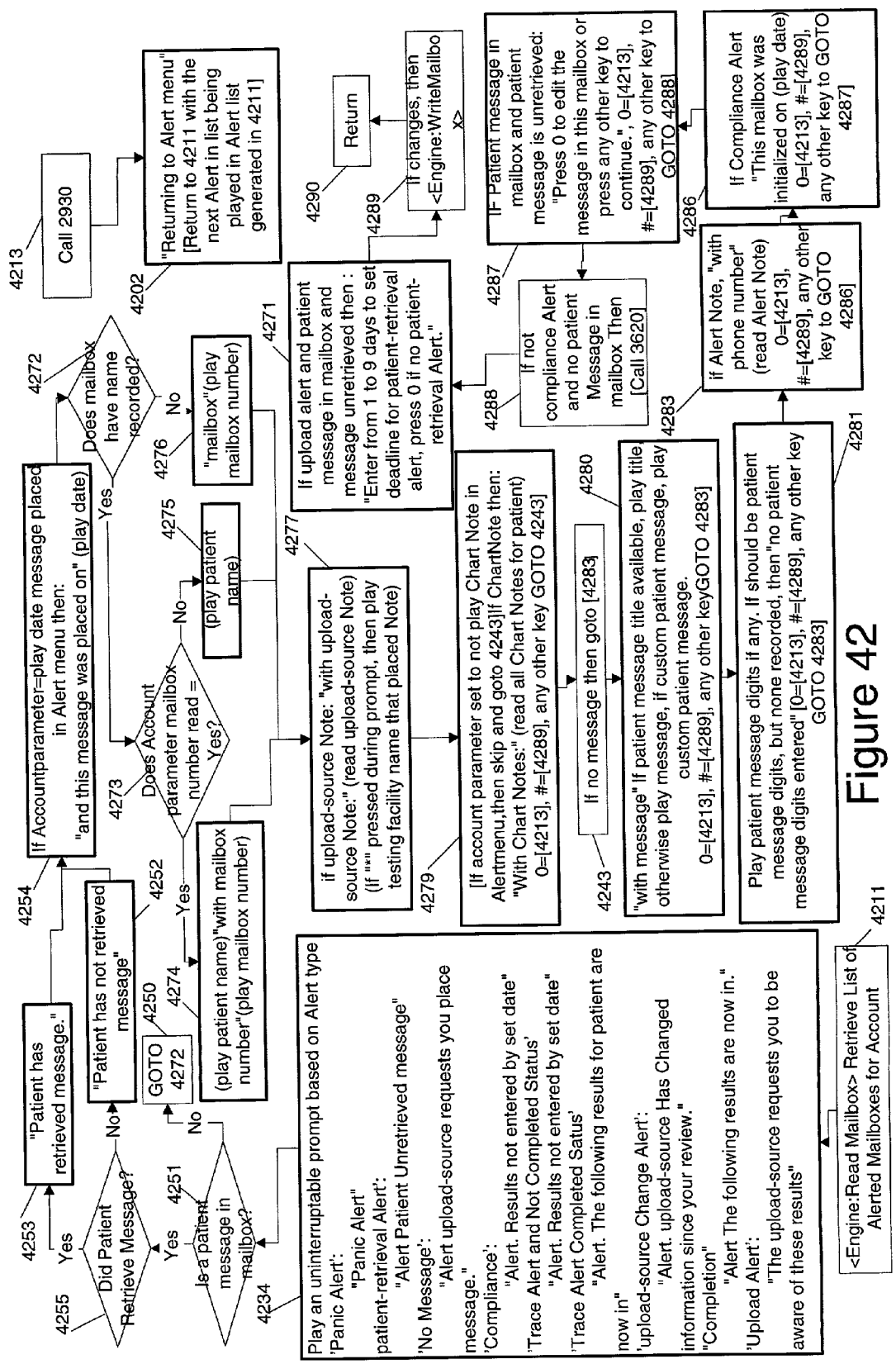
FIG. 42 illustrates a logic flow diagram for an account owner to access alert information in the account in a medical information system in accordance with the present disclosure.

FIG. 42 illustrates a logic flow diagram for an account owner to access his or her alerts. The alerts are presented in a pre-determined order, which, for example, could be as follows: panic alerts, patient-retrieval alerts, no-message alerts, compliance alerts, trace alerts with non-completed status, trace alerts with completed status, upload-source-change alerts, completion alerts, and upload-source upload alerts.

Control is transferred to logic block 4211 where the engine reads the mailbox database and retrieves the list of alerted mailboxes for the account. Control is then transferred to logic block 4234 where a non-interruptible prompt is played based on the type of the alert selected from the list to be read at that time. The alert types and the corresponding prompts are as follows:

Panic alert: "Panic alert"

Patient-retrieval alert: "Alert: Patient unretrieved message"

No-Message alert: "Alert: upload-source requests you place a patient message in this mailbox Compliance alert: "Alert: Results have not been entered by set date"

Trace alert (Non-Completed Status): "Alert: The patient results have not been entered by set date"

Trace alert (Completed Status): "Alert: The following results for patients are now in"

Upload-source-change alert: "Alert: Upload-source has changed information since your review"

Completion alert: "Alert: The following results are now in"

Upload-source alert: "Alert: The upload-source requests you are aware of these results."

Control is then transferred to logic block 4251 where a determination is made whether or not a patient message is in the mailbox. If not, control is transferred to logic block 4250 which transfers control to logic block 4272 where the system proceeds as described below. If there is a patient message in the mailbox being accessed, control is transferred to logic block 4255 where it is determined whether or not the patient has retrieved the message. If so, control is transferred to logic block 4253 where the account owner is so informed. If not, control is transferred to logic block 4252 where the account owner is informed that the patient has not retrieved the message in the mailbox.

From logic block 4253 or logic block 4252 control is transferred to logic block 4254 where, if the appropriate account parameter is set to allow reading of date on which the message was placed in the mailbox at this point, the account owner is so informed of this information. If the aforementioned parameter is not set to allow this, the account owner is not so informed at this point. Control is then transferred from logic block 4254 to logic block 4272 where it is determined whether or not the mailbox has the patient name recorded. If not, control passes to logic block 4276 where the system plays the prompt "mailbox" followed by the mailbox number before passing control to logic block 4277. If the name is recorded, control passes to logic block 4273 where a determination is made whether or not the account has a parameter set to read mailbox numbers at this point. If not, control passes to logic block 4275 where the patient name is read prior to control passing to logic block 4277. If the account is set to play mailbox numbers, control passes from logic block 4273 to logic block 4274 where the system first plays the patient name to the account owner followed by the prompt "with mailbox number" which is followed by reading the mailbox number. Control is then passed to logic block 4277.

In logic block 4277, if the mailbox has an upload-source note, the system plays a prompt "with upload-source note" and then plays the upload-source note. If the account owner presses "*" here, the system plays the prompt "This result was uploaded by" followed by the name of the upload-source that uploaded this result. Control is then transferred to logic block 4279 where if the account has a parameter set not to play chart notes in this alert menu control is transferred to logic block 4243. If this is not the case and the mailbox has chart note(s), where the chart note(s) are read. If the user presses any touch tone key besides "0" or "#" while in this logic block, control is transferred to logic block 4243 at that point. At the completion of the chart note read in logic block 4279 control passes to logic block 4243 where control is transferred to logic block 4283 if there is no patient message in the mailbox. Otherwise control passes to logic block 4280 where the title of the patient message is played unless there is no title available in which case the patient message is played. If the user presses any touch tone key besides "0" or "#" while in this logic block, control is transferred to logic block 4283 at that point. At the completion of the patient message or patient message title read, control is next transferred to logic block 4281 where any patient message digits are played if the patient message is the type that has patient message digits; if the patient message is not of this type, control is passed directly to logic block 4283. If the user presses any touch tone key besides "0" or "#" while in logic block 4281, control is transferred to logic block 4283 at that point.

In an embodiment, in logic block 4277, if the mailbox from which information presented to the account owner has a panic alert, then the panic alert is deleted from the mailbox automatically or at the users option.

In an embodiment, once alert information has been presented to the account owner, the appropriate alert is set to saved status, or at the users option deleted.

In logic block 4283 the system reads the phone number of the patient that is in the alert note. If the user presses any touch tone key besides "0" or "#" while in this logic block, control is transferred to logic block 4286 at that point. From logic block 4283 control passes to logic block 4286 where if the alert is a compliance alert, the system states the date on which the mailbox was initialized. If the user presses any touch tone key besides "0" or "#" while in this logic block, control is transferred to logic block 4287 at that point. From logic block 4286 control passes to logic block 4287 where the user is told, if there is a patient message in the mailbox and the patient message has not been retrieved by the patient, to "Press 0 to edit the message in this mailbox or press any other key to continue." If the user presses any touch tone key besides "0" or "#" while in this logic block, control is transferred to logic block 4288 at that point except in the case of not a compliance alert in mailbox and no patient message, then control is transferred to logic block 3620. Control is then transferred to 4271.

If the user presses "0" in logic block 4287, control is next transferred to logic block 4213 where the system proceeds as described below.

Control is then passed to logic block 4288 whereupon, if the alert is not a compliance alert and there is no patient message in the mailbox, control is transferred to logic block 3620 illustrated in FIG. 36 which illustrates a logic flow diagram for placing a patient message in a mailbox in response to a no-message alert. When control returns to logic block 4288 from logic illustrated in FIG. 36 or if control is not transferred to logic illustrated in FIG. 36 from logic block 4288, control passes to logic block 4271 where if the alert is an upload-source alert and there is an unretrieved patient message in the mailbox, the account owner is prompted to "Enter from one to nine days to set a deadline for patient retrieval or press "0" for no patient-retrieval alert."

Control is then transferred to 4289 where, if there are changes to the mailbox data fields, these are written by the engine to the mailbox database. Control passes then to logic block 4290 which returns the control to the logic block that passed control originally to logic block 4211.

Note that in logic blocks 4279, 4280, 4281, 4283, 4286, or 4287 if the account owner interrupts with "0" control is transferred to logic block 4213 and the system proceeds as described below or if the account owner interrupts with "#" control is transferred to logic block 4289 and the system proceeds as noted above.

If control is transferred to logic block 4213 control passes to logic block 2930 illustrated in FIG. 29 which illustrates a logic flow diagram for editing a patient message without reading the message. On return of control from logic illustrated in FIG. 29 to logic block 4213 control passes to logic block 4202 where the user is informed that the system is returning to the alert menu and control is passed to logic block 4211.

Figure 43:
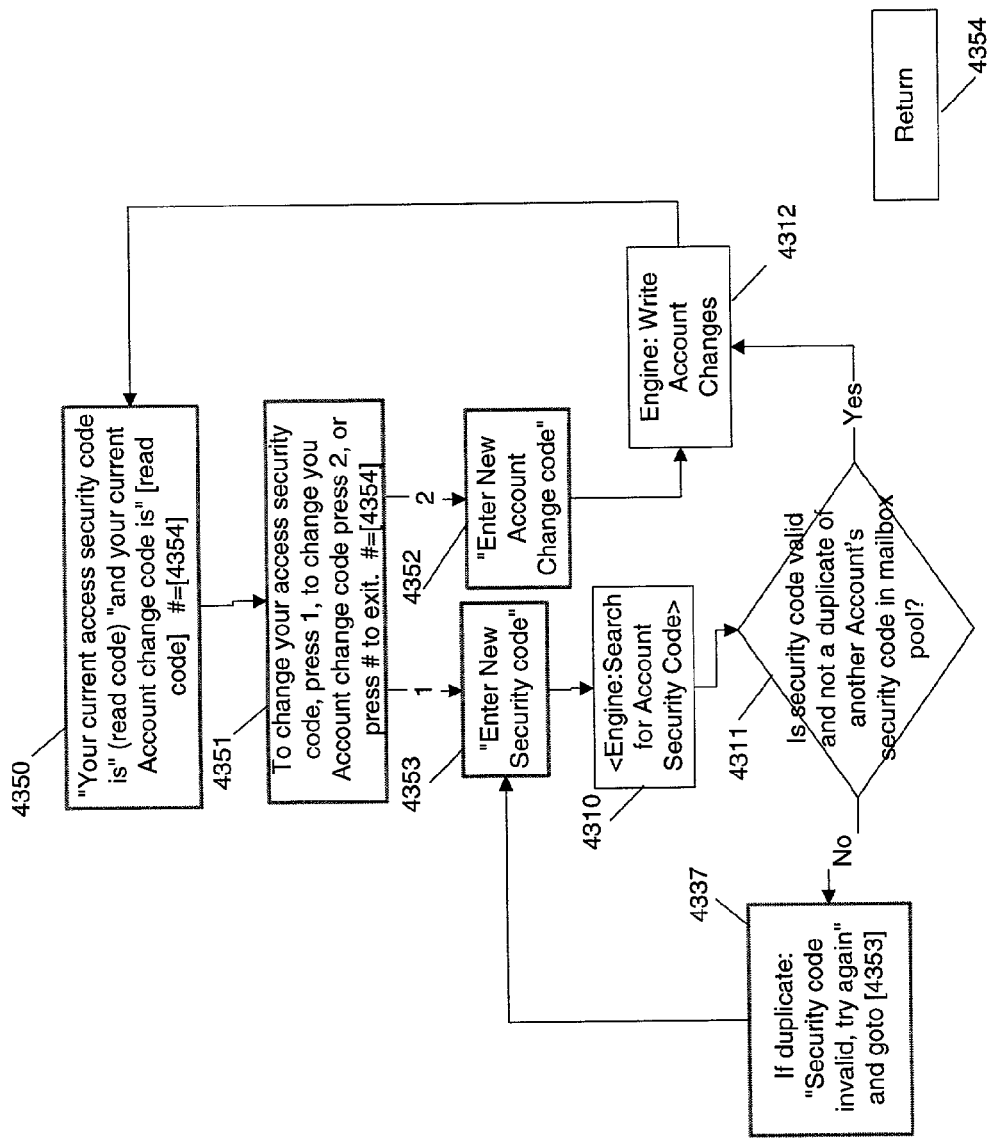
FIG. 43 illustrates a logic flow diagram for changing the access security code and/or account change code for an account owner in a medical information system in accordance with the present disclosure.

FIG. 43 illustrates a logic flow diagram for changing the access security code and/or account change code for an account. Control is passed to logic block 4350 where the user is informed of the current access security code and the current account change code. If the user enters "#" here, control is transferred to logic block 4354 where control passes back to the logic block that transferred control to logic block 4350. If "#" is not entered, control then transfers to logic block 4351 where the user is asked to press "1" to change the access security code and to press "2" to change the account change code or to press "#" to exit. If the user presses "2", control is transferred to logic block 4352 where the user is prompted to enter the new account change code; control then passes to logic block 4312 where the engine writes the changes to the account database prior to transferring control back to logic block 4350. If the user presses "1" in response to the prompt of logic block 4351, control is passed to logic block 4353 where the user is prompted to enter a new security code. Control then passes to logic block 4310 where the engine searches for the entered code to see that the code entered is not already in use, and then control passes to logic block 4311. If a duplicate is found, control is transferred to logic block 4337 and the account owner is informed that the code is invalid. Control then passes back to logic block 4353 where the account owner is prompted to enter another. If the entered code is acceptable, control passes to logic block 4312 where the engine updates the account database prior to transferring control back to logic block 4350.

Figure 44:
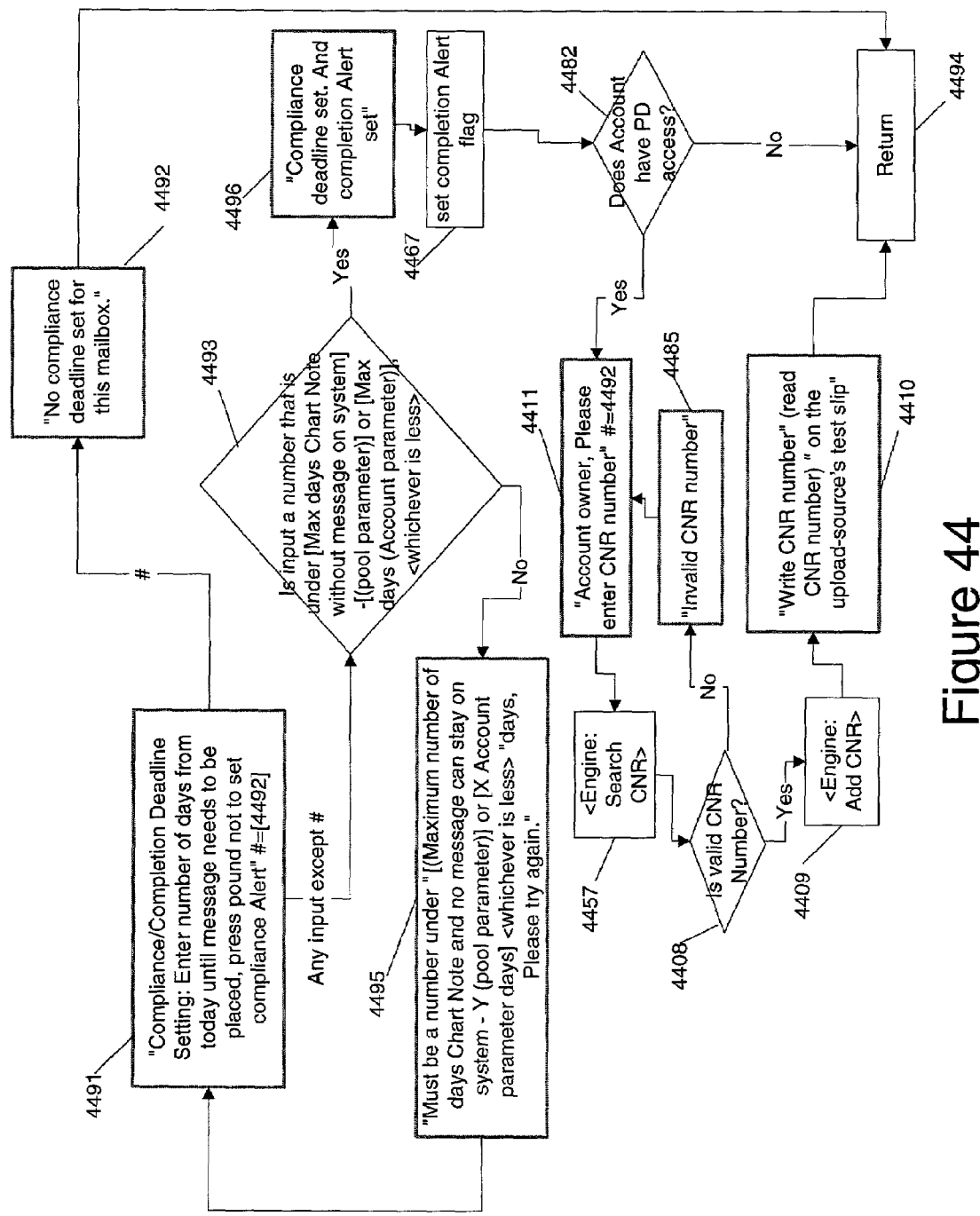
FIG. 44 illustrates a logic flow diagram for completion and compliance alert information entry in a medical information system in accordance with the present disclosure.

FIG. 44 illustrates a logic flow diagram for completion and compliance alert information entry in the system. Control is passed to logic block 4491 where the user is requested to enter the number of days from the present day until the patient message needs to be placed to avoid activating the alert. The user is told to enter "#" to cancel setting a compliance or completion alert. If the user enters "#", control is transferred to logic block 4492 where a prompt announces that no compliance deadline will be set for this mailbox and control is passed to logic block 4494 and the system proceeds as described below.

Otherwise, control is transferred to logic block 4493 where a determination is made whether or not the input is less than the smaller of two parameters: (a) the maximum number of days that a chart note may remain on the system without a patient message in the mailbox (a pool parameter) and (b) an account parameter for the maximum value of the time period being set. If this is not true, then control is transferred to logic block 4495, where the user is informed of these parameter limits and asked to reset the deadline and control is returned to logic block 4491. If the input is smaller than the above two parameters, control is transferred to logic block 4496 where the user is informed that the compliance deadline and completion alert have been set. Control then passes to logic block 4467 where the completion alert flag is set for the mailbox and then is passed to logic block 4482 where a determination is made whether or not the mailbox is part of an account with access to a patient database. If not, control is passed to logic block 4494 whence control is returned to the logic block that passed the control originally to logic block 4491. If this is an account with PD access, control passes to logic block 4411 where the account owner is prompted to enter a CNR number before passing to logic block 4457 where the engine does a search for the CNR. Control passes next to logic block 4408 where a determination is made whether or not the entered number is a valid CNR. If not, control passes to logic block 4485 where the user is so informed and then to logic block 4411 for re-entry of a CNR. If a valid CNR number is entered as determined in logic block 4408 then control passes to logic block 4409 in which the engine adds the CNR to the mailbox database. Control is then transferred to logic block 4410 where the account owner is requested to write the CNR and upload-source instructions on the lab test slip which is given to an upload-source; control then passes to logic block 4494 for processing as noted above.

FIG. 45 illustrates a logic flow diagram for deleting or saving an alert that has been accessed in the system. Control is passed via logic block 4563 to logic block 4211 illustrated in FIG. 42 which illustrates a logic flow diagram for an account owner to access alerts in the account. When control returns to logic block 4563 from logic illustrated in FIG. 42 control is passed to logic block 4562 where the account owner is asked to press "1" to delete the alert or any other key to save the alert. If "1" is pressed the alert is deleted and control is passed to logic block 4565 where a determination is made if there are more entries in the list of alerted mailboxes. If yes, control transfers to logic block 4564 which causes the next alerted mailbox to be selected. Control then passes to logic block 4563 for processing as above. If, a determination is made in logic block 4565 that there are no further alerts, control passes to logic block 4566 and thence is returned to the logic block that originally passed the control to logic block 4563.

If "#" or any other key but "1" is entered in logic block 4562, control is passed to logic block 4561 where the current alert is saved and a determination is made if there are more panic alerts. If there are more panic alerts, control is passed to logic block 4564 for processing as described above. If there are not more panic alerts, control passes to logic block 4566 where the system proceeds as noted above.

FIG. 46 illustrates a logic flow diagram for replacing patient-retrieval alert information. Control is transferred to logic block 4601 where the account owner is informed that he or she will be prompted regarding replacing the patient-retrieval alert information. Control is then passed to logic block 4602 where the account owner is prompted to enter the number of days until the patient-retrieval alert should be activated or to press "0" to not set a patient-retrieval alert. If "0" is entered, control passes to logic block 4604 where the account owner is informed that there is no patient-retrieval alert set for this mailbox and control is passed to logic block 4606 where the account owner is informed that the edit is complete. Control then passes to logic block 4607 whence control is returned to the logic block that originally passed control to logic block 4601.

If the account owner enters a digit in the range of "1" to "9" inclusive in response to the prompt in logic block 4602, control is passed to logic block 4603 where the account owner is informed that he or she will be alerted if the patient does not retrieve the message within the deadline date. Control then transfers to logic block 4605 where if the alert has been set and the system is configured to prompt for alert notes, the account owner is prompted to record an alert note. Control then passes to logic block 4606 to be processed as described above.

Figure 47:
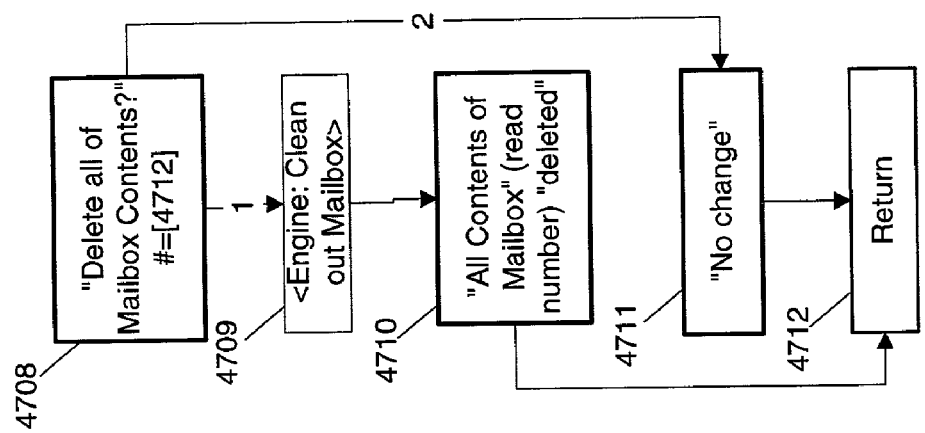
FIG. 47 illustrates a logic flow diagram for deleting mailbox contents in a medical information system in accordance with the present disclosure.

FIG. 47 illustrates a logic flow diagram for deleting the contents of a mailbox. Control is passed to logic block 4708 where the account owner is asked to press "1" to delete all the mailbox contents or "2" to not make any changes. If "2" is entered, control transfers to logic block 4711 where the account owner is informed no change was made in the mailbox and control is passed to logic block 4712 whence control returns to the logic block that originally transferred control to logic block 4708.

If the account owner enters "1" in response to the prompt in logic block 4708, control is transferred to logic block 4709 where the mailbox is cleaned out—i.e., all data from the mailbox record is removed except for the security code and the mailbox is removed from any lists and collections for both the account owner and the upload-source except the collection of unused mailboxes to which the mailbox is added. Control then passes to logic block 4710 where the account owner is informed that all contents of the mailbox were deleted. Control then passes to logic block 4712 whence control returns to the logic block that originally transferred control to logic block 4708.

FIG. 48 illustrates a logic flow diagram for re-recording a patient name in the system. Control is passed to logic block 4814 where the account owner is asked to replace the patient name. Control then passes to logic block 3910 illustrated in FIG. 39 which illustrates a logic flow diagram for recording a patient name. Upon return of control to logic block 4815 from logic illustrated in FIG. 39 the control is transferred to logic block 4816 where the patient name just recorded is played. Control then transfers to logic block 4817 where the account owner is asked to press "2" to re-record the name or "1" to install the name. If "2" is entered, control transfers back to logic block 4815 and the system proceeds as previously described. If "1" is pressed, control passes to logic block 4818 where the account owner is informed that the edit is completed before control passes to logic block 4819 and thence to the logic block that originally transferred control to logic block 4814.

FIG. 49 illustrates a logic flow diagram for on-line training in the system. Control is passed to logic block 4901 where the account owner is informed of the on-line help menu by the following prompt: "Press one for an explanation of how to set up mailboxes and place patient messages; press two for information on alerts; press three to learn about advanced features; press four to submit a suggestion or testimonial; press "#" to return to the main menu." On pressing "#" control is transferred to logic block 4999 whence control returns to the logic block that transferred control to logic block 4901 originally.

On pressing "1" control is transferred to logic block 4902 where the appropriate prompt is played and thence back to logic block 4901.

On pressing "2" control is transferred to logic block 4905 where the appropriate prompt is played and thence back to logic block 4901.

On pressing "3" control is transferred to logic block 4903 where an appropriate informational message is played that includes a query as to whether the account owner desires to be prompted to place the patient's phone number on the system when placing a patient-retrieval alert. If the account owner chooses to do this, control is transferred to logic block 4904 which causes the engine to set this feature to be enabled in the account parameters. If the account owner chooses not to have this feature, control is transferred to logic block 4920 where the engine disables this feature. Control is transferred from logic block 4904 or logic block 4920 to logic block 4906 where the account owner is informed that the system is returning to the on-line help menu and control is transferred to logic block 4901.

On pressing "4" control passes via logic block 4922 to logic block 3115 illustrated in FIG. 31 which illustrates a logic flow diagram for placing suggestions in the system. Upon return of control from logic illustrated in FIG. 31 to logic block 4922 control is passed back to logic block 4901.

Figure 50:
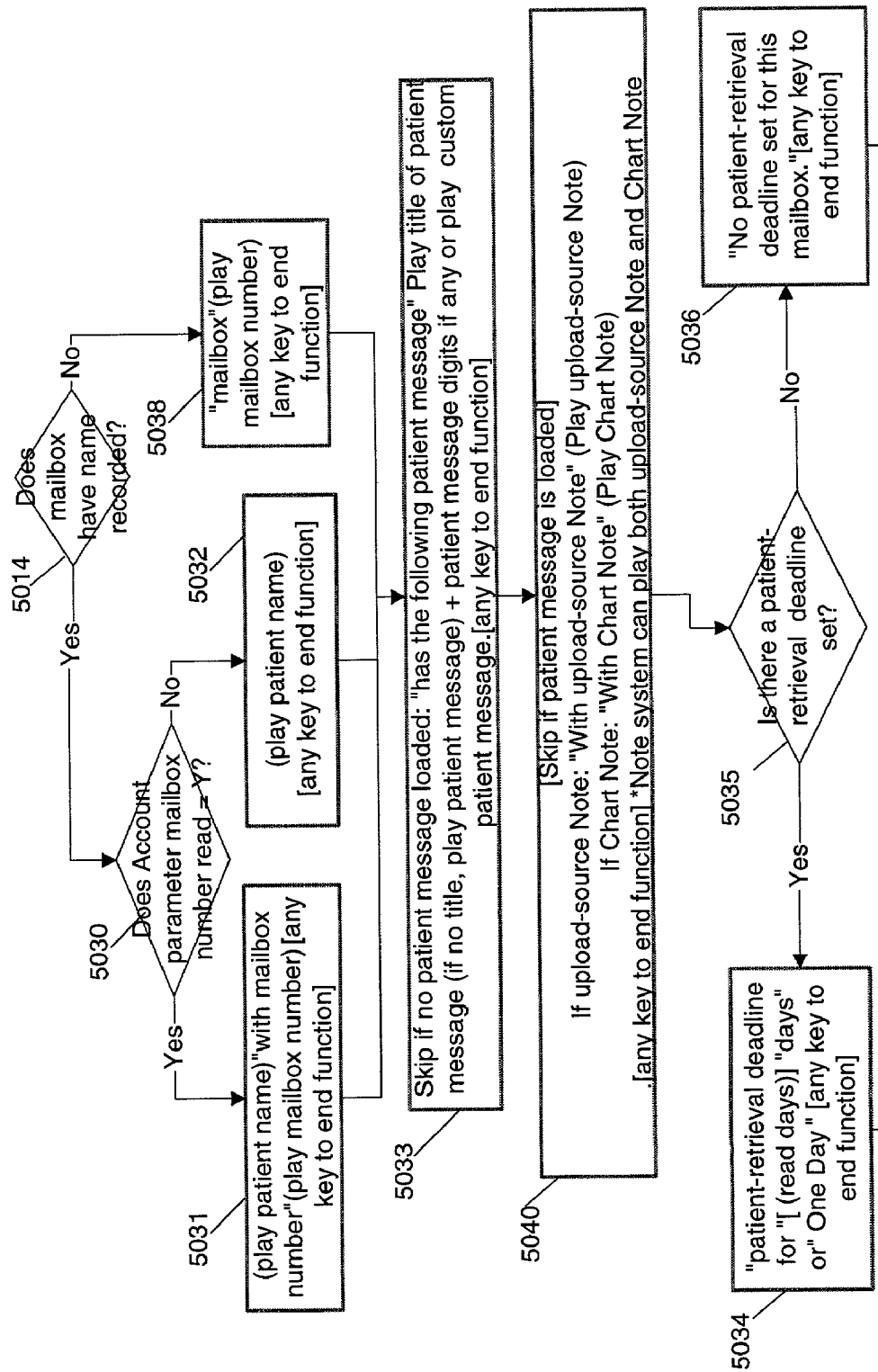
FIG. 50 illustrates a logic flow diagram for reading a patient mailbox content in a medical information system in accordance with the present disclosure.

FIG. 50 illustrates a logic flow diagram for reading the contents of a patient mailbox in the system. Control is passed to logic block 5014 where a determination is made if the mailbox record has a patient name recorded. If not, control is passed to logic block 5038 where the system first reads the prompt "mailbox" and then the number of the mailbox; control then passes to logic block 5033.

If a determination is made in logic block 5014 that there is a recorded name in the mailbox, control passes to logic block 5030 where a determination is made whether or not an account parameter is set such that the mailbox number is read at this point. If not, control is passed to logic block 5032 where the patient name is played prior to control passing to logic block 5033. If the mailbox number is to be read, control passes to logic block 5031 where the system proceeds as follows: The patient name is played followed by the prompt "with mailbox number" and then the mailbox number is read. Control then passes to logic block 5033. In logic block 5033, if there is no patient message in the mailbox, control passes directly to logic block 5040. If there is a patient message in the mailbox, the system plays the title of the patient message and any patient message digits or if the title is not available, then the patient message and any patient message digits. Control then passes to logic block 5040 and thence directly to logic block 5035 if there is patient message loaded in the mailbox. If the latter is not the case, the system first plays any upload-source notes associated with the mailbox and then any chart notes associated with the mailbox before passing control to logic block 5035 where a determination is made if there is a patient-retrieval alert deadline set.

If there is no patient-retrieval alert deadline set, control passes to logic block 5036 where the user is informed of this and thence to logic block 5037 where control is returned to the logic block that originally transferred control to logic block 5014.

If there is a patient retrieval deadline set, control passes to logic block 5034 where the user is informed of this and the number of days this alert is set for and thence to logic block 5037 where control is returned to the logic block that originally transferred control to logic block 5014.

Note that in logic blocks 5031,5032,5038,5033,5040, 5034, or 5036 that if the account owner presses any key, the function in the respective logic block ends and control passes to the succeeding logic block as indicated.

FIG. 51 illustrates a logic flow diagram for replacing a patient message in the system. Control is passed to logic block 5101 where the user is prompted to press one to re-record the patient message or to enter a pre-recorded patient message code to place a new pre-recorded patient message. If the user enters "1", control is transferred via logic block 5109 to logic block 3806 illustrated in FIG. 38 which illustrates a logic flow diagram for recording information on the system with no review. When control returns from logic illustrated in FIG. 38 to logic block 5109, control is passed next to logic block 5111 and the system proceeds as described below.

If the user enters a pre-recorded patient message code in response to the prompt of logic block 5101, control passes to logic block 5131 wherein the engine retrieves the pre-recorded patient message code. Control next passes to logic block 5106 where a determination is made whether or not the entry is a valid pre-recorded patient message code. If not, control passes to logic block 5104 where the user is so informed; then control is transferred back to logic block 5101. If the entry is a valid pre-recorded patient message code, control passes to logic block 5108 where a determination is made whether or not the patient message is a pre-recorded patient message with patient message digits. If not, control passes to logic block 5111 where the system proceeds as described below. If the patient message is a patient message with patient message digits, control passes to logic block 5110 where the user is prompted to enter the test value. Control then passes via logic block 5111 to logic block 5014 illustrated in FIG. 50 which illustrates a logic flow diagram for reading the contents of a patient mailbox. The patient message is read here and then control is passed to logic block 5199 where, if the patient message is not time sensitive or the account is configured with the alert feature not enabled, control is transferred to logic block 5115. Otherwise, control is transferred to logic block 5112 where the user is prompted to enter the number of days until the patient-retrieval alert should be activated or "0" to not set a patient-retrieval alert. If the user enters "0", control is passed to logic block 5114 which informs the user that no patient-retrieval alert is set for this mailbox and then control passes to logic block 5115. If a digit from "1" to "9" inclusive is entered, control passes to logic block 5118 where the user is informed when the system will activate the patient-retrieval alert. Control then passes to logic block 5119 where, if the account is configured to prompt for alert notes, the user is prompted to enter the patient's phone number. Control then passes to logic block 5115 where the user is informed that the edit is complete before control is transferred to logic block 5116 and thence to the logic block that originally transferred control to logic block 5101.

Figure 52:
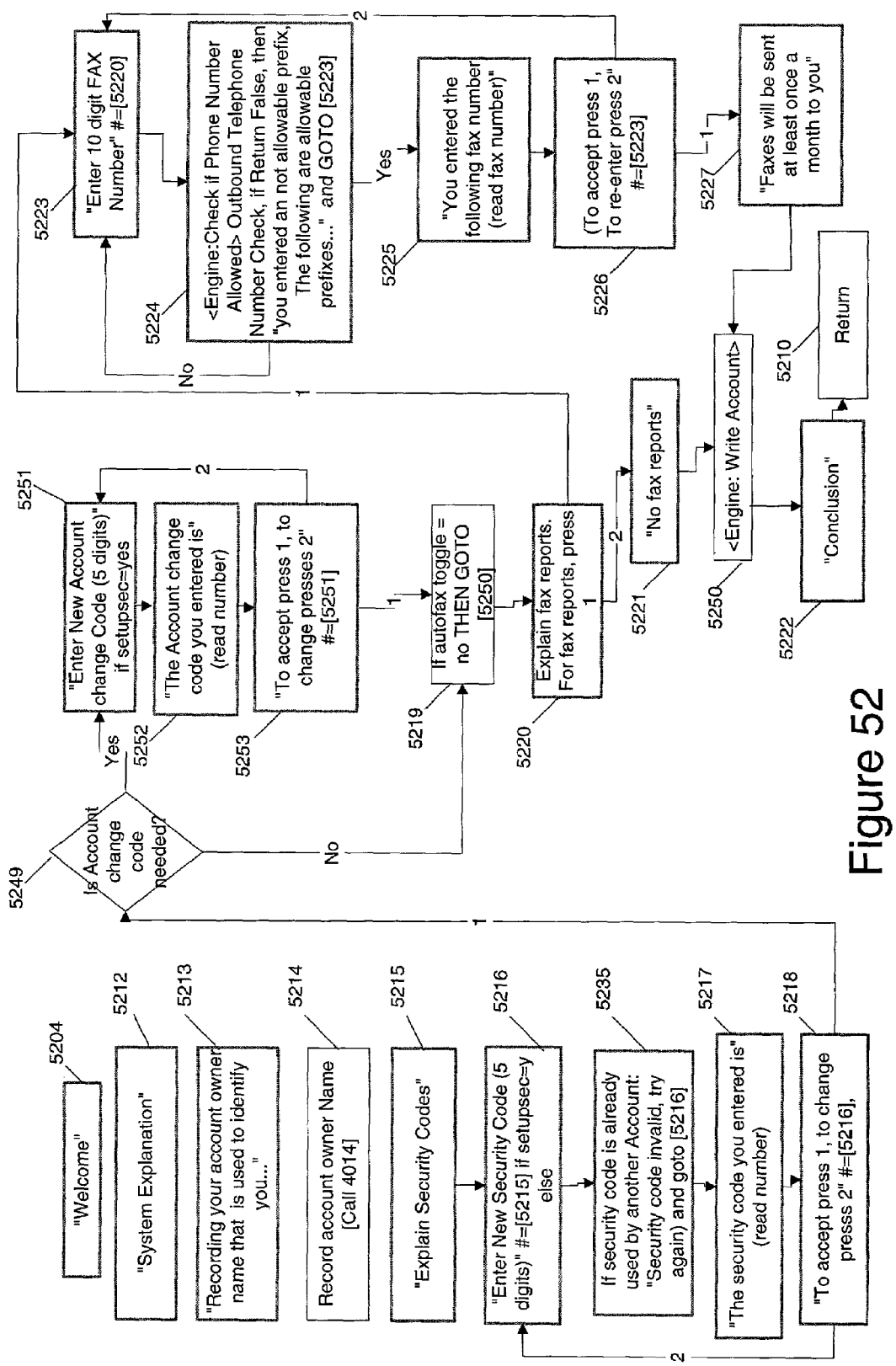
FIG. 52 illustrates a logic flow diagram of an account owner entering a medical information system for the first time and recording an account owner name and selecting a personal security code and fax number and, if appropriate, a new account change code according to the present disclosure.

FIG. 52 illustrates a logic flow diagram for an account owner entering the system for the first time and recording an account owner name and selecting a personal security code and fax number and, if appropriate, a new account change code. Control is transferred to logic block 5204 where the account owner is greeted and then passes to logic block 5212 where the operation of the system is briefly explained. The prompt played here is appropriate to the type of account. Control then passes to logic block 5213 where the account owner is prompted to record the name patients will hear when they call for results. Control then transfers via logic block 5214 to logic block 4014 illustrated in FIG. 40 which illustrates a logic flow diagram for recording an account owner's name. Upon return of control from logic illustrated in FIG. 40 to logic block 5214 control passes to logic block 5215 where security codes are explained in a prompt appropriate for the account. The existence of a second security code, the account change code, for accounts with the appropriate parameter settings is explained here. This is a different code so that, for example, laboratory personnel may enter the system to leave messages using the account's security code, but only persons who know a separate account change code would be able to change the account settings using logic as illustrated in FIG. 24.

Control then passes to logic block 5216 where the account owner is prompted to enter a new security code and then to logic block 5235 where the engine checks to see if this security code is in use by another account on the system. If this is the case, the system requests another code and transfers control back to logic block 5216. If the entered code is acceptable, control is transferred to logic block 5217 where the entry is read back to the account owner. Control then passes to logic block 5218 where the account owner is asked to press "1" to accept the code and "2" to change the code. If the user presses "2", control is transferred back to logic block 5216 and the system proceeds as described above.

If the account owner presses "1", control is transferred to logic block 5249 where a determination is made whether or not an account change code is needed. If not, control transfers to logic block 5219 and the system proceeds as described below. If an account change code is needed, control transfers to logic block 5251 where the account owner is prompted to enter a new account change code and then to logic block 5252 where this entry is read back. The account owner is then prompted in logic block 5253 to press "1" to accept this entry and "2" to change entry. If the account owner presses "2", control passes back to logic block 5251 and the system proceeds as described above. If the account owner presses "1", control is passed to logic block 5219 where a determination is made whether or not the system is configured to have automatic fax reports sent to the account owner. If not, control is transferred to logic block 5250 where the engine writes the entered account information to the appropriate databases and the system proceeds as described below.

If the system is configured to send automatic fax reports to the account owner, control is transferred from logic block 5219 to logic block 5220 where a prompt explains the fax report option to the account owner. If the account owner then chooses not to have fax reports by pressing "2", control is transferred to logic block 5221 where the account owner is informed that these will not be sent and then to logic block 5250 where the system proceeds as described below.

If the account owner chooses to have fax reports sent in response to the prompt of logic block 5220 by pressing "1", control is passed to logic block 5223 where the account owner is prompted to enter a ten digit fax number. Control then passes to logic block 5224 where the engine checks if the fax number entered is an allowable number on the system. If not, the account owner is so informed and also informed of allowed prefixes and area codes and control transfers back to logic block 5223 for re-entry. If the number entered is allowable, control transfers to logic block 5225 where the fax number is read back to the account owner and then to logic block 5226 where the account owner is prompted to enter "1" to accept and "2" to re-enter a fax number. If "2" is entered, control passes back to logic block 5223 where the system proceeds as described.

If "1" is entered, control passes to logic block 5227 where a prompt informs the account owner that faxes will be sent at least monthly. Control then passes to logic block 5250 where the engine writes the entered account information to the appropriate databases. Control is then transferred to logic block 5222 where the account owner is informed that the system is ready for patient message entry. Control then passes to logic block 5210 whereupon control is transferred to the logic block that originally passed control to logic block 5204.

FIG. 53 illustrates a logic flow diagram for an account owner to access a list of patient names and messages and upload-source notes uploaded into the system by one or more upload-sources. Control is passed to logic block 5375 wherein the engine retrieves a list of upload events and then passes to logic block 5301 where a determination is made whether or not there are any uploaded patient messages and upload-source notes to review. If not, control passes to logic block 5309 where the user is informed that there are no items on this list prior to control being passed to logic block 5310 whence control returns to the logic block that originally passed control to logic block 5375.

If there are uploaded patient messages and upload-source notes to review as determined in logic block 5301, control is transferred to logic block 5302 where the account owner learns of the number of messages and upload-source notes uploaded by upload-sources that are to be reviewed prior to control passing to logic block 5303 where the account owner is informed that information from these upload results is to be played. Control is then transferred via logic block 5304 to logic block 4100 illustrated in FIG. 41 which illustrates a logic flow diagram for accessing a list of patients and their messages entered on a particular day on the system. Upon return of control from logic illustrated in FIG. 41 to logic block 5304, control is passed to logic block 5350 where a prompt indicating the end of the list is played.

Control then passes to logic block 5305 where the account owner is told to press "1" to clear the list of uploaded patients just played or "2" to save the list and exit. If the account owner presses any key but "1", control is transferred to logic block 5307 where the list is saved and the account owner is so informed prior to control transferring to logic block 5308 whence control is passed to logic block 5310 to be processed as noted above. If the account owner presses "1" in response to the prompt of logic block 5305, control passes to logic block 5350 where the engine deletes the collection of upload events just played prior to the passage of the control to logic block 5306 where a prompt informs the user that the list has been cleared. Control then passes to logic block 5308 where the system proceeds as previously described.

FIG. 54 illustrates a logic flow diagram for an administrator to access an account's parameters in the system. Control is passed to logic block 5420 where a prompt states that "This account has the following account settings" before control passes to logic block 5421 where the system informs the administrator whether or not the account is currently activated or not. Control then passes to logic block 5422 where the security code of the account is played and then to logic block 5423 where, if there is an account change code, this is played. Control then passes to logic block 5424 where the number of faxes left for the account for this month is played. Control is then transferred to logic block 5425 where the administrator is informed if the account is set for prompting to record the alert note or not. Control then passes to logic block 5426 where the system informs the user if the account owner is on beginning or advanced menu's. Control then passes to logic block 5427 where the number of unused mailboxes left on the account is read or the system informs the user that the account is configured to have no limit on the number of mailboxes; if there are no mailboxes left for this account, this information is also stated here. Control then passes to logic block 5430 whence control is returned to the logic block that originally transferred control to logic block 5420.

FIG. 55 illustrates a logic flow diagram for setting the number of mailboxes on an account in the system. Control is transferred to logic block 5501 where a determination is made whether or not the system is configured so that the number of mailboxes allowed is limited or not. If the number of mailboxes for the account is not limited, control is transferred to logic block 5503 where this is stated prior to control passing to logic block 5504 for the system to proceed as described below. If there is a limit on mailboxes for the account, control is passed to logic block 5502 where the number of unused mailboxes remaining in the account is stated before control is passed to logic block 5504.

In logic block 5504 the administrator is prompted to press "1" to change the account's configuration or any other key to keep the same account configuration. If any key except "1" is pressed, control passes to logic block 5505 whence control is returned to the logic block that passed control originally to logic block 5501. If "1" is entered in response to the prompt in logic block 5504, control is passed to logic block 5506 where the administrator is prompted to press "1" for unlimited mailboxes and "2" for a new amount of mailboxes. If "1" is entered, control passes to logic block 5508 and the number of mailboxes for the account is set to be unlimited. If "2" is entered, control passes to logic block 5507 where the administrator is prompted to enter the new amount of mailboxes. From logic block 5508 or logic block 5507 control is passed to logic block 5509 whence control passes back to logic block 5501 for processing as described above.

Figure 56:
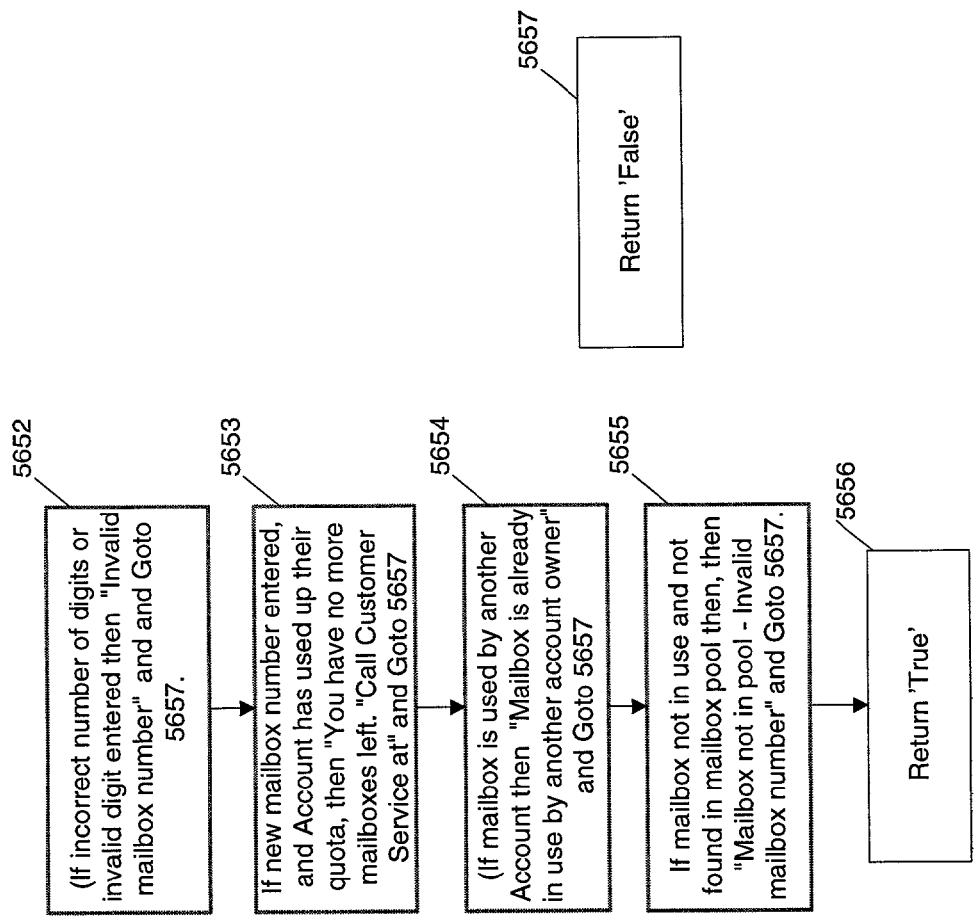
FIG. 56 illustrates a logic flow diagram to check whether or not a mailbox number is valid on an account in a medical information system in accordance with the present disclosure.

FIG. 56 illustrates a logic flow diagram to check whether or not a mailbox number is valid on an account in the system. Control is passed to logic block 5652 where a determination is made whether or not an incorrect number of digits or an invalid key was entered; if this is the case, a prompt so stating is played and control is passed to logic block 5657 whence "False" is returned to the logic block that originally passed control to logic block 5652. If no errors in entry are detected in logic block 5652, control is passed to logic block 5653 where a determination is made whether or not the account has any more mailboxes left. If not, the account owner is advised to call customer service. If there are mailboxes left, control is transferred to logic block 5654 where a determination is made whether or not the mailbox is in use on another account. If so, the account owner is so informed. If not, control is passed to logic block 5655 where, if the mailbox is not in use and is not found in the mailbox pool, the account owner is so informed and is informed that this is an invalid mailbox number. Otherwise, control transfers to logic block 5656, which causes "True" to be returned to the logic block that originally passed control to logic block 5652.

Figure 57:
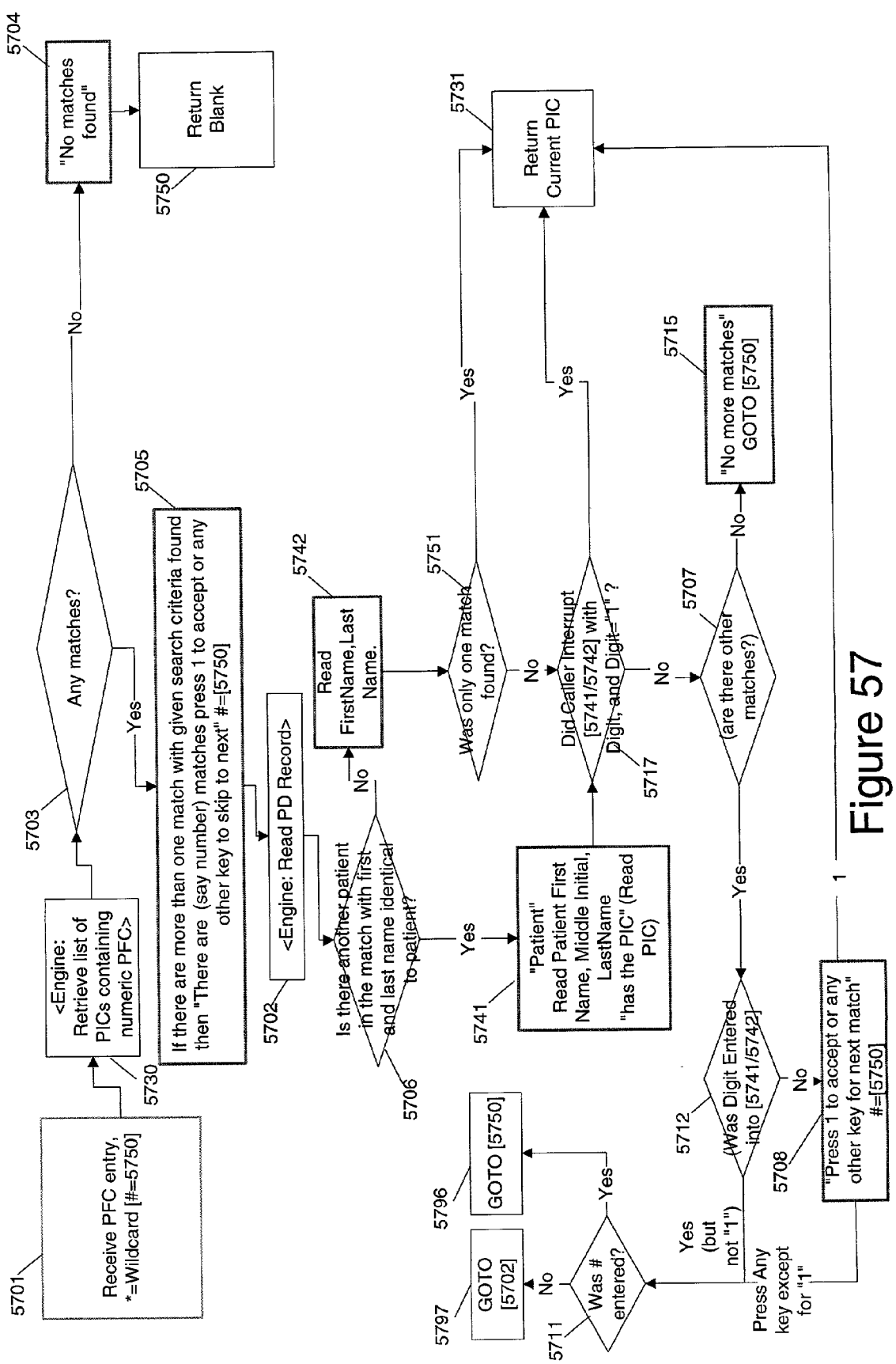
FIG. 57 illustrates a logic flow diagram in a medical information system with patient database access for locating a patient identification code from a patient finder code entry in accordance with the present disclosure.

FIG. 57 illustrates a logic flow diagram in a system with patient database access for locating a patient identification code (PIC) from a patient finder code (PFC) entry. Control is received in logic block 5701 where the PFC is entered. The key "*" acts as a wildcard in the entry and can represent any digit from "1" to "9". Control passes from logic block 5701 to logic block 5730 where the engine retrieves a list of PICs containing the entered PFC. Control then passes to logic block 5703 where a determination is made whether or not there are any matches of PIC's to the PFC. If not, control passes to logic block 5704 where this is stated prior to control passing to logic block 5750 which causes "Blank" to be return to the logic block that originally transferred control to logic block 5701.

If there are matches found in logic block 5703 then control passes to logic block 5705 where, if the number of matches is one or greater, the number of matches is stated and the user is requested to press "1" to accept a match or any other key to skip to the next match. Control then passes to logic block 5702 where the engine reads the PD record of the match. Control then passes to logic block 5706 where a determination is made whether or not there is another patient in the matches found with first and last name identical to the patient in the PD record just played. If not, control is passed to logic block 5742 where the first and last name of the patient are played. Control then passes to logic block 5751 where a determination is made whether or not only one match was found. If this is the case then control passes to logic block 5731. In logic block 5731 the current PIC is returned to the logic block that originally transferred control to logic block 5701.

If a determination is made in logic block 5751 that more than one match was found, control passes to logic block 5717 where the system proceeds as described below.

If in logic block 5706 a determination is made that there is another patient with identical first and last names, control is transferred to logic block 5741 where the patient first name, middle initial, and last name is read along with the PIC. Control then transfers to logic block 5717 where a determination is made whether or not the user interrupted with a digit and if that digit was "1". If yes, control is transferred to logic block 5731 for processing as described above. If not, control is transferred to logic block 5707 where a determination is made whether or not there are other matches. If not, control is transferred to logic block 5715 where the user is so informed and thence to logic block 5750 where the system proceeds as previously described. If there are other matches, control passes to logic block 5712 where the system accesses if a digit was entered in logic block 5741 or logic block 5742. If not, control passes to logic block 5708 where the user is asked to press "1" to accept or any other key to proceed to the next match. If the user presses "1", control passes to logic block 5731 and the system proceeds as described previously. If any other key besides "1" is pressed, control passes to logic block 5711 were a determination is made if "#" was entered. If so, control passes via logic block 5796 to logic block 5750 and the system proceeds as described before. If not, control passes to logic block 5702 via logic block 5797 for processing as described above.

FIG. 58 illustrates a logic flow diagram in a system with patient database access for placing a patient message or chart note. Control is passed to logic block 5800 where a determination is made in the situation where a new mailbox number has been entered, if the account has any remaining unused mailboxes. If not, control passes to logic block 5822 where the user is informed that there are no mailboxes left and control is passed to logic block 5899 whence control is returned to the logic block that originally passed the control to logic block 5800.

If the above is not true, control passes from logic block 5800 to logic block 5801 where the user is asked to enter the patient PFC or to press "#" to return to the main menu. If "#" is pressed, control passes to the logic block that originally transferred control to logic block 5800 via logic block 5815. When a PFC is entered in response to the prompt of logic block 5801, control passes via logic block 5842 to logic block 5701 of the logic flow diagram illustrated in FIG. 57 that illustrates how to locate a PIC using a PFC. Upon return of control from logic illustrated in FIG. 57 to logic block 5842 control is passed to logic block 5843 where a determination is made if a PIC was returned.

If not, control passes back to logic block 5801 and the system proceeds as described before. If so, control is transferred via logic block 5841 to logic block 5901 illustrated in FIG. 59 which illustrates a logic flow diagram in a system with patient database access for recording a chart note, a patient message or patient name or placing a pre-recorded patient message or setting a completion/compliance alert. When control is passed back from FIG. 59 to logic block 5841, the engine writes the changes to the mailbox database; if "Main Menu" is returned control is transferred to logic block 5815 and the system progresses as described above. Subsequent to the engine writing changes to the database, control is transferred to logic block 5871 where a determination is made if a message was recorded.

If not, control is transferred to logic block 5801 and the system progresses as heretofore described. If a message was recorded, control is transferred to logic block 5850 where the engine adds the mailbox information to the database. Control then passes via logic block 5862 to logic block 2322 illustrated in FIG. 23 which illustrates a logic flow diagram for setting an alert note and the number of days until a patient-retrieval alert is activated. Upon return of control from logic illustrated in FIG. 23 to logic block 5862 the engine writes the changes to the database and control is transferred to logic block 5801 where the system proceeds as previously described.

Figure 59:
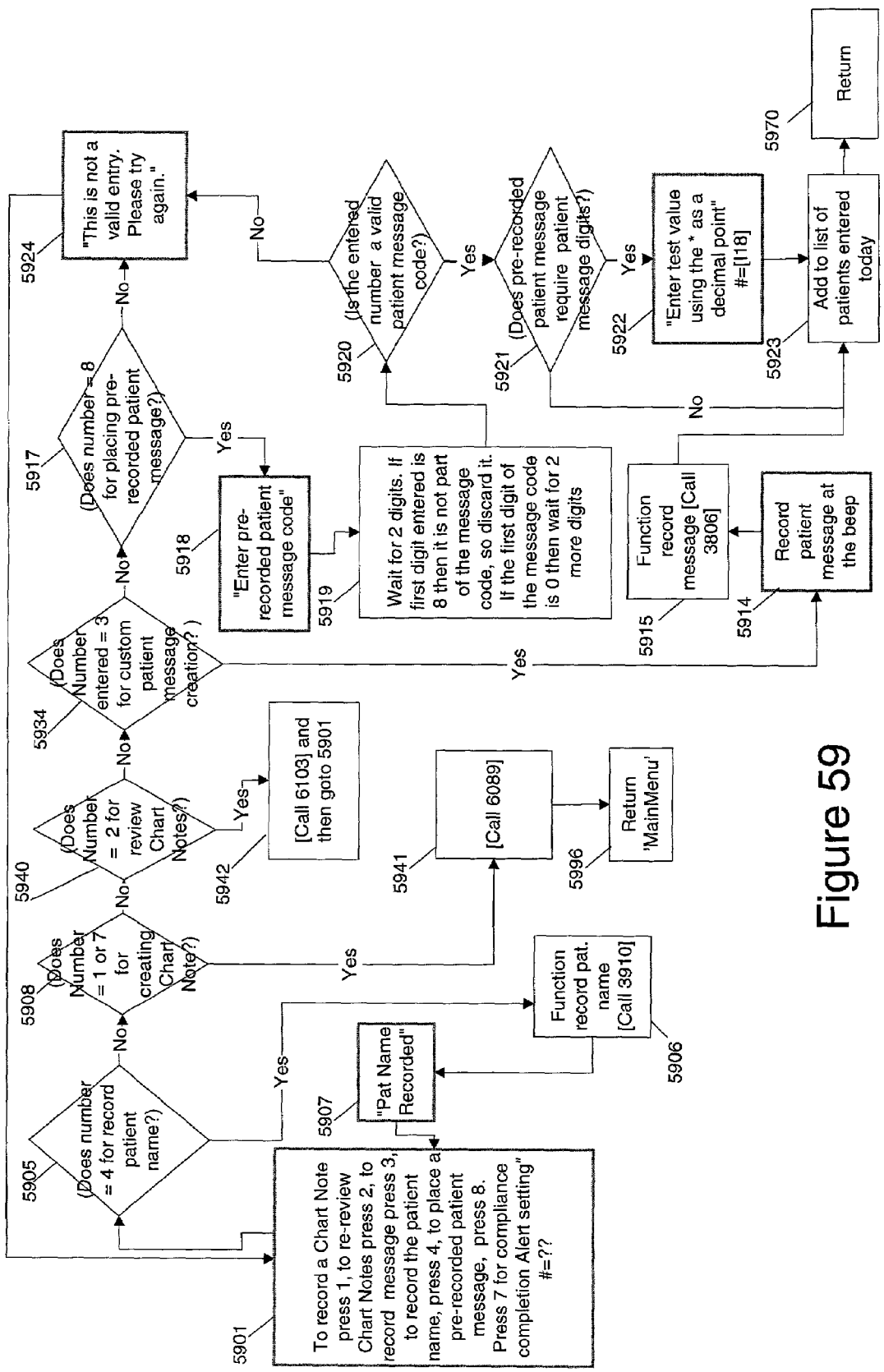
FIG. 59 illustrates a logic flow diagram in a medical information system with patient database access for reviewing chart notes or for recording a chart note, a patient message, or the patient name or to place a pre-recorded patient message or set a completion/compliance alert in accordance with the present disclosure.

FIG. 59 illustrates a logic flow diagram in a system with patient database access for recording a chart note, a patient message, placing a pre-recorded patient message, recording a patient name, or setting a completion/compliance alert. Control is received in logic block 5901 where the user is requested to press "1" to record a chart note, press "2" to re-review chart notes, press "3" to record a patient message, press "4" to record a patient name, press "8" to place a pre-recorded patient message, or press "7" to set a completion/compliance alert. Control is then transferred to logic block 5905 where a determination is made whether or not four was pressed. If so, control is transferred via logic block 5906 to logic block 3910 illustrated in FIG. 39 which illustrates logic for recording a patient name. On return of control from logic illustrated in FIG. 39 to logic block 5906 control is transferred then to logic block 5907 where a prompt states that the patient name was recorded before control is transferred back to logic block 5901.

If a determination is made in logic block 5905 that four was not entered, control is transferred to logic block 5908 where a determination is made whether or not one or seven was entered. If so, control is transferred via logic block 5941 to logic block 6089 illustrated in FIG. 60 which illustrates a logic flow diagram in a system with patient database access for recording a chart note or appending or replacing a chart note in a mailbox. Upon return of control from logic illustrated in FIG. 60 to logic block 5941 control is transferred to logic block 5996 whereupon "Main Menu" is returned to the logic block that originally transferred control to logic block 5901.

If "1" or "7" was not entered in logic block 5908, control is transferred to logic block 5940 where a determination is made whether or not "2" was entered. If so, control is transferred via logic block 5942 to logic block 6103 illustrated in FIG. 61 which illustrates a logic flow diagram in a system with patient database access for reading chart notes for specific PIC and account. Upon return of control to logic block 5942 from logic illustrated in FIG. 61 control is passed to logic block 5901 and the system proceeds as described before.

If a determination is made that "2" was not entered in logic block 5940, control passes to logic block 5934 where a determination is made whether or not "3" was entered. If so, control is passed to logic block 5914 where the user is prompted to record a patient message at the beep. Control then passes via logic block 5915 to logic block 3806 illustrated in FIG. 38 that illustrates a logic flow diagram for recording information on the system with no review. When control returns from logic illustrated in FIG. 38 to logic block 5915 control is next passed to logic block 5923 whereupon the mailbox is added to the list of patients entered today. Control then passes to logic block 5970 whence control is returned to the logic block that originally passed control to logic block 5901.

If "3" is not entered in logic block 5934, control passes to logic block 5917 where a determination is made whether or not "8" was entered. If not, control passes to logic block 5924 where the account owner is informed that an invalid entry was made and asked to make another entry attempt. Control is then passed back to logic block 5901 and the system proceeds as described before.

If a determination is made in logic block 5917 that "8" was entered, control passes to logic block 5918 where the user is prompted to enter a pre-recorded patient message code. Control then passes to logic block 5919 where the system receives two digits; if the first digit entered is "8" or "0" the system waits for two additional digits. Control is then transferred to logic block 5920 where a determination is made whether or not the entered number is a valid pre-recorded patient message code. If not, control passes to logic block 5924 where the user is so informed prior to control being passed back to logic block 5901 where the system proceeds as described above.

If a determination is made that a valid pre-recorded patient message code was entered in logic block 5920, then control passes to logic block 5921 where a determination is made whether or not the patient message type requires patient message digits for a test result. If not, control passes to logic block 5923 where the system proceeds as described above. If so, control passes to logic block 5922 where the user is prompted to enter the test value on the touch tone key pad and thence to logic block 5923 where the system proceeds as described above.

Figure 60:
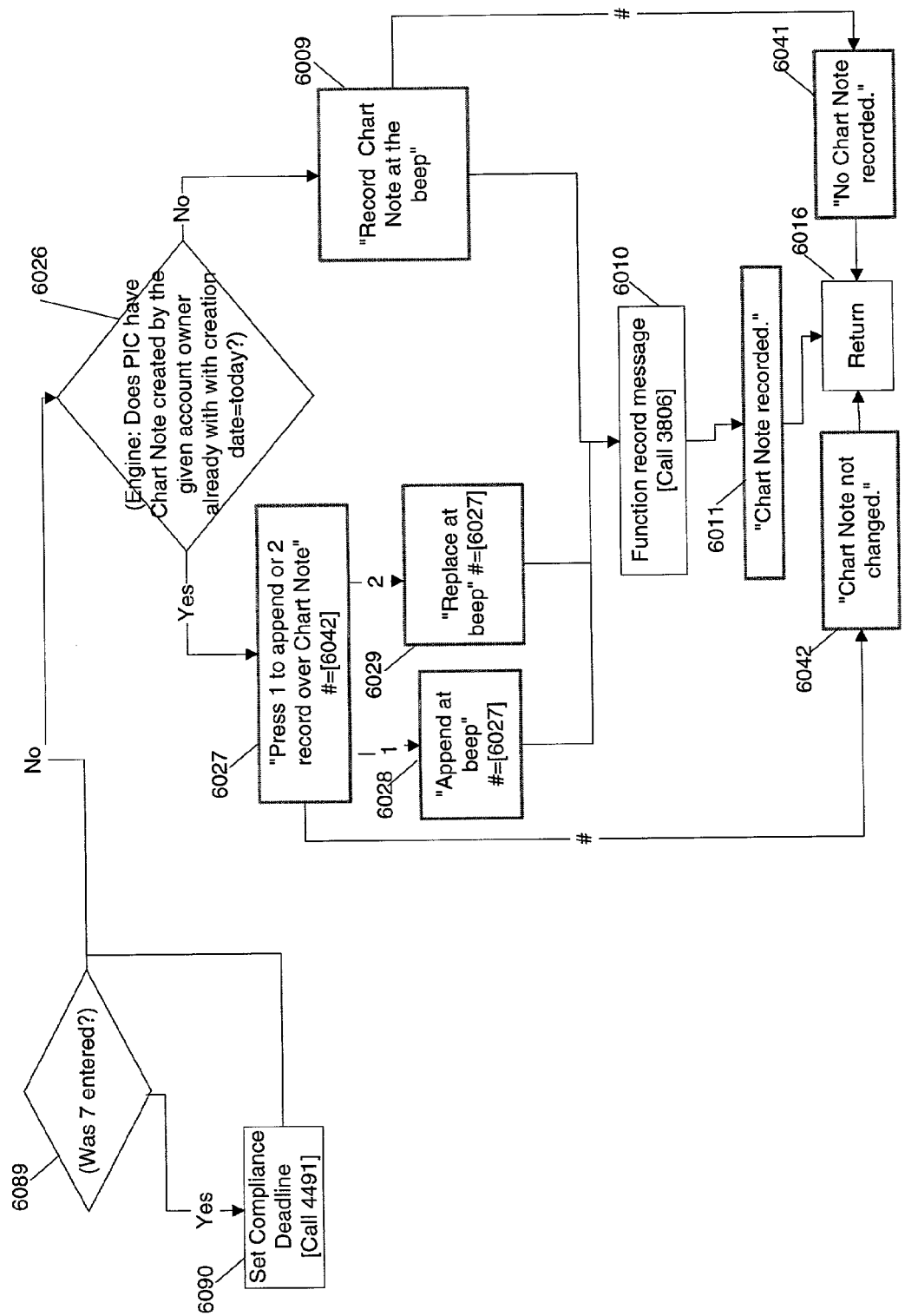
FIG. 60 illustrates a logic flow diagram in a medical information system with patient database access for recording a chart note or appending or replacing a chart note for a mailbox in accordance with to the present disclosure.

FIG. 60 illustrates a logic flow diagram in a system with patient database access for recording a chart note or appending or replacing a chart note in a mailbox. Control is received in logic block 6089 where a determination is made whether or not "7" was entered in the logic block that passed control to logic illustrated in FIG. 60. If so, control is transferred to logic block 4491 illustrated in FIG. 44, which illustrates a logic flow diagram for entry of completion and compliance alert information. Upon return of control from logic illustrated in FIG. 44 to logic block 6090 the control passes to logic block 6026 to be processed as described below.

If a determination is made in logic block 6089 that "7" was not entered, control passes to logic block 6026 where the engine determines if the PIC already has a chart note created by this account owner on the current date. If not, control passes to logic block 6009 where the account owner is prompted to record a chart note at the beep. If the account owner presses "#", control then is passed to logic block 6041 where the account owner is informed no chart note was recorded and control is then passed to logic block 6016. From here control is returned to the logic block that originally passed control to logic block 6089. If the account owner does not press "#", control is passed from logic block 6009 to logic block 6010 to be processed as described below.

If a determination is made in logic block 6026 that the PIC has a chart note already created on the current date by the account owner, control passes to logic block 6027. Here the account owner is asked to press "1" to append to the chart note or "2" to record over the current chart note. If the account owner presses "1", control passes to logic block 6028 where the account owner is prompted to "append at beep" and control is passed to logic block 6010. If the account owner presses "2" in response to the prompt in logic block 6027, control passes to logic block 6029 where the account owner is prompted to "replace at beep" and control is passed to logic block 6010. If the account owner presses "#" in logic block 6027, control is passed to logic block 6042 where a prompt states that the chart note was not changed; control then passes to logic block 6016 and is processed as described below.

In logic block 6010 control is transferred to logic block 3806 illustrated in FIG. 38 which illustrates a logic flow diagram for recording information on the system with no review. Upon return of control from logic illustrated in FIG. 38 to logic block 6010 control is transferred from logic block 6010 to logic block 6011 where the account owner is informed that the chart note has been recorded. Control then passes to logic block 6016 whence control is returned to the logic block that originally passed control to logic block 6089.

Figure 61:
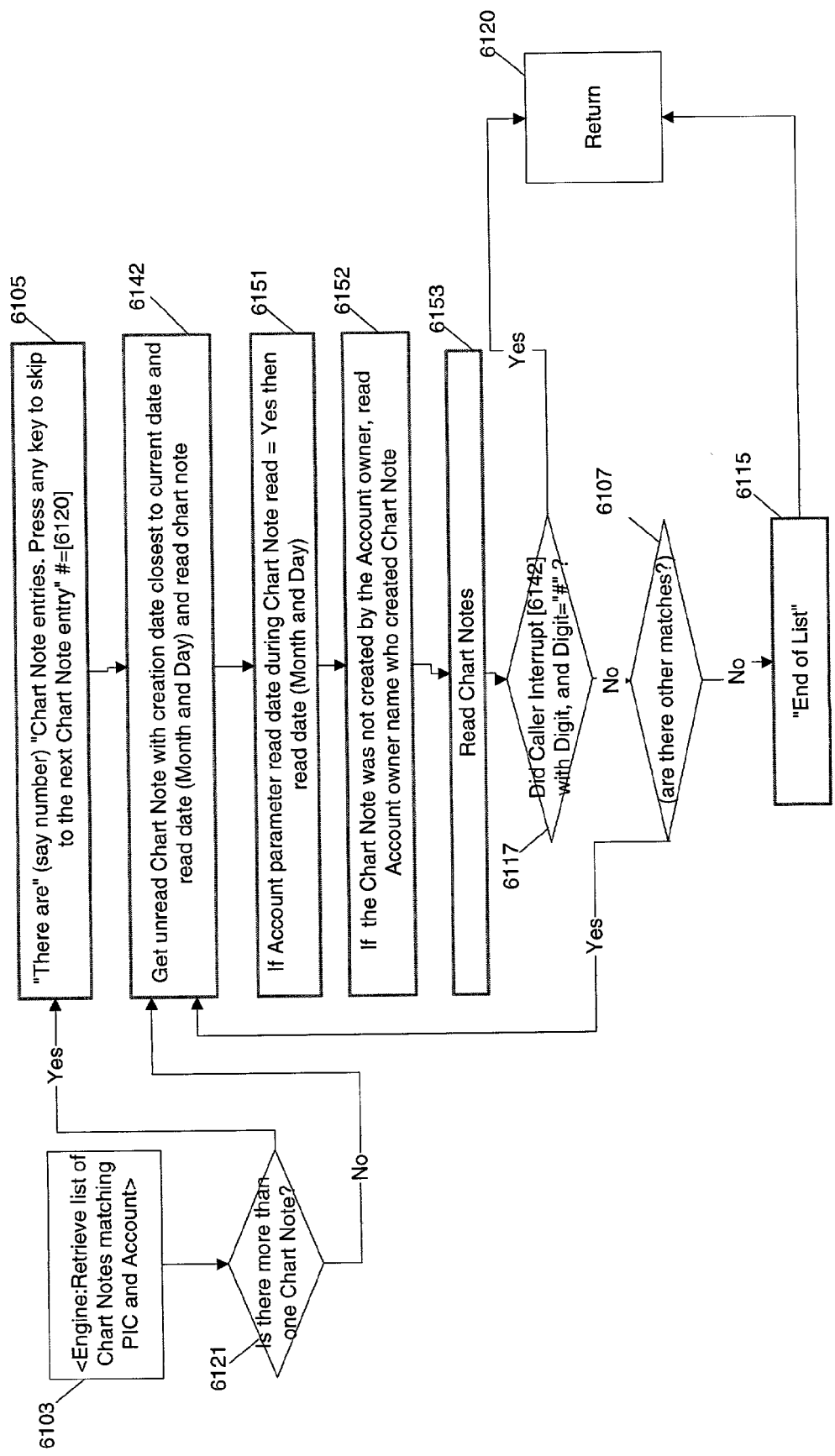
FIG. 61 illustrates a logic flow diagram in a medical information system with patient database access for reading chart notes associated with a specific patient identification code and account in accordance with the present disclosure.

FIG. 61 illustrates a logic flow diagram in a system with patient database access for reading chart notes associated with a specific patient identification code and account. Control is transferred to logic block 6103 where the engine retrieves a list of chart notes matching the PIC and account number. Control then passes to logic block 6121 where a determination is made if there is more than one chart note. If not, control passes to logic block 6142 and the system proceeds as described below. If there are more than one chart note as determined in logic block 6121, control passes to logic block 6105 where the account owner is informed of the number of chart notes and told to press any key to skip to the next chart note entry during the subsequent reading of the chart notes. Control then passes to logic block 6142 where the engine retrieves a chart note that has not as yet been read during this access and with creation date closest to the current date.

From logic block 6142 control is passed to logic block 6151 where the date of the chart note recording is read if an account parameter is set for doing this. Control then passes to logic block 6152 where if the account owner did not create the chart note, the name of the account owner who created the chart note is read.

Control then passes to logic block 6153 where the chart note is then read. An account parameter determines a choice in the reading order of chart notes: The order may be that the current accessing account owner's chart notes are first read in chronological order from the most recently placed to the oldest and then other account owners' chart notes for this PIC are read in chronological order. An alternate choice is to read all chart notes in chronological order regardless of which account owner placed them.

Control then passes to logic block 6117 where a determination is made whether or not the caller interrupted with pressing a touch tone key and if the key was "#". If yes, control is transferred to logic block 6120 whence control is returned to the logic block that originally passed control to logic block 6103. If a key other than "#" was pressed, control passes to logic block 6107 where a determination is made whether or not there are other matches. If so, control is passed back to logic block 6142 and the system proceeds as previously described. If not, control is transferred to logic block 6115 where the "End of the List" prompt is played and control then passes to logic block 6120 and the system proceeds as described previously.

FIG. 62 illustrates a logic flow diagram in a system with patient database access for editing data in a mailbox. Control is transferred to logic block 6201 where the user is informed that this is the edit menu and asked to enter a patient PFC or "#" to return to the main menu.

If "#" is entered, control is transferred to logic bloc 6299 where any edit flags that have been set are cleared before control is transferred to logic block 6230. From logic block 6230 control is returned to the logic block that originally transferred control logic block 6201.

If a PFC is entered, control then passes via logic block 6202 to logic block 5701 illustrated in FIG. 57 which illustrates a logic flow diagram in a system with patient database access for finding a PIC from a PFC entry. Upon return of control to logic block 6202 from logic illustrated in FIG. 57 control passes to logic block 6232 where a determination is made whether or not a PIC was returned. If not, control passes back to logic block 6201 where the system proceeds as previously described. If a PIC is returned, then control passes to logic block 6252 where an edit flag is set that prevents other account owners or patients from entering any system mailbox with that PIC while this flag is set. Control is next transferred via logic block 6203 to logic block 6302 illustrated in FIG. 63 which illustrates a logic flow diagram in a system with patient database access for retrieving and presenting a list of mailboxes that have a specific PIC and that have unretrieved patient messages. If no such mailboxes are found when control is returned to logic block 6203, control is passed via logic block 6250 to logic block 6251 where the user is so informed and thence control is returned to logic block 6201. Otherwise control is returned from logic illustrated in FIG. 63 to logic block 6203 from where control is transferred to logic block 6250 and then to logic block 6204.

In logic block 6204 a prompt informs the user of four options that exist for editing the contents of the mailbox. These are accessible to the user by pressing the digits from one to four on the touch tone telephone. The numbered choices include: Deleting the patient message in which case control is transferred via logic block 6221 to logic block 4708 illustrated in FIG. 47 which illustrates a logic flow diagram for deleting the contents of a mailbox; Replacing the patient message in the mailbox in which case control is transferred via logic block 6222 to logic block 5101 illustrated in FIG. 51 which illustrates a logic flow diagram for replacing the patient message in a mailbox; Re-recording the patient name in which case control is transferred via logic block 6223 to logic block 4814 illustrated in FIG. 48 which illustrates a logic flow diagram for re-recording a patient name in a mailbox; and Replace alert information including the alert note in which case control is transferred via logic block 6224 to logic block 4601 illustrated in FIG. 46 which illustrates a logic flow diagram for replacing alert information in a mailbox. Control is returned to the respective logic blocks that transferred the control initially to each of the above figures and then is transferred back to logic block 6204 via logic block 6219 in all cases except for logic block 6221. In this latter case control is then transferred to logic block 6220 where the edit flag that was set for the PIC to prevent other user entry is cleared and then transferred to logic block 6201. If "#" is entered at logic block 6204, control is transferred to logic block 6220 to clear the edit flag and thence to logic block 6201.

Figure 63:
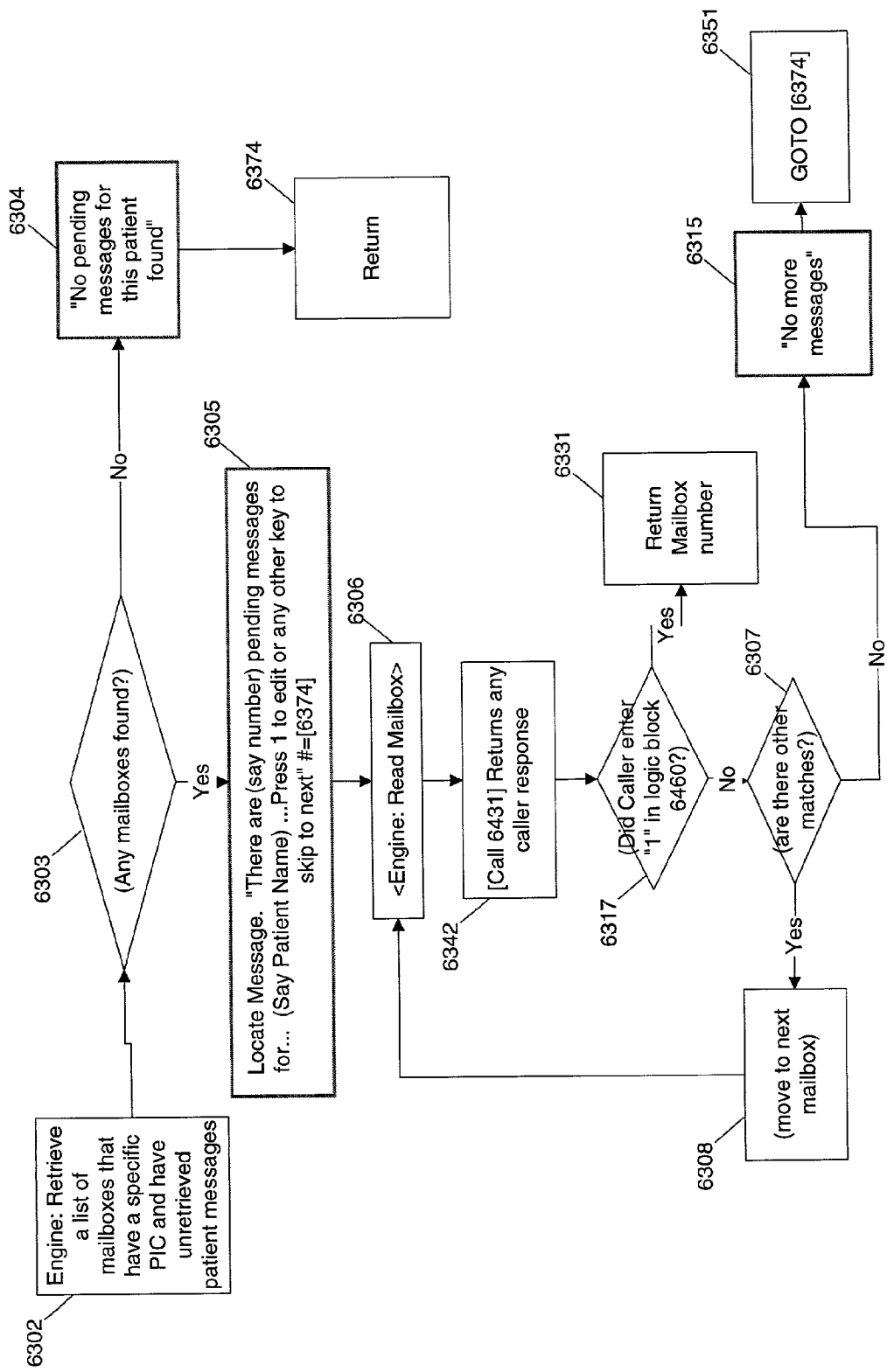
FIG. 63 illustrates a logic flow diagram in a medical information system with patient database access for retrieving and presenting a list of mailboxes that have a specific patient identification code and have unretrieved patient messages in accordance with the present disclosure.

FIG. 63 illustrates a logic flow diagram in a system with patient database access for retrieving and presenting a list of mailboxes that have a specific identification code and have unretrieved patient messages. Control is passed to logic block 6302 where the engine retrieves a list of mailboxes that have a specific PIC and unretrieved patient messages. Control then passes to logic block 6303 where a determination is made whether or not any such mailboxes are found. If none are found, control is passed to logic block 6304 where the account owner is informed that there are no pending patient messages for this patient. Control is then passed to logic block 6374 where control is thereupon returned to the logic block that originally transferred control to logic block 6302.

If such mailboxes are determined to exist in logic block 6303 control is passed to logic block 6305 where the number of such patient messages is read to the user along with the patient name. The user is asked to press "1" to edit the patient message or any other key to skip to the next patient message in the subsequent reading of the mailbox content. Control is then passed to logic block 6306 where the engine reads the mailbox information. Control then passes via logic block 6342 to logic block 6431 illustrated in FIG. 64 which illustrates a logic flow diagram in a system with patient database access for presenting the data in a mailbox. Upon return of control from logic illustrated in FIG. 64 to logic block 6342 control is passed to logic block 6317 where a determination is made if the user entered "1" or not. If not, control is transferred to logic block 6307 where a determination is made whether or not there are other matches. If so, control is transferred to logic block 6308 where the system is caused to access the next mailbox in the list being presented prior to the control being transferred back to logic block 6306 for processing as above. If there are no other matches, control is then transferred to logic block 6315 where the user is informed that there are no more patient messages. Control then transfers to logic block 6351 whence control returns to logic block 6374 and the system proceeds as described above.

If a determination is made in logic block 6317 that the user entered "1", then control is transferred to logic block 6331 where the mailbox number is returned to the logic block that originally transferred control to logic block 6302.

FIG. 64 illustrates a logic flow diagram in a system with patient database access for presenting the data in a particular mailbox. Control is transferred to logic block 6431 where the patient name is played along with the mailbox number. Control is then transferred to logic block 6433 where the title of the patient message if the title is available or the patient message and patient message digits are played. Control then transfers to logic block 6440 where the upload-source notes of the mailbox are played. If the user enters "*" after an upload-source note is played, the system reads the name of the upload-source of the upload-source note to the user. Control then passes to logic block 6450 where, if the system has a parameter set to allow this and if a chart note exists, the chart note(s) associated with the particular mailbox are read. Control is then transferred to logic block 6435 where a determination is made whether or not a patient-retrieval alert deadline is set. If not, control transfers to logic block 6436 where the user is so informed. Control then passes to logic block 6460 where the user is asked to press "1" to accept or any other key for the next patient message. Control then transfers to logic block 6437 where the digit entered and control is returned to the logic block that originally transferred control to logic block 6431.

If a determination is made that there is a patient-retrieval alert deadline set in logic block 6435 then control is transferred to logic block 6434 where the user is informed of the patient-retrieval alert deadline and then control is passed to logic block 6460 where the system proceeds as previously described.

If the account owner presses "1" in logic block 6431, 6433, 6440, or 6450, control is transferred to logic block 6435 and the system proceeds as described above. If the account owner enters any other key in logic block 6431,

6433, 6440, or 6450 control is transferred to logic block 6437 and the system proceeds as described above.

Figure 65:
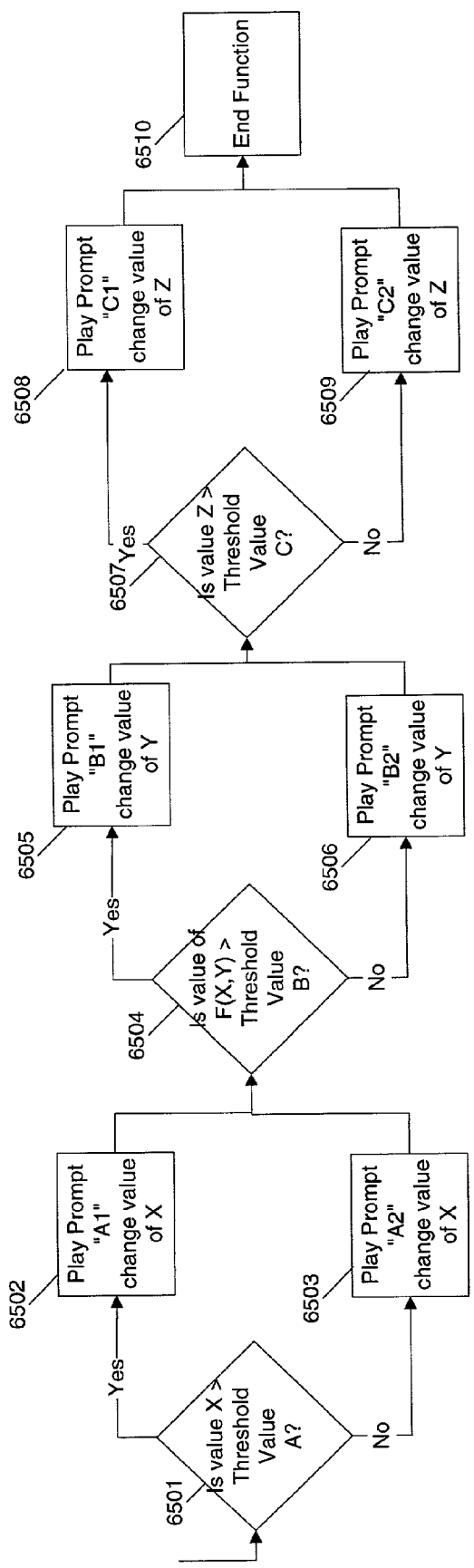
FIG. 65 illustrates a logic flow diagram for a system that possesses an array of prompts appropriate for each prompted step from which prompts are chosen to be used which fit the user's level of familiarity with the system in accordance with the present disclosure.

FIG. 65 illustrates a logic flow diagram for a system that possesses an array of prompts appropriate for each prompted step. The particular prompts from these arrays that are used by the system are automatically chosen in accordance to the user's experience with the system or the user's demonstrated ability to use the system. Values X, Y, and Z represent parameters that are related to the user's experience and use of the system such as, for example, the number of entries into the system, the number of times that a logic block has been accessed by a user, the time period a user listens to a prompt before pushing a key in response to the prompt. The mathematical function, $F(X,Y)$, represents a combination of values of parameters X and Y that has the same dimensions as X or Y.

The flow diagram in FIG. 65 illustrates how prompts are chosen from an array. Prompt "A1" and Prompt "A2" represent different prompts for a particular step in the system. Prompt "B1" and Prompt "B2" represent different prompts for a succeeding step; Prompt "C1" and Prompt "C2" represent different prompts that may be suitably used at another succeeding step in the system. Threshold values A, B, and C represent values of the parameters and/or functions X, $F(X,Y)$, and Z above which the system changes prompts as described below.

Control is transferred to logic block 6501 where a determination is made whether or not the parameter X is greater than the threshold value A. If so, control transfers to logic block 6502 which results in Prompt "A1" being used by the system at this step and an increment to the value of X. If X is not greater than A, control transfers to logic block 6503 whereupon Prompt "A2" is used by the system at this step and an increment is made to the value of X.

Control then passes from logic block 6502 or logic block 6503 to logic block 6504 where a determination is made whether or not the value of a mathematical function $F(X,Y)$ is greater than the threshold value B. If so, control transfers to logic block 6505 which results in Prompt "B1" being used by the system at this step and an increment to the value of Y. If $F(X,Y)$ is not greater than B in logic block 6504, control transfers to logic block 6506 whereupon Prompt "B2" is used by the system at this step and an increment is made to the value of Y.

Control then passes from logic block 6505 or logic block 6506 to logic block 6507 where a determination is made whether or not the value of parameter Z is greater than the threshold value C. If so, control transfers to logic block 6508 which results in Prompt "C1" being used by the system at this step and an increment to the value of Z. If Z is not greater than C in logic block 6507, control transfers to logic block 6509 whereupon Prompt "C2" is used by the system at this step and an increment is made to the value of Z.

This method allows system prompts to be adapted to match the user's experience with the system. In different embodiments threshold values A, B, and C may increase with lack of user accessing the system for a prolonged, defined time period.

FIG. 66 illustrates a logic block diagram for message uploading from an upload-source into the medical information server. Test results are received in logic block 6601 and passed to logic block 6607 or logic block 6602. In logic block 6607 the test results are compared to previously determined parameters specific for the test and consistent with the standards of the upload-source and system account owner. On the basis of these comparisons codes for pre-recorded patient messages and alert information are chosen and an upload file containing these and the corresponding patient identification and other information is formed in logic block 6605. In logic block 6602 an expert system functions similarly to choose instruction codes for pre-recorded patient messages and alerts responsive to the criteria of the account owner account for formation of an upload file in logic block 6605.

The expert system uses rules responsive to the criteria of the account owner who ordered the tests being reported. This allows standard patient messages to be used for tests that are commonly done as a group. For example, assume a screening battery of blood tests is done such as one containing the following: Fasting Blood Glucose, Sodium, Potassium, Carbon Dioxide, Chloride, Blood Urea Nitrogen, Creatinine, Uric Acid, Albumin, Total Protein, Serum Alanine Transaminase, Alkaline Phosphatase, Calcium, and Phosphorous. If all the tests return normal except for a fasting blood glucose of 125 when the upper normal is 110, the patient message chosen by the expert system might be:

"All your tests, including those of liver and kidney function and blood proteins, were normal except for a slightly elevated blood sugar. This should be repeated again in six weeks to check that there is not any progression. If you notice signs of diabetes, such as increased thirst or weight loss or frequent urination, you should set up an office visit promptly."

If all the results were within normal limits except for a glucose of 160 and a carbon dioxide of 16, the expert system criteria could result in a patient message like the following with a patient-retrieval alert and panic alert set by the expert system:

"Your blood tests indicate a higher than normal blood sugar with possible complications that should be evaluated promptly. Please contact me immediately to arrange an appointment."

Control passes from logic block 6605 to logic block 6606 wherein the upload file is inputted into the Medical Information Server according to the present invention. The function then ends in logic block 6607.

The foregoing descriptions of various embodiments have been provided for the purposes of illustration and description. It is not intended to be exhaustive or to limit the invention to the precise forms disclosed. Obviously, many modifications and variations will become apparent to practitioners skilled in the art after appreciating the above disclosure. The various examples and embodiments given herein were chosen in order to elucidate various principles of the disclosure and their practical applications, thereby enabling those skilled in the art to carry out various other embodiments and/or modifications in accordance with the present disclosure as may be suited for particular situations. It is intended that the scope of exclusivity under this application be equitably defined in accordance with claims appended hereto and their equivalents.

What is claimed is:

1. A machine-implemented notifying method which is able to notify responsible parties of notification-worthy events occurring in an automation-assisted medical messaging system, where at least two of the following messaging transactions can take place in the medical messaging system:

(0.1) a medical service provider orders one or more medical tests to be performed on a given patient where one or more deadlines may be indicated for the performance of the tests and/or for the reporting of corresponding test results to the medical service provider;

(0.2) an upload source automatically uploads test results and/or other for-provider information into a machine-implemented mailbox, where the mailbox corresponds to a given patient, and where the mailbox is structured to allow a medical service provider to access the uploaded test results and/or other for-provider information of the corresponding mailbox;

(0.3) the upload source automatically uploads test result changes and/or other informational changes into the machine-implemented mailbox of the given patient;

(0.4) an expert system automatically analyzes test results and/or other for-provider information, generates a notification urgency value for the analyzed information, where the generated notification urgency value is indicative of whether a corresponding predefined threshold has been exceeded where the threshold has been established for the analyzed type of test results and/or other for-provider information;

(0.5) a medical service provider places a message for retrieval by a given patient where the placed message asks the given patient to contact the medical service provider, and where said requested contacting by the given patient may have a time deadline associated therewith;

(0.6) a medical service provider is allowed to review uploaded test results and/or other for-provider information uploaded into the machine-implemented mailbox of a given patient;

(0.7) after review of uploaded test results and/or other for-provider information, a medical service provider is allowed to place and/or approve for placement, corresponding, for-patient information in the mailbox for retrieval by the given patient, where one or more deadlines may be indicated for retrieval by the patient of the placed, for-patient information; and (0.8) a patient is allowed to attempt to access a corresponding patient mailbox even if there is no for-patient information placed in that mailbox;

said notifying method comprising:

(a) testing the messaging transactions of the medical messaging system and responsively generating corresponding alerts for retrieval by one or more alertable parties, where the generated and retrievable alerts can be deleted after they are retrieved, where the generated and retrievable alerts are designated as belonging to at least one category in a set of predefined alert categories, where the predefined alert categories include at least two of the following alert categories:

(a.1) a panic alert category indicative of a failure of an alertable party to timely retrieve a placed alert of a lesser urgency than the panic alert being currently generated, where timely retrieval of the less urgent alert is constituted by retrieval of the less urgent alert before expiration of a deadline established for retrieval of the less urgent alert;

(a.2) a patient retrieval alert category indicative of a failure of a patient to timely retrieve a placed, for-patient message before expiration of a deadline established for retrieval of the placed, for-patient message;

(a.3) a missing message alert category indicative of a failure of a responsible party to timely place a for-patient message in a corresponding mailbox before expiration of a deadline established for placing the for-patient message;

(a.4) a test noncompliance alert category indicative of a failure of a corresponding one or more test results to be uploaded into a given mailbox before expiration of a respective one or more deadlines established for completion of correspondingly ordered tests and for reporting of the corresponding test results;

(a.5) a traced test noncompliance alert category indicative of a failure of a corresponding one or more of plural test results to be uploaded into a given mailbox before expiration of a respective one or more deadlines established for completion of a correspondingly ordered set of plural tests, where the plural tests are pre-designated as belonging to a traced set of tests;

(a.6) a traced test completion alert category indicative of successful and timely uploading of a corresponding one or more of plural test results into a given mailbox before expiration of a respective one or more deadlines established for completion of a correspondingly ordered set of plural tests, where the plural tests are pre-designated as belonging to a traced set of tests;

(a.7) a changed upload alert category indicative of a change of upload information in a given mailbox after a medical service provider has accessed for-provider information that was earlier uploaded into the given mailbox, where change of upload information alters validity of the earlier uploaded information;

(a.8) a test completion alert category indicative of a successful uploading of a corresponding one or more test results into a given mailbox;

(a.9) an upload alert category indicative of for-provider information having been automatically uploaded into a given mailbox where the upload source is indicating via the upload alert, a desire for the medical service provider to be aware of the automatically uploaded, for-provider information;

(a.10) a patient attempt alert category indicative of a patient attempting to retrieve for-patient information from a mailbox that does not contain for-patient information; and (a.11) a timed upload alert category indicative of for-provider information having been automatically uploaded into a given mailbox where the upload source is indicating via the timed upload alert, a desire for the medical service provider to be aware of the automatically uploaded, for-provider information before expiration of an established deadline;

(b) collecting generated alerts that have not yet been deleted and determining the respective categories into which the collected alerts belong; and (c) presenting to a medical service provider and/or to another responsible and notifiable party information indicating the category of one or more of the collected alerts.

2. The machine-implemented notifying method of claim 1 wherein the at least two alert categories include said test completion alert category (a.8).

3. The machine-implemented notifying method of claim 1 wherein the at least two alert categories include said test noncompliance alert category (a.4).

4. The machine-implemented notifying method of claim 1 wherein the at least two alert categories include said changed upload alert category (a.7).

5. The machine-implemented notifying method of claim 1 wherein the at least two alert categories include said patient attempt alert category (a.10).

6. The machine-implemented notifying method of claim 1 wherein the at least two alert categories include said timed upload alert category (a.11) and where the upload source has determined that the uploaded information deserves the issuance of a panic alert if the timed upload alert is not responded to before expiration of the established deadline.

7. The machine-implemented notifying method of claim 1 wherein said predefined alert categories are ordered according to a predefined priority scheme and the step of presenting includes
(c.1) presenting information about alerts in a higher priority one of said at least two alert categories to the medical service provider and/or other responsible and notifiable party before presenting information about alerts in a lower priority one of said at least two alert categories.

8. The machine-implemented notifying method of claim 7 wherein the at least two alert categories include said panic alert category (a.1) and the panic alert category is ordered as the highest priority one of said predefined alert categories.

9. The machine-implemented notifying method of claim 1 wherein said predefined alert categories are ordered according to a predefined priority scheme and the step of presenting includes
(c.1) presenting information about how many collected alerts are present in a given one or more of said at least two alert categories to the medical service provider and/or other responsible and notifiable party before presenting more detailed information about the alerts of the one or more alert categories.

10. The machine-implemented notifying method of claim 9 wherein said information about how many collected alerts are present in a given one or more of said at least two alert categories is machine-vocalized to the medical service provider and/or other responsible and notifiable party.

11. The machine-implemented notifying method of claim 1 wherein the predefined alert categories, to which respective ones of the generated and retrievable alerts are designated, include:
(a.12) at least four of said categories (a.1) through (a.11).

12. The machine-implemented notifying method of claim 1 wherein the predefined alert categories, to which respective ones of the generated and retrievable alerts are designated, include:
(a.12) at least eight of said categories (a.1) through (a.11).

13. An automated notification system for notifying responsible parties of notification-worthy events occurring in an automation-assisted medical messaging system, where at least two of the following messaging transactions can take place in the medical messaging system:
(0.1) a medical service provider orders one or more medical tests to be performed on a given patient where one or more deadlines may be indicated for the performance of the tests and/or for the reporting of corresponding test results to the medical service provider;
(0.2) an upload source automatically uploads test results and/or other for-provider information into a machine-implemented mailbox, where the mailbox corresponds to a given patient, and where the mailbox is structured to allow a medical service provider to access the uploaded test results and/or other for-provider information of the corresponding mailbox;
(0.3) the upload source automatically uploads test result changes and/or other informational changes into the machine-implemented mailbox of the given patient;
(0.4) an expert system automatically analyzes test results and/or other for-provider information, generates a notification urgency value for the analyzed information, where the generated notification urgency value is indicative of whether a corresponding predefined threshold has been exceeded where the threshold has been established for the analyzed type of test results and/or other for-provider information;
(0.5) a medical service provider places a message for retrieval by a given patient where the placed message asks the given patient to contact the medical service provider, and where said requested contacting by the given patient may have a time deadline associated therewith;
(0.6) a medical service provider is allowed to review uploaded test results and/or other for-provider information uploaded into the machine-implemented mailbox of a given patient;
(0.7) after review of uploaded test results and/or other for-provider information, a medical service provider is allowed to place and/or approve for placement, corresponding, for-patient information in the mailbox for retrieval by the given patient, where one or more deadlines may be indicated for retrieval by the patient of the placed, for-patient information; and
(0.8) a patient is allowed to attempt to access a corresponding patient mailbox even if there is no for-patient information placed in that mailbox;
said automated notification system comprises:
(a) one or more alert event detectors which monitor the messaging transactions of the medical messaging system and responsively generate corresponding alerts for retrieval by one or more alertable parties, where the generated and retrievable alerts can be deleted after they are retrieved, where the generated and retrievable alerts are machine designated as belonging to at least one category in a set of predefined alert categories, where the predefined alert categories include at least two of the following alert categories:
(a.1) a panic alert category indicative of a failure of an alertable party to timely retrieve a placed alert of a lesser urgency than the panic alert being currently generated, where timely retrieval of the less urgent alert is constituted by retrieval of the less urgent alert before expiration of a deadline established for retrieval of the less urgent alert;
(a.2) a patient retrieval alert category indicative of a failure of a patient to timely retrieve a placed, for-patient message before expiration of a deadline established for retrieval of the placed, for-patient message;
(a.3) a missing message alert category indicative of a failure of a responsible party to timely place a for-patient message in a corresponding mailbox before expiration of a deadline established for placing the for-patient message;
(a.4) a test noncompliance alert category indicative of a failure of a corresponding one or more test results to be uploaded into a given mailbox before expiration of a respective one or more deadlines established for completion of correspondingly ordered tests and for reporting of the corresponding test results;
(a.5) a traced test noncompliance alert category indicative of a failure of a corresponding one or more of plural test results to be uploaded into a given mailbox before expiration of a respective one or more deadlines established for completion of a correspondingly ordered set of plural tests, where the plural tests are pre-designated as belonging to a traced set of tests;

(a.6) a traced test completion alert category indicative of successful and timely uploading of a corresponding one or more of plural test results into a given mailbox before expiration of a respective one or more deadlines established for completion of a correspondingly ordered set of plural tests, where the plural tests are pre-designated as belonging to a traced set of tests;

(a.7) a changed upload alert category indicative of a change of upload information in a given mailbox after a medical service provider has accessed for-provider information that was earlier uploaded into the given mailbox, where change of upload information alters validity of the earlier uploaded information;

(a.8) a test completion alert category indicative of a successful uploading of a corresponding one or more test results into a given mailbox;

(a.9) an upload alert category indicative of for-provider information having been automatically uploaded into a given mailbox where the upload source is indicating via the upload alert, a desire for the medical service provider to be aware of the automatically uploaded, for-provider information;

(a.10) a patient attempt alert category indicative of a patient attempting to retrieve for-patient information from a mailbox that does not contain for-patient information; and (a.11) a timed upload alert category indicative of for-provider information having been automatically uploaded into a given mailbox where the upload source is indicating via the timed upload alert, a desire for the medical service provider to be aware of the automatically uploaded, for-provider information before expiration of an established deadline;

(b) an alerts collector which collects generated alerts that have not yet been deleted and identifies the respective categories into which the collected alerts belong; and (c) an alerts presenter which can present to a medical service provider and/or to another responsible and notifiable party information indicating the category of one or more of the collected alerts.

14. The automated notification system of claim 13 wherein said predefined alert categories are ordered according to a predefined priority scheme and the alerts presenter includes:

(c.1) a presentation prioritizer which causes presentation of information about alerts in a higher priority one of said at least two alert categories to surpass presentation of information about alerts in a lower priority one of said at least two alert categories.

15. The automated notification system of claim 14 wherein said surpassing of presentation includes at least one of serially presenting the higher priority information before the lower priority information, or listing the higher priority information before the lower priority information.

16. The automated notification system of claim 14 wherein said presentation of information includes indicating how many collected alerts are present in a given one or more of said at least two alert categories.

17. The automated notification system of claim 14 wherein said presentation of information about the alerts includes a machine-vocalized presentation.

18. The automated notification system of claim 13 wherein the predefined alert categories, to which respective ones of the generated and retrievable alerts are designated, include at least eight of said categories (a.1) through (a.11).

19. A machine-implemented alert forwarding method which is able to alert responsible parties of alert-worthy events occurring in an automation-assisted medical messaging system, wherein operations within the medical messaging system are characterized by:

(0.1) a medical service provider orders one or more medical tests to be performed on a given one or more patients;

(0.2) corresponding test results are generated;

(0.3) a machine-implemented upload source automatically uploads the generated test results and/or corresponding other for-provider information into one or more machine-implemented mailboxes, where each mailbox is structured to allow a medical service provider to access the uploaded test results and/or other for-provider information;

(0.4) an expert system automatically analyzes the test results and/or other for-provider information and generates an alert flag for the analyzed information if the analyzed information is outside of predefined bounds;

(0.5) the generated alert flags are logically associated with the uploaded test results and/or other for-provider information uploaded into the machine-implemented mailbox;

(0.6) the generated alert flags are assigned deadlines by which review is to occur of their corresponding uploaded test results and/or other uploaded for-provider information;

(0.7) a medical service provider is allowed to review uploaded test results and/or other for-provider information uploaded into the machine-implemented mailbox;

(0.8) one or more, supplementally notifiable persons are designated;

(0.9) the medical service provider and/or the one or more, supplementally notifiable persons can be presented with respective alert indicators corresponding to said, generated alert flags, if any;

(0.10) inhibiting deletion of the associated alert flag, if any, of uploaded test results and/or other uploaded for-provider information until the corresponding uploaded information is reviewed;

said alert forwarding method comprising:

(a) automatically finding undeleted alert flags and determining if review by a responsible medical service provider has taken place for the associated uploaded test results and/or other uploaded for-provider information; and (b) if the assigned deadline of the corresponding and not-yet-deleted alert flag has passed and if it is automatically determined that a responsible medical service provider has not yet reviewed the logically-associated, uploaded test results and/or other uploaded for-provider information, then automatically forwarding a corresponding notification alert signal to at least one of said supplementally notifiable persons where the notification alert signal identifies the uploaded information that has not yet been reviewed.

* * * * *